(12) United States Patent
Okano et al.

(10) Patent No.: US 9,249,409 B2
(45) Date of Patent: Feb. 2, 2016

(54) METHOD FOR DETECTION OF CANCER

(75) Inventors: Fumiyoshi Okano, Kamakura (JP);
Kana Suzuki, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 803 days.

(21) Appl. No.: 12/739,689

(22) PCT Filed: Oct. 23, 2008

(86) PCT No.: PCT/JP2008/069275
§ 371 (c)(1),
(2), (4) Date: Apr. 23, 2010

(87) PCT Pub. No.: WO2009/054475
PCT Pub. Date: Apr. 30, 2009

(65) Prior Publication Data
US 2010/0297646 A1 Nov. 25, 2010

(30) Foreign Application Priority Data

Oct. 25, 2007 (JP) .................................. 2007-277697
Oct. 25, 2007 (JP) .................................. 2007-277747
Oct. 26, 2007 (JP) .................................. 2007-279512
Oct. 26, 2007 (JP) .................................. 2007-279580
Sep. 30, 2008 (JP) .................................. 2008-254170

(51) Int. Cl.
*G01N 33/53* (2006.01)
*G01N 33/574* (2006.01)
*C12N 15/10* (2006.01)

(52) U.S. Cl.
CPC ...... *C12N 15/1037* (2013.01); *G01N 33/57484* (2013.01); *G01N 2333/4727* (2013.01); *G01N 2333/723* (2013.01)

(58) Field of Classification Search
CPC ....................... G01N 33/564; G01N 33/57484
See application file for complete search history.

(56) References Cited

U.S. PATENT DOCUMENTS

| 6,355,623 B2 * | 3/2002 | Seidman et al. ................. 514/45 |
| 2003/0124579 A1 * | 7/2003 | Mack et al. ........................ 435/6 |
| 2004/0029114 A1 * | 2/2004 | Mack et al. ........................ 435/6 |
| 2004/0175721 A1 * | 9/2004 | Doxsey ............................. 435/6 |
| 2011/0219464 A1 * | 9/2011 | Domon et al. .................... 800/13 |

FOREIGN PATENT DOCUMENTS

| JP | 2005-506033 A | 3/2005 |
| JP | 2006-517094 A | 7/2006 |
| JP | 2007-512804 A | 5/2007 |
| WO | WO 02/30268 A2 | 4/2002 |
| WO | WO 02/083876 A2 | 10/2002 |
| WO | WO 03/009814 A2 | 2/2003 |
| WO | WO 2004/024887 A2 | 3/2004 |
| WO | WO 2004/080148 A2 | 9/2004 |
| WO | WO 2005/040414 A1 | 5/2005 |

OTHER PUBLICATIONS

American Cancer Society teaches in Staging (American Cancer Society, http://www.cancer.org/Treatment/UnderstandingYour Diagnosis/staging, downloaded May 31, 2011).*
Looijenga et al. (Cancer Res. Jan. 5, 2006 66:290-302).*
Infante et al. (J. Cell. Biol. Apr. 5, 1999 145:83-98).*
Harlow and Lane (Antibodies, a Laboratory Manual, Cold Spring Harbor Laboratory Press, 1988, p. 238).*
Guinn et al. (Proc. Amer. Assoc. Cancer Res 2004 45: Abstract #5452).*
TRIP11 protein, human (MeSH-NCBI Dec. 22, 1997).*
Matsushita et al (FEBS Letters, 1999, vol. 443, pp. 348-352).*
Singh et al (Glycobiology, 2001, vol. 11, pp. 587-592).*
Nesslinger et al. (Clin. Cancer Res. Mar. 1, 2007 13(5): 1493-1502).*
Guinn et al. (Biochem. Biophys. Res. Comm 2005 335:1293-1304).*
"Predicted: similar to CG4452-PA, isoform A [*Canis familiaris*]," Protein; Translations of Life, XP-002597394, one page, Aug. 30, 2005.
Albrecht, Walter et al., "Testicular tumor markers: Corner-stones in the management of malignant germ cell tumors," J. Lab. Med., XP-007914538, 28 (2), pp. 109-115, Jan. 1, 2004.
Search Report dated Feb. 10, 2011 for Application No. 08842391.8.
Clinical Tests, Dec. 2003, vol. 47, No. 13, pp. 1641-1654.
Guasch et al., "FGFR1 is fused to the centrosome-associated protein CEP 110 in the 8p12 stem cell myeloproliferative disorder with t(8;9)(p12;q33)," Blood, Mar. 1, 2000, vol. 95, No. 5, pp. 1788-1796.
Infante et al., "GMAP-210, A Cis-Golgi Network-associated Protein, is a Minus End Microtubule-binding Protein," The Journal of Cell Biology, vol. 145, No. 1, Apr. 5, 1999, pp. 83-98.
Lee et al., "Two classes of proteins dependent on either the presence or absence of thyroid hormone for interaction with the thyroid hormone receptor," Mol. Endocrinol., vol. 9, 1995, pp. 243-254. (English Abstract only).
Naokazu et al., "Protein, Nucleic Acid and Enzyme," Science Links Japan, vol. 50, No. 11, 2005, ISSN No. 0039-9450, pp. 1405-1412.
Ou et al., "CEP 110 and ninein are located in a specific domain of the centrosome associated with centrosome maturation," Journal of Cell Science, vol. 115, 2002, pp. 1825-1835.
Tanaka et al., "Cloning and characterization of the human Calmegin gene encoding putative testis-specific chaperone," Gene, vol. 204, Nos. 1/2, Dec. 19, 1997, ISN No. 0378-1119(19971219)204:1-2; 1-U, pp. 159-163.
Waters et al., "Cancer clues from studies of pet dogs with cancer an offer unique help in the fight against human malignancies while also improving care for man's best friend," Scientific American, Inc., 2006, pp. 95-101.

* cited by examiner

*Primary Examiner* — Peter J Reddig
(74) *Attorney, Agent, or Firm* — Birch, Stewart, Kolasch & Birch, LLP

(57) ABSTRACT

A method for detecting a cancer(s) based on an expression of prescribed polypeptides is disclosed. These polypeptides were isolated, by the SEREX method using a cDNA library derived from canine testis and serum from a cancer-bearing dog, as a polypeptide which binds to an antibody existing in serum derived from cancer-bearing living body. Because these polypeptides react with antibodies specifically existing in serum of a cancer patient, cancers in a living body can be detected by measuring the antibody in a sample. Cancers in a living body can also be detected by measuring the antigen protein of the antibody per se or mRNA encoding it.

12 Claims, 9 Drawing Sheets

METHOD FOR DETECTION OF CANCER

TECHNICAL FIELD

The present invention relates to a novel method for detecting a cancer(s).

BACKGROUND ART

Cancers are the commonest cause for death among all of the causes for death, and the main therapies therefor are palliative treatment in which surgical treatment is combined with radiotherapy and chemotherapy. By virtue of the advance in medical technology, cancers have become such diseases that can be highly possibly cured if they can be found in the early stage. Therefore, a detection method of cancer which can be easily carried out by testing serum, urine or the like without physical and economical burden to patients is demanded.

Recently, methods wherein tumor products such as tumor markers are measured have been widely used as diagnostic methods using blood or urine. Examples of the tumor product include tumor-related antigens, enzymes, specific proteins, metabolites, tumor genes, products of tumor genes, and tumor-suppressor genes. In some cancers, a carcinoembryonic antigen CEA, glycoproteins CA19-9 and CA125, a prostate-specific antigen PSA, calcitonin which is a peptide hormone produced in thyroid and the like are utilized as tumor markers in cancer diagnosis. However, in most types of cancers, there are no tumor markers useful for cancer diagnosis. Further, since most of the tumor markers currently known exist only in very small amounts (e.g., in the order of pg/mL) in body fluid, their detection requires a highly sensitive measurement method or a special technique. Under such circumstances, if a novel cancer test method by which various cancers can be detected by simple operations is provided, its use for diagnosis of various cancers are expected to be developed.

The method would be very useful if it further enables diagnosis of cancers developed in invisible parts, assessment of the stage of cancer progression, assessment of the grade of cancer malignancy, follow-up of postoperative patients, diagnosis of recurrence, diagnosis of metastasis, monitoring of therapy and the like, in addition to detection of cancers.

More particularly, if a method which enables diagnosis of cancers developed in invisible parts is provided, it would be useful for early detection of cancers in parts where cancers are hardly realized, for example, the inside of the abdominal cavity. Further, even in cases where the tumor is too small to be found visually, detection of such cancers that cannot be found by ultrasonography, CT (computed tomography) or MRI (magnetic resonance imaging) is also made possible.

The stage of cancer progression is classified based on the extent of expansion of the tumor at the primary site and whether or not metastasis has occurred to a regional lymph node or a distant organ. In general, the disease stage is classified into 5 stages, wherein a larger number indicates a more advanced state. Although, strictly speaking, the definition varies depending on organs, the disease stage 0 indicates a cancer staying within epithelium and the stage 1V indicates a cancer with distant metastasis. If the stage of cancer progression as described above can be determined, determination of an appropriate therapeutic strategy and, in addition, assessment of therapeutic effects of anticancer drugs are made possible. In regard to the determination of the therapeutic strategy, for example, some of prostate cancers are low malignant and hardly progress, hence do not require treatment; and others are progressive and metastasize to bones and/or the like, causing pain and death of patients. Since hormonotherapy and extirpative surgery are accompanied by side effects, it is necessary to appropriately judge and determine the therapeutic approach. Further, if whether the selected anticancer drug is appropriate or not, when to end the administration of the anticancer drug and the like can be appropriately judged, the physical and economical burden on the patient can also be reduced. Therefore, it is important that the stage of progression can be assessed.

One of the characteristics of cancer cells is blastogenesis, that is, dedifferentiation. Except for a part of cancers, lower-differentiated cancer cells such as those poorly differentiated or undifferentiated grow more rapidly after the metastasis, and the prognosis is poor. Such cancers are said to be highly malignant. Conversely, highly-differentiated cancer cells, that is, those showing a high degree of cell differentiation maintain the structural and functional traits of the organ from which they were originated, and can be said to be less malignant. If such cancer malignancy can be determined, it is made possible to secure a larger margin of excision of the tumor in cases where its malignancy is high even if the size of the tumor is small, as well as to follow up the patient, paying attention to larger areas in the surrounding tissues.

In cases where diagnosis of the postoperative course including recurrence and metastasis is possible, diagnosis of whether the tumor has been completely excised by the operation is made possible. Since recurrence is likely to occur in cases where the excision was incomplete, this can be used as a basis for judging whether a more careful follow up of the patient at short intervals is necessary and, in some cases, for deciding whether an early reoperation should be carried out. Furthermore, recurrent cancer can be found at its early stage with a high possibility. In the case of distant metastasis, its detection is likely to be late, but if a method which enables diagnosis of metastasis is provided, a basis for deciding whether the region to be checked should be extended in addition to the site where the tumor was excised and the vicinity thereof can be obtained.

If monitoring of therapy is possible, an appropriate therapeutic method or combination of therapeutic methods can be selected among various therapeutic methods to optimize the therapy. If one can see the therapeutic effects of anticancer agents, selection of the dosing periods and the types and doses of anticancer agents may be made easier. Further, after excision of the tumor, one can know presence/absence of remaining tumor, and during follow up of the patient, one can have a clue to find metastasis or recurrence as early as possible, so that initiation of early treatment is possible. If monitoring of a therapeutic effect is possible, whether the therapeutic approach was appropriate and whether the therapeutic approach should be changed to another can be judged.

It is known that dogs age 7 times faster than human. Recently, a companion animal is kept as a member of a family and often has a lifestyle similar to that of its owner. Therefore, if the companion animal is suffering from cancer, it is possible to predict that the owner has a high risk of development of cancer in the future. If accurate diagnosis of cancer in companion animals is possible, it is expected to be useful as a clue for prophylaxis of cancer in the owners.

It is said that about 6,390,000 and about 17,640,000 dogs are currently kept in Japan and the U.S., respectively. Since, in addition to rabies vaccination, combination vaccines such as pentavalent, heptavalent and octavalent vaccines have become popular, occurrence of highly lethal infectious diseases such as canine parvovirus infection, canine distemper virus infection, canine parainfluenza (kennel cough), canine adenovirus type II infection (kennel cough), canine infectious hepatitis, canine coronavirus infection and leptospirosis decreased. Therefore, the average life expectancy of dogs increased, and aged dogs of 7 years old or older occupy 35.5% of the total number of the kept dogs. As the causes of death, cancer, hypertension, cardiac diseases and the like are consistently increasing like in human. In the U.S., about 4,000,000 dogs/year are diagnosed as cancer, and it is also said that about 1,600,000 dogs in Japan potentially have a certain tumor.

However, there exist no simple diagnostic agents for animal cancers so far, and in the field of animal healthcare, test methods such as photography by X-ray, CT and MRI are not commonly used. Their diagnosis is carried out by palpation, simple blood test and a test by radiography, which largely depend on experience of a veterinarian. Although some veterinarians have begun to employ a test method using serum, human tumor markers are used in the method since canine tumor markers have not been found yet.

Accurate diagnosis of cancer requires an abdominal operation, and there are large problems of the physical burden to a dog and the economical burden to its owner. If diagnosis of cancers can be conveniently carried out in companion animals such as dogs and cats, early detection and accurate diagnosis of the cancers are made possible, which is useful for treatment of the cancers in the companion animals. Further, if a method which enables such simple diagnosis of cancers using serum is provided, it is expected that the method not only makes it possible to diagnose cancers but also contributes a great deal to periodic health examination, preoperative diagnosis and determination of the therapeutic strategy.

Unlike in human, medical examination is not popular in companion animals. Therefore, in many cases, tumor in a companion animal is found at its late stage, and the owner realizes the tumor and takes his animal only after the tumor has grown bigger. In cases where the grown tumor is malignant, surgical therapy such as operation and administration of an anticancer agent or the like are very often too late. Therefore, in cases where the cancer was judged as malignant by a veterinarian, anticancer drug therapy is generally carried out without operation. Even in cases where an operation is carried out, the operation must be strictly controlled to secure the margin and prevent dispersion of blood and cells during the operation. It is desirable to start anticancer drug therapy immediately after the operation and to follow up the patient at short intervals. It is expected that early detection of cancers is made easier if the above-described diagnosis is adopted into the medical examination of dogs, so-called "dog dock", which is recently being popularized.

On the other hand, in the case of a benign tumor, an operation can be decided to be carried out even if the tumor is large. All that is required is to care the excised area, and there is no need for treatment with neither expensive anticancer drugs nor being nervous about the follow up.

In view of the above-described circumstances, if a simple means for detecting cancers with a high sensitivity which can be applied to cancer diagnosis in animals is provided, accurate and efficient therapy is made possible, which is highly advantageous to both owners and veterinarians.

Non-patent Literature 1: Investigation by Ministry of Health, Labour and Welfare, 2004
Non-patent Literature 2: Nikkei Science, 2007, March, pp. 80-88
Non-patent Literature 3: Clinical Tests, 2003, December, vol. 47, No. 13, p. 1641-1654
Non-patent Literature 4: Statistics of Diseases of Dogs and Cats, 2005, January
Non-patent Literature 5: Companion Animal Health Products: 2006 Edition By Tim Wesley, ANIMAL PHARM REPORTS
Non-patent Literature 6: Expansion of Cancer and Stage of Progression. Hideaki Tsukuma, Department of Cancer Control and Statistics, Osaka Medical Center for Cancer and Cardiovascular Diseases
Non-patent Literature 7: Proteins, Nucleic Acids and Enzymes, vol. 50, No. 11, p. 1405-1412
Non-patent Literature 8: J Cell Sci. 115: 1825-35
Non-patent Literature 9: Blood. 95: 1788-96
Non-patent Literature 10: Mol Endocrinol. 9: 243-54 (1995)
Non-patent Literature 11: J Cell Biol. 145: 83-98 (1999)

DISCLOSURE OF THE INVENTION

Problems to be Solved by the Invention

An object of the present invention is to provide means for detecting a cancer(s) which is useful in diagnosing a cancer(s).

Means for Solving the Problem

The present inventors intensively studied to obtain a cDNA encoding a protein which binds to an antibody existing in serum derived from a tumor-bearing living body by the SEREX method using a cDNA library derived from canine testis and serum of a tumor-bearing dog, which cDNA was used to prepare a polypeptide having the amino acid sequence shown in SEQ ID NO:2, a canine calmegin protein having the amino acid sequence shown in SEQ ID NO:16, a canine centrosomal protein (which may be hereinafter abbreviated as CEP) having the amino acid sequence shown in SEQ ID NO:26, and the canine thyroid hormone receptor interactor 11 (which may be hereinafter described as "TRIP11") having the amino acid sequence shown in SEQ ID NO:45. Further, based on a human gene homologous to the obtained gene, a polypeptide having the amino acid sequence shown in SEQ ID NO:4, a human calmegin protein having the amino acid sequence shown in SEQ ID NO:18, a human CEP having the amino acid sequence shown in SEQ ID NO:28, and a human TRIP11 having the amino acid sequence shown in SEQ ID NO:47 were prepared. The inventors found that genes encoding these proteins are specifically expressed in canine and human testis and malignant cancer cells (see, Examples A-1, B-1, C-1 and D-1), and that recombinant proteins prepared based on the amino acid sequences of these proteins specifically react with the serum in cancer-bearing living body, as well as that each of the above-mentioned polypeptides and homologous factors thereof can be specifically detected in a cancer-bearing living body by an antibody prepared by using the respective recombinant proteins, thereby completing the present invention.

That is, the present invention provides a method for detecting a cancer(s), which is applied to a sample separated from a living body and comprises measuring an expression of at least one of the polypeptides (a) to (d) below:

(a) a polypeptide produced in said living body and having a reactivity to bind to an antibody against a polypeptide having the amino acid sequence shown in SEQ ID NO:2 or 4 by antigen-antibody reaction;

(b) calmegin;

(c) a polypeptide having a reactivity to bind to an antibody against a centrosomal protein having the amino acid sequence shown in SEQ ID NO:26, 28 or 42 by antigen-antibody reaction;

(d) thyroid hormone receptor interactor 11.

The present invention also provides a reagent for detecting a cancer(s), comprising a polypeptide which immunologically reacts with an antibody induced in a living body against any one of the polypeptides (i) to (l) below:

(i) a polypeptide having the amino acid sequence shown in SEQ ID NO:2 or 4;

(j) calmegin;

(k) a centrosomal protein having the amino acid sequence shown in SEQ ID NO:26, 28 or 42;

(l) thyroid hormone receptor interactor 11.

The present invention further provides a reagent for detecting a cancer(s), comprising an antibody which immunologically reacts with any one of the polypeptides (m) to (p) below or antigen-binding fragment thereof:

(m) a polypeptide produced in a living body and having a reactivity to bind to an antibody against a polypeptide having the amino acid sequence shown in SEQ ID NO:2 or 4 by antigen-antibody reaction;

(n) calmegin;

(o) a polypeptide produced in a living body and having a reactivity to bind to an antibody against a centrosomal protein having the amino acid sequence shown in SEQ ID NO:26, 28 or 42 by antigen-antibody reaction;

(p) thyroid hormone receptor interactor 11.

The present invention still further provides a reagent for detecting a cancer(s), comprising a polynucleotide which specifically hybridizes with a partial region of the base sequence shown in any one of SEQ ID NOs:1, 3, 15, 17, 25, 27, 41, 44 and 46 in SEQUENCE LISTING.

EFFECTS OF THE INVENTION

By the present invention, a novel method for detecting a cancer(s) was provided. As will be concretely described in Examples below, recombinant polypeptides prepared based on the amino acid sequence shown in SEQ ID NO:2 or 4, the amino acid sequence of calmegin, the amino acid sequence of CEP shown in SEQ ID NO:26, 28 or 42 and the amino acid sequence of TRIP11 react with antibodies which specifically exist in serum of cancer patients. Therefore, cancers in a living body can be detected by measuring the antibody in a sample according to the method of the present invention. Cancers in a living body can also be detected by measuring the antigen protein per se which the antibody recognizes. Because the method of the present invention makes it possible to detect invisible small cancers and cancers which exist in a deep part of a body, it is also useful for early detection of cancers in medical examinations and the like. If the method of the present invention is used in following-up of the patients after cancer therapy, recurrence of the cancer can be detected in its early stage. Moreover, the method of the present invention makes it possible to assess the stage of cancer progression such as growth of the tumor, invasion of the tumor to the surrounding tissues, and metastasis of the cancer to lymph nodes and distant organs. Furthermore, the method of the present invention makes it possible to assess the grade of cancer malignancy, because patients suffering from more malignant cancer have more amount of the antibody mentioned above in serum compared to those suffering from less malignant cancer. Furthermore, based on the increase or decrease of the above-mentioned antibody in serum, how much the administered anticancer drug is effective, or whether a portion of the tumor is left in the patient after extirpation of the tumor can be assessed, as well as a clue to find metastasis and/or recurrence as early as possible can be obtained during the follow-up. Thus, by the method of the present invention, monitoring of the therapy, which provides a basis for adoption of the therapeutic approach, such as whether the therapeutic approach applied to a patient is appropriate or not, whether the approach should be changed to another or not, or whether any therapy should be started or not, can be attained. Furthermore, as shown in the Examples below, mRNAs encoding a polypeptide having the amino acid sequence shown in SEQ ID NO:2 or 4, calmegin, CEP having the amino acid sequence shown in SEQ ID NO:26, 28 or 42, and encoding TRIP11 are highly expressed specifically in the testis and cancer cells. Therefore, cancers can be detected by measuring the mRNAs.

BEST MODE FOR CARRYING OUT THE INVENTION

Figure 1:
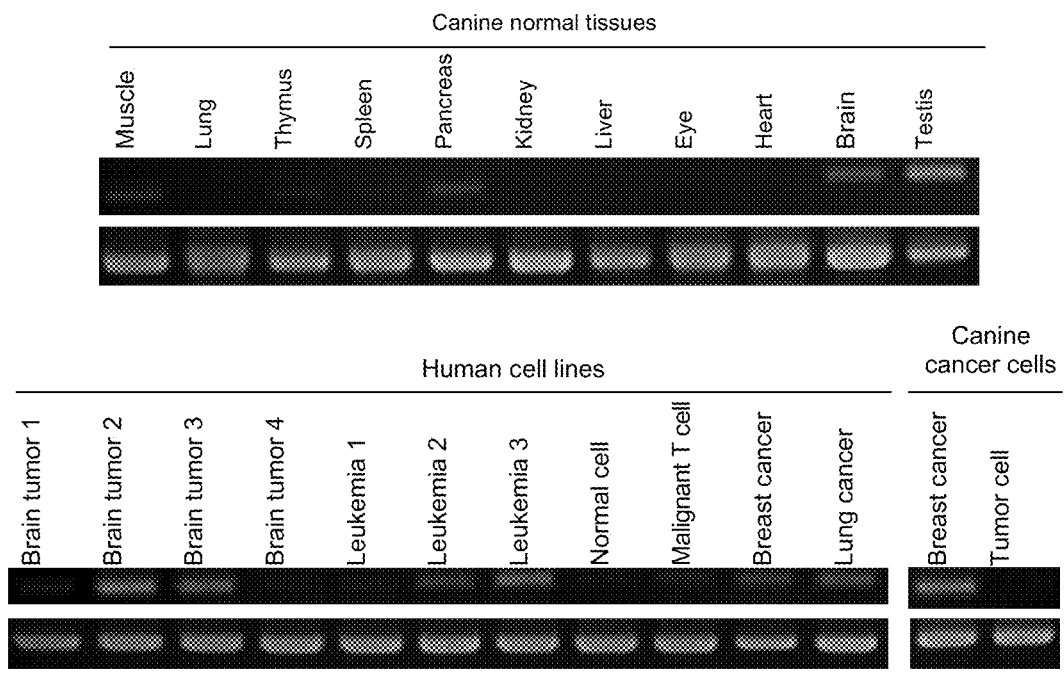
FIG. 1 shows the expression pattern of the gene identified in Example A-1 in normal tissues and tumor cell lines. Reference numeral 1: the expression pattern of the identified gene; Reference numeral 2: the expression pattern of the GAPDH gene.
Figure 2:
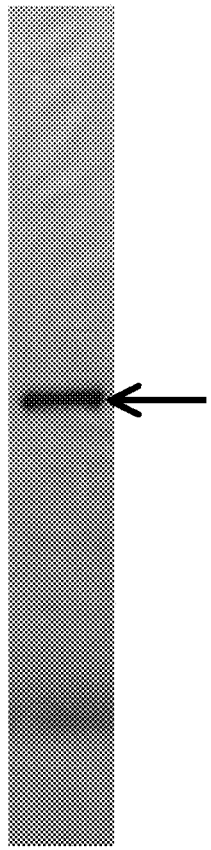
FIG. 2 shows the detection by Coomassie staining of the recombinant canine protein, which is an example of the polypeptide used in the present invention, produced in *E. coli* and purified in Example A. Reference numeral 3: the band for the recombinant canine protein.

In the method of the present invention, the expression of a prescribed polypeptide is measured using a sample separated from a living body. The method for measuring the expression of a polypeptide using the sample includes a method in which an antibody against the polypeptide, which antibody is contained in the sample, is measured by immunoassay (Method 1); a method in which the polypeptide per se contained in the sample is measured by immunoassay (Method 2); and a method in which mRNA contained in the sample which encodes the polypeptide is measured (Method 3). In the method of the present invention, the expression of the polypeptide may be measured by any of these three methods. In the present invention, the term "measurement" includes detection, quantification and semi-quantification.

The above-mentioned prescribed polypeptide whose expression is measured in the method of the present invention is at least one of the polypeptides (a) to (d) below:

(a) a polypeptide produced in the living body and having a reactivity to bind to an antibody against a polypeptide having the amino acid sequence shown in SEQ ID NO:2 or 4 by antigen-antibody reaction;

(b) calmegin;

(c) a polypeptide having a reactivity to bind to an antibody against a centrosomal protein having the amino acid sequence shown in SEQ ID NO:26, 28 or 42 by antigen-antibody reaction;

(d) thyroid hormone receptor interactor 11.

As shown in the following Examples, cancers are successfully detected even by measuring the expression of just one of these polypeptides. Therefore, in the present invention, the expression of just one of the polypeptides (a) to (d) may be measured, as well as two or more of the polypeptides (a) to (d) may be measured in combination. When two or more polypeptides are measured, cancers can be detected with higher accuracy (see, Example E below).

The polypeptide (a) is a polypeptide which is produced in a living body and has a reactivity to bind to an antibody against a polypeptide having the amino acid sequence shown in SEQ ID NO:2 or 4 by antigen-antibody reaction. In other words, the prescribed polypeptide whose expression should be measured is a polypeptide which has the same antigenicity as a canine-derived polypeptide of SEQ ID NO:2 or as a human-derived polypeptide of SEQ ID NO:4.

Specific examples of such a polypeptide include a canine-derived polypeptide of SEQ ID NO:2 and a human-derived polypeptide of SEQ ID NO:4. These polypeptides are the very corresponding antigen of "an antibody against a polypeptide having the amino acid sequence shown in SEQ ID NO:2 or 4", and thus included in the above-mentioned prescribed polypeptide. Specific examples of the polypeptide also include a polypeptide which is derived from other mammals and has the same antigenicity as the above-mentioned canine- or human-derived polypeptide (such a polypeptide is hereinafter referred to as "homologous factor", and the human-derived polypeptide as described above may also be referred to as "human homologous factor" of the canine-derived polypeptide).

SEQ ID NO:2 shows the amino acid sequence of the polypeptide with unknown function identified in the Examples below as a polypeptide which binds to an antibody existing specifically in serum derived from a cancer-bearing dog (the antibody may also be hereinafter referred to as "cancer-specific antibody" of dogs), which identification was carried out by the SEREX method using a canine testis-derived cDNA library and serum of cancer-bearing dogs (see, Example A-1). Therefore, cancers in dogs can be detected by measuring this cancer-specific antibody against a polypeptide of SEQ ID NO:2 in accordance with Method 1 above (see, Examples A-3 and A-4). Cancers in dogs can also be detected by measuring the polypeptide of SEQ ID NO:2 per se, which is the antigen, in accordance with Method 2 above (see, Examples A-5 and A-6). Moreover, since the expression of mRNA encoding the antigen polypeptide is significantly high in the testis and cancer cells as shown in the following Examples (see, Example A-1), cancers in dogs can also be detected by measuring the mRNA. It is noted that, although the amino acid sequence of the canine polypeptide shown in SEQ ID NO:2 is registered in the NCBI database under the Accession No. XP_535343 (protein) and Accession No. XM_535343 (coding gene), its function has not been reported yet.

SEQ ID NO:4 shows the amino acid sequence of the human homologous factor of the canine-derived polypeptide described above, which was found by BLAST homology search. The base sequence encoding the human homologous factor and the amino acid sequence thereof are shown in SEQ ID NOs:3 and 4, respectively, and also registered in the NCBI database under Accession No. NP_689873 (protein) and Accession No. NM_152660 (coding gene). Similarly to the canine-derived polypeptide described above, any functions of the human homologous factor have not been reported. As concretely shown in the following Examples, similarly to the canine-derived polypeptide of SEQ ID NO:2, the expression level of mRNA encoding the human homologous factor is significantly high in human testis and cancer cells, and an antibody against the human homologous factor is not detected in healthy humans. Therefore, cancers in humans can be detected by determining the expression of a polypeptide of SEQ ID NO:4 in the humans.

Specific examples of the homologous factor in other mammals which has the same antigenicity as the above-mentioned canine-derived polypeptide or the human homologous factor thereof include, for example, the polypeptide which specifically exists in cancer-bearing cats as shown in the following Examples. This feline polypeptide immunologically reacts with not only an antibody prepared by using as an immunogen the canine-derived polypeptide of SEQ ID NO:2, but also an antibody prepared by using as an immunogen the human homologous factor of SEQ ID NO:4 (see, Examples A-5 and A-6). Therefore, this feline polypeptide is the feline homologous factor which has the same antigenicity as the above-described canine- and human-derived polypeptides, and included in the scope of a polypeptide "which has a reactivity to bind to an antibody against a polypeptide having the amino acid sequence shown in SEQ ID NO:2 or 4 by antigen-antibody reaction", whose expression is to be measured in the present invention. As concretely described in the Examples below, an antibody induced in cats against the feline homologous factor is detected only in cancer-bearing cats and not detected in healthy cats. The feline homologous factor per se, which is the antigen, is also detected only in cancer-bearing cats and not detected in healthy cats. Therefore, by measuring the expression of the homologous factor in mammals other than dogs and humans, cancers in the mammals can be detected.

The polypeptide (a) described above is preferably a polypeptide having the amino acid sequence shown in SEQ ID NO:2 in SEQUENCE LISTING, or a polypeptide which has a homology of not less than 95% thereto and is produced in a living body. The homology between the canine-derived polypeptide (SEQ ID NO:2) and the human homologous factor thereof (SEQ ID NO:4) is 93% in terms of base sequence and 99% in terms of amino acid sequence. Although dogs and humans are genetically distant, the homologous factor in such a genetically distant species shares a very high homology of 99% at amino acid level. Therefore, it is believed that the homologous factor in mammals other than human also shares as high homology as not less than 95% with the canine-derived polypeptide of SEQ ID NO:2.

The above-described polypeptide (b), Calmegin, was identified as a protein which is expressed specifically at the time of differentiation of a spermatid, and has a chaperone activity in vitro. Since it is expressed only in testis and disappears in a mature sperm, calmegin is considered to have a function to fold proteins involved in differentiation of spermatid (Non-patent Literature 7: Naokazu Inoue, Ryo Yamaguchi and Masahito Ikawa, Protein, Nucleic Acid and Enzyme, vol. 50, No. 11, 1405-1412). However, there has been no report showing that the protein is expressed in a cancer and useful for cancer diagnosis and the like.

SEQ ID NO:16 shows the amino acid sequence of canine calmegin. The canine calmegin having this amino acid sequence was identified as a polypeptide which binds to an antibody existing specifically in serum derived from a cancer-bearing dog, which identification was carried out by the SEREX method using a canine testis-derived cDNA library and serum of cancer-bearing dogs (see, Example B-1). That is, in cancer-bearing dogs, an antibody against calmegin having the amino acid sequence shown in SEQ ID NO:16 is specifically induced. Therefore, cancers in dogs can be detected by measuring the above-mentioned antibody against calmegin having the amino acid sequence shown in SEQ ID NO:16 in accordance with Method 1 above (see, Examples B-3 and B-4). Cancers in dogs can also be detected by measuring calmegin of SEQ ID NO:16 per se, which is the antigen, in accordance with Method 2 above (see, Examples B-5 and B-6). Moreover, since the expression of mRNA encoding calmegin is significantly high in the testis and cancer cells as shown in the following Examples (see, Example B-1), cancers in dogs can also be detected by measuring the mRNA.

In the method of the present invention, not only the canine calmegin of SEQ ID NO:16 but also calmegin in other mammals (hereinafter also referred to as "homologous factor" of canine calmegin; in cases where the simple term "calmegin" is used, not only canine calmegin but also other mammalian calmegin are referred to by the term) may be measured. As concretely described in the Example below, similarly to canine calmegin of SEQ ID NO:16, the expression level of mRNA encoding human calmegin is also significantly high in human testis and cancer cells, and an antibody against human calmegin is not detected in healthy humans. An antibody against feline calmegin is detected only in cancer-bearing cats and not detected in healthy cats. Therefore, by measuring the expression of calmegin in mammals other than dogs, cancers in the mammals can also be detected. Besides canine calmegin, examples of the calmegin to be measured in the method of the present invention include, but not limited to, human calmegin, feline calmegin and the like. The base sequence encoding human calmegin and the amino acid sequence thereof are shown in SEQ ID NOs:17 and 18 in SEQUENCE LISTING, respectively, and the homology between human calmegin and canine calmegin is 90% in terms of base sequence and 89% in terms of amino acid sequence. Although dogs and humans are genetically distant, the calmegin in such genetically distant species share a very high homology of 89% at amino acid level. Therefore, it is believed that calmegin in mammals other than human also shares as high homology as not less than about 80% with canine calmegin. That is, calmegin to be measured in the method of the present invention preferably has a homology of not less than 80%, more preferably not less than 85% to canine calmegin shown in SEQ ID NO:16, although not restricted thereto.

The polypeptide (c) described above is a polypeptide which has a reactivity to bind to an antibody against centrosomal protein (CEP) having the amino acid sequence shown in SEQ ID NO:26, 28 or 42 by antigen-antibody reaction. In other words, the polypeptide (c) described above is a polypeptide which has the same antigenicity as canine-derived CEP of SEQ ID NO:26 or 42 or human-derived CEP of SEQ ID NO:28.

Specific examples of such a prescribed CEP include canine-derived CEP of SEQ ID NO:26 or 42, and human-derived CEP of SEQ ID NO:28. These CEPs are the very corresponding antigen of "an antibody against CEP having the amino acid sequence shown in SEQ ID NO:26, 28 or 42", and thus included in a prescribed CEP as mentioned above. Specific examples of the CEP also include CEP derived from other mammals which has the same antigenicity as the above-mentioned canine- or human-derived CEP (such CEP is hereinafter referred to as "homologous factor", and human-derived CEP mentioned above may also be referred to as "human homologous factor" of canine-derived CEP).

SEQ ID NO:26 shows the amino acid sequence of canine CEP identified as a polypeptide which binds to an antibody existing specifically in serum derived from a cancer-bearing dog (hereinafter also referred to as a canine "cancer-specific antibody"), which identification was carried out by the SEREX method using a canine testis-derived cDNA library and serum of cancer-bearing dogs (see, Example C-1). Therefore, cancers in dogs can be detected by measuring the above-mentioned antibody against canine CEP having the amino acid sequence shown in SEQ ID NO:26 in accordance with Method 1 above (see, Examples C-3 and C-4). Cancers in dogs can also be detected by measuring CEP of SEQ ID NO:26 per se, which is the antigen, in accordance with Method 2 above (see, Examples C-5 and C-6). Moreover, since the expression of mRNA encoding CEP of SEQ ID NO:26 is significantly high in the testis and cancer cells as shown in the following Examples (see, Example C-1), cancers in dogs can also be detected by measuring the mRNA. CEP is a protein which is required by the centrosome to control microtubules, and also involved in maturation of the centrosome. Frequent occurrence of chromosomal translocation is known in a part of myeloproliferative disorders, and since the CEP gene exists at the point where the translocation occurs, it is considered to have a certain relationship with the disorders. However, there has been no report showing that the protein is expressed in a cancer and useful for cancer diagnosis (Non-patent Literature 8: J Cell Sci. 115:1825-35; Non-patent Literature 9: Blood. 95:1788-96).

SEQ ID NO:42 shows the amino acid sequence of a known canine CEP registered in a database, which was found as a protein sharing very high homology with the obtained canine CEP mentioned above by BLAST search (see, Example C-1). The base sequence of this known canine CEP is shown in SEQ ID NO:41. Similarly to canine CEP of SEQ ID NO:26, canine CEP of SEQ ID NO:42 is also considered to be highly expressed in cancer-bearing dogs, and cancers in dogs can be detected by determining the expression of this known canine CEP as concretely described in the following Examples.

SEQ ID NO:28 shows the amino acid sequence of a human homologous factor of the canine-derived CEP mentioned above, which amino acid sequence was found by BLAST homology search. The base sequence encoding the human homologous factor and the amino acid sequence thereof are shown in SEQ ID NOs:27 and 28 in SEQUENCE LISTING, respectively. As concretely described in the Examples below, similarly to canine-derived CEP of SEQ ID NO:26, the expression level of mRNA encoding the human homologous factor is significantly high in human testis and cancer cells, and an antibody against the human homologous factor is not detected in healthy humans. Therefore, cancers in humans can be detected by determining the expression of CEP of SEQ ID NO:28 in the humans.

Specific examples of the homologous factor in other mammals which has the same antigenicity as the above-described canine-derived CEP or as the human homologous factor thereof include, for example, CEP which specifically exists in cancer-bearing cats as shown in the following Examples. The feline CEP immunologically reacts with not only an antibody prepared by using as an immunogen canine-derived CEP of SEQ ID NO:26 or 42, but also an antibody prepared by using as an immunogen the human homologous factor of SEQ ID NO:28 (see, Examples C-5 and C-6). Therefore, this feline CEP is a feline homologous factor which has the same antigenicity as the above-mentioned canine- and human-derived CEPs, and thus included in the scope of a CEP "which has a reactivity to bind to an antibody against CEP having the amino acid sequence shown in SEQ ID NO:26, 28 or 42 by antigen-antibody reaction", whose expression is to be measured in the present invention. As concretely described in the Examples below, an antibody induced in cats against the feline homologous factor is detected only in cancer-bearing cats and not detected in healthy cats. The feline homologous factor per se, which is the antigen, is also detected only in cancer-bearing cats and not detected in healthy cats. Therefore, by measuring the homologous factor in mammals other than dogs and humans, cancers in the mammals can also be detected.

Preferably, the CEP whose expression should be measured in the detection method of the present invention is CEP having the amino acid sequence shown in SEQ ID NO:26 or 42 in SEQUENCE LISTING, or a polypeptide which has a homology of not less than 80% thereto and is produced in a living body. The homology between canine-derived CEP and human homologous factor thereof is 87% in terms of base sequence and 84% in terms of amino acid sequence. Although dogs and humans are genetically distant, the homologous factor in such a genetically distant species shares very high homology of 84% at amino acid level. Therefore, it is believed that the homologous factor in mammals other than human also shares as high homology as not less than 80% with the canine CEP.

The above-described polypeptide (d), TRIP11 (thyroid hormone receptor interactor 11), was first identified as a factor which interacts with the thyroid hormone receptor β, and its binding to Golgi bodies and microtubules also became evident, so that it is considered to play a role in maintaining the shapes of these organelles by making links between Golgi bodies, microtubules and the like. However, there has been no report showing that the protein is expressed in a cancer and useful for cancer diagnosis and the like (Non-patent Literature 10: Mol Endocrinol. 9:243-54 (1995); Non-patent Literature 11: J Cell Biol. 145: 83-98 (1999)).

SEQ ID NO:45 shows the amino acid sequence of canine TRIP11. The canine TRIP11 having this amino acid sequence was identified as a polypeptide which binds to an antibody existing specifically in serum derived from a cancer-bearing dog, which identification was carried out by the SEREX method using a canine testis-derived cDNA library and serum of cancer-bearing dogs (see, Example D-1). That is, in cancer-bearing dogs, an antibody against TRIP11 having the amino acid sequence shown in SEQ ID NO:45 is specifically induced. Therefore, cancers in dogs can be detected by measuring the above-mentioned antibody against TRIP11 having the amino acid sequence shown in SEQ ID NO:45 in accordance with Method 1 above (see, Examples D-3 and D-4). Cancers in dogs can also be detected by measuring TRIP11 of SEQ ID NO:45 per se, which is the antigen, in accordance with Method 2 above (see, Examples D-5 and D-6). Moreover, since the expression of mRNA encoding TRIP11 is significantly high in the testis and cancer cells as shown in the following Examples (see, Example D-1), cancers in dogs can also be detected by measuring the mRNA.

In the method of the present invention, not only canine TRIP11 of SEQ ID NO:45 but also TRIP11 in other mammals (hereinafter also referred to as "homologous factor" of canine TRIP11; in cases where the simple term "TRIP11" is used, not only canine TRIP11 but also other mammalian TRIP11 are referred to by the term) may be measured. As concretely described in the Example below, similarly to canine TRIP11 of SEQ ID NO:45, the expression level of mRNA encoding human TRIP11 is also significantly high in human testis and cancer cells, and an antibody against human TRIP11 is not detected in healthy humans. An antibody against feline TRIP11 is detected only in cancer-bearing cats and not detected in healthy cats. Therefore, by measuring the expression of TRIP11 in mammals other than dog, cancers in the mammals can also be detected. Besides canine TRIP11, examples of the TRIP11 to be measured in the method of the present invention include, but not limited to, human TRIP11, feline TRIP11 and the like. The base sequence encoding human TRIP11 and the amino acid sequence thereof are shown in SEQ ID NOs:46 and 47 in SEQUENCE LISTING, respectively, and the homology between canine TRIP11 and human TRIP11 is 88% in terms of base sequence and 86% in terms of amino acid sequence. Although dogs and humans are genetically distant, the TRIP11 s in such genetically distant species share very high homology of 86% at amino acid level with each other. Therefore, it is believed that TRIP11 in mammals other than human also shares as high homology as not less than about 75% with canine TRIP11. That is, the TRIP11 whose expression should be measured in the method of the present invention preferably has a homology of not less than 75%, more preferably not less than 80% to the amino acid sequence of canine TRIP11 shown in SEQ ID NO:45, although not restricted thereto.

It should be noted that the term "having the amino acid sequence" in the present invention means that amino acid residues are aligned in that order. Accordingly, for example, "a polypeptide having the amino acid sequence shown in SEQ ID NO:2" means a polypeptide having a size of 306 amino acid residues, whose amino acid sequence is Met Ala Ala Leu . . . (snip) . . . Ile Thr Ser Pro as shown in SEQ ID NO:2.

Further, "a polypeptide having the amino acid sequence shown in SEQ ID NO:2" may be abbreviated as "a polypeptide of SEQ ID NO:2". This also applies to the term "having the base sequence". It should be noted that the term "polypeptide" in the present invention means a molecule formed by peptide bonding of a plurality of amino acids, and includes not only polypeptide molecules having a large number of amino acids constituting them, but also low molecular weight molecules having a small number of amino acids (oligopeptides) and full-length proteins. Thus, in the present invention, proteins consisting of the full length of SEQ ID NO:2, 4, 16, 18, 26, 28, 42, 45 or 47 are also included in "polypeptide".

In Method 1 above, measurement of the cancer-specific antibody which may exist in the sample can be easily carried out by immunoassay using an antigenic substance which immunologically reacts with the antibody. The immunoassay per se is a conventional well-known method as explained in detail below. Examples of the antigenic substance which may be used in the immunoassay include a polypeptide of SEQ ID NO:2, 16, 26, 42 or 45, which induces the antibody in cancer-bearing dogs. As antibodies have the cross-reactivity, a molecule may be bound to an antibody which is induced against another immunogen, as long as the molecule has any structure thereon which is similar to the epitope of the immunogen. For example, polypeptides having high amino acid sequence homology to each other often have epitopes with similar structures, and in such cases both polypeptides may have the same antigenicity. As concretely described in the Examples below, canine-derived polypeptide of SEQ ID NO:2, 16, 26, 42 or 45 immunologically reacts with not only an antibody induced in cancer-bearing dogs against the polypeptide but also an antibody induced in cancer-bearing cats against a feline homologous factor. The human homologous factor immunologically reacts with the above-described antibodies induced in cancer-bearing dogs and cats. Therefore, in Method 1 of the present invention, any mammalian homologous factors may be used as an antigen in the immunoassay.

Antigenic substances having a large molecular weight and a complex structure, such as proteins, usually have a plurality of sites with different structures on their surface. Therefore, such a large, complex antigenic substance induces a plurality of kinds of antibodies which respectively recognize each of the sites in a living body. That is, an antibody induced in a living body against an antigenic substance such as a protein is a polyclonal antibody, which is a mixture of a plurality of kinds of antibodies. The cancer-specific antibodies found by the present inventors, which specifically exist in the serum from cancer-bearing living bodies and specifically bind to a polypeptide of SEQ ID NO:2, 16, 26, 42 or 45 or homologous factors thereof by antigen-antibody reaction, are also a polyclonal antibody. It should be noted that, in the present invention, the term "polyclonal antibody" means an antibody which exists in serum from a living body having an antigenic substance therein and is induced in the living body against the antigenic substance.

In the Example A below, a polypeptide consisting of the entire region of SEQ ID NO:2 and a polypeptide consisting of the entire region of SEQ ID NO:4, which is the human homologous factor, were prepared as an antigen for immunoassay of the cancer-specific antibody, and the reactivity of these polypeptides with the antibody in the serum derived from a cancer-bearing living body was confirmed. In the Example B below, a polypeptide consisting of the entire region of SEQ ID NO:16 (canine calmegin) and a polypeptide consisting of the entire region of SEQ ID NO:18 (human calmegin), which is the human homologous factor thereof, were prepared, and the reactivity of these polypeptides with the antibody in the serum derived from a cancer-bearing living body was confirmed. In the Example C below, a polypeptide consisting of a region of 1514th to 2339th amino acids of SEQ ID NO:26 (canine CEP) and a polypeptide consisting of a region of 1513rd to 2325th amino acids of SEQ ID NO:28 (human CEP) were prepared, and the reactivity of these polypeptides with the antibody in the serum derived from a cancer-bearing living body was confirmed. In the Example D below, a polypeptide consisting of a region of 237th to 1023rd amino acids of SEQ ID NO:45 (canine TRIP11) and a polypeptide consisting of a region of 236th to 1023rd amino acids of SEQ ID NO:47 (human TRIP11) were prepared, and the reactivity of these polypeptides with the antibody in the serum derived from a cancer-bearing living body was confirmed. However, since the antibodies mentioned above are polyclonal, a polypeptide consisting of the full length of SEQ ID NO:2, 16, 26, 42 or 45 or a homologous factor thereof of course binds to the antibody. A fragment of the polypeptide can also bind to the antibody contained in the serum from a cancer-bearing living body, since the polyclonal antibody may include antibodies which recognize the structure of the fragment. That is, not only a polypeptide consisting of the full length of SEQ ID NO:2, 16, 26, 42 or 45 or a homologous factor thereof but also a fragment thereof may be used in measurement of the polyclonal antibody specifically contained in the serum of a cancer-bearing living body, and is useful for detection of a cancer(s).

Thus, a polypeptide used as an antigen for immunoassay in Method 1 of the present invention is not restricted to a polypeptide consisting of the full length of SEQ ID NO:2, 16, 26, 42 or 45 or a homologous factor thereof (e.g. SEQ ID NO:4, 18, 28, 47, etc.), and includes a polypeptide fragment which consists of not less than 7 consecutive, preferably not less than 10 consecutive amino acids of the amino acid sequence shown in SEQ ID NO:2, 16, 26, 42 or 45 or of a homologous factor thereof, and immunologically reacts with a polyclonal antibody against a canine-derived polypeptide of SEQ ID NO:2, 16, 26, 42 or 45 or a homologous factor thereof (the polypeptide fragment may also be hereinafter referred to as "specifically-reactive partial polypeptide" for convenience). It should be noted that, as known in the art, a polypeptide having not less than about 7 amino acid residues can exert its antigenicity.

However, in cases where the number of the amino acid residues are too small, the possibility that the antigen polypeptide may cross-react with antibodies against proteins which exist in the sample and are different from the canine-derived polypeptide of SEQ ID NO:2, 16, 26, 42 or 45 or the homologous factor thereof is increased. Therefore, in view of attaining a high accuracy in the immunoassay, a polypeptide fragment consisting of a large number of the amino acid residues is preferred as an antigen used in the immunoassay. For example, in the case of a polypeptide of SEQ ID NO:2 or a homologous factor thereof, it is desired that the number of the amino acid residues of the used polypeptide fragment should be preferably not less than 30, more preferably not less than 100, still more preferably not less than 200, still more preferably not less than 250. In the case of canine calmegin of SEQ ID NO:16 or a homologous factor thereof, it is desired that the number of the amino acid residues should be preferably not less than 30, more preferably not less than 100, still more preferably not less than 200, still more preferably not less than 400, still more preferably not less than 550. In the case of canine CEP of SEQ ID NO:26 or 42 or a homologous factor thereof, it is desired that the number of the amino acid residues should be preferably not less than 30, more preferably not less than 100, still more preferably not less than 300, still more preferably not less than 600, and the number of the amino acid residues may be not less than 1000, not less than 1500, or not less than 2000. In the case of canine TRIP11 of SEQ ID NO:45 or a homologous factor thereof, it is desired that the number of the amino acid residues should be preferably not less than 30, more preferably not less than 100, still more preferably not less than 300, still more preferably not less than 600, and the number of the residues may be not less than 1000, or not less than 1500.

Specific examples of the polypeptide used as an antigen include the following polypeptides:

(e) a polypeptide having the amino acid sequence shown in SEQ ID NO:2 or 4;

(f) a polypeptide having the amino acid sequence shown in SEQ ID NO:16 or 18;

(g) a polypeptide consisting of not less than 500 consecutive amino acids of the amino acid sequence shown in SEQ ID NO:26 and comprising not less than 500 consecutive amino acids located in the region of 1514th to 2339th amino acids of SEQ ID NO:26, or a polypeptide consisting of not less than 500 consecutive amino acids of the amino acid sequence shown in SEQ ID NO:28 and comprising not less than 500 consecutive amino acids located in the region of 1513rd to 2325th amino acids of SEQ ID NO:28;

(h) a polypeptide consisting of not less than 500 consecutive amino acids of the amino acid sequence shown in SEQ ID NO:45 and comprising not less than 500 consecutive amino acids located in the region of 237th to 1023rd amino acids of SEQ ID NO:45, or a polypeptide consisting of not less than 500 consecutive amino acids of the amino acid sequence shown in SEQ ID NO:47 and comprising not less than 500 consecutive amino acids located in the region of 236th to 1023rd amino acids of SEQ ID NO:47.

Preferred examples of the polypeptide (g) above (a polypeptide of SEQ ID NO:26 or a fragment thereof, or a polypeptide of SEQ ID NO:28 or a fragment thereof) include a fragment which comprises a region of 1514th to 2339th amino acids of the amino acid sequence shown in SEQ ID NO:26 and consists of not more than 1000 amino acids, and a fragment which comprises a region of 1513rd to 2325th amino acids of the amino acid sequence shown in SEQ ID NO:28 and consists of not more than 1000 amino acids. More preferred examples thereof include a fragment consisting of a region of 1514th to 2339th amino acids (SEQ ID NO:35) of the amino acid sequence shown in SEQ ID NO:26, and a fragment consisting of a region of 1513rd to 2325th amino acids (SEQ ID NO:36) of the amino acid sequence shown in SEQ ID NO:28.

Preferred examples of the polypeptide (h) above (a polypeptide of SEQ ID NO:45 or a fragment thereof, or a polypeptide of SEQ ID NO:47 or a fragment thereof) include a fragment which comprises a region of 237th to 1023rd amino acids of the amino acid sequence shown in SEQ ID NO:45 and consists of not more than 1000 amino acids, and a fragment which comprises a region of 236th to 1023rd amino acids of the amino acid sequence shown in SEQ ID NO:47 and consists of not more than 1000 amino acids. More preferred examples thereof include a fragment consisting of a region of 237th to 1023rd amino acids (SEQ ID NO:54) of the amino acid sequence shown in SEQ ID NO:45, and a fragment consisting of a region of 236th to 1023rd amino acid (SEQ ID NO:55) of the amino acid sequence shown in SEQ ID NO:47.

It is well-known in the art that, in general, there are cases where a protein antigen retains substantially the same antigenicity as the original even if the amino acid sequence of the protein is modified such that a small number of amino acids are substituted, deleted and/or inserted. Therefore, the polypeptides each of which has the same amino acid sequence as the polypeptide of SEQ ID NO:2, 16, 26, 42 or 45 or the homologous factor thereof except that a small number of amino acid residues are substituted, deleted and/or inserted, whose sequence has a homology of not less than 80%, preferably not less than 90%, more preferably not less than 95%, still more preferably not less than 98% to the sequence of the original polypeptide, and which polypeptide specifically binds to a polyclonal antibody against a polypeptide having the amino acid sequence shown in SEQ ID NO:2, 16, 26, 42 or 45 or a homologous factor thereof by antigen-antibody reaction (the polypeptides may also be hereinafter referred to as "specifically-reactive modified polypeptide" for convenience), may also be used for detection of cancers. Preferably, the specifically-reactive modified polypeptide has the same amino acid sequence as the polypeptide of SEQ ID NO:2, 16, 26, 42 or 45 or a homologous factor thereof (preferably having the sequence shown in SEQ ID NO:4, 18, 28 or 47) except that one or several amino acid residues are substituted, deleted and/or inserted.

As used herein, the term "homology" of amino acid sequences means a value expressed in percentage which is calculated by aligning two amino acid sequences to be compared such that the number of matched amino acid residues is the maximum, and dividing the number of the matched amino acid residues by the number of the total amino acid residues. When the above-described alignment is carried out, a gap(s) is/are inserted into one or both of the two sequences to be compared as required. Such alignment of sequences can be carried out using a well-known program such as BLAST, FASTA and CLUSTAL W. When a gap(s) is/are inserted, the above-described number of the total amino acid residues is calculated by counting one gap as one amino acid residue. When the thus counted numbers of the total amino acid residues are different between the two sequences to be compared, homology (%) is calculated by dividing the number of matched amino acid residues by the number of total amino acid residues in the longer sequence. The 20 types of amino acids constituting the naturally occurring proteins may be classified into groups each of which has similar properties, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the polypeptides. Therefore, in cases where the amino acid residue(s) of the polypeptide of SEQ ID NO:2, 16, 26, 42 or 45 or a homologous factor thereof is/are substituted, the probability that the ability to bind to the corresponding antibody can be maintained may be made high by conducting the substitution(s) within the same group.

The polypeptides which contain the above-described polypeptide used in the present invention as a partial sequence (i.e., the polypeptides used in the present invention which have other (poly)peptide(s) added at one or both ends thereof) and which specifically bind to a polyclonal antibody against a polypeptide of SEQ ID NO:2, 16, 26, 42 or 45 or a homologous factor thereof (the polypeptides may also be hereinafter referred to as "specifically-reactive added polypeptide" for convenience) may also be used for detection of cancers.

The above-described polypeptides used in the present invention may be prepared by chemical synthesis such as the Fmoc method (fluorenylmethyloxycarbonyl method), the tBoc method (t-butyloxycarbonyl method) or the like, or prepared by a conventional method using a commercially available peptide synthesizer. The polypeptides may also be easily prepared by a known genetic engineering method. For example, the desired polypeptides may be obtained by extracting RNAs from a tissue expressing a gene encoding a polypeptide of SEQ ID NO:2, 16, 26, 42 or 45 or a homologous factor thereof, preparing cDNA of the gene by RT-PCR, inserting the full length or a desired part of the cDNA into an expression vector, and then introducing the vector into a host cell. The base sequences of cDNAs encoding the canine polypeptide of SEQ ID NO:2, canine calmegin of SEQ ID NO:16, canine CEPs of SEQ ID NOs:26 and 42, and canine TRIP11 of SEQ ID NO:45 are shown in SEQ ID NO:1, SEQ ID NO:15, SEQ ID NOs:25 and 41, and SEQ ID NO:44, respectively, and the base sequences of cDNAs encoding human homologous factors of the above polypeptides are shown in SEQ ID NO:3, SEQ ID NO:17 (human calmegin), SEQ ID NO:27 (human CEP), and SEQ ID NO:47 (human TRIP11), respectively. Therefore, referring to these base sequences, primers used in RT-PCR may easily be designed. Further, as explained below, genes encoding a homologous factor in mammals other than human may be amplified by using primers designed in reference to the base sequences of canine polypeptides and human homologous factors. Therefore, cDNAs encoding e.g. a feline homologous factor may easily be prepared in the same manner as described above. Extraction of RNAs, RT-PCR, insertion of cDNA into a vector, and introduction of a vector into a host cell may be performed by a well-known method as described below. Vectors and host cells which may be used are well-known, and various vectors and host cells are commercially available.

The above-described host cells are not restricted as long as they can express the above-described polypeptide, and examples thereof include prokaryotic cells such as *E. coli*; and eukaryotic cells such as mammalian cultured cells including monkey kidney cells COS 1 and Chinese hamster ovary cells CHO, budding yeast, fission yeast, silkworm cells, and *Xenopus laevis* egg cells.

In cases where prokaryotic cells are used as the host cells, an expression vector having the origin that enables its replication in a prokaryotic cell, a promoter, a ribosome binding site, a DNA cloning site, a terminator and the like is used as the expression vector. Examples of the expression vector for *E. coli* include the pUC system, pBluescriptII, pET expression system and pGEX expression system. By incorporating DNA encoding the above-described polypeptide into such an expression vector and transforming prokaryotic host cells with the vector, followed by culturing the obtained transformant, the polypeptide encoded by the above-described DNA can be expressed in the prokaryotic host cells. In this case, the polypeptide can also be expressed as a fusion protein with another protein. The DNA encoding the above-described polypeptide may be obtained by preparing cDNA by RT-PCR as described above, or may be synthesized by a conventional method using a commercially available nucleic acid synthesizer as explained below. It should be noted that the base sequences of cDNAs encoding polypeptides of SEQ ID NOs: 2, 4, 16, 18, 26, 28, 42, 45 and 47 are shown in SEQ ID NOs:1, 3, 15, 17, 25, 27, 41, 44 and 46 in SEQUENCE LISTING, respectively.

In cases where eukaryotic cells are used as the host cells, an expression vector for eukaryotic cells having a promoter, splicing site, poly(A) addition site and the like is used as the expression vector. Examples of such an expression vector include pKA1, pCDM8, pSVK3, pMSG, pSVL, pBK-CMV, pBK-RSV, the EBV vector, pRS, pcDNA3, pMSG and pYES2. In the same manner as described above, by incorporating DNA encoding the polypeptide used in the present invention into such an expression vector and transforming eukaryotic host cells with the vector, followed by culturing the obtained transformant, the polypeptide encoded by the above-described DNA can be expressed in the eukaryotic host cells. In cases where pIND/V5-His, pFLAG-CMV-2, pEGFP—N1 or pEGFP-C1 was used as the expression vector, the above-described polypeptide can be expressed as a fusion protein having various added tags such as His tag, FLAG tag, myc tag, HA tag or GFP.

Introduction of the expression vector to the host cells can be carried out using a well-known method such as electroporation, the calcium phosphate method, the liposome method or the DEAE dextran method.

Isolation and purification of a polypeptide of interest from the host cells can be carried out by a combination of known separation operations. Examples of the operations include treatment by a denaturant such as urea or by a surfactant; ultrasonication treatment; enzyme digestion; salting-out and solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method include those in the form of a fusion protein with another arbitrary protein. Examples thereof include fusion proteins with glutathione S-transferase (GST) and with a His tag. Such a polypeptide in the form of a fusion protein is also included in the specifically-reactive added polypeptide described above, and may be used in Method 1 of the present invention. Further, in some cases, a polypeptide expressed in a transformed cell is modified in various ways in the cell after translation thereof. Such a polypeptide having a post-translational modification may also be used in Method 1 of the present invention, as long as it has an ability to bind to a polyclonal antibody against a polypeptide of SEQ ID NO:2 or 4. Examples of such a post-translational modification include elimination of N-terminus methionine, N-terminus acetylation, glycosylation, limited degradation by an intracellular protease, myristoylation, isoprenylation and phosphorylation.

Measurement of the antibody in a sample may easily be carried out by immunoassay using the above-described polypeptide as an antigen. Immunoassays per se are well-known in the art, and includes, when classified based on the reaction mode, sandwich method, competition method, agglutination method, Western blot method and the like. When classified based on the label, immunoassays include radioimmunoassay, fluorescence immunoassay, enzyme immunoassay, biotin immunoassay and the like, and the immunoassay of the above-described antibody may be carried out by any of these immunoassays. Although not restricted, the sandwich ELISA and competition method may be preferably used as an immunoassay of the above antibody in the present invention, as these methods are simple and do not require a large-scale apparatus. In cases where enzymes are used as a label of antibodies, the used enzyme is not particularly restricted as long as it satisfies such conditions that the turnover number is large, that the enzyme is stable even when it is bound to an antibody, that it specifically colors its substrate and the like. For example, enzymes used in an ordinary enzyme immunoassay such as peroxidase, β-galactosidase, alkaline phosphatase, glucose oxidase, acetylcholinesterase, glucose-6-phosphate dehydrogenase, and malate dehydrogenase may be used. Enzyme inhibitors, coenzymes and the like may also be used. Binding of these enzymes with an antibody may be carried out by a known method using a cross-linking agent such as a maleimide compound. As a substrate, known substances may be used depending on the kind of the used enzyme. For example, in cases where peroxidase is used as an enzyme, 3,3',5,5'-tetramethylbenzidine may be used; and in cases where alkaline phosphatase is used as an enzyme, para-nitrophenol or the like may be used. As a radioisotope, those used in an ordinary radioimmunoassay such as $^{125}$I and $^3$H may be used. As a fluorescent dye, one used in an ordinary fluorescent antibody technique such as fluorescein isothiocyanate (FITC), tetramethylrhodamine isothiocyanate (TRITC) or the like may be used.

These immunoassays per se are well-known in the art, and so it is not necessary to explain these immunoassays in the present specification. Briefly, in sandwich immunoassays, for example, the above-mentioned polypeptide used as an antigen is immobilized on a solid phase, and then reacted with a sample such as a serum. After washing the solid phase, the resultant is reacted with an appropriate secondary antibody. After washing the solid phase, the secondary antibody bound to the solid phase is measured. In the method for detecting a cancer(s) according to the present invention, it is preferred to immobilize an antigen polypeptide on a solid phase, because immobilization on a solid phase makes it possible to easily remove the unbound secondary antibody. As the secondary antibody, for example, anti-dog IgG antibody may be used in cases where the sample is obtained from dogs. The secondary antibody bound to a solid phase may be measured by labeling the secondary antibody with a labeling substance exemplified above. The thus measured amount of the secondary antibody corresponds to the amount of the above-mentioned antibody in a serum sample. In cases where an enzyme is used as a labeling substance, the amount of the antibody may be measured by adding a substrate which is decomposed by the enzymatic activity to develop a color, and then optically measuring the amount of decomposed substrate. In cases where a radioisotope is used as a labeling substance, the amount of radiation from the radioisotope may be measured with a scintillation counter or the like.

In Method 2 of the present invention, at least one polypeptide selected from the group consisting of the polypeptide of SEQ ID NO:2 or a homologous factor thereof, calmegin, CEP of SEQ ID NO:26 or 42 or a homologous factor thereof and TRIP11, which may be contained in a sample obtained from a living body, is measured. As explained above, the abundance of the cancer-specific antibody which immunologically reacts with the polypeptide of SEQ ID NO:2 or a homologous factor thereof, calmegin in dogs, humans or the like, CEP of SEQ ID NO:26 or 42 or a homologous factor thereof, or TRIP11 in dogs, humans or the like is significantly high in cancer patients, which indicates that the production of these polypeptides or homologous factors thereof, which are the antigen of the cancer-specific antibody, is significantly high in cancer patients. As concretely described in the Examples below, cancers can also be detected by measuring the antigen per se. Therefore, similarly to Method 1 above, cancers in a living body can be detected by measuring the polypeptide of SEQ ID NO:2 or a homologous factor thereof, calmegin, CEP of SEQ ID NO:26 of 42 or a homologous factor thereof, or TRIP11 per se.

Measurement of the polypeptide in a sample may easily be carried out by a well-known immunoassay. Specifically, for example, the polypeptide of SEQ ID NO:2, 16, 26, 42 or 45 or a homologous factor thereof which may exist in a sample may be measured by preparing an antibody or antigen-binding fragment thereof which immunologically reacts with the polypeptide of SEQ ID NO:2, 16, 26, 42 or 45 or a homologous factor thereof, and then carrying out an immunoassay using the prepared antibody or fragment thereof. Because antibodies have a cross-reactivity as explained above, not only a canine-derived polypeptide of SEQ ID NO:2, 16, 26, 42 or 45 but also a homologous factor in other mammals, for example, a human homologous factor of SEQ ID NO:4, 18, 28 or 47 or a feline homologous factor, may be measured by using the antibody or antigen-binding fragment thereof which immunologically reacts with the canine-derived polypeptide of SEQ ID NO:2, 16, 26, 42 or 45. Immunoassays per se are a well-known, conventional method as described above.

The term "antigen-binding fragment" herein means fragment such as Fab fragment or F(ab')$_2$ fragment of the antibody, which exhibits antigen-binding property of the antibody. Although the antibody may be either a polyclonal antibody or monoclonal antibody, a monoclonal antibody is preferred for immunoassays and the like, because the reproducibility is high. Methods for preparing a polyclonal or monoclonal antibody using a polypeptide as an immunogen are well-known, and may be easily carried out by a conventional method. For example, antibodies against the polypeptide may be induced by immunizing an animal with an immunogen, the polypeptide conjugated to a carrier protein such as keyhole limpet hemocyanin (KLH) or casein, together with an adjuvant. Then antibody-producing cells such as spleen cells or lymphocytes are collected from the immunized animal and fused with myeloma cells to prepare hybridomas. Among the hybridomas, one producing the antibody which binds to the protein of SEQ ID NO:2, 16, 26, 42 or 45 or a homologous factor thereof is selected and proliferated, and then the antibody whose corresponding antigen is the above-mentioned protein may be collected from the culture supernatant. The above-described method is a conventional well-known method.

In Method 3 of the present invention, mRNA encoding any one of the polypeptides selected from the group consisting of the polypeptide of SEQ ID NO:2 or a homologous factor thereof, calmegin, CEP of SEQ ID NO:26 or 42 or a homologous factor thereof and TRIP11, which may be contained in a sample obtained from a living body, is measured. As concretely described in the Examples below, the expression level of mRNA encoding the canine-derived polypeptide of SEQ ID NO:2 or the human homologous factor thereof shown in SEQ ID NO:4; mRNA encoding canine calmegin of SEQ ID NO:16 or human calmegin of SEQ ID NO:18; mRNA encoding canine CEP of SEQ ID NO:26 or 42 or the human homologous factor thereof shown in SEQ ID NO:28; and mRNA encoding canine TRIP11 of SEQ ID NO:45 or human TRIP11 of SEQ ID NO:47 is significantly high in cancer cells. Therefore, cancers in a living body can be detected by measuring the mRNA in a sample.

For example, mRNA in a sample may be quantified by a conventional method such as real-time detection RT-PCR using the mRNA as a template, and may also be roughly quantified based on the staining intensity in a conventional Northern blotting. The sequence of cDNAs encoding the polypeptides of SEQ ID NOs:2, 4, 16, 18, 26, 28, 42, 45 and 47 are shown in SEQ ID NOs:1, 3, 15, 17, 25, 27, 41, 44 and 46, respectively. Referring to these sequences, a polynucleotide which specifically hybridizes with a partial region of the base sequence shown in SEQ ID NO:1, 3, 15, 17, 25, 27, 41, 44 or 46 (hereinafter referred to as "polynucleotide for cancer detection") may be prepared, and using the polynucleotide as a probe or a primer for nucleic acid amplification, the amount of the mRNA in a sample may be measured. As explained below, mRNA encoding homologous factors in mammals other than dogs and humans may also be measured by using a polynucleotide which specifically hybridizes with a partial region of the base sequence shown in SEQ ID NO:1 or 3. Similarly, mRNA encoding calmegin in mammals other than dogs and humans may also be measured by using a polynucleotide which specifically hybridizes with a partial region of the base sequence shown in SEQ ID NO:15 or 17; mRNA encoding homologous factors in mammals other than dogs and humans may also be measured by using a polynucleotide which specifically hybridizes with a partial region of the base sequence shown in SEQ ID NO:25, 27 or 41; and mRNA encoding TRIP11 in mammals other than dogs and humans may also be measured by using a polynucleotide which specifically hybridizes with a partial region of the base sequence shown in SEQ ID NO:44 or 46. In the present invention, polynucleotide may be RNA or DNA.

The term "specifically hybridize" used herein means that a certain sequence hybridizes only with the subject partial region and does not substantially hybridize with the other regions under ordinary hybridization conditions.

The term "ordinary hybridization condition" refers to a condition used for annealing in the ordinary PCR or the ordinary detection with probes. For example, in the case of PCR with Taq polymerase, the term refers to a reaction condition at an appropriate annealing temperature of about 54° C. to 60° C. using a common buffer such as one containing 50 mM KCl, 10 mM Tris-HCl (pH 8.3 to 9.0) and 1.5 mM $MgCl_2$. In the case of Northern hybridization, the term refers to a reaction condition at an appropriate hybridization temperature of 42° C. to 65° C. using a common hybridization solution such as one containing 5×SSPE, 50% formamide, 5×Denhardt's solution and 0.1 to 0.5% SDS. It should be noted, however, that the appropriate annealing temperature and hybridization temperature are not restricted to those exemplified above, and may be determined based on Tm of the primer or the probe and on the empirical rules. Those skilled in the art can easily determine the appropriate temperature.

The term "does not substantially hybridize" means that a hybridization does not occur at all or, even if it occurs, the degree of the hybridization with regions other than the subject partial region is considerably lower than that of the hybridization with the subject region so that the hybridization with other regions can be relatively ignored. Examples of the polynucleotide which specifically hybridizes under such conditions include those having a certain homology to the subject partial region, for example, those having a homology of not less than 70%, preferably not less than 80%, more preferably not less than 90%, still more preferably not less than 93%, still more preferably not less than 95%, still more preferably not less than 98% to the subject partial region. Most preferably, the polynucleotide has the same base sequence as the subject partial region. The same definition as for the homology of amino acid sequences applies to the homology of base sequences. Even if a polynucleotide for cancer detection comprises any region which does not hybridizes with the subject region at its end, a probe consisting of such a polynucleotide may be used for detecting cancers as long as a region which hybridizes with the subject region occupies about half or more of the whole probe. Similarly, a primer consisting of such a polynucleotide can normally anneal to the subject region to allow the extension reaction to occur and thus may be used for detecting cancers, as long as a region which hybridizes with the subject region occupies about half or more of the whole primer and is located at the 3'-end of the primer. It should be noted that, in cases where polynucleotides for cancer detection comprise any region which does not hybridizes with the subject region at its end, the homology to the subject base sequence is calculated based only on the region which hybridizes with the subject region, ignoring the non-hybridizing region.

In the present invention, the term "partial region" refers to a region consisting of a part of the base sequence shown in SEQ ID NO:1, 3, 15, 17, 25, 27, 41, 44 or 46. A "partial region" preferably consists of not less than 18 consecutive bases. It is understood that "base sequence shown in SEQ ID NO:1" as used herein includes not only the base sequence expressly written in the SEQ ID NO:1, but also the sequence complementary thereto. Thus, for example, the phrase "a polynucleotide having the base sequence shown in SEQ ID NO:1" includes a single strand polynucleotide having the base sequence expressly written in the SEQ ID NO:1, a single strand polynucleotide having the sequence complementary thereto, and a double strand polynucleotide composed of these single strand polynucleotides. When the polynucleotides used in the present invention or polynucleotides encoding the polypeptides used in the present invention are prepared, any one of these base sequences should be appropriately selected, and those skilled in the art can easily carry out the selection.

In view of assuring specificity, the number of bases of the polynucleotide for cancer detection is preferably not less than 18 bases. In cases where the polynucleotide is used as a probe, the size is preferably not less than 18 bases, more preferably not less than 20 bases, and not more than the full length of the coding region. In cases where the polynucleotide is used as a primer, the size is preferably not less than 18 bases, and preferably not more than 50 bases. Preferred examples of the polynucleotide for cancer detection include those consisting of not less than 18 consecutive bases of the base sequence shown in SEQ ID NO:1, 3, 15, 17, 25, 27, 41, 44 or 46.

It is apparent for those skilled in the art who refer to the present specification that a polynucleotide which specifically hybridizes with a partial region of SEQ ID NO:1, 15, 25 or 44 is used for measurement of mRNA encoding a canine polypeptide of SEQ ID NO:2, 16, 26 or 45, respectively; and that a polynucleotide which specifically hybridizes with a partial region of SEQ ID NO:3, 17, 27 or 46 is used for a measurement of mRNA encoding a human homologous factor of SEQ ID NO:4, 18, 28 or 47, respectively. It should be noted that homologous factors usually share high homology with each other even at a base sequence level. For example, SEQ ID NOs:1 and 3 share 93% homology, SEQ ID NOs:15 and 17 share 90% homology, SEQ ID NOs:25 and 27 share 87% homology, and SEQ ID NOs:44 and 46 share 88% homology, which are very high homology. Thus, a polynucleotide specifically hybridizing with a partial region of SEQ ID NO:1, 15, 25 or 44 may also specifically hybridize with the corresponding partial region of SEQ ID NO:3, 17, 27 or 46, respectively. As practically demonstrated in the Examples below, for example, by using a set of primers having the base sequences shown in SEQ ID NOs:7 and 8, respectively, mRNA encoding the canine-derived polypeptide of SEQ ID NO:2 and mRNA encoding the human homologous factor of SEQ ID NO:4 both may be measured, because the respective primers specifically hybridize with not only a partial region of SEQ ID NO:1 but also a partial region of SEQ ID NO:3 (Example A). By using a set of primers having the base sequences shown in SEQ ID NOs:19 and 20, respectively, mRNA encoding the canine calmegin of SEQ ID NO:16 and mRNA encoding the human homologous factor, the human calmegin of SEQ ID NO:18, both may be measured, because the respective primers specifically hybridize with not only a partial region of SEQ ID NO:15 but also a partial region of SEQ ID NO:17 (Example B). By using a set of primers having the base sequences shown in SEQ ID NOs:29 and 30, respectively, mRNA encoding the canine CEP of SEQ ID NO:26 or 42 and mRNA encoding the human homologous factor, the human CEP of SEQ ID NO:28, both may be measured, because the respective primers specifically hybridize with a partial region of SEQ ID NO:25, a partial region of SEQ ID NO:27, and also a partial region of SEQ ID NO:41 (Example C). By using a set of primers having the base sequences shown in SEQ ID NOs:48 and 49, respectively, mRNA encoding the canine TRIP11 of SEQ ID NO:45 and mRNA encoding the human homologous factor, the human TRIP11 of SEQ ID NO:47, both may be measured, because the respective primers specifically hybridize with not only a partial region of SEQ ID NO:44 but also a partial region of SEQ ID NO:46 (Example D). Thus, for example, by using the polynucleotide specifically hybridizing with a partial region of the canine base sequence shown in SEQ ID NO: 1; SEQ ID NO:15; SEQ ID NO:25; or SEQ ID NO:44, not only mRNA encoding the canine polypeptide of SEQ ID NO:2; SEQ ID NO:16; SEQ ID NOs:26 and 42; or SEQ ID NO:45 but also mRNA encoding the human homologous factor thereof, the polypeptide of SEQ ID NO:4; SEQ ID NO:18; SEQ ID NO:28; or SEQ ID NO:47, may be measured, respectively. Furthermore, mRNA encoding the homologous factor in other mammals such as cats may also be measured by using the same polynucleotides.

In designing a polynucleotide for cancer detection, it is more desirable to select a partial region in which homology between SEQ ID NOs:1 and 3; SEQ ID NOs:15 and 17; SEQ ID NOs:25 and 27; or SEQ ID NOs:44 and 46 is especially high (preferably a partial region having the same sequence). It is expected that a region especially highly homologous between dog and human also shares very high homology with a certain partial region of the homologous genes in other animal species. Therefore, by selecting a partial region in such a manner, the accuracy of measurement of mRNA which encodes homologous factors in animal species other than dog and human can be more improved.

The methods per se for measuring a test nucleic acid using a polynucleotide which specifically hybridizes with a partial region of the test nucleic acid as a primer for a gene-amplification method such as PCR or as a probe are well-known, and include Northern blotting, in situ hybridization and the like, as well as RT-PCR as described in detail in the following Examples. Any of these well-known measurement methods may be used for measuring mRNA level in the present invention.

The nucleic acid-amplification methods per se such as PCR are well-known in the art, and the reagent kits and apparatuses are also commercially available, so that they may be easily carried out. That is, for example, a test nucleic acid serving as a template (e.g., cDNA of the gene encoding the protein having the amino acid sequence shown in SEQ ID NO:2, 4, 16, 18, 26, 28, 45 or 47) and a pair of polynucleotides for cancer detection (primers) are mixed in a known buffer in the presence of Taq polymerase and dNTP, and the steps of denaturation, annealing and extension are carried out by changing the temperature of the reaction mixture. Usually, the denaturation step is carried out at 90 to 95° C., the annealing step is carried out at Tm between the template and the primers or a vicinity thereof (preferably within ±4° C.), and the extension step is carried out at 72° C. which is the optimum temperature of Taq polymerase. The reaction time of each step is selected from about 30 seconds to 2 minutes. By repeating this thermal cycle for about 25 to 40 times, the region between a pair of primers is amplified. The nucleic acid-amplification method is not restricted to PCR, and other nucleic acid-amplification methods well-known in the art may also be employed. By carrying out the nucleic acid-amplification method using a pair of the above-described polynucleotides for cancer detection as primers and using the test nucleic acid as a template, the test nucleic acid is amplified. In contrast, in cases where the test nucleic acid is not contained in the sample, the amplification does not occur. Therefore, by detecting the amplification product, whether the test nucleic acid exists in the sample or not may be determined. Detection of the amplification product may be carried out by a method in which the reaction solution after the amplification is subjected to electrophoresis and then the bands are stained with ethidium bromide or the like, or by a method in which the amplification product after electrophoresis is immobilized on a solid phase such as a nylon membrane; a labeled probe which specifically hybridizes with the test nucleic acid is hybridized with the test nucleic acid; and then the label is detected after washing. Alternatively, the test nucleic acid in the sample may be quantified by the so-called realtime detection PCR using a quencher fluorescent dye and a reporter fluorescent dye. Since the kits for realtime detection PCR are also commercially available, realtime detection PCR may also be carried out easily. The test nucleic acid may also be semi-quantified based on the intensity of the electrophoretic band. The test nucleic acid may be mRNA or cDNA reverse-transcribed from mRNA. In cases where mRNA is amplified as the test nucleic acid, NASBA method (3SR method, TMA method) using the above-described pair of primers may also be employed. NASBA method per se is well-known, and kits therefor are commercially available, so that NASBA method may easily be carried out using the above-described pair of primers.

As the probe, a labeled probe obtained by labeling the above-described polynucleotide for cancer detection with a fluorescent label, radioactive label, biotin label or the like may be used. The methods per se for labeling a polynucleotide are well-known. Whether the test nucleic acid exists in the sample or not may be determined by immobilizing the test nucleic acid or amplification product thereof on a solid phase, hybridizing the labeled probe therewith, and measuring the label bound to the solid phase after washing. Alternatively, the polynucleotide for cancer detection may be immobilized on a solid phase to hybridize the test nucleic acid therewith and detect the test nucleic acid bound to the solid phase by a labeled probe or the like. In such a case, the polynucleotide for cancer detection immobilized on the solid phase is also called a probe. The methods for measuring a test nucleic acid using a polynucleotide probe are also well-known in the art, and may be attained by bringing a polynucleotide probe into contact with the test nucleic acid in a buffer at Tm or a vicinity thereof (preferably within ±4° C.) so as to hybridize them, and then measuring the hybridized labeled probe or the test nucleic acid bound to the immobilized probe. Such a method includes well-known methods such as Northern blot and in situ hybridization, and Southern blot. Any of such known methods may be used in the present invention.

In the detection method of the present invention, whether the subject living body suffers from cancer or not or the like is determined based on the expression level of the polypeptide measured as described above. Although the cancer detection may be attained simply by measuring the expression of the polypeptide in the subject living body, it is preferred to obtain the normal reference value by determining the expression level of the polypeptide (the amount of the antibody, polypeptide or mRNA) in one or more samples from healthy individuals to compare the measured value in the subject living body with the normal reference value, in view of increasing the measurement accuracy. In order to further increase the measurement accuracy, the cancer reference value may be obtained by determining the expression level of the polypeptide in samples obtained from many patients who have been revealed to suffer from cancer to compare the measured value of the subject living body with both of the normal and cancer reference values. The above mentioned reference values may be determined by expressing the expression level of the polypeptide in each sample in values and calculating the average value thereof. The normal and cancer reference values may be determined beforehand by measuring the expression level of the polypeptide in many healthy and cancer subjects. Thus, the predetermined reference values may also be used when comparing the measured value with the reference values in the present invention.

In cases where cancer detection is carried out based on the expression levels of two or more of the above-described four polypeptides, the subject living body may be judged to suffer from cancer when the expression level of any one polypeptide indicates cancer (see, Example E below).

The detection method of the present invention may be carried out in combination with diagnosis using other cancer antigens and/or cancer markers so that the detection accuracy of cancers can be more improved. For example, in measuring the above-mentioned cancer-specific antibody according to the present invention, other polypeptide(s) highly expressed in cancer tissues may be used as an antigen in the same manner as the above-described polypeptides. The method of the present invention may also be carried out in combination with diagnosis using known cancer markers.

By the detection method of the present invention, cancers in a living body can be detected. Especially, as described in the following Examples, the method of the present invention can detect even an invisible small cancer or a cancer which exists in a deep part of a body, and thus the method is useful for early detection of cancers. Further, by applying the detection method of the present invention to patients in the follow-up period after cancer therapy, the recurrent cancer, if any, can be detect in its early stage.

If the more cancer cells expressing the prescribed polypeptide to be measured in the present invention proliferate in a cancer-bearing living body, the more the polypeptides and mRNAs encoding them accumulate in the body, which causes the increased amount of the antibodies against the above-mentioned polypeptides in the serum. On the other hand, the more cancer cells decrease, the more the accumulated polypeptides and mRNAs encoding them decrease in the body, which causes the decreased amount of the antibodies against the above-mentioned polypeptides in the serum. Thus, if the expression level of the prescribed polypeptide is high, it can be determined that tumor growth and/or metastasis of cancer occurs, i.e., the stage of progression of cancer is advanced. Indeed, as concretely described in the Examples below, it was observed that the amount of the above-mentioned antibody increases in the serum of cancer-bearing body along with the cancer progression such as tumor growth or metastasis. Hence, the stage of cancer progression can be detected by the method of the present invention.

Further, as shown in the Example below, when compared between the same kind of tumors, a malignant one produces significantly more amount of the antibodies than a benign one. Therefore, if the expression level of the prescribed polypeptides is high, it can be determined that the grade of cancer malignancy is higher. That is, the grade of cancer malignancy can also be detected by the method of the present invention.

Furthermore, the effect of the cancer therapy can be monitored based on the increase or decrease of the expression level of the prescribed polypeptides. As described in the Example below, compared to the cancer-bearing state, individuals receiving an anticancer drug for prevention of recurrence after tumor extirpation show decreased expression of the polypeptides. This applies to benign tumors. That is, in cases where the expression of the polypeptides can be observed, the decreased expression of the polypeptides is observed when complete extirpation of the benign tumor is attained. Therefore, by observing the expression level of the above-mentioned polypeptides on individuals during or after cancer therapy, a clue to assess how much the administered anticancer drug was effective, or whether a portion of the tumor is left in the patient after extirpation of the tumor can be obtained, as well as a clue to find metastasis and/or recurrence as early as possible can be obtained during the follow-up. If cancer is appropriately treated in a patient, the expression level of the polypeptides becomes lower in the patient after therapy than before therapy. In such a case, it can be judged that the effect of the therapy which was (is being) performed on the patient is good. In cases where the expression level of the polypeptides increases or is sustained, or once decreases and then increases, it can be judged that the effect of the therapy is not good enough. Thus, a useful basis for adoption of the therapeutic approach can be obtained. For example, it can be judged, based on the above-described change of the expression level, whether the therapeutic approach should be changed to another, whether or how the dose of the anticancer drug should be changed, and so on.

Cancers to be detected by the method of the present invention are those expressing at least one polypeptide selected from the group consisting of the polypeptide of SEQ ID NO:2 or a homologous factor thereof, calmegin, CEP of SEQ ID NO:26 or 42 or a homologous factor thereof, and TRIP11. Examples of the cancer to be detected include, but not limited to, brain tumor; squamous cell carcinomas of head, neck, lung, uterus and esophagus; melanoma; adenocarcinomas of lung and uterus; renal cancer; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; chronic lymphocytic leukemia; lymphoma; gastrointestinal lymphoma; digestive organ lymphoma; small cell or medium cell lymphoma; adrenomedullaiy tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor);

poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); and leiomyosarcoma. The living bodies to which the method of the present invention applies are mammals, preferably humans, dogs and cats.

The sample subjected to the method of the present invention include body fluids such as blood, serum, plasma, ascites and pleural effusion, and tissues and cells. Particularly, serum, plasma, ascites and pleural effusion may be preferably used in Method 1 and Method 2 above. A tissue sample and cell sample are preferred in the case of Method 3 above in which mRNA is measured.

The polypeptides used as an antigen for immunoassay in Method 1 (i.e., a canine-derived polypeptide of SEQ ID NO:2, SEQ ID NO:16, SEQ ID NO:26 or 42 or SEQ ID NO:45 and homologous factors thereof, specifically-reactive partial polypeptides, specifically-reactive modified polypeptides, and specifically-reactive added polypeptides) may be provided as a reagent for detecting a cancer(s). The reagent may consist only of the above-mentioned polypeptide, or may contain various additives useful for stabilizing the polypeptide and the like. The reagent may also be provided in the form of being immobilized on a solid phase such as a plate or membrane.

The antibodies or antigen-binding fragments thereof which immunologically react with the canine polypeptide of SEQ ID NO:2, SEQ ID NO:16, SEQ ID NO:26 or 42 or SEQ ID NO:45 or a homologous factor thereof, which are used for measuring the canine polypeptide or the homologous factor thereof by immunoassay, may also be provided as a reagent for detecting a cancer(s). The reagent may also consist only of the above-mentioned antibody or antigen-binding fragment thereof, or may contain various additives useful for stabilizing the antibody or antigen-binding fragment thereof and the like. The antibody or antigen-binding fragment thereof may also be in the form of being conjugated with a metal such as manganese or iron. Since such a metal-conjugated antibody or antigen-binding fragment thereof accumulates in a site in which a large amount of antigen protein exists when administered to a body, the existence of cancer cells which produce the antigen protein can be detected by measuring the metal by MRI or the like.

Furthermore, the above-described polynucleotides for cancer detection used for measuring mRNA in Method 3 may also be provided as a reagent for detecting a cancer(s). The reagent may also consist only of the polynucleotide, or may contain various additives useful for stabilizing the polynucleotide and the like. The polynucleotide for cancer detection contained in the reagent is preferably a primer or a probe. The conditions and preferred examples of the polynucleotide for cancer detection are as already described above.

EXAMPLES

The present invention will now be described more concretely by way of Examples.

Example A-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly (A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host $E.\ coli$ cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from squamous cell carcinoma was used. The serum was stored at −80° C. and pretreated immediately before use. The method of the pretreatment of the serum was as follows. That is, host $E.\ coli$ cells (XL1-Blue MRF') were infected with λ ZAP Express phage to which no foreign gene was inserted, and then cultured on NZY plate medium at 37° C. overnight. Subsequently, the buffer of 0.2 M NaHCO$_3$, pH 8.3 containing 0.5 M NaCl was added to the plate, and the plate was left to stand at 4° C. for 15 hours, followed by collecting the supernatant as an $E.\ coli$/phage extract. Thereafter, the collected $E.\ coli$/phage extract was allowed to flow through an NHS column (manufactured by GE Healthcare Bio-Science) to immobilize proteins derived from the $E.\ coli$/phage thereon. The serum from the canine patients was allowed to flow through and react with this protein-immobilized column to remove antibodies adsorbed on $E.\ coli$ and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 µl of a solution prepared to contain a host E. coli (XL1-Blue MRF') such that the absorbance OD$_{600}$ should be 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1,000×g for 15 minutes, and the supernatant was recovered as a phagemid solution. Subsequently, 200 µl of a solution prepared to contain a phagemid host E. coli (SOLR) such that the absorbance OD$_{600}$ should be 1.0 was mixed with 10 µl of a purified phage solution, and the reaction was allowed to proceed at 37° C. for 15 minutes. Thereafter, 50 µl of the reaction mixture was plated on ampicillin (final concentration: 50 µg/ml)-containing LB agar medium, and cultured at 37° C. overnight. A single colony of transformed SOLR was recovered and cultured in ampicillin (final concentration: 50 µg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:1 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the gene (Accession No. XM_535343) encoding a protein (Accession No. XP_535343) whose function is unknown. The human homologous factor of this gene was the gene (Accession No. NM_152660) encoding a protein (Accession No. NP_689873) whose function is also unknown (homology: base sequence, 93%; amino acid sequence, 99%). The base sequence of the human homologous factor is shown in SEQ ID NO:3, and the amino acid sequence thereof is shown in SEQ ID NO:4.

(4) Analysis of Expression in Each Tissue

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:7 and 8) specific to the obtained canine gene and its human homologous gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl, and the reaction was carried out with 30 cycles of 94° C. for 30 seconds, 55° C. for 30 seconds and 72° C. for 1 minute using Thermal Cycler (manufactured by BIO RAD). The gene-specific primers having the base sequences shown in the above-described SEQ ID NOs:7 and 8 were those which amplify the regions of the 87th to 606th bases of the base sequence of SEQ ID NO:1 and the 173rd to 695th bases of the base sequence of SEQ ID NO:3, and can be used for investigation of the expression of both the canine gene and its human homologous gene. As a control for comparison, primers (described in SEQ ID NOs:9 and 10) specific to GAPDH were used simultaneously. As a result, as shown in FIG. 1, strong expression of the obtained canine gene was observed in testis among the normal dog tissues, and on the other hand, strong expression was observed in the canine breast cancer cell line. Expression of the human homologous gene was confirmed, as is the case with the canine gene, only in testis among the human normal tissues, but the expression was detected in brain tumor, leukemia, breast cancer and lung cancer cells among human cancer cell lines. Thus, the human homologous gene was also confirmed to be specifically expressed in testis and cancer cells.

In FIG. 1, reference numeral 1 in the ordinate indicates the expression pattern of the above identified gene, and reference numeral 2 indicates the expression pattern of the GAPDH gene as a control for comparison.

Example A-2

Preparation of Novel Cancer Antigen Proteins (1) Preparation of Recombinant Protein Based on the gene of SEQ ID NO:1 obtained in Example A-1, a recombinant protein was prepared by the following method. Respective reagents and the attached buffer were mixed such that the mixture should contain 1 µl of the vector which was prepared from the phagemid solution obtained in Example A-1 and was subjected to the sequence analysis, 0.4 µM each of two kinds of primers having NdeI and XhoI restriction sites (described in SEQ ID NOs:11 and 12), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 1 minute using Thermal Cycler (manufactured by BIO RAD). Using the above-described two kinds of primers, the region encoding the entire amino acid sequence of SEQ ID NO:2 is obtained. After the PCR, the amplified DNA was subjected to electrophoresis using 1% agarose gel, and a DNA fragment of about 930 by was purified using QIAquick Gel Extraction Kit (manufactured by QIAGEN).

The purified DNA fragment was ligated into a cloning vector pCR-Blunt (manufactured by Invitrogen). E. coli was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and XhoI and purified using QIAquick Gel Extraction Kit, followed by inserting the gene sequence of interest into an expression vector for E. coli, pET16b (manufactured by Novagen) that had been treated with NdeI and XhoI. Usage of this vector enables production of a His-tag fusion recombinant protein. E. coli for expression, BL21 (DE3), was transformed with this plasmid, and expression of the protein of interest was induced in *E. coli* with 1 mM IPTG.

On the other hand, based on the gene of SEQ ID NO:3, a recombinant protein of the human homologous gene was prepared by the following method. Respective reagents and the attached buffer were mixed such that the mixture should contain 1 µl of the cDNA prepared in Example A-1 whose expression could be confirmed by the RT-PCR method in various tissues/cells, 0.4 µM each of two kinds of primers having EcoRV and EcoRI restriction sites (described in SEQ ID NOs:13 and 14), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 1 minute using Thermal Cycler (manufactured by BIO RAD). Using the above-described two kinds of primers, the region encoding the entire amino acid sequence of SEQ ID NO:4 is obtained. After the PCR, the amplified DNA was subjected to electrophoresis using 1% agarose gel, and a DNA fragment of about 930 by was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRV and EcoRI and purified using QIAquick Gel Extraction Kit, followed by inserting the gene sequence of interest into an expression vector for *E. coli*, pET30a (manufactured by Novagen) that had been treated with EcoRV and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:1 and SEQ ID NO:3, respectively, were cultured in ampicillin (final concentration: 100 µg/ml)-containing LB medium at 37° C. until the absorbance at 600 nm reached about 0.7, and then IPTG was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in 50 mM Tris-HCl buffer (pH 8.0) and subjected to sonication on ice. The sonicated solution of *E. coli* was centrifuged at 6,000 rpm for 20 minutes to obtain the supernatant as the soluble fraction and the precipitate as the insoluble fraction.

The insoluble fraction was suspended in 50 mM Tris-HCl buffer (pH 8.0) and centrifuged at 6,000 rpm for 15 minutes. This operation was repeated twice and an operation of removal of proteases was carried out.

The residue was suspended in 6M guanidine hydrochloride (manufactured by Sigma Aldrich Japan), 0.15 M sodium chloride-containing 50 mM Tris-HCl buffer (pH 8.0), and the resulting suspension was left to stand at 4° C. for 15 hours to denature proteins. Thereafter, the suspension was centrifuged at 6,000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride, 0.15 M sodium chloride-containing 50 mM Tris-HCl buffer (pH 8.0)), followed by leaving it to stand at 4° C. overnight to allow adsorption to the nickel-chelated carrier. The supernatant was recovered by centrifugation of this column carrier at 1,500 rpm for 5 minutes, and the column carrier was suspended in phosphate-buffered saline, followed by refilling the column with the resulting suspension.

The fraction that was not adsorbed to the column was washed away with 10 column volumes of 0.5 M sodium chloride-containing 0.1 M acetate buffer (pH 4.0), and elution was immediately carried out with 0.5 M sodium chloride-containing 0.1 M acetate buffer (pH 3.0). Six column volumes of the eluted fraction was collected in each elution step. Elution of the proteins of interest was confirmed by Coomassie staining carried out according to a conventional method. Based on the result, the eluted fractions were desalted and concentrated to obtain the material to be solid-phased for diagnosis.

Example A-3

Cancer Diagnosis Using Recombinant Canine Protein (1) Cancer Diagnosis in Dogs

Blood samples were collected from 486 canine patients in which malignant or benign tumors were found and 6 healthy dogs, and sera were separated therefrom. Using the recombinant canine protein prepared in Example A-2 and anti-dog IgG antibody, the IgG antibody titer of the sera which specifically react with the recombinant protein was measured by ELISA.

As for immobilization of the prepared protein on a solid phase, 100 µL/well of a solution of the recombinant protein diluted to 50 µg/mL with phosphate buffered saline was added to a 96-well Immobilizer Amino plate (manufactured by Nunc), and the plate was left to stand at 4° C. overnight. As for blocking, 100 µL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. Serum was 500-fold diluted with the blocking solution, and 100 µL/well of the diluted serum was added to the plate, followed by shaking the plate at room temperature for 3 hours to allow the reaction to proceed. After washing the wells 3 times with phosphate buffered saline containing 0.05% Tween20 (manufactured by Wako Pure Chemicals) (hereinafter referred to as PBS-T), 100 µL/well of HRP-conjugated dog IgG antibody (Goat anti Dog IgG-h+l HRP conjugated: manufactured by BETHYL Laboratories) 3,000-fold diluted with the blocking solution was added thereto, and the plate was shaken at room temperature for 1 hour to allow the reaction to proceed. After washing the wells 3 times with PBS-T, 100 µl/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 µl/well of 0.5 M sulfuric acid solution (manufactured by Sigma Aldrich Japan), and then the absorbance was measured at 450 nm with a microplate reader. As a control, a plate on which the prepared recombinant protein was not immobilized and a plate with which the serum from a cancer-bearing dog was not reacted were measured in the same manner as above.

Among the total 486 samples used in the above-described cancer diagnosis, 311 samples were definitely diagnosed as malignant by pathological diagnosis using the extirpated tumor tissue.

Specifically, the samples were diagnosed as cancer such as malignant melanoma; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; squamous cell carcinoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); leiomyosarcoma or the like.

Figure 3:
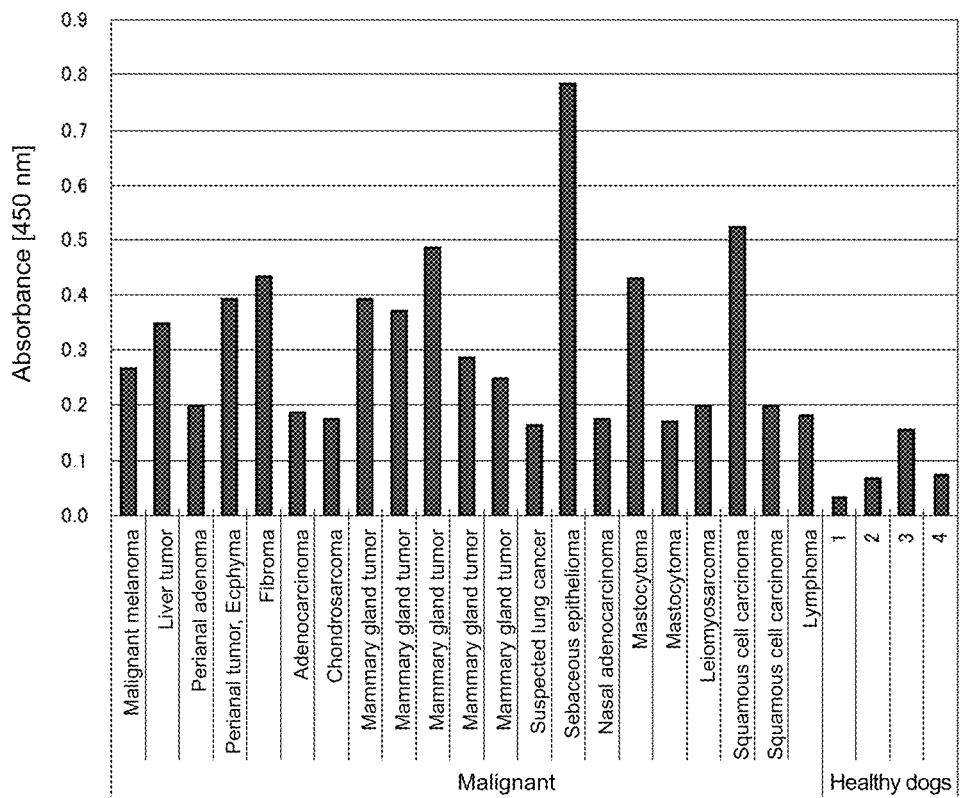
FIG. 3 shows some of the results of cancer diagnosis in cancer-bearing dogs carried out using the recombinant canine protein prepared in Example A.

As shown in FIG. 3, sera from these cancer-bearing dogs showed a significantly high antibody titer against the recombinant protein. It was revealed that, by diagnosing a sample showing twice the average value of healthy canine samples as malignant, 192 samples i.e. 61.7% of the malignant cases could be successfully diagnosed as malignant. The details of these 192 cancer samples are as follows. It is noted that the following number of each cancer case is a cumulative total, as some samples contained multiple primaries.

Malignant melanoma, 10 cases; lymphoma, 9 cases; pheochromocytoma, 1 case; granulosa cell tumor, 1 case; hepatocellular carcinoma, 3 cases; angioma, 1 case; malignant testicular tumor, 9 cases; intraoral tumor, 4 cases; perianal adenocarcinoma, 7 cases; osteosarcoma, 3 cases; fibrosarcoma, 8 cases; ductal carcinoma, 19 cases; chondrosarcoma, 1 case; mammary adenocarcinoma, 35 cases; combined mammary adenocarcinoma, 24 cases; lung cancer, 1 case; sebaceous adenocarcinoma, 2 cases; nasal adenocarcinoma, 2 cases; mastocytoma, 26 cases; adrenomedullary tumor, 1 case; leiomyosarcoma, 2 cases; squamous cell carcinoma, 7 cases; chronic lymphocytic leukemia, 1 case; undifferentiated sarcoma, 1 case; malignant mixed tumor, 2 cases; hemangiopericytoma, 1 case; tumor in the left knee joint, 1 case; tumor in the posterior segment of the left lobe of the lung, 1 case; bladder cancer (transitional cell carcinoma), 1 case; soft part sarcoma (spindle cell tumor), 1 case; ceruminous adenocarcinoma, 1 case; multicentric lymphoma, 2 cases; liposarcoma, 1 case; synovial sarcoma, 1 case; invasive trichoepithelioma, 1 case; anal sac adenocarcinoma, 1 case.

The above-described diagnostic method was also carried out using pleural effusion samples and ascites samples collected from terminal cancer dogs. As a result, values similar to those detected in serum samples could be detected, and hence cancer diagnosis could be successfully attained.

Figure 4:
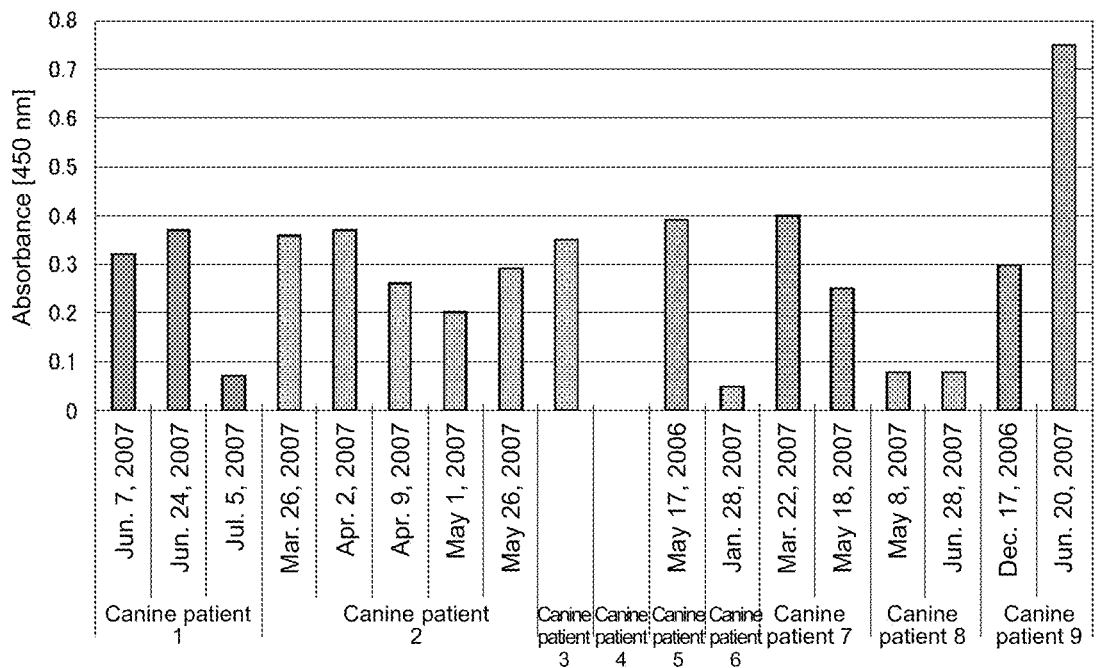
FIG. 4 shows some of the results of detailed cancer diagnosis in cancer-bearing dogs carried out using the recombinant canine protein prepared in Example A.

Furthermore, it was confirmed that diagnostic approaches such as diagnosis of cancers existing in an invisible part of the body, assessment of cancer stage and grade, follow-up of postoperative patients, diagnosis of recurrence and metastasis and the like can also be attained by applying the above-described diagnostic method. The followings are several of the practical examples of the detailed diagnosis shown in FIG. 4.

(2)-1 Diagnosis of Invisible Tumors

In Canine Patient 1 (Flat-Coated Retriever), any tumors were not found on Jun. 7, 2007. But about 20 days later, on Jun. 24, 2007, a pedunculated tumor with a diameter of 2 mm was found on the gum at the root of the canine tooth. The tumor was ligated at its pedunculated part and excised on the day it found. The absorbance at 450 nm observed before the tumor became visible with the naked eye was 0.32, which was significantly high and not so different from the absorbance at the time of finding tumor, 0.37. The result indicates that it is possible to diagnose cancers even in an invisible part such as an intraperitoneal part by the method of the present invention.

Rise of the value was observed before the tumor became visible with the naked eye, which is considered to have been a sign of tumor development. Thus, the method of the present invention is useful in medical examinations such as periodic health examination.

Canine Patient 1 was again checked by the serodiagnosis 2 weeks after the tumor excision. As a result, the absorbance at 450 nm greatly decreased to 0.07. Thus, it was also confirmed that the cancer antigen-expressing tumor which had caused the increased antibody titer was completely removed (see, (2)-4, Follow-Up of Postoperative Patients).

(2)-2 Assessment of Stage of Cancer Progression

The stage of cancer progression is determined based on the size or depth of the tumor, how much the tumor exerts influence on the surrounding tissues, whether the tumor metastasizes or not, and the like. It was revealed herein that the detected value is higher than before if the metastasis occurs, i.e., the cancer has advanced. The following is another example of assessment of stage of a certain cancer case, which received anticancer drug therapy.

Canine Patient 2 (Mixed Breed) underwent tumor extirpation by amputating the right hind leg on Oct. 13, 2006. According to the pathological diagnosis using the extirpated tumor, it was a highly-malignant mastocytoma at Grade II rather close to Grade III. On Mar. 12, 2007, metastasis and recurrence were found in the right groin and liver, and anticancer drug therapy (vinblastine and prednisolone) was started without any surgical operations. Administration of anticancer drugs was started at the time of finding the metastasis and recurrence, and drugs were administered 1, 2, 4 and 8 weeks thereafter again. The serodiagnosis was carried out each time drugs were administered to find that the absorbance at 450 nm was 0.36, 0.37, 0.26, 0.20 and 0.29, respectively. The value gradually decreased with anticancer drugs administered with short intervals from the start to the 4th week, which indicates that the progression of cancer could be suppressed. However, the value increased again in the 8th week, when 1 month had passed since the previous administration, which indicates that the cancer began to advance again. It was also confirmed clinically that the tumor grew larger at that time. The result obtained in Canine Patient 2 revealed that the stage of cancer progression can also be assessed by this method, and that the effect of anticancer drug therapy can also be assessed as shown above.

(2)-3 Assessment of Grade of Cancer Malignancy

Basaliomas include malignant type and benign type. Recently, according to the new WHO classification, malignant basaliomas are called basal cell carcinoma, and benign basaliomas are called trichoblastoma.

Canine Patient 3 (Beagle) was diagnosed as basal cell carcinoma (malignant). The serodiagnosis was carried out at the time of the surgery to find that the absorbance at 450 nm was 0.35. On the other hand, in Canine Patient 4 (Mixed Breed) diagnosed as trichoblastoma (benign), the serodiagnosis carried out at the time of the surgery revealed that the absorbance at 450 nm was 0, not detected at all. Thus, even in the case of the same basaliomas, malignant basal cell carcinoma and benign trichoblastoma can be distinctively diagnosed.

Next example is mammary gland tumors. Mammary gland tumors include malignant tumors such as mammary adenocarcinoma and mammary gland malignant mixed tumor, and benign mammary tumors which do not show malignant symptoms. Canine Patient 5 (Yorkie) underwent extirpation of mammary gland malignant mixed tumor and mammary adenocarcinoma on May 17, 2006. In general, the complete excision of mixed tumors in mammary gland is easy because they are poorly invasive to the surrounding tissues even if they are malignant, and thus the postoperative course of the patients is usually uneventful. However, Canine Patient 5 had been diagnosed as highly malignant tumor, because the pathological diagnosis using the extirpated tissue revealed that some components of the specimen from Canine Patient showed an invasive nature. On the other hand, mammary adenocarcinoma is a highly invasive tumor which often recurs and metastasizes. Although invasion of the tumor cells was not observed in the specimen from Canine Patient 5, it had been pointed out that highly malignant components possibly proliferated in other region out of the specimen. Thus, the findings in the pathological diagnosis clearly taught that Canine Patient 5 was suffering from highly malignant mammary cancer. A blood sample was collected during the surgery and the serodiagnosis was carried out to find that the absorbance at 450 nm was 0.39. Canine Patient 6 (Yorkshire Terrier) underwent extirpation of mammary tumor on Jan. 28, 2007. According to the pathological diagnosis using the extirpated tissue, atypism of cells was low, and thus Canine Patient 6 was diagnoses as benign mastadenoma without malignant findings. A blood sample was collected during the surgery and the serodiagnosis was carried out to find that the absorbance at 450 nm was 0.05. The results in the two cases above revealed that highly malignant tumors show a higher value than low malignant, benign tumors.

(2)-4 Follow-Up of Postoperative Patients

Canine Patient 7 (Shih Tzu) visited the hospital due to an intraoral tumor and underwent the extirpation on Mar. 22, 2007. The serodiagnosis was carried out at that time to find that the absorbance at 450 nm was 0.40. In addition, based on the pathological diagnosis using the extirpated tissue, Canine Patient 7 was diagnosed as malignant acanthomatous epulis. This kind of tumor often recurs if excision is insufficient, though distant metastasis seldom happens. Thus, it is important whether the tumor can be completely excised by surgery or not. According to the follow up on May 18, 2007, the absorbance at 450 nm was 0.25, and hence the antibody titer was decreased. The recurrence has not been found till August of 2007. Thus, it is considered that the value obtained in the serodiagnosis became lower than that obtained at the time of surgery because the tumor could be completely excised from Canine Patient 7.

(2)-5 Diagnosis of Recurrence

Canine Patient 8 (Husky) underwent an extirpation of mammary adenocarcinoma on May 8, 2007. The serodiagnosis was carried out at the time of the surgery to find that the absorbance at 450 nm was 0.08. The pathological diagnosis using the extirpated tissue revealed that highly atypical epithelial cells proliferated and mainly formed ductal structures, and thus this patient was diagnosed as primary breast adenocarcinoma. It was said that the patient was at a high risk of recurrence or metastasis to lymph nodes or distant organs, as many cancer cells had already entered the lymph vessels at that time. On Jun. 28, 2007, about 1-and-a-half month after the surgery, metastasis was found at the same site. The value detected by the serodiagnosis carried out then was 0.08, which did not decrease at all. Thus, it is considered that the value of the serodiagnosis stayed unchanged from the beginning of May to the end of June because the tumor could not have been completely excised or recurrence would have occurred in Canine Patient 8.

(2)-6 Diagnosis of Metastasis

Canine Patient 9 (Scottish Terrier), repeatedly undergoing metastasis and recurrence, was diagnosed as mammary tumor in February of 2003; intraoral malignant melanoma in August of 2003; malignant melanoma of the lip in January of 2005; and as intraoral melanoma on Apr. 13, 2005, all of which were excised by surgery. This patient visited the hospital again on Dec. 17, 2006 for follow-up after the recurrence of intraoral melanoma in April of 2005, and the serodiagnosis was carried out at that time to find that the absorbance at 450 nm was 0.3. Half a year later, on Jun. 20, 2007, the patient again visited the hospital because of the hypertrophy of cervical and malar lymph nodes. In the case of lymphomas, hypertrophy of lymph nodes is systemically observed. Because Canine Patient 9 had only two swollen lymph nodes, this patient was clinically diagnosed as probable metastatic lymphoma. The diagnosis according to the present invention also revealed that it was a tumor which had metastasized from the tumor previously existed in this patient as the absorbance at 450 nm greatly increased to 0.75.

(2)-7 Therapy Monitoring

Canine Patient 11 (Miniature Dachshund) underwent tumor extirpation on Apr. 19, 2007. According to the pathological diagnosis using the extirpated tumor, the patient was suffering from moderately-malignant combined mammary adenocarcinoma with a high probability of invasive and metastatic development. The serodiagnosis was carried out at that time to reveal that the absorbance at 450 nm was 0.26. On Jun. 3, 2008, about 1 year after the extirpation, the serodiagnosis was carried out to find that the absorbance at 450 nm greatly decreased to 0.13. Although any recurrent tumors were not found with the naked eye, an anticancer drug (INTERCAT) was administered once-weekly for 2 months to prevent recurrence. The serodiagnosis was carried out 2, 4, and 6 weeks after the administration of the anticancer drug started to reveal that the absorbance at 450 nm was 0.09, 0.07 and 0.08, respectively. These results obtained in Canine Patient 11 confirmed that the value becomes lower than that detected in a cancer-bearing state if tumors can be completely removed, as well as that the value does not increase if anticancer drug treatment successfully prevents cancer metastasis, and thus change in treated patients can be followed. In addition, the diagnosis of recurrence can also be carried out as shown in Canine Patient 8, which confirms that the therapy monitoring can also be made possible.

(2)-8 Diagnosis of Malignancy of Recurrent Tumor

Canine Patient 12 (Chihuahua) underwent tumor extirpation on Apr. 27, 2007. According to the pathological diagnosis using the extirpated tumor, this patient was suffering from ductal carcinoma originated from mammary ductal epithelium, i.e., malignant breast cancer. On Jun. 29, 2008, about 1 year thereafter, tumor was found again and extirpated. According to the pathological diagnosis using the extirpated tumor, although tumor cells which were originated from mammary ductal epithelium formed irregular glandular cavities and developed to reduplicate toward the lumens, the constituting cells had an almost uniformly egg-shaped nucleus and atypism of the cells was low, and therefore the tumor was diagnosed as benign mammary adenocarcinoma. The serodiagnosis was carried out but the absorbance at 450 nm was 0.02, hardly detected. The results observed in Canine Patients 8 and 12 confirmed that the value of the serodiagnosis does not decrease or is sustained in cases where the recurrent tumor is malignant, and is hardly detected in cases where the tumor is benign.

(2)-9 Prognosis of Canine Patient Bearing Benign Tumor

Canine Patient 13 (Toy Poodle) underwent tumor extirpation on Oct. 9, 2007. The pathological diagnosis using the extirpated tumor revealed that mammary epithelial cells and myoepithelial cells were both proliferated to form the tumor, but that both of them did not show any malignant findings, and therefore this patient was diagnosed as benign mixed tumor. According to the serodiagnosis carried out at that time, the absorbance at 450 nm was 0.07, slightly detected. On Jun. 5, 2008, 8 months thereafter, a blood sample was collected again and the serodiagnosis was carried out to find that the absorbance at 450 nm was 0, not detected at all. Recurrence was not found clinically at that time. These results indicated that, even in the case where tumor is benign, complete removal of the tumor results in the decreased value of the serodiagnosis if a detectable value can be observed in cancer-bearing state, and hence prognosis can be attained.

(3) Diagnosis in Cats

Next, cancer-bearing cats and healthy cats were diagnosed. Using the above-described recombinant canine protein and anti-cat IgG antibody, the IgG antibody titer of feline serum which specifically reacts with the polypeptide was measured in the same manner as described above. As a secondary antibody, HRP-conjugated anti-cat IgG antibody (PEROXIDASE-CONJUGATED GOAT IgG FRACTION TO CAT IgG (WHOLE MOLECULE): manufactured by CAPPEL RESERCH REAGENTS) 8,000-fold diluted with the blocking solution was used.

Feline Patient 1 (Chinchilla) underwent tumor extirpation of mammary adenocarcinoma on Aug. 17, 2005. The absorbance at 450 nm was 0.32. In Feline Patient 2 (Himalayan), which underwent extirpation of ductal carcinoma on Oct. 17, 2006, the absorbance at 450 nm was 0.18. On the other hand, the absorbance was not detected in healthy cats at all.

Thus, similarly to dogs, the absorbance value was detected in samples from cats suffering from cancer, while the absorbance value was not detected at all in samples from healthy cats. Hence, similarly to dogs, cancers in cats can also be detected by this method using a recombinant canine protein.

(4) Diagnosis in Healthy Human

Using the above-described recombinant canine protein and anti-human IgG antibody above, the IgG antibody titer of healthy human serum which specifically reacts with the polypeptide was measured in the same manner as described above. As a secondary antibody, HRP-conjugated anti-human IgG antibody (HRP-Goat Anti-Human IgG(H+L) Conjugate: manufactured by Zymed Laboratories) 10,000-fold diluted with the blocking solution was used. As a positive control, an immobilized ovalbumin antigen prepared by immobilizing 50 µg/ml ovalbumin in phosphate buffered saline on a solid phase was used. As a result, in Healthy Human 1, the absorbance at 450 nm observed on an ovalbumin antigen was 0.25, while the absorbance at 450 nm observed on the recombinant protein was 0, not detected at all. Similarly, in Healthy Human 2, the absorbance at 450 nm observed on an ovalbumin antigen was 0.18, while the absorbance at 450 nm observed on the recombinant protein was 0, not detected at all.

Example A-4

Cancer Diagnosis Using Recombinant Human Protein

Using the recombinant human protein prepared in Example A-2, the IgG antibody titer of human, canine and feline sera which react with the protein was measured in the same manner as in Example A-3.

The diagnosis was carried out using healthy human serum. In the same manner as in Example A-3 (4), ovalbumin antigen was used as a positive control. As a result, the absorbance value was detected in the case where ovalbumin was immobilized on a solid phase, while the absorbance value was hardly detected in the case where a human calmegin protein was immobilized on a solid phase.

Similarly, in healthy dogs and cats, the absorbance at 450 nm was hardly detected in the case where the protein was immobilized on a solid phase.

On the other hand, Canine Patient 10 (Shih Tzu) underwent extirpation of mammary adenocarcinoma on Jun. 21, 2007. According to the pathological diagnosis using the extirpated tissue, the mammary gland tissue contained highly atypical, invasive cells, and grew to form adenomatous hyperplasia showing large and small massive structures. Hence, this patient was diagnosed as malignant tumor. In this Canine Patient 10, the absorbance at 450 nm was 0.29. The malignancy diagnosis was carried out using additional 310 serum samples which had been diagnosed as malignant based on the pathological diagnosis. As a result, by diagnosing a sample showing twice the average value of healthy canine samples as malignant, 189 samples i.e. 60.8% of the malignant cases could be successfully diagnosed as malignant. Moreover, in Feline Patient 3 (Mixed Breed), which underwent extirpation of mammary adenocarcinoma on Apr. 3, 2007, the absorbance at 450 nm was 0.14.

The above-described results indicate that the diagnosis can be similarly attained in humans, dogs and cats even by using the recombinant human protein.

Furthermore, pleural effusion and ascites samples collected from terminal cancer dogs were subjected to the diagnosis using the recombinant human protein in the same manner as the recombinant canine protein. As a result, values similar to those detected in serum samples could be detected, and hence cancer diagnosis could be successfully attained.

Example A-5

Cancer Diagnosis by Measuring Antigen Polypeptide (1)

Mice and rabbits were immunized with the recombinant canine polypeptide prepared in Example A-2 to obtain an antibody specific to this antigen. Using this polyclonal antibody, detection of the antigen polypeptide per se contained in the serum from cancer bearing living body was carried out by sandwich ELISA. Using anti-mouse IgG antibody, the amount of the protein in the serum which specifically reacts with the prepared polyclonal antibody specific to the protein was measured by sandwich ELISA.

As for immobilization of a primary antibody on a solid phase, 100 μL/well of the rabbit antiserum 20-fold diluted with phosphate buffered saline was added to a 96-well Immobilizer Amino plate (manufactured by Nunc), and the plate was shaken at room temperature for 2 hours. As for blocking, 100 μL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. To the plate, 100 μL/well of the serum from cancer-bearing body diluted with the blocking solution was added, and the plate was shaken at room temperature for 3 hours to allow the reaction to proceed. As for the diluted serum, a 10-fold serial dilution ranging 10 to 1,000-fold was prepared. After washing the wells 3 times with phosphate buffered saline containing 0.05% Tween20 (manufactured by Wako Pure Chemicals) (hereinafter referred to as PBS-T), 100 μL/well of mouse antiserum 200-fold diluted with the blocking solution was added thereto, and the plate was shaken at room temperature for 1 hour to allow the reaction to proceed. After washing the wells 3 times with PBS-T, 100 of HRP-conjugated mouse IgG antibody (Stabilized Goat Anti Mouse HRP conjugated: manufactured by PIERCE) 2,000-fold diluted with the blocking solution was added thereto as a tertiary antibody, and the plate was shaken at room temperature for 1 hour to allow the reaction to proceed. After washing the wells 3 times with PBS-T, 100 μl/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 μl/well of 0.5 M sulfuric acid solution (manufactured by Sigma Aldrich Japan), and then the absorbance was measured at 450 nm with a microplate reader. As a control, a plate on which the rabbit antiserum was not immobilized and a plate with which serum from a cancer-bearing body was not reacted were measured in the same manner as described above.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody prepared by using the recombinant canine polypeptide as an immunogen.

Example A-6

Cancer Diagnosis by Measuring Antigen Polypeptide (2)

Mice and rabbits were immunized with the recombinant human protein prepared in Example A-2 to obtain an antibody specific to this antigen. In the same manner as in Example 5, detection of the antigen polypeptide per se contained in the serum from cancer-bearing body was carried out by sandwich ELISA using this polyclonal antibody.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody prepared by using the recombinant human polypeptide as an immunogen.

Example B-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly (A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from tumor proximal to the anus was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 µl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 µl of a solution prepared to contain a host *E. coli* (XL1-Blue MRF') such that the absorbance OD$_{600}$ should be 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1,000×g for 15 minutes, and the supernatant was recovered as a phagemid solution. Subsequently, 200 µl of a solution prepared to contain a phagemid host *E. coli* (SOLR) such that the absorbance OD$_{600}$ should be 1.0 was mixed with 10 µl of a purified phage solution, and the reaction was allowed to proceed at 37° C. for 15 minutes. Thereafter, 50 µl of the reaction mixture was plated on ampicillin (final concentration: 50 µg/ml)-containing LB agar medium, and cultured at 37° C. overnight. A single colony of transformed SOLR was recovered and cultured in ampicillin (final concentration: 50 µg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:15 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the calmegin gene. The human homologous factor of the canine calmegin gene was human calmegin (homology: base sequence, 90%; amino acid sequence, 89%). The base sequence of human calmegin is shown in SEQ ID NO:17, and the amino acid sequence thereof is shown in SEQ ID NO:18.

(4) Analysis of Expression in Each Tissue

Figure 5:
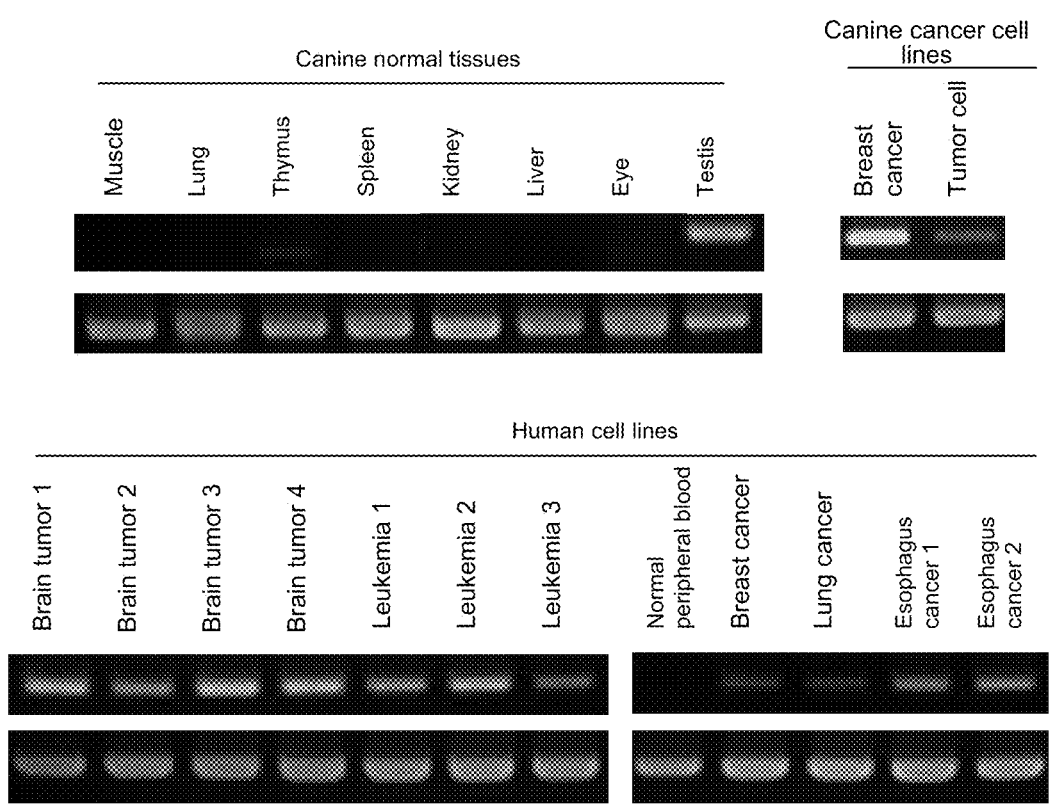
FIG. 5 shows the expression pattern of the gene encoding calmegin protein in normal tissues and tumor cell lines. Reference numeral 1: the expression pattern of the gene encoding calmegin protein; Reference numeral 2: the expression pattern of the GAPDH gene.
Figure 6:
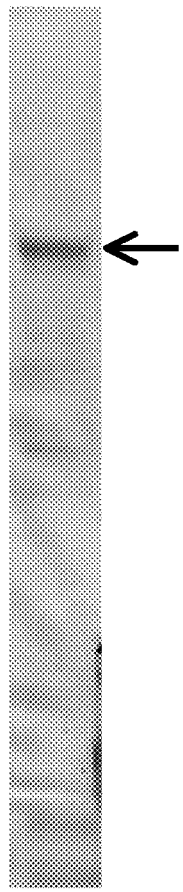
FIG. 6 shows the detection by Coomassie staining of canine calmegin, which is an example of the polypeptide used in the present invention, produced in *E. coli* and purified in Example B. Reference numeral 3: the band for the canine calmegin protein.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Super-script First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:19 and 20) specific to the obtained gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 and the reaction was carried out with 30 cycles of 94° C. for 30 seconds, 55° C. for 30 seconds and 72° C. for 1 minute using Thermal Cycler (manufactured by BIO RAD). The above-described gene-specific primers were those which amplify the regions of the 755th to 1318th bases of the base sequence of SEQ ID NO:15 (canine calmegin gene) and the 795th to 1358th bases of the base sequence of SEQ ID NO:17, and can be used for investigation of the expression of both the canine calmegin gene and the human calmegin gene. As a control for comparison, primers (described in SEQ ID NOs:9 and 10) specific to GAPDH were used simultaneously. As a result, as shown in FIG. 5, strong expression was observed in testis among the normal dog tissues, and on the other hand, strong expression was observed in canine tumor cell lines. Expression of the human calmegin gene was confirmed, as is the case with the canine calmegin gene, only in testis among the normal tissues, but the expression was detected in brain tumor, leukemia and esophagus cancer cells among cancer cell lines. Thus, the human calmegin gene was also confirmed to be specifically expressed in testis and cancer cells.

In FIG. 5, reference numeral 1 in the ordinate indicates the expression pattern of the calmegin gene, and reference numeral 2 indicates the expression pattern of the GAPDH gene as a control for comparison.

Example B-2

Preparation of Canine and Human Calmegin Proteins (1) Preparation of Recombinant Protein Based on the gene of SEQ ID NO:15 obtained in Example B-1, a recombinant protein was prepared by the following method. Respective reagents and the attached buffer were mixed such that the mixture should contain 1 µl of the vector that was prepared from the phagemid solution obtained in Example B-1 and was subjected to the sequence analysis, 0.4 µM each of two kinds of primers having BamHI and EcoRI restriction sites (described in SEQ ID NOs:21 and 22), 0.2 mM dNTP and 1.25 U of PrimeSTAR HS polymerase (manufactured by Takara Shuzo Co., Ltd.) in a total volume of 50 and PCR was carried out with 30 cycles of 98° C. for 10 seconds, 55° C. for 15 seconds and 72° C. for 2 minutes using Thermal Cycler (manufactured by BIO RAD). Using the above-described two kinds of primers, the region encoding the entire amino acid sequence of SEQ ID NO:16 is obtained. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and EcoRI and purified using QIAquick Gel Extraction Kit, followed by inserting the gene sequence of interest into an expression vector for *E. coli*, pET30a (manufactured by Novagen) that had been treated with BamHI and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

Based on the gene of SEQ ID NO:17, a recombinant protein of the human homologous gene was prepared by the following method. Respective reagents and the attached buffer were mixed such that the mixture should contain 1 µl of the cDNA prepared in Example B-1 whose expression could be confirmed by the RT-PCR method in various tissues/cells, 0.4 µM each of two kinds of primers having EcoRI and XhoI restriction sites (described in SEQ ID NOs:23 and 24), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 2 minutes using Thermal Cycler (manufactured by BIO RAD). Using the above-described two kinds of primers, the region encoding the entire amino acid sequence of SEQ ID NO:18 is obtained. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRI and XhoI and purified using QIAquick Gel Extraction Kit, followed by inserting the gene sequence of interest into an expression vector for *E. coli*, pET30a (manufactured by Novagen) that had been treated with EcoRI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:15 and SEQ ID NO:17, respectively, were cultured in kanamycin (final concentration: 30 µg/nip-containing LB medium at 37° C. until the absorbance at 600 nm reached about 0.7, and then IPTG was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of *E. coli* cells was suspended in 20 mM phosphate buffer (pH 7.0) and subjected to sonication on ice. The sonicated solution of *E. coli* was centrifuged at 6,000 rpm for 20 minutes to obtain the supernatant as the soluble fraction and the precipitate as the insoluble fraction.

The soluble fraction was placed in an cation-exchange column (carrier: SP Sepharose (trademark) Fast Flow (GE Health Care); column volume: 5 mL;

equilibration buffer: 20 mM phosphate buffer (pH 7.0)). The column was washed with 10 column volumes of 20 mM phosphate buffer (pH 7.0), and then elution was immediately carried out with density gradient of salt by 0.3 M-1.0 M sodium chloride-containing 20 mM phosphate buffer (pH 7.0). Six column volumes of the eluted fraction was collected in each elution step.

Among these eluted fractions, all the fractions eluted with 0.3 M sodium chloride-containing 20 mM phosphate buffer (pH 7.0) and the 1st fraction eluted with 1.0 M sodium chloride-containing 20 mM phosphate buffer (pH 7.0) were combined, and the resulting solution was subjected to additional purification by a secondary column.

For the secondary column, a column carrier Bio gel HT Type II (BioRad) was used. The column volume was 5 mL. The column was equilibrated with 10 column volumes of 0.3 M sodium chloride-containing 20 mM phosphate buffer (pH 7.0), and the above-described eluted fractions were placed in the column. The fractions that were not adsorbed to the column was washed away with 10 column volumes of 0.3 M sodium chloride-containing 20 mM phosphate buffer (pH 7.0) and 0.1 M phosphate buffer (pH 7.0). Immediately thereafter, elution was carried out with 0.2 M phosphate buffer (pH 7.0). Six column volumes of the eluted fraction was collected in each elution step. Elution of the proteins of interest was confirmed by Coomassie staining carried out according to a conventional method. Based on the result, the eluted fractions were desalted and concentrated to obtain the material to be solid-phased for diagnosis.

Example B-3

Cancer Diagnosis Using Canine Calmegin Protein (1) Cancer Diagnosis in Dogs

Blood samples were collected from 486 canine patients in which malignant or benign tumors were found and 6 healthy dogs, and sera were separated therefrom. Using the canine calmegin protein prepared in Example B-2 and anti-dog IgG antibody, the IgG antibody titer of the sera which specifically react with the protein was measured by ELISA.

As for immobilization of the prepared protein on a solid phase, 100 µL/well of a solution of the recombinant protein diluted to 50 µg/mL with phosphate buffered saline was added to a 96-well Immobilizer Amino plate (manufactured by Nunc), and the plate was left to stand at 4° C. overnight. As for blocking, 100 µL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. Serum was 1,000-fold diluted with the blocking solution, and 100 µL/well of the diluted serum was added to the plate, followed by shaking the plate at room temperature for 3 hours to allow the reaction to proceed. After washing the wells 3 times with phosphate buffered saline containing 0.05% Tween20 (manufactured by Wako Pure Chemicals) (hereinafter referred to as PBS-T), 100 µL/well of HRP-conjugated dog IgG antibody (Goat anti Dog IgG-h+l HRP conjugated: manufactured by BETHYL Laboratories) 3,000-fold diluted with the blocking solution was added thereto, and the plate was shaken at room temperature for 1 hour to allow the reaction to proceed. After washing the wells 3 times with PBS-T, 100 µl/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 µl/well of 0.5 M sulfuric acid solution (manufactured by Sigma Aldrich Japan), and then the absorbance was measured at 450 nm with a microplate reader. As a control, a plate on which the prepared recombinant protein was not immobilized and a plate with which the serum from a cancer-bearing dog was not reacted were measured in the same manner as above.

Among the total 486 samples used in the above-described cancer diagnosis, 311 samples were definitely diagnosed as malignant by pathological diagnosis using the extirpated tumor tissue.

Specifically, the samples were diagnosed as cancer such as malignant melanoma; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; squamous cell carcinoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); leiomyosarcoma or the like.

Figure 7:
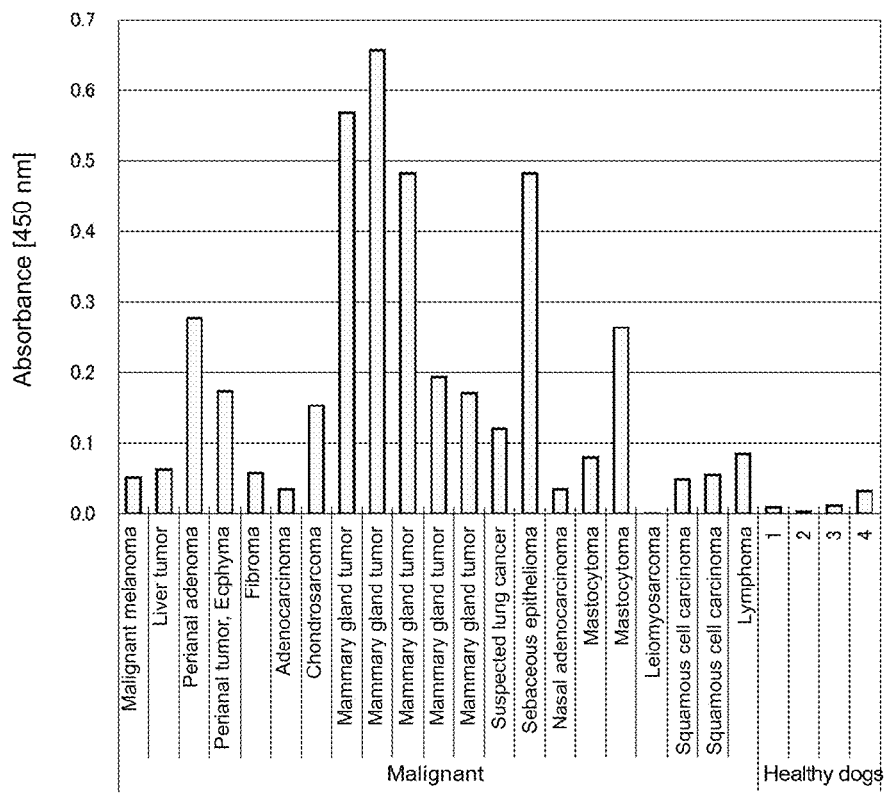
FIG. 7 shows some of the results of cancer diagnosis in cancer-bearing dogs carried out using the canine calmegin protein prepared in Example B.

As shown in FIG. 7, sera from these cancer-bearing dogs showed a significantly high antibody titer against the recombinant protein. It was revealed that, by diagnosing a sample showing twice the average value of healthy canine samples as malignant, 177 samples i.e. 56.9% of the malignant cases could be successfully diagnosed as malignant. The details of these 177 cancer samples are as follows. It is noted that the following number of each cancer case is a cumulative total, as some samples contained multiple primaries.

Malignant melanoma, 10 cases; lymphoma, 10 cases; pheochromocytoma, 1 case; granulosa cell tumor, 1 case; hepatocellular carcinoma, 4 cases; sweat gland carcinoma, 5 cases; angioma, 1 case; malignant testicular tumor, 7 cases; intraoral tumor, 4 cases; perianal adenocarcinoma, 11 cases; osteosarcoma, 4 cases; fibrosarcoma, 7 cases; chondrosarcoma, 2 case; mammary adenocarcinoma, 35 cases; combined mammary adenocarcinoma, 27 cases; lung cancer, 2 cases; sebaceous adenocarcinoma, 2 cases; nasal adenocarcinoma, 2 cases; mastocytoma, 25 cases; adrenomedullary tumor, 1 case; leiomyosarcoma, 1 case; squamous cell carcinoma, 5 cases; chronic lymphocytic leukemia, 1 case; germinoma, 1 case; malignant fibrous histiocytoma, 1 case; metastatic malignant epithelioma, 1 case; mammary ductal carcinoma, 1 case; angiosarcoma, 1 case; tubular mammary adenocarcinoma, 1 case; invasive trichoepithelioma, 1 case; prostate cancer, 1 case; bronchial adenocarcinoma, 1 case.

The above-described diagnostic method was also carried out using pleural effusion samples and ascites samples collected from terminal cancer dogs. As a result, values similar to those detected in serum samples could be detected, and hence cancer diagnosis could be successfully attained.

Figure 8:
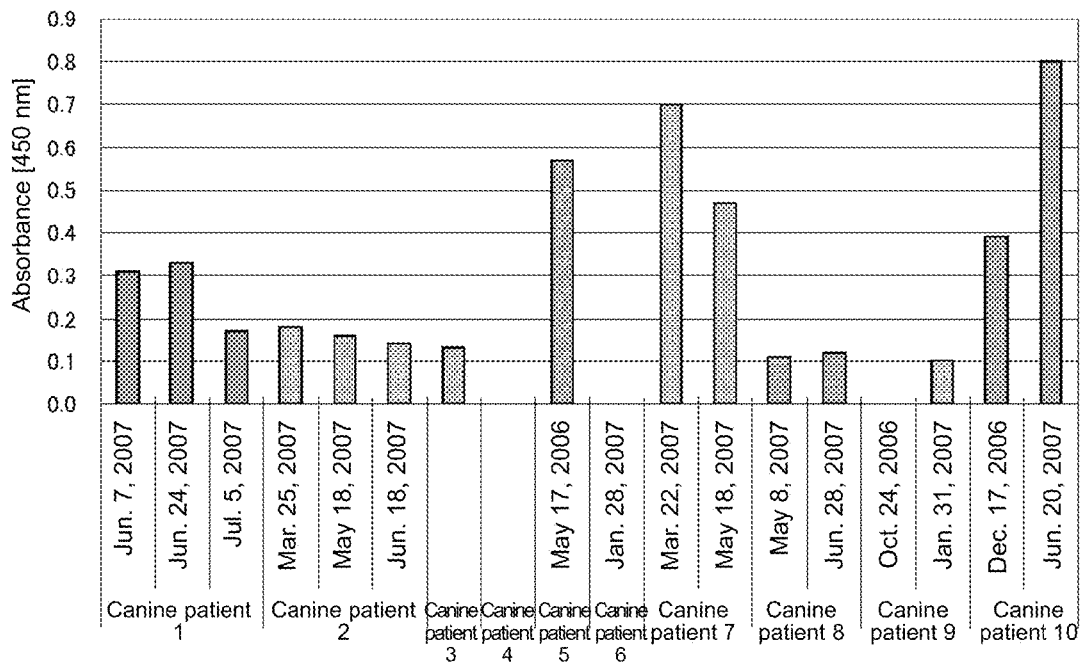
FIG. 8 shows some of the results of detailed cancer diagnosis in cancer-bearing dogs carried out using the canine calmegin protein prepared in Example B.

Furthermore, it was confirmed that diagnostic approaches such as diagnosis of cancers existing in an invisible part of the body, assessment of cancer stage and grade, follow-up of postoperative patients, diagnosis of recurrence and metastasis and the like can also be attained by applying the above-described diagnostic method. The followings are several of the practical examples of the detailed diagnosis shown in FIG. 8.

(2)-1 Diagnosis of Invisible Tumors

In Canine Patient 1 (Flat-Coated Retriever), any tumors were not found on Jun. 7, 2007. But about 20 days later, on Jun. 24, 2007, a pedunculated tumor with a diameter of 2 mm was found on the gum at the root of the canine tooth. The tumor was ligated at its pedunculated part and excised on the day it found. The absorbance at 450 nm observed before the tumor became visible with the naked eye was 0.31, which was significantly high and not so different from the absorbance at the time of finding tumor, 0.33. This result indicates that it is possible to diagnose cancers even in an invisible part such as an intraperitoneal part by the method of the present invention.

Rise of the value was observed before the tumor became visible with the naked eye, which is considered to have been a sign of tumor development. Thus, the method of the present invention is useful in medical examinations such as periodic health examination.

Canine Patient 1 was again checked by the serodiagnosis 2 weeks after the tumor excision. As a result, the absorbance at 450 nm was greatly reduced to 0.17. Thus, it was also confirmed that the cancer antigen-expressing tumor which had caused the increased antibody titer was completely removed (see, (2)-4, Follow-Up of Postoperative Patients).

(2)-2 Assessment of Stage of Cancer Progression

The stage of cancer progression is determined based on the size or depth of the tumor, how much the tumor exerts influence on the surrounding tissues, whether the tumor metastasizes or not, and the like. It was revealed herein that the detected value is higher than before if the metastasis occurs, i.e., the cancer has advanced. The following is another example of a stage assessment of a certain cancer case, which received anticancer drug therapy.

Canine Patient 2 (Miniature Dachshund) visited the hospital with chief complaints of nausea and emaciation on Feb. 21, 2007, and two massive tumors were found in the abdominal cavity. This patient underwent tumor extirpation on Feb. 23, 2007. The swollen right kidney weighed 433 g. The neighboring lymph node was well-vascularized and weighed 42 g. Based on the pathological diagnosis using the extirpated tissue, the patient was diagnosed as multicentric malignant lymphoma. It was said that there was a probability that the tumor cells would spread into other organs in the abdominal cavity, as a disseminated spread of tumor cells was observed in the adipose tissue. The anticancer drug administration (Oncovin) was started postoperatively on Mar. 1, 2007, and the serodiagnosis was carried out 3 times, i.e., on the day the administration was started, and 2 and 3 months thereafter. As a result, the absorbance at 450 nm was 0.18, 0.16, and 0.14, respectively. The value had gradually decreased since the start of the administration, which confirmed that the anticancer drug took effect. Thus, it was confirmed that cancer progression could be inhibited. Hence, the results in Canine Patient 2 confirmed that the stage of cancer progression can also be assessed. In addition, it was confirmed that the effect of anticancer drug therapy can also be assessed as described above.

(2)-3 Assessment of Grade of Cancer Malignancy

Basaliomas include malignant type and benign type. Recently, according to the new WHO classification, malignant basaliomas are called basal cell carcinoma, and benign basaliomas are called trichoblastoma.

Canine Patient 3 (Beagle) was diagnosed as basal cell carcinoma (malignant). The serodiagnosis was carried out at the time of the surgery to find that the absorbance at 450 nm was 0.13. On the other hand, in the case of Canine Patient 4 (Mixed Breed) diagnosed as trichoblastoma (benign), the serodiagnosis carried out at the time of the surgery revealed that the absorbance at 450 nm was 0, not detected at all. Thus, even in the case of the same basaliomas, malignant basal cell carcinoma and benign trichoblastoma can be distinctively diagnosed.

Next example is mammary gland tumors. Mammary gland tumors include malignant tumors such as mammary adenocarcinoma and mammary gland malignant mixed tumor, and benign mammary tumors which do not show malignant symptoms. Canine Patient 5 (Yorkie) underwent extirpation of mammary gland malignant mixed tumor and mammary adenocarcinoma on May 17, 2006. In general, the complete excision of mixed tumors in mammary gland is easy because they are poorly invasive to the surrounding tissues even if they are malignant, and thus the postoperative course of the patients is usually uneventful. However, Canine Patient 5 had been diagnosed as highly malignant tumor, because the pathological diagnosis using the extirpated tissue revealed that some components of the specimen from Canine Patient 5 showed an invasive nature. On the other hand, mammary adenocarcinoma is a highly invasive tumor which often recurs and metastasizes. Although invasion of tumor cells was not observed in the specimen from Canine Patient 5, it had been pointed out that highly malignant components possibly proliferated in other region out of the specimen. Thus, the findings in the pathological diagnosis clearly taught that Canine Patient 5 was suffering from highly malignant mammary cancer. A blood sample was collected during the surgery and the serodiagnosis was carried out to find that the absorbance at 450 nm was 0.57. On the other hand, Canine Patient 6 (Yorkshire Terrier) underwent extirpation of mammary tumor on Jan. 28, 2007. According to the pathological diagnosis using the extirpated tissue, atypism of cells was low, and thus Canine Patient 6 was diagnoses as benign mastadenoma without malignant findings. A blood sample was collected during the surgery and the serodiagnosis was carried out to find that the absorbance at 450 nm was 0. The results in the two cases above revealed that highly malignant tumors show a higher value than low malignant, benign tumors.

(2)-4 Follow-Up of Postoperative Patients

Canine Patient 7 (Shih Tzu) visited the hospital due to an intraoral tumor and underwent the extirpation on Mar. 22, 2007. The serodiagnosis was carried out then to find that the absorbance at 450 nm was 0.70. In addition, based on the pathological diagnosis using the extirpated tissue, Canine Patient 7 was diagnosed as malignant acanthomatous epulis. This kind of tumor often recurs if excision is insufficient, though distant metastasis seldom happens. Thus, it is important whether the tumor can be completely excised by surgery or not. According to the follow-up on May 18, 2007, the absorbance at 450 nm decreased to 0.47. The recurrence has not been found till August of 2007. Thus, it is considered that the value obtained by the serodiagnosis became lower than that obtained at the time of surgery because the tumor could be completely excised from Canine Patient 7.

(2)-5 Diagnosis of Recurrence

Canine Patient 8 (Husky) underwent extirpation of mammary adenocarcinoma on May 8, 2007. The serodiagnosis was carried out at the time of the surgery to find that the absorbance at 450 nm was 0.11. The pathological diagnosis using the extirpated tissue revealed that highly atypical epithelial cells proliferated and mainly formed ductal structures, and thus this patient was diagnosed as primary breast adenocarcinoma. It was said that the patient was at a high risk of recurrence or metastasis to lymph nodes or distant organs, as many cancer cells had already entered the lymph vessels at that time. On Jun. 28, 2007, about 1-and-a-half-month after the surgery, metastasis was found at the same site. The value detected by the serodiagnosis increased to 0.12. Thus, it was confirmed that the value detected by the serodiagnosis was higher in the end of June than in the beginning of May because the tumor could not have been completely excised or recurrence would have occurred in Canine Patient 8.

Canine Patient 9 (Sheltie) underwent extirpation of ductal carcinoma on Oct. 24, 2006. The serodiagnosis carried out at that time revealed that the absorbance at 450 nm was approximately 0, hardly detected. About 3 months later, on Jan. 31, 2007, this patient visited the hospital because of cancer recurrence and underwent extirpation again. According to the pathological diagnosis using the extirpated tissue, many cancer cells having egg-shaped atypical nuclei invaded lymph vessels and metastasis was observed in the inguinal lymph node, and thus the patient was diagnosed as ductal carcinoma (breast cancer) with a probability of distant metastasis. The serodiagnosis was carried out at that time to find that the absorbance at 450 nm increased to 0.10. Thus, similarly to above, it was revealed that the value of the serodiagnosis increased 3 months later because the tumor could not have been completely excised or recurrence of the tumor would have occurred in Canine Patient 9.

(2)-6 Diagnosis of Metastasis

Canine Patient 10 (Scottish Terrier), repeatedly undergoing metastasis and recurrence, was diagnosed as mammary tumor in February of 2003; intraoral malignant melanoma in August of 2003; malignant melanoma of the lip in January of 2005; and as intraoral melanoma on Apr. 13, 2005, all of which were excised by surgery. This patient visited the hospital again on Dec. 17, 2006 for follow-up after the recurrence of intraoral melanoma in April of 2005, and the serodiagnosis was carried out at that time to find that the absorbance at 450 nm was 0.39. Half a year later, on Jun. 20, 2007, the patient again visited the hospital because of the hypertrophy of cervical and malar lymph nodes. In the case of lymphomas, hypertrophy of lymph nodes is systemically observed. Because Canine Patient 10 had only two swollen lymph nodes, this patient was clinically diagnosed as probable metastatic lymphoma. The diagnosis according to the present invention also revealed that it was a tumor which had metastasized from the tumor previously existed in this patient as the absorbance at 450 nm greatly increased to 0.80.

Canine Patient 11 (Shiba Inu) underwent extirpation of oral malignant melanoma of the right lip on Mar. 11, 2006. This patient has a history of anticancer drug treatment (cyclophosphamide) from Jun. 10 to Sep. 26 in 2006, and has received BIREMO S, which contains organic germanium as a main ingredient, since May 23, 2006. On Mar. 20, 2007, this patient underwent extirpation of a tumor which was considered to be metastasis from the tumor mentioned above, and the serodiagnosis was carried out. As a result, the absorbance at 450 nm was 0.06. Based on the pathological diagnosis using the tissue extirpated at that time, Canine Patient 11 was diagnosed as metastatic malignant melanoma. On Jun. 27, 2007, three months after the extirpation of metastatic melanoma, metastasis occurred in this patient again. The tumor which was extirpated on Mar. 20, 2007 existed in the right cervical part, and this time tumor occurred on the opposite side. As for the shape of the tumor, a black mass was formed similarly to the previous tumor. The tumor, having the size of 3.1×3.2×0.8 cm, was also clinically diagnosed as metastasis. The serodiagnosis was carried out again to find that the absorbance at 450 nm increased to 0.19, which indicated that it was metastatic tumor.

(2)-7 Therapy Monitoring

Canine Patient 11 (Miniature Dachshund) underwent tumor extirpation on Apr. 19, 2007. According to the pathological diagnosis using the extirpated tumor, the patient was suffering from moderately-malignant combined mammary adenocarcinoma with a high probability of invasive and metastatic development. The serodiagnosis was carried out at that time to find that the absorbance at 450 nm was 0.30. On Jun. 3, 2008, about 1 year after the extirpation, the serodiagnosis was carried out to find that the absorbance at 450 nm decreased to 0.25. Although any recurrent tumors were not found with the naked eye, an anticancer drug (INTERCAT) was administered once-weekly for 2 months to prevent recurrence. The serodiagnosis was carried out 2, 4, and 6 weeks after the administration of the anticancer drug started to reveal that the absorbance at 450 nm was 0.25, 0.19 and 0.19, respectively. These results obtained in Canine Patient 11 confirmed that the value becomes lower than that detected in a cancer-bearing state if tumors can be completely removed, as well as that the value does not increase if anticancer drug treatment successfully prevents cancer metastasis, and thus change in treated patients can be followed. In addition, the diagnosis of recurrence can also be carried out as shown in Canine Patient 8, which confirms that the therapy monitoring can also be made possible.

(2)-8 Diagnosis of Malignancy of Recurrent Tumor

Canine Patient 12 (Chihuahua) underwent tumor extirpation on Apr. 27, 2007. According to the pathological diagnosis using the extirpated tumor, this patient was suffering from ductal carcinoma originated from mammary ductal epithelium, i.e., malignant breast cancer. On Jun. 29, 2008, about 1 year thereafter, tumor was found again and extirpated. According to the pathological diagnosis using the extirpated tumor, although tumor cells which were originated from mammary ductal epithelium formed irregular glandular cavities and developed to reduplicate toward the lumens, the constituting cells had an almost uniformly egg-shaped nucleus and atypism of the cells was low, and therefore the tumor was diagnosed as benign mammary adenocarcinoma. The serodiagnosis was carried out but the absorbance at 450 nm was 0, not detected at all. The results observed in Canine Patients 8 and 12 revealed that the value of the serodiagnosis does not decrease or is sustained in cases where the recurrent tumor is malignant, and is not detected in cases where the tumor is benign.

(2)-9 Prognosis of Canine Patient Bearing Benign Tumor

Canine Patient 13 (Toy Poodle) underwent tumor extirpation on Oct. 9, 2007. According to the pathological diagnosis using the extirpated tumor, mammary epithelial cells and myoepithelial cells were both proliferated to form the tumor, but both of them did not show any malignant findings, and therefore it was diagnosed as benign mixed tumor. The serodiagnosis showed the result that the absorbance at 450 nm was 0.13, slightly detected. On Jun. 5, 2008, 8 months thereafter, a blood sample was collected again and the serodiagnosis was carried out to find that the absorbance at 450 nm was 0, not detected at all. Recurrence was not found clinically at that time. These results confirmed that, even in the case where tumor is benign, complete removal of the tumor results in the decreased value in serodiagnosis if a detectable value can be observed in cancer-bearing state, and thus prognosis can be attained.

(3) Diagnosis in Cats

Next, cancer-bearing cats and healthy cats were diagnosed. Using the above-described canine calmegin protein and anti-cat IgG antibody, the IgG antibody titer of feline serum which specifically reacts with the polypeptide was measured in the same manner as described above. As a secondary antibody, HRP-conjugated anti-cat IgG antibody (PEROXIDASE-CONJUGATED GOAT IgG FRACTION TO CAT IgG (WHOLE MOLECULE): manufactured by CAPPEL RESERCH REAGENTS) 8,000-fold diluted with the blocking solution was used.

Feline Patient 1 (Chinchilla) underwent tumor extirpation of mammary adenocarcinoma on Aug. 17, 2005. The absorbance at 450 nm was 0.22. In Feline Patient 2 (Himalayan), which underwent extirpation of ductal carcinoma on Oct. 17, 2006, the absorbance at 450 nm was 0.21. On the other hand, the absorbance was not detected in healthy cats at all.

Thus, similarly to dogs, the absorbance value was detected in samples from cats suffering from cancer, while the absorbance value was not detected at all in samples from healthy cats. Hence, similarly to dogs, cancers in cats can also be diagnosed by this method using a canine calmegin protein.

(4) Diagnosis in Healthy Human

Using the above-described canine calmegin protein and anti-human IgG antibody above, the IgG antibody titer of healthy human serum which specifically reacts with the protein was measured in the same manner as described above. As a secondary antibody, HRP-conjugated anti-human IgG antibody (HRP-Goat Anti-Human IgG(H+L) Conjugate: manufactured by Zymed Laboratories) 10,000-fold diluted with the blocking solution was used. As a positive control, an immobilized ovalbumin antigen prepared by immobilizing 50 μg/ml ovalbumin in phosphate buffered saline on a solid phase was used. As a result, in Healthy Human 1, the absorbance at 450 nm observed on an ovalbumin antigen was 0.25, while the absorbance at 450 nm observed on the recombinant protein was 0.03, hardly detected.

Example B-4

Cancer Diagnosis Using Human Calmegin Protein

Using the human calmegin protein prepared in Example B-2, the IgG antibody titer of human, canine and feline sera which react with the protein was measured in the same manner as in Example B-3.

The diagnosis was carried out using healthy human serum. In the same manner as in Example B-3 (4), ovalbumin antigen was used as a positive control. As a result, the absorbance value was detected in the case where ovalbumin was immobilized on a solid phase, while the absorbance value was hardly detected in the case where a human calmegin protein was immobilized on a solid phase.

Similarly, in healthy dogs and cats, the absorbance at 450 nm was hardly detected in the case where the protein was immobilized on a solid phase.

On the other hand, Canine Patient 12 (Shih Tzu) underwent extirpation of mammary adenocarcinoma on Jun. 21, 2007. According to the pathological diagnosis using the extirpated tissue, the mammary gland tissue contained highly atypical, invasive cells, and grew to form adenomatous hyperplasia showing large and small massive structures. Hence, this patient was diagnosed as malignant tumor. In this Canine Patient 12, the absorbance at 450 nm was 0.70. The malignancy diagnosis was carried out using additional 310 serum samples which had been diagnosed as malignant based on the pathological diagnosis. As a result, by diagnosing a sample showing twice the average value of healthy canine samples as malignant, 171 samples i.e. 55.0% of the malignant cases could be successfully diagnosed as malignant. Moreover, in Feline Patient 3 (Mixed Breed), which underwent extirpation of mammary adenocarcinoma on Apr. 3, 2007, the absorbance at 450 nm was 0.38.

The above described results indicates that the diagnosis can be similarly attained in humans, dogs and cats even by using a human calmegin protein.

Furthermore, pleural effusion and ascites samples collected from terminal cancer dogs were subjected to the diagnosis using the recombinant human protein in the same manner as the recombinant canine protein. As a result, values similar to those detected in serum samples could be detected, and hence cancer diagnosis could be successfully attained.

Example B-5

Cancer Diagnosis by Measuring Antigen Polypeptide (1)

Mice and rabbits were immunized with the recombinant canine protein prepared in Example B-2 to obtain an antibody specific to this antigen. Using this polyclonal antibody, detection of the antigen polypeptide per se contained in the serum from cancer bearing living body was carried out by sandwich ELISA. Using anti-mouse IgG antibody, the amount of the protein in the serum which specifically reacts with the prepared polyclonal antibody specific to the protein was measured by sandwich ELISA.

As for immobilization of a primary antibody on a solid phase, 100 μL/well of the rabbit antiserum 20-fold diluted with phosphate buffered saline was added to a 96-well Immobilizer Amino plate (manufactured by Nunc), and the plate was shaken at room temperature for 2 hours. As for blocking, 100 μL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. To the plate, 100 μL/well of the serum from cancer-bearing body diluted with the blocking solution was added, and the plate was shaken at room temperature for 3 hours to allow the reaction to proceed. As for the diluted serum, a 10-fold serial dilution ranging 10 to 1,000-fold was prepared. After washing the wells 3 times with phosphate buffered saline containing 0.05% Tween20 (manufactured by Wako Pure Chemicals) (hereinafter referred to as PBS-T), 100 μL/well of mouse antiserum 200-fold diluted with the blocking solution was added thereto, and the plate was shaken at room temperature for 1 hour to allow the reaction to proceed. After washing the wells 3 times with PBS-T, 100 μL/well of HRP-conjugated mouse IgG antibody (Stabilized Goat Anti Mouse HRP conjugated: manufactured by PIERCE) 2000-fold diluted with the blocking solution was added thereto as a tertiary antibody, and the plate was shaken at room temperature for 1 hour to allow the reaction to proceed. After washing the wells 3 times with PBS-T, 100 μL/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 μl/well of 0.5 M sulfuric acid solution (manufactured by Sigma Aldrich Japan), and then the absorbance was measured at 450 nm with a microplate reader. As a control, a plate on which the rabbit antiserum was not immobilized and a plate with which serum from a cancer-bearing body was not reacted were measured in the same manner as described above.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody prepared by using the recombinant canine polypeptide as an immunogen.

Example B-6

Cancer Diagnosis by Measuring Antigen Polypeptide (2)

Mice and rabbits were immunized with the recombinant human protein prepared in Example B-2 to obtain an antibody specific to this antigen. In the same manner as in Example B-5, detection of the antigen polypeptide per se contained in the serum from cancer-bearing body was carried out by sandwich ELISA using this polyclonal antibody.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody prepared by using the recombinant human polypeptide as an immunogen.

Example C-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly (A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack II Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from squamous cell carcinoma was used. The serum was stored at −80° C. and pretreated immediately before use. The method of the pretreatment of the serum was as follows. That is, host E. coli cells (XL1-Blue MRF') were infected with λ ZAP Express phage to which no foreign gene was inserted, and then cultured on NZY plate medium at 37° C. overnight. Subsequently, the buffer of 0.2 M NaHCO$_3$, pH 8.3 containing 0.5 M NaCl was added to the plate, and the plate was left to stand at 4° C. for 15 hours, followed by collecting the supernatant as an E. coli/phage extract. Thereafter, the collected E. coli/phage extract was allowed to flow through an NHS column (manufactured by GE Healthcare Bio-Science) to immobilize proteins derived from the E. coli/phage thereon. The serum from the canine patients was allowed to flow through and react with this protein-immobilized column to remove antibodies adsorbed on E. coli and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host E. coli (XL1-Blue MRF') such that the absorbance OD$_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1,000×g for 15 minutes, and the supernatant was recovered as a phagemid solution. Subsequently, 200 μl of a solution prepared to contain a phagemid host E. coli (SOLR) such that the absorbance OD$_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:25 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene has 99% homology (which was calculated only in the overlapping region) to the registered CEP gene described in SEQ ID NO:41 in terms of base sequence and amino acid sequence, so that the gene was judged as the CEP gene. The obtained human homologous factor of the canine CEP was human CEP (homology to the CEP gene described in SEQ ID NO:25: base sequence, 87%; amino acid sequence, 84%). The base sequence of human CEP is shown in SEQ ID NO:27, and the amino acid sequence thereof is shown in SEQ ID NO:28.

(4) Analysis of Expression in Each Tissue

Figure 9:
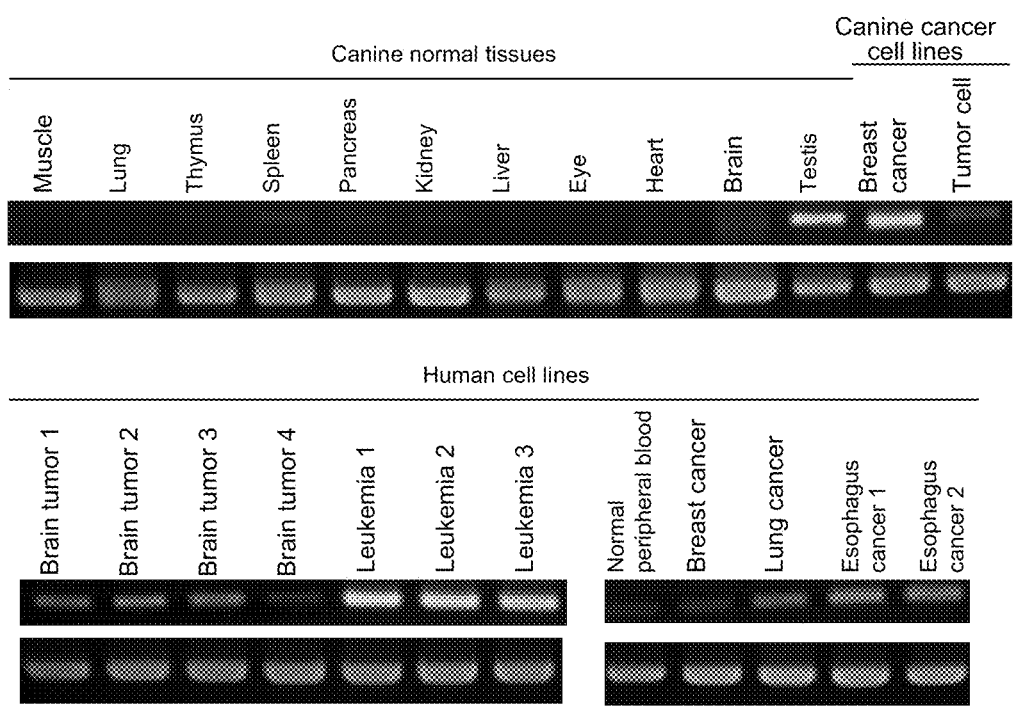
FIG. 9 shows the expression pattern of the gene encoding CEP in normal tissues and tumor cell lines. Reference numeral 1: the expression pattern of the gene encoding CEP; Reference numeral 2: the expression pattern of the GAPDH gene.
Figure 10:
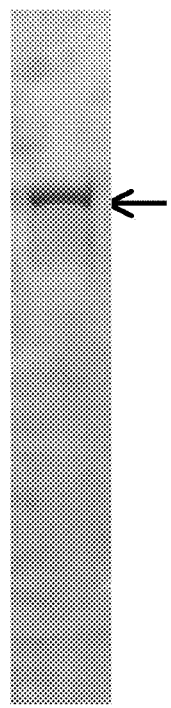
FIG. 10 shows the detection by Coomassie staining of the polypeptide derived from canine CEP, which is an example of the polypeptide used in the present invention, produced in *E. coli* and purified in Example C. Reference numeral 3: the band for the polypeptide derived from canine CEP.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:29 and 30) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for 30 seconds and 72° C. for 30 seconds using Thermal Cycler (manufactured by BIO RAD). The above-described gene-specific primers were those which amplify the regions of the 4582nd to 5124th bases of the base sequences of SEQ ID NOs:25 and 41 (canine CEP gene) and the 4610th to 5152nd bases of the base sequence of SEQ ID NO:27 (human CEP gene), and can be used for investigation of the expression of both the canine CEP gene and the human CEP gene. As a control for comparison, primers (described in SEQ ID NOs:9 and 10) specific to GAPDH were used simultaneously. As a result, as shown in FIG. 9, strong expression of the canine CEP gene was observed in testis among the normal dog tissues, and on the other hand, strong expression was observed in the canine breast cancer cell line. Expression of the human CEP gene was confirmed, as is the case with the canine CEP gene, only in testis among the human normal tissues, but the expression was detected in brain tumor, leukemia and esophagus cancer cells among human cancer cell lines, and especially, strong expression was observed in the leukemia cell line. Thus, the human CEP gene was also confirmed to be specifically expressed in testis and cancer cells.

In FIG. 9, reference numeral 1 in the ordinate indicates the expression pattern of the CEP gene, and reference numeral 2 indicates the expression pattern of the GAPDH gene as a control for comparison.

Example C-2

Preparation of Polypeptides Derived from Canine and Human CEPs (1) Preparation of Recombinant Protein Based on the gene of SEQ ID NO:25 obtained in Example C-1, a recombinant protein was prepared by the following method. Respective reagents and the attached buffer were mixed such that the mixture should contain 1 µl of the vector that was prepared from the phagemid solution obtained in Example C-1 and was subjected to the sequence analysis, 0.4 µM each of two kinds of primers having BamHI and SalI restriction sites (described in SEQ ID NOs:31 and 32), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 7 minutes using Thermal Cycler (manufactured by BIO RAD). Using the above-described two kinds of primers, a region encoding an amino acid region (SEQ ID NO:35) of 1514th to 2339th amino acids of SEQ ID NO:26 is obtained. After the PCR, the amplified DNA was subjected to electrophoresis using 1% agarose gel, and a DNA fragment of about 2.5 kbp was purified using QIAquick Gel Extraction Kit (manufactured by QIAGEN).

In the same manner, PCR was carried out using two kinds of primers described in SEQ ID NOs:37 and 38 to obtain the region encoding the entire amino acid sequence of SEQ ID NO:26. After the PCR, the amplified DNA was subjected to electrophoresis using 1% agarose gel, and a DNA fragment of about 7.0 kbp was purified using QIAquick Gel Extraction Kit (manufactured by QIAGEN).

Moreover, PCR was carried out using two kinds of primers described in SEQ ID NOs:37 and 43 to obtain the region encoding the entire amino acid sequence of SEQ ID NO:42. After the PCR, the amplified DNA was subjected to electrophoresis using 1% agarose gel, and a DNA fragment of about 7.8 kbp was purified using QIAquick Gel Extraction Kit (manufactured by QIAGEN).

Each of the purified DNA fragments was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

Further, based on the gene of SEQ ID NO:27, a recombinant protein of the human homologous gene was prepared by the following method. Respective reagents and the attached buffer were mixed such that the mixture should contain 1 µl of the cDNA prepared in Example C-1 whose expression could be confirmed by the RT-PCR method in various tissues/cells, 0.4 µM each of two kinds of primers having BamHI and SalI restriction sites (described in SEQ ID NOs:33 and 34), 0.2 mM dNTP and 1.25 U of PrimeSTAR HS polymerase (manufactured by Takara Shuzo Co., Ltd.) in a total volume of 50 and PCR was carried out with 30 cycles of 98° C. for 10 seconds, 55° C. for 5 seconds and 72° C. for 7 minutes using Thermal Cycler (manufactured by BIO RAD). Using the above-described two kinds of primers, a region encoding an amino acid region (SEQ ID NO:36) of 1513rd to 2325th amino acids of SEQ ID NO:28 is obtained. After the PCR, the amplified DNA was subjected to electrophoresis using 1% agarose gel, and a DNA fragment of about 2.5 kbp was purified using QIAquick Gel Extraction Kit (manufactured by QIAGEN).

In the same manner, PCR was carried out using two kinds of primers described in SEQ ID NOs:39 and 40 to obtain the region encoding the entire amino acid sequence of SEQ ID NO:28. After the PCR, the amplified DNA was subjected to electrophoresis using 1% agarose gel, and a DNA fragment of about 7.0 kbp was purified using QIAquick Gel Extraction Kit (manufactured by QIAGEN).

Each of the purified DNA fragments was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed a part of SEQ ID NO:26 and a part of SEQ ID NO:28, respectively, were cultured in kanamycin (final concentration: 30 µg/ml)-containing LB medium at 37° C. until the absorbance at 600 nm reached about 0.7, and then IPTG was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in phosphate-buffered saline and subjected to sonication on ice. The sonicated solution of *E. coli* was centrifuged at 7,000 rpm for 20 minutes to obtain the supernatant as the soluble fraction and the precipitate as the insoluble fraction. The insoluble fraction was suspended in 4% Triton X-100 solution and the resulting suspension was centrifuged at 7,000 rpm for 20 minutes. This operation was repeated twice and an operation of removal of proteases was carried out. The residue was suspended in 8 M urea (manufactured by Sigma Aldrich Japan)-containing 10 mM Tris-HCl, 100 mM phosphate buffer (hereinafter referred to as 8 M urea solution) and a protease inhibitor cocktail solution, and the resulting suspension was left to stand at 4° C. for 15 hours to denature proteins.

Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 8M urea solution), followed by leaving it to stand at 4° C. overnight. The supernatant was recovered by centrifugation of this column carrier at 1,500 rpm for 5 minutes, and the column carrier was suspended in phosphate-buffered saline followed by refilling the column with the resulting suspension. The fraction that was not adsorbed to the column was washed away with 5 column volumes of 8 M urea solution, 10 column volumes of 0.5 M sodium chloride-containing 0.1 M acetate buffer (pH 5.0) and 10 mM imidazole-containing 20 mM phosphate buffer (pH 8.0), and elution was immediately carried out with a five-step density gradient of 100 mM-500 mM imidazole. Five column volumes of the eluted fraction was collected in each elution step. Elution of the proteins of interest was confirmed by Coomassie staining carried out according to a conventional method. Based on the result, the eluted fractions were desalted and concentrated to obtain the material to be solid-phased for diagnosis.

In the same manner, the recombinant *E. coli* cells that expressed the full-length of SEQ ID NOs:26, 28 and 42, respectively, were cultured and the proteins of interest were purified to obtain the material to be solid-phased for diagnosis.

Example C-3

Cancer Diagnosis Using Polypeptide Derived from Canine CEP (1) Cancer Diagnosis in Dogs Blood samples were collected from 486 canine patients in which malignant or benign tumors were found and 6 healthy dogs, and sera were separated therefrom. Using the partial polypeptide of canine CEP (SEQ ID NO:35; 1514th to 2339th amino acid region of SEQ ID NO:26) prepared in Example C-2 and anti-dog IgG antibody, the IgG antibody titer of the sera which specifically react with the polypeptide was measured by ELISA.

As for immobilization of the prepared protein on a solid phase, 100 µL/well of a solution of the recombinant protein diluted to 50 µg/mL with phosphate buffered saline was added to a 96-well Immobilizer Amino plate (manufactured by Nunc), and the plate was left to stand at 4° C. overnight. As for blocking, 100 µL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. Serum sample was 500-fold diluted with the blocking solution, and 100 µL/well of the diluted serum was added to the plate, followed by shaking the plate at room temperature for 3 hours to allow the reaction to proceed. After washing the wells 3 times with phosphate buffered saline containing 0.05% Tween20 (manufactured by Wako Pure Chemicals) (hereinafter referred to as PBS-T), 100 µL/well of HRP-conjugated dog IgG antibody (Goat anti Dog IgG-h+l HRP conjugated: manufactured by BETHYL Laboratories) 3,000-fold diluted with the blocking solution was added thereto, and the plate was shaken at room temperature for 1 hour to allow the reaction to proceed. After washing the wells 3 times with PBS-T, 100 µl/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 µl/well of 0.5 M sulfuric acid solution (manufactured by Sigma Aldrich Japan), and then the absorbance was measured at 450 nm with a microplate reader. As a control, a plate on which the prepared recombinant protein was not immobilized and a plate with which the serum from a cancer-bearing dog was not reacted were measured in the same manner as above.

Among the total 486 samples used in the above-described cancer diagnosis, 311 samples were definitely diagnosed as malignant by pathological diagnosis using the extirpated tumor tissue.

Specifically, the samples were diagnosed as cancer such as malignant melanoma; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; squamous cell carcinoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); leiomyosarcoma or the like.

Figure 11:
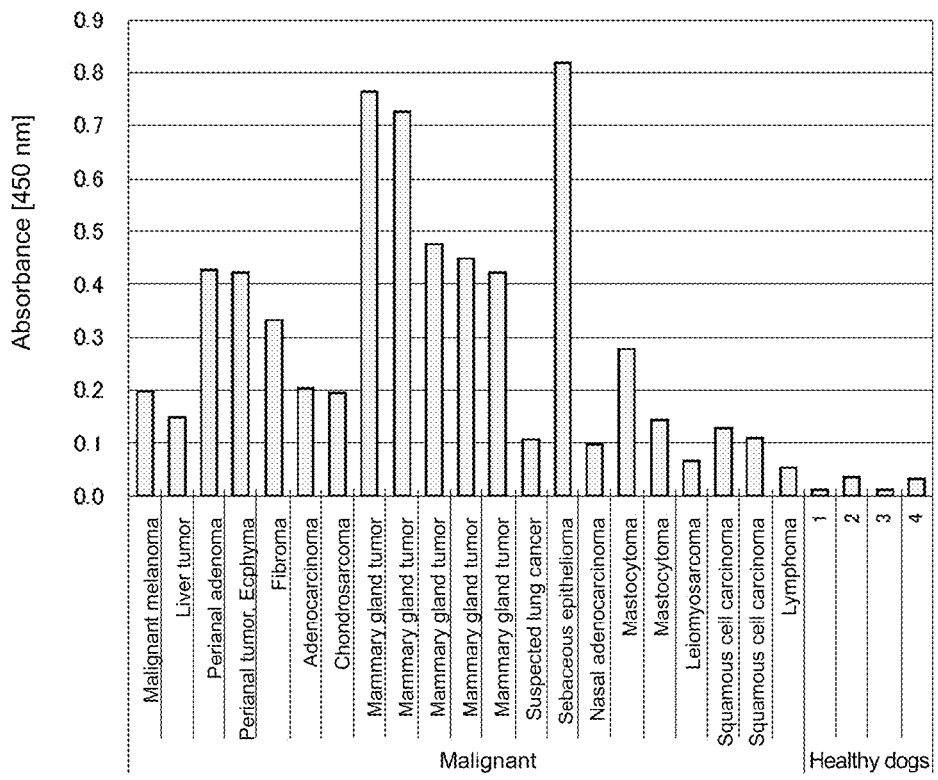
FIG. 11 shows some of the results of cancer diagnosis in cancer-bearing dogs carried out using the polypeptide derived from canine CEP prepared in Example C.

As shown in FIG. 11, sera from these cancer-bearing dogs showed a significantly high antibody titer against the recombinant protein. It was revealed that, by diagnosing a sample showing twice the average value of healthy canine samples as malignant, 197 samples i.e. 63.3% of the malignant cases could be successfully diagnosed as malignant. The details of these 197 cancer samples are as follows. It is noted that the following number of each cancer case is a cumulative total, as some samples contained multiple primaries.

Malignant melanoma, 8 cases; lymphoma, 9 cases; pheochromocytoma, 1 case; suppurative inflammation, 1 case; granulosa cell tumor, 1 case; hepatocellular carcinoma, 5 cases; angioma, 1 case; malignant testicular tumor, 6 cases; intraoral tumor, 5 cases; perianal adenocarcinoma, 12 cases; osteosarcoma, 4 cases; fibrosarcoma, 8 cases; ductal carcinoma, 10 cases; chondrosarcoma, 2 cases; mammary adenocarcinoma, 35 cases; combined mammary adenocarcinoma, 24 cases; lung cancer, 2 cases; sebaceous adenocarcinoma, 2 cases; nasal adenocarcinoma, 2 cases; mastocytoma, 24 cases; adrenomedullary tumor, 1 case; leiomyosarcoma, 1 case; squamous cell carcinoma, 4 cases; chronic lymphocytic leukemia, 1 case; undifferentiated sarcoma, 1 case; malignant mixed tumor, 1 case; tumor in the posterior segment of the left lobe of the lung, 1 case; tumor in the right infra-axillary region, 1 case; tumor in the elbow of the right forelimb, 1 case; bladder cancer (transitional cell carcinoma), 1 case; metastatic malignant melanoma, 3 cases; amelanotic malignant melanoma, 1 case; adenocarcinoma of the large intestine, 1 case; plasmacytoma, 1 case; histiocytic sarcoma, 1 case; liposarcoma, 1 case; poorly differentiated sarcoma, 1 case; synovial sarcoma, 1 case; malignant hemangiopericytoma, 1 case; apocrine sweat gland carcinoma, 3 cases; bronchial adenocarcinoma, 1 case.

The above-described diagnostic method was also carried out using pleural effusion samples and ascites samples collected from terminal cancer dogs. As a result, values similar to those detected in serum samples could be detected, and hence cancer diagnosis could be successfully attained.

Figure 12:
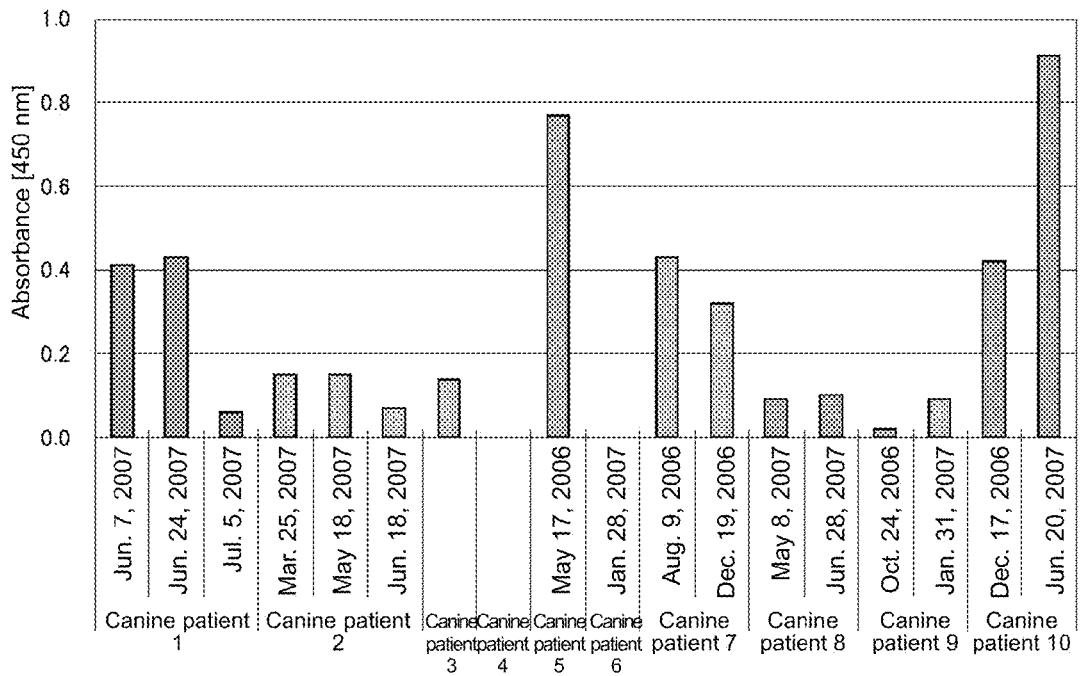
FIG. 12 shows some of the results of detailed cancer diagnosis in cancer-bearing dogs carried out using the polypeptide derived from canine CEP prepared in Example C.

Furthermore, it was confirmed that diagnostic approaches such as diagnosis of cancers existing in an invisible part of the body, assessment of cancer stage and grade, follow-up of postoperative patients, diagnosis of recurrence and metastasis and the like can also be attained by applying the above-described diagnostic method. The followings are several of the practical examples of the detailed diagnosis shown in FIG. 12.

(2)-1 Diagnosis of Invisible Tumors

In Canine Patient 1 (Flat-Coated Retriever), any tumors were not found on Jun. 7, 2007. But about 20 days later, on Jun. 24, 2007, a pedunculated tumor with a diameter of 2 mm was found on the gum at the root of the canine tooth. The tumor was ligated at its pedunculated part and excised on the day it found. The absorbance at 450 nm observed before the tumor became visible with the naked eye was 0.41, which was significantly high and not so different from the absorbance at the time of finding tumor, 0.43. The result indicates that it is possible to diagnose cancers even in an invisible part such as an intraperitoneal part by the method of the present invention.

Rise of the value was observed before the tumor became visible with the naked eye, which is considered to have been a sign of tumor development. Thus, the method of the present invention is useful in medical examinations such as periodic health examination.

Canine Patient 1 was again checked by the serodiagnosis 2 weeks after the tumor excision. As a result, the absorbance at 450 nm was greatly reduced to 0.06. Thus, it was also confirmed that the cancer antigen-expressing tumor which had caused the increased antibody titer was completely removed (see, (2)-4, Follow-Up of Postoperative Patients).

(2)-2 Assessment of Stage of Cancer Progression

The stage of cancer progression is determined based on the size or depth of the tumor, how much the tumor exerts influence on the surrounding tissues, whether the tumor metastasizes or not, and the like. It was revealed herein that the detected value is higher than before if the metastasis occurs, i.e., the cancer has advanced. The following is another example of a stage assessment of a certain cancer case, which received anticancer drug therapy.

Canine Patient 2 (Miniature Dachshund) visited the hospital with chief complaints of nausea and emaciation on Feb. 21, 2007, and two massive tumors were found in the abdominal cavity. This patient underwent tumor extirpation on Feb. 23, 2007. The swollen right kidney weighed 433 g. The neighboring lymph node was well-vascularized and weighed 42 g. Based on the pathological diagnosis using the extirpated tissue, the patient was diagnosed as multicentric malignant lymphoma. It was said that there was a probability that the tumor cells would spread into other organs in the abdominal cavity, as a disseminated spread of tumor cells was observed in the adipose tissue. The anticancer drug administration (Oncovin) was started postoperatively on Mar. 1, 2007, and the serodiagnosis was carried out 3 times, i.e., on the day the administration was started, and 2 and 3 months thereafter. As a result, the absorbance at 450 nm was 0.15, 0.15, and 0.07, respectively. The value had gradually decreased since the start of the administration, which confirmed that the anticancer drug took effect. Thus, it was confirmed that cancer progression could be inhibited. Hence, the results in Canine Patient 2 confirmed that the stage of cancer progression can also be assessed. In addition, it was confirmed that the effect of anticancer drug therapy can also be assessed as described above.

(2)-3 Assessment of Grade of Cancer Malignancy

Basaliomas include malignant type and benign type. Recently, according to the new WHO classification, malignant basaliomas are called basal cell carcinoma, and benign basaliomas are called trichoblastoma.

Canine Patient 3 (Beagle) was diagnosed as basal cell carcinoma (malignant). The serodiagnosis was carried out at the time of the surgery to find that the absorbance at 450 nm was 0.14. On the other hand, in Canine Patient 4 (Mixed Breed) diagnosed as trichoblastoma (benign), the serodiagnosis carried out at the time of the surgery revealed that the absorbance at 450 nm was 0, not detected at all. Thus, even in the case of the same basaliomas, malignant basal cell carcinoma and benign trichoblastoma can be distinctively diagnosed.

Next example is mammary gland tumors. Mammary gland tumors include malignant tumors such as mammary adenocarcinoma and mammary gland malignant mixed tumor, and benign mammary tumors which do not show malignant symptoms. Canine Patient 5 (Yorkie) underwent extirpation of mammary gland malignant mixed tumor and mammary adenocarcinoma on May 17, 2006. In general, the complete excision of mixed tumors in mammary gland is easy because they are poorly invasive to the surrounding tissues even if they are malignant, and thus the postoperative course of the patients is usually uneventful. However, Canine Patient 5 had been diagnosed as highly malignant tumor, because the pathological diagnosis using the extirpated tissue revealed that some components of the specimen from Canine Patient 5 showed an invasive nature. On the other hand, mammary adenocarcinoma is a highly invasive tumor which often recurs and metastasizes. Although invasion of the tumor cells was not observed in the specimen from Canine Patient 5, it had been pointed out that highly malignant components possibly proliferated in other region out of the specimen. Thus, the findings in the pathological diagnosis clearly taught that Canine Patient 5 was suffering from highly malignant mammary cancer. A blood sample was collected during the surgery and the serodiagnosis was carried out to find that the absorbance at 450 nm was 0.77. On the other hand, Canine Patient 6 (Yorkshire Terrier) underwent extirpation of mammary tumor on Jan. 28, 2007. According to the pathological diagnosis using the extirpated tissue, atypism of cells was low, and thus Canine Patient 6 was diagnosed as benign mastadenoma without malignant findings. A blood sample was collected during the surgery and the serodiagnosis was carried out to find that the absorbance at 450 nm was 0. The results in the two cases above revealed that highly malignant tumors show a higher value than low malignant, benign tumors.

(2)-4 Follow-Up of Postoperative Patients

Canine Patient 7 (Mixed Breed) underwent extirpation of perianal adenoma in August of 2003 and on Aug. 9, 2006. The tumor extirpated on Aug. 9, 2006 was clinically diagnosed as recurrence, because the similar tumor again occurred at the same site. The pathological diagnosis using the tissue extirpated at the second time revealed that tumor cells were highly invasive and atypical showing anisokaryosis and dyskaryosis, and also that a lot of dividing nuclei were observed. Thus, the patient was diagnosed as malignant tumor. According to the diagnostic pathologist, it is necessary to pay attention to local recurrence or metastasis which would occur again. The serodiagnosis was carried out at that time. As a result, the absorbance at 450 nm was 0.43. On Dec. 19, 2006, about 4 months after the surgery, the serodiagnosis was carried out again on the patient in the course of follow-up. As a result, the absorbance at 450 nm decreased to 0.32. Neither recurrence nor metastasis has been found till August of 2007. Thus, it is considered that the value obtained in the serodiagnosis became lower than that obtained at the time of surgery because the tumor could be completely extirpated in Canine Patient 7.

(2)-5 Diagnosis of Recurrence

Canine Patient 8 (Husky) underwent an extirpation of mammary adenocarcinoma on May 8, 2007. According to the serodiagnosis carried out at the time of the surgery, the absorbance at 450 nm was 0.09. The pathological diagnosis using the extirpated tissue revealed that highly atypical epithelial cells proliferated and mainly formed ductal structures, and thus this patient was diagnosed as primary breast adenocarcinoma. It was said that the patient was at a high risk of recurrence or metastasis to lymph nodes or distant organs, as many cancer cells had already entered the lymph vessels at that time. On Jun. 28, 2007, about 1-and-a-half month after the surgery, metastasis was found at the same site. The serodiagnosis was carried out at that time to find that the value increased to 0.10. Thus, it was confirmed that the value detected by the serodiagnosis was higher in the end of June than in the beginning of May because the tumor could not have been completely excised or recurrence would have occurred in Canine Patient 8.

Canine Patient 9 (Sheltie) underwent extirpation of ductal carcinoma on Oct. 24, 2006. The serodiagnosis was carried out at that time. As a result, the absorbance at 450 nm was 0.02. About 3 months later, on Jan. 31, 2007, this patient visited the hospital because of cancer recurrence and underwent extirpation again. According to the pathological diagnosis using the extirpated tissue, many cancer cells having egg-shaped atypical nuclei invaded lymph vessels and metastasis was observed in the inguinal lymph node, and thus the patient was diagnosed as ductal carcinoma (breast cancer) with a probability of distant metastasis. The serodiagnosis was carried out at that time to find that the absorbance at 450 nm increased to 0.09. Thus, similarly to above, it was confirmed that the value of the serodiagnosis increased 3 months later because the tumor could not have been completely excised or recurrence of the tumor would have occurred in Canine Patient 9.

(2)-6 Diagnosis of Metastasis

Canine Patient 10 (Scottish Terrier), repeatedly undergoing metastasis and recurrence, was diagnosed as mammary tumor in February of 2003; intraoral malignant melanoma in August of 2003; malignant melanoma of the lip in January of 2005; and as intraoral melanoma on Apr. 13, 2005, all of which were excised by surgery. This patient visited the hospital again on Dec. 17, 2006 for follow-up after the recurrence of intraoral melanoma in April of 2005, and the serodiagnosis was carried out at that time. As a result, the absorbance at 450 nm was 0.42. Half a year later, on Jun. 20, 2007, the patient again visited the hospital because of the hypertrophy of cervical and malar lymph nodes. In the case of lymphomas, hypertrophy of lymph nodes is systemically observed. Because Canine Patient 10 had only two swollen lymph nodes, this patient was clinically diagnosed as probable metastatic lymphoma. The diagnosis according to the present invention also revealed that it was a metastatic tumor from one which had previously existed in this patient, as the absorbance at 450 nm greatly increased to 0.91.

(2)-7 Therapy Monitoring

Canine Patient 12 (Mixed Breed) underwent tumor extirpation on Jul. 27, 2007. The pathological diagnosis using the extirpated tumor revealed that breast cancer grew continuously in the mammary ducts. Thus, this patient was diagnosed as ductal carcinoma. According to the serodiagnosis carried out at that time, the absorbance at 450 nm was 0.24. Cancer recurrence has not been found up to this time, i.e. 13 months after the extirpation. The serodiagnosis was again carried out on Sep. 3, 2007, about 1 month after the extirpation; Oct. 12, 2007, 2 months after the extirpation; and on Jun. 1, 2008, 10 month after the extirpation. As a result, the absorbance at 450 nm was 0.18, 0.18 and 0.12, respectively.

These results obtained in Canine Patient 12 confirmed that the value becomes lower than that detected in a cancer-bearing state if tumors can be completely removed, as well as that the value does not increase unless cancer recurs, and thus change in treated patients can be followed. In addition, the diagnosis of recurrence can also be carried out as shown in Canine Patient 8, which confirms that the therapy monitoring can also be made possible.

(2)-8 Diagnosis of Malignancy of Recurrent Tumor

Canine Patient 13 (Golden Retriever) underwent tumor extirpation on May 1, 2005. The pathological diagnosis using the extirpated tumor revealed that the tumor in this patient was malignant neoplastic lesion originated from mammary ductal epithelium, i.e., malignant mammary ductal carcinoma and malignant papillary carcinoma continuously growing through the mammary ducts. On Jun. 28, 2008, about 3 years thereafter, tumor was found again and thus extirpation was carried out. The pathological diagnosis using the extirpated tumor revealed that nothing but severe infiltration of inflammatory cells such as neutrophils, macrophages, plasma cells and the like could be observed around surgical sutures under the skin which was considered to be the previous surgical wound, and thus the patient was diagnosed as having no neoplastic lesions. According to the serodiagnosis carried out at that time, the absorbance at 450 nm was 0, not detected at all. The results observed in Canine Patients 8, 9 and 13 indicated that the value of the serodiagnosis does not decrease or is sustained in cases where the recurrent tumor is malignant, and is not detected in cases where the tumor is benign.

(2)-9 Prognosis of Canine Patient Bearing Benign Tumor

Canine Patient 14 (Toy Poodle) underwent tumor extirpation on Oct. 9, 2007. The pathological diagnosis using the extirpated tumor revealed that mammary epithelial cells and myoepithelial cells were both proliferated to form the tumor, but that both of them did not show any malignant findings, and therefore this patient was diagnosed as benign mixed tumor. According to the serodiagnosis carried out at that time, the absorbance at 450 nm was 0.05, slightly detected. On Jun. 5, 2008, 8 months thereafter, a blood sample was collected again and the serodiagnosis was carried out to find that the absorbance at 450 nm was 0, not detected at all. Recurrence was not found clinically at that time. These results indicated that, even in the case where tumor is benign, complete removal of the tumor results in the decreased value of the serodiagnosis if a detectable value can be observed in cancer-bearing state, and hence prognosis can be attained.

(3) Diagnosis in Cats

Next, cancer-bearing cats and healthy cats were diagnosed. Using the above-described partial polypeptide of canine CEP and anti-cat IgG antibody, the IgG antibody titer of feline serum which specifically reacts with the polypeptide was measured in the same manner as described above. As a secondary antibody, HRP-conjugated anti-cat IgG antibody (PEROXIDASE-CONJUGATED GOAT IgG FRACTION TO CAT IgG (WHOLE MOLECULE): manufactured by CAPPEL RESERCH REAGENTS) 8,000-fold diluted with the blocking solution was used.

Feline Patient 1 (Chinchilla) underwent extirpation of mammary adenocarcinoma on Aug. 17, 2005. The absorbance at 450 nm was 0.48. In Feline Patient 2 (Himalayan), which underwent extirpation of ductal carcinoma on Oct. 17, 2006, the absorbance at 450 nm was 0.18. On the other hand, the absorbance was not detected in healthy cats at all.

Thus, similarly to dogs, the absorbance value was detected in samples from cats suffering from cancer, while the absorbance value was not detected at all in samples from healthy cats. Hence, similarly to dogs, cancers in cats can also be detected by this method using a polypeptide derived from canine CEP.

(4) Diagnosis in Healthy Human

Using the above-described partial polypeptide of canine CEP and anti-human IgG antibody above, the IgG antibody titer of healthy human serum which specifically reacts with the polypeptide was measured in the same manner as described above. As a secondary antibody, HRP-conjugated anti-human IgG antibody (HRP-Goat Anti-Human IgG(H+L) Conjugate: manufactured by Zymed Laboratories) 10,000-fold diluted with the blocking solution was used. As a positive control, an immobilized ovalbumin antigen prepared by immobilizing 50 µg/ml ovalbumin in phosphate buffered saline on a solid phase was used. As a result, in Healthy Human 1, the absorbance at 450 nm observed on an ovalbumin antigen was 0.25, while the absorbance at 450 nm observed on the recombinant protein was 0.02, hardly detected. Similarly, in Healthy Human 2, the absorbance at 450 nm observed on an ovalbumin antigen was 0.18, while the absorbance at 450 nm observed on the recombinant protein was 0.03, hardly detected.

Further, the diagnosis was carried out in the same manner as described above using a full-length canine CEP having the sequence shown in SEQ ID NO:26 prepared in Example C-2. As a result, the diagnosis can be similarly attained in humans, dogs and cats.

Furthermore, the diagnosis was carried out in the same manner as described above using a full-length canine CEP having the sequence shown in SEQ ID NO:42 prepared in Example C-2. As a result, the diagnosis can be similarly attained in humans, dogs and cats.

Example C-4

Cancer Diagnosis Using Polypeptide Derived from Human CEP

Using the partial polypeptide of human CEP (SEQ ID NO:36; 1513rd to 2325th amino acid region of SEQ ID NO:28) prepared in Example C-2, the IgG antibody titer of human, canine and feline sera which react with the polypeptide was measured in the same manner as in Example C-3.

The diagnosis was carried out using healthy human serum. In the same manner as in Example C-3 (4), ovalbumin antigen was used as a positive control. As a result, the absorbance value was detected in the case where ovalbumin was immobilized on a solid phase, while the absorbance value was hardly detected in the case where the partial polypeptide of human CEP was immobilized on a solid phase.

Similarly, in healthy dogs and cats, the absorbance at 450 nm was hardly detected in the case where the polypeptide was immobilized on a solid phase.

On the other hand, Canine Patient 11 (Shih Tzu) underwent extirpation of mammary adenocarcinoma on Jun. 21, 2007. According to the pathological diagnosis using the extirpated tissue, the mammary gland tissue contained highly atypical, invasive cells, and grew to form adenomatous hyperplasia showing large and small massive structures. Hence, this patient was diagnosed as malignant tumor. In Canine Patient 11, the absorbance at 450 nm was 0.33. The malignancy diagnosis was carried out using additional 310 serum samples which had been diagnosed as malignant by pathological diagnosis. As a result, by diagnosing a sample showing twice the average value of healthy canine samples as malignant, 185 samples i.e. 59.5% of the malignant cases could be successfully diagnosed as malignant.

Moreover, in Feline Patient 3 (Mixed Breed), which underwent extirpation of mammary adenocarcinoma on Apr. 3, 2007, the absorbance at 450 nm was 0.15.

The above described results indicated that the diagnosis can also be similarly carried out in humans, dogs and cats by using a polypeptide derived from human CEP.

Furthermore, pleural effusion and ascites samples collected from terminal cancer dogs were subjected to the diagnosis using the recombinant human protein in the same manner as the recombinant canine protein. As a result, values similar to those detected in serum samples could be detected, and hence cancer diagnosis could be successfully attained.

In addition, the diagnosis was carried out in the same manner as described above using a full-length human CEP having the sequence shown in SEQ ID NO:28 prepared in Example C-2. As a result, the diagnosis could also be similarly carried out in humans, dogs and cats.

Example C-5

Cancer Diagnosis by Measuring Antigen Polypeptide (1)

Mice and rabbits were immunized with the recombinant canine protein having the sequence shown in SEQ ID NO:35 prepared in Example C-2 to obtain an antibody specific to this antigen. Using this polyclonal antibody, detection of the antigen polypeptide per se contained in the serum from cancer bearing living body was carried out by sandwich ELISA. Using anti-mouse IgG antibody, the amount of the protein in the serum which specifically reacts with the prepared polyclonal antibody specific to the protein was measured by sandwich ELISA.

As for immobilization of a primary antibody on a solid phase, 100 μL/well of the rabbit antiserum 20-fold diluted with phosphate buffered saline was added to a 96-well Immobilizer Amino plate (manufactured by Nunc), and the plate was shaken at room temperature for 2 hours. As for blocking, 100 μL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. To the plate, 100 μL/well of the serum from cancer-bearing body diluted with the blocking solution was added, and the plate was shaken at room temperature for 3 hours to allow the reaction to proceed. As for the diluted serum, a 10-fold serial dilution ranging 10 to 1,000-fold was prepared. After washing the wells 3 times with phosphate buffered saline containing 0.05% Tween20 (manufactured by Wako Pure Chemicals) (hereinafter referred to as PBS-T), 100 μL/well of mouse antiserum 200-fold diluted with the blocking solution was added thereto, and the plate was shaken at room temperature for 1 hour to allow the reaction to proceed. After washing the wells 3 times with PBS-T, 100 μL/well of HRP-conjugated mouse IgG antibody (Stabilized Goat Anti Mouse HRP conjugated: manufactured by PIERCE) 2,000-fold diluted with the blocking solution was added thereto as a tertiary antibody, and the plate was shaken at room temperature for 1 hour to allow the reaction to proceed. After washing the wells 3 times with PBS-T, 100 Owen of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 μl/well of 0.5 M sulfuric acid solution (manufactured by Sigma Aldrich Japan), and then the absorbance was measured at 450 nm with a microplate reader. As a control, a plate on which the rabbit antiserum was not immobilized and a plate with which serum from a cancer-bearing body was not reacted were measured in the same manner as described above.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody which was prepared by using the recombinant canine polypeptide as an immunogen.

In addition, the diagnosis was carried out in the same manner as described above using an antibody which was prepared by using as an immunogen the full-length canine CEP having the sequence shown in SEQ ID NO:26 prepared in Example C-2.

As a result, cancers could also be diagnosed in dogs and cats by this method in which the antigen polypeptide was detected with an antibody which was prepared by using a full-length canine CEP as an immunogen.

Furthermore, the diagnosis was carried out in the same manner as described above using an antibody which was prepared by using as an immunogen the full-length canine CEP having the sequence shown in SEQ ID NO:42 prepared in Example C-2.

As a result, cancers could also be diagnosed in dogs and cats by this method in which the antigen polypeptide was detected with an antibody which was prepared by using a full-length canine CEP as an immunogen.

Example C-6

Cancer Diagnosis by Measuring Antigen Polypeptide (2)

Mice and rabbits were immunized with the recombinant human protein having the sequence shown in SEQ ID NO:36 prepared in Example C-2 to obtain an antibody specific to this antigen. In the same manner as in Example C-5, detection of the antigen polypeptide per se contained in the serum from cancer-bearing living body was carried out by sandwich ELISA using this polyclonal antibody.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody prepared by using the recombinant human polypeptide as an immunogen.

In addition, the diagnosis was carried out in the same manner as described above using an antibody which was prepared by using as an immunogen the full-length human CEP having the sequence shown in SEQ ID NO:28 prepared in Example C-2.

As a result, cancers could also be diagnosed in dogs and cats by this method in which the antigen polypeptide was detected with an antibody which was prepared by using a full-length human CEP as an immunogen.

Example D-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly (A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host E. coli cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M NaHCO$_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance OD$_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1,000×g for 15 minutes, and the supernatant was recovered as a phagemid solution. Subsequently, 200 μl of a solution prepared to contain a phagemid host *E. coli* (SOLR) such that the absorbance OD$_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:44 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the TRIP11 gene. The human homologous factor of canine TRIP11 was human TRIP11 (homology: base sequence, 88%; amino acid sequence, 86%). The base sequence of human TRIP11 is shown in SEQ ID NO:46, and the amino acid sequence thereof is shown in SEQ ID NO:47.

(4) Analysis of Expression in Each Tissue

Figure 13:
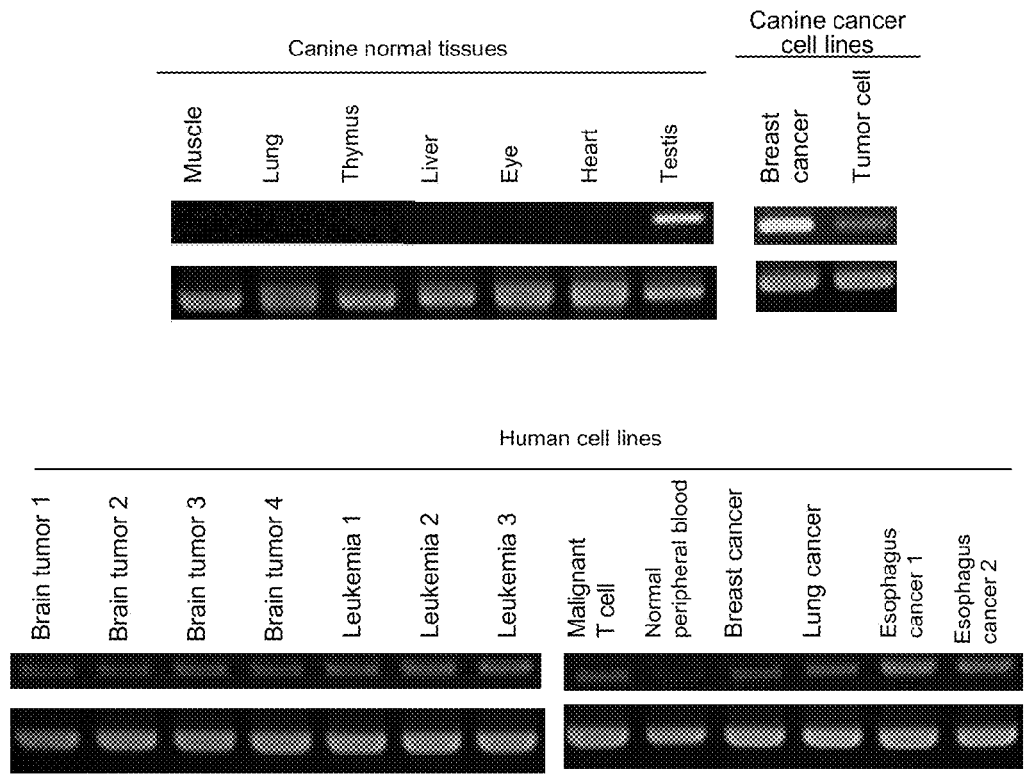
FIG. 13 shows the expression pattern of the gene encoding the TRIP11 protein in normal tissues and tumor cell lines. Reference numeral 1: the expression pattern of the gene encoding the TRIP11 protein; Reference numeral 2: the expression pattern of the GAPDH gene.
Figure 14:
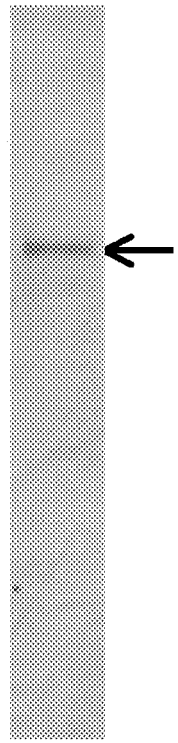
FIG. 14 shows the detection by Coomassie staining of the polypeptide derived from canine TRIP11, which is an example of the polypeptide used in the present invention, produced in *E. coli* and purified in Example D. Reference numeral 3: the band for the polypeptide derived from canine TRIP11.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:48 and 49) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for 30 seconds and 72° C. for 1.5 minutes using Thermal Cycler (manufactured by BIO RAD). The above-described gene-specific primers are those which amplify the regions of the 1519th to 2957th bases of the base sequence of SEQ ID NO:44 (canine TRIP11 gene) and the 1872nd to 3310th bases of the base sequence of SEQ ID NO:46 (human TRIP11 gene), and can be used for investigation of the expression of both the canine TRIP11 gene and the human TRIP11 gene. As a control for comparison, primers (described in SEQ ID NOs:9 and 10) specific to GAPDH were used simultaneously. As a result, as shown in FIG. 13, strong expression of the canine TRIP11 gene was observed in testis among the normal dog tissues, and on the other hand, strong expression was observed in the canine breast cancer cell line. Expression of the human TRIP11 gene was confirmed, as is the case with the canine TRIP11 gene, only in testis among the human normal tissues, but the expression was detected in many types of cancer cell lines such as brain tumor, leukemia, breast cancer, lung cancer and esophagus cancer cell lines among human cancer cell lines. Thus, the human TRIP11 gene was also confirmed to be specifically expressed in testis and cancer cells.

In FIG. 13, reference numeral 1 in the ordinate indicates the expression pattern of the TRIP11 gene, and reference numeral 2 indicates the expression pattern of the GAPDH gene as a control for comparison.

Example D-2

Preparation of Canine and Human TRIP11 Proteins (1) Preparation of Recombinant Protein Based on the gene of SEQ ID NO:44 obtained in Example D-1, a recombinant protein was prepared by the following method. Respective reagents and the attached buffer were mixed such that the mixture should contain 1 µl of the vector which was prepared from the phagemid solution obtained in Example D-1 and was subjected to the sequence analysis, 0.4 µM each of two kinds of primers having SalI and XhoI restriction sites (described in SEQ ID NOs:50 and 51), 0.2 mM dNTP and 1.25 U of PrimeSTAR HS polymerase (manufactured by Takara Shuzo Co., Ltd.) in a total volume of 50 and PCR was carried out with 30 cycles of 98° C. for 10 seconds, 55° C. for 5 seconds and 72° C. for 6 minutes using Thermal Cycler (manufactured by BIO RAD). Using the above-described two kinds of primers, a region encoding an amino acid region (SEQ ID NO:54) of 237th to 1023rd amino acids of SEQ ID NO:45 is obtained. After the PCR, the amplified DNA was subjected to electrophoresis using 1% agarose gel, and a DNA fragment of about 2.4 kbp was purified using QIAquick Gel Extraction Kit (manufactured by QIAGEN).

In the same manner, PCR was carried out using two kinds of primers described in SEQ ID NOs:56 and 57 to obtain a region encoding the entire amino acid sequence of SEQ ID NO:45. After the PCR, the amplified DNA was subjected to electrophoresis using 1% agarose gel, and a DNA fragment of about 6.0 kbp was purified using QIAquick Gel Extraction Kit (manufactured by QIAGEN).

Each of the purified DNA fragments was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes SalI and XhoI and purified using QIAquick Gel Extraction Kit, followed by inserting the gene sequence of interest into an expression vector for *E. coli*, pET30b (manufactured by Novagen) that had been treated with SalI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

Further, based on the gene of SEQ ID NO:46, a recombinant protein of the human homologous gene was prepared by the following method. Respective reagents and the attached buffer were mixed such that the mixture should contain 1 µl of the cDNA prepared in Example D-1 whose expression could be confirmed by the RT-PCR method in various tissues/cells, 0.4 µM each of two kinds of primers having NdeI and KpnI restriction sites (described in SEQ ID NOs:52 and 53), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 6 minutes using Thermal Cycler (manufactured by BIO RAD). Using the above-described two kinds of primers, a region encoding an amino acid region (SEQ ID NO:55) of 236th to 1023rd amino acids of SEQ ID NO:47 is obtained. After the PCR, the amplified DNA was subjected to electrophoresis using 1% agarose gel, and a DNA fragment of about 2.4 kbp was purified using QIAquick Gel Extraction Kit (manufactured by QIAGEN).

In the same manner, PCR was carried out using two kinds of primers described in SEQ ID NOs:58 and 59 to obtain a region encoding the entire amino acid sequence of SEQ ID NO:47. After the PCR, the amplified DNA was subjected to electrophoresis using 1% agarose gel, and a DNA fragment of about 6.0 kbp was purified using QIAquick Gel Extraction Kit (manufactured by QIAGEN).

Each of the purified DNA fragments was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and KpnI and purified using QIAquick Gel Extraction Kit, followed by inserting the gene sequence of interest into an expression vector for *E. coli*, pET30b (manufactured by Novagen) that had been treated with NdeI and KpnI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Proteins

The above-obtained recombinant *E. coli* cells that expressed a part of SEQ ID NO:44 and a part of SEQ ID NO:46, respectively, were cultured in kanamycin (final concentration: 30 µg/ml)-containing LB medium at 37° C. until the absorbance at 600 nm reached about 0.7, and then IPTG was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in phosphate-buffered saline and subjected to sonication on ice. The sonicated solution of *E. coli* was centrifuged at 7,000 rpm for 15 minutes to obtain the supernatant as the soluble fraction and the precipitate as the insoluble fraction.

The insoluble fraction was suspended in 4% Triton X-100 solution and the resulting suspension was centrifuged at 7,000 rpm for 10 minutes. This operation was repeated twice and an operation of removal of proteases was carried out. Thereafter, the residue was suspended in phosphate-buffered saline and an operation of removal of the surfactant was carried out.

The residue was suspended in 6M guanidine hydrochloride (manufactured by Sigma Aldrich Japan)-containing 20 mM phosphate buffer (pH 8.0), and the resulting suspension was left to stand at 4° C. for 15 hours to denature proteins. Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride-containing 20 mM phosphate buffer (pH 8.0)). The fraction that was not adsorbed to the column was washed away with 10 column volumes of 6 M sodium chloride-containing 20 mM phosphate buffer (pH 8.0) and 10 mM imidazole-containing 20 mM phosphate buffer (pH 8.0), and elution was immediately carried out with a four-step density gradient of 50 mM-500 mM imidazole. Five column volumes of the eluted fractions was collected in each elution step. Elution of the proteins of interest was confirmed by Coomassie staining carried out according to a conventional method. Based on the result, the eluted fractions were desalted and concentrated to obtain the material to be solid-phased for diagnosis.

In the same manner, the recombinant *E. coli* cells that expressed the full-length of SEQ ID NOs:45 and 47, respectively, were cultured, and the proteins of interest were purified to obtain the material to be solid-phased for diagnosis.

Example D-3

Cancer Diagnosis Using Polypeptide Derived from Canine TRIP11

(1) Cancer Diagnosis in Dogs

Blood samples were collected from 486 canine patients in which malignant or benign tumors were found and 6 healthy dogs, and sera were separated therefrom. Using the partial polypeptide of canine TRIP11 (SEQ ID NO:54; 237th to 1023rd amino acid region of SEQ ID NO:45) prepared in Example D-2 and anti-dog IgG antibody, the IgG antibody titer of the sera which specifically react with the polypeptide was measured by ELISA.

As for immobilization of the prepared protein on a solid phase, 100 µL/well of a solution of the recombinant protein diluted to 50 µg/mL with phosphate buffered saline was added to a 96-well Immobilizer Amino plate (manufactured by Nunc), and the plate was left to stand at 4° C. overnight. As for blocking, 100 µL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. Serum sample was 1,000-fold diluted with the blocking solution, and 100 µL/well of the diluted serum was added to the plate, followed by shaking the plate at room temperature for 3 hours to allow the reaction to proceed. After washing the wells 3 times with phosphate buffered saline containing 0.05% Tween20 (manufactured by Wako Pure Chemicals) (hereinafter referred to as PBS-T), 100 µL/well of HRP-conjugated dog IgG antibody (Goat anti Dog IgG-h+l HRP conjugated: manufactured by BETHYL Laboratories) 3,000-fold diluted with the blocking solution was added thereto, and the plate was shaken at room temperature for 1 hour to allow the reaction to proceed. After washing the wells 3 times with PBS-T, 100 µl/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 µl/well of 0.5 M sulfuric acid solution (manufactured by Sigma Aldrich Japan), and then the absorbance was measured at 450 nm with a microplate reader. As a control, a plate on which the prepared recombinant protein was not immobilized and a plate with which the serum from a cancer-bearing dog was not reacted were measured in the same manner as above.

Among the total 486 samples used in the above-described cancer diagnosis, 311 samples were definitely diagnosed as malignant by pathological diagnosis using the extirpated tumor tissue.

Specifically, the samples were diagnosed as cancer such as malignant melanoma; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; squamous cell carcinoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); leiomyosarcoma or the like.

Figure 15:
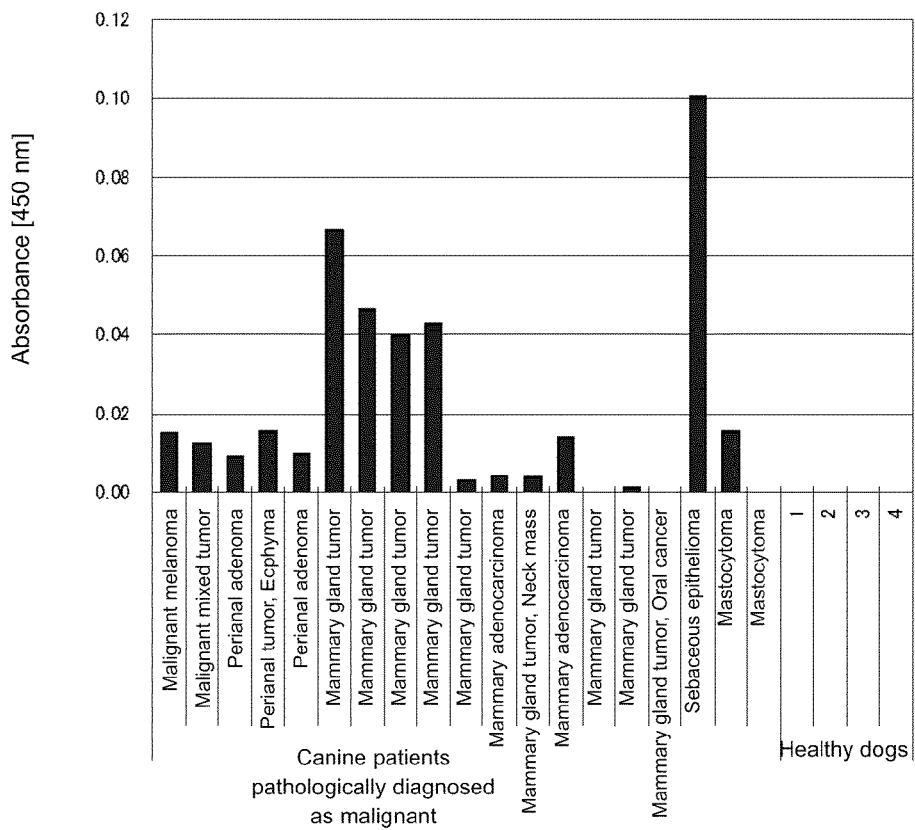
FIG. 15 shows some of the results of cancer diagnosis in cancer-bearing dogs carried out using the polypeptide derived from canine TRIP11 prepared in Example D.
Figure 16:
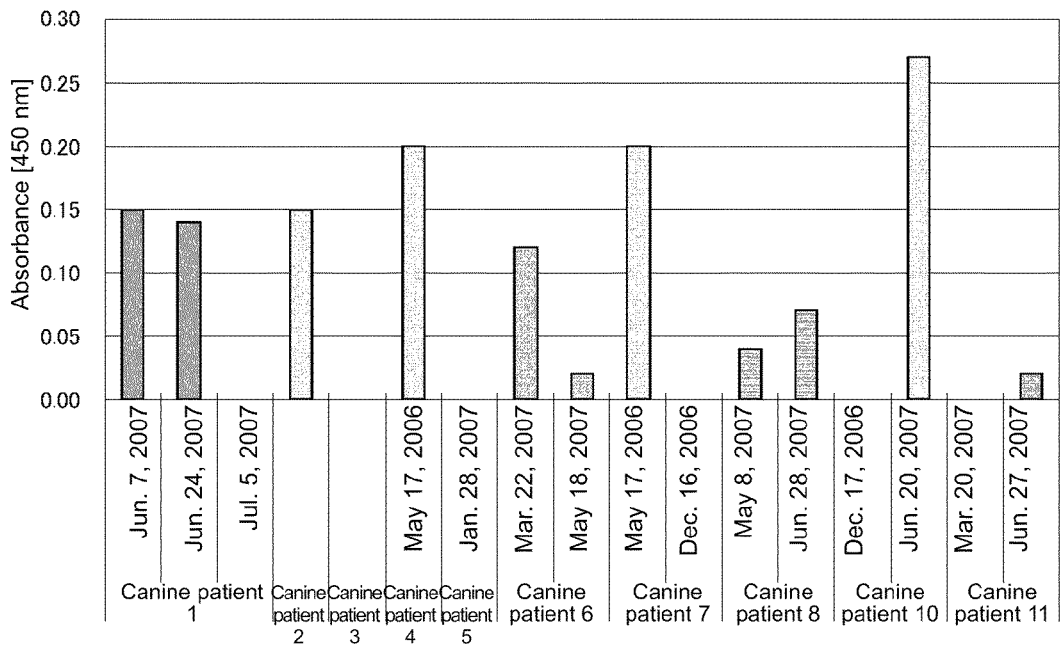
FIG. 16 shows some of the results of detailed cancer diagnosis in cancer-bearing dogs carried out using the polypeptide derived from canine TRIP11 prepared in Example D.

As shown in FIG. 15, sera from these cancer-bearing dogs showed a significantly high antibody titer against the recombinant protein. It was revealed that, by diagnosing a sample showing twice the average value of healthy canine samples as malignant, 78 samples i.e. 25.1% of the malignant cases could be successfully diagnosed as malignant. The details of these 78 cancer samples are as follows. It is noted that the following number of each cancer case is a cumulative total, as some samples contained multiple primaries.

Malignant melanoma, 4 cases; lymphoma, 5 cases; suppurative inflammation, 1 case; granulosa cell tumor, 1 case; hepatocellular carcinoma, 2 cases; malignant testicular tumor, 2 cases; intraoral tumor, 3 cases; perianal adenoma, 5 cases; osteosarcoma, 2 cases; ductal carcinoma, 6 cases; mammary adenocarcinoma, 16 cases; combined mammary adenocarcinoma, 8 cases; lung cancer, 1 case; sebaceous adenocarcinoma, 2 cases; mastocytoma, 6 cases; leiomyosarcoma, 2 cases; squamous cell carcinoma, 4 cases; malignant mixed tumor, 1 case; metastatic malignant melanoma, 1 case; mammary ductal carcinoma, 1 case; apocrine carcinoma, 1 case; gastric adenocarcinoma, 1 case; multicentric lymphoma, 1 case; seminoma, 1 case; plasmacytoma, 1 case.

The above-described diagnostic method was also carried out using pleural effusion samples and ascites samples collected from terminal cancer dogs. As a result, values similar to those detected in serum samples could be detected, and hence cancer diagnosis could be successfully attained.

Furthermore, it was confirmed that diagnostic approaches such as diagnosis of cancers existing in an invisible part of the body, assessment of cancer stage and grade, follow-up of postoperative patients, diagnosis of recurrence and metastasis and the like can also be attained by applying the above-described diagnostic method. The followings are several of the practical examples of the detailed diagnosis shown in FIG. 4.

(2)-1 Diagnosis of Invisible Tumors

In Canine Patient 1 (Flat-Coated Retriever), any tumors were not found on Jun. 7, 2007. But about 20 days later, on Jun. 24, 2007, a pedunculated tumor with a diameter of 2 mm was found on the gum at the root of the canine tooth. The tumor was ligated at its pedunculated part and excised on the day it found. The absorbance at 450 nm observed before the tumor became visible with the naked eye was 0.15, which was significantly high and not so different from the absorbance at the time of finding tumor, 0.14. The result indicates that it is possible to diagnose cancers even in an invisible part such as an intraperitoneal part by the method of the present invention.

Rise of the value was observed before the tumor became visible with the naked eye, which is considered to have been a sign of tumor development. Thus, the method of the present invention is useful in medical examinations such as periodic health examination.

Canine Patient 1 was again checked by the serodiagnosis 2 weeks after the tumor excision. As a result, the absorbance at 450 nm was 0, not detected. Thus, it was also confirmed that the cancer antigen-expressing tumor which had caused the increased antibody titer was completely removed (see, (2)-4, Follow-Up of Postoperative Patients).

(2)-2 Assessment of Stage of Cancer Progression

The stage of cancer progression is determined based on the size or depth of the tumor, how much the tumor exerts influence on the surrounding tissues, whether the tumor metastasizes or not, and the like. It was revealed herein that the detected value is higher than before if the metastasis occurs, i.e., the cancer has advanced.

(2)-3 Assessment of Grade of Cancer Malignancy

Basaliomas include malignant type and benign type. Recently, according to the new WHO classification, malignant basaliomas are called basal cell carcinoma, and benign basaliomas are called trichoblastoma.

Canine Patient 2 (Beagle) was diagnosed as basal cell carcinoma (malignant).

The serodiagnosis was carried out at the time of the surgery. As a result, the absorbance at 450 nm was 0.15. On the other hand, in Canine Patient 3 (Mixed Breed) diagnosed as trichoblastoma (benign), the serodiagnosis carried out at the time of the surgery revealed that the absorbance at 450 nm was 0, not detected at all. Thus, even in the case of the same basaliomas, malignant basal cell carcinoma and benign trichoblastoma can be distinctively diagnosed.

Next example is mammary gland tumors. Mammary gland tumors include malignant tumors such as mammary adenocarcinoma and mammary gland malignant mixed tumor, and benign mammary tumors which do not show malignant symptoms. Canine Patient 4 (Yorkie) underwent extirpation of mammary gland malignant mixed tumor and mammary adenocarcinoma on May 17, 2006. In general, the complete excision of mixed tumors in mammary gland is easy because they are poorly invasive to the surrounding tissues even if they are malignant, and thus the postoperative course of the patients is usually uneventful. However, Canine Patient 4 had been diagnosed as highly malignant tumor, because the pathological diagnosis using the extirpated tissue revealed that some components of the specimen from Canine Patient 4 showed an invasive nature. On the other hand, mammary adenocarcinoma is a highly invasive tumor which often recurs and metastasizes. Although invasion of the tumor cells was not observed in the specimen from Canine Patient 4, it had been pointed out that highly malignant components possibly proliferated in other region out of the specimen. Thus, the findings in the pathological diagnosis clearly taught that Canine Patient 4 was suffering from highly malignant mammary cancer. A blood sample was collected during the surgery and the serodiagnosis was carried out to find that the absorbance at 450 nm was 0.20. Canine Patient 5 (Yorkshire Terrier) underwent extirpation of mammary tumor on Jan. 28, 2007. According to the pathological diagnosis using the extirpated tissue, atypism of cells was low, and thus Canine Patient 5 was diagnoses as benign mastadenoma without malignant findings. A blood sample was collected during the surgery and the serodiagnosis was carried out to find that the absorbance at 450 nm was 0. The results in the two cases above revealed that highly malignant tumors show a higher value than low malignant, benign tumors.

(2)-4 Follow-Up of Postoperative Patients

Canine Patient 6 (Shih Tzu) visited the hospital due to an intraoral tumor and underwent the extirpation on Mar. 22, 2007. The serodiagnosis was carried out at that time. As a result, the absorbance at 450 nm was 0.12. In addition, based on the pathological diagnosis using the extirpated tissue, Canine Patient 6 was diagnosed as malignant acanthomatous epulis. This kind of tumor often recurs if excision is insufficient, though distant metastasis seldom happens. Thus, it is important whether the tumor can be completely excised by surgery or not. According to the follow up on May 18, 2007, the absorbance at 450 nm was 0.02 and hence the antibody titer was decreased. Recurrence has not been found till August of 2007. Thus, it is considered that the value detected by the serodiagnosis became lower than that obtained at the time of surgery because the tumor could be completely excised from Canine Patient 6.

Canine Patient 7 (Yorkie) was diagnosed by the serodiagnosis using a serum sample collected on May 17, 2006, and the absorbance at 450 nm was 0.20. This patient visited the hospital on Dec. 16, 2006 for follow-up, and the serodiagnosis was carried out again. As a result, the absorbance at 450 nm was 0. No recurrence nor metastasis has been found till August of 2007. Thus, it is considered that the value detected by the serodiagnosis became lower than that obtained at the time of surgery because the tumor could be completely excised from Canine Patient 7.

(2)-5 Diagnosis of Recurrence

Canine Patient 8 (Husky) underwent an extirpation of mammary adenocarcinoma on May 8, 2007. The serodiagnosis was carried out at the time of the surgery, and the absorbance at 450 nm was 0.04. The pathological diagnosis using the extirpated tissue revealed that highly atypical epithelial cells proliferated and mainly formed ductal structures, and thus this patient was diagnosed as primary breast adenocarcinoma. It was said that the patient was at a high risk of recurrence or metastasis to lymph nodes or distant organs, as many cancer cells had already entered the lymph vessels at that time. On Jun. 28, 2007, about one and a half months after the surgery, metastasis was found at the same site. The serodiagnosis was carried out at that time to find that the value increased to 0.07. Thus, it was confirmed that the value detected by the serodiagnosis was higher in the end of June than in the beginning of May because the tumor could not have been completely excised or recurrence would have occurred in Canine Patient 8.

(2)-6 Diagnosis of Metastasis

Canine Patient 9 (Scottish Terrier), repeatedly undergoing metastasis and recurrence, was diagnosed as mammary tumor in February of 2003; intraoral malignant melanoma in August of 2003; malignant melanoma of the lip in January of 2005; and as intraoral melanoma on Apr. 13, 2005, all of which were excised by surgery. This patient visited the hospital again on Dec. 17, 2006 for follow-up after the recurrence of intraoral melanoma in April of 2005, and the serodiagnosis was carried out at that time to find that the absorbance at 450 nm was 0. Half a year later, on Jun. 20, 2007, the patient again visited the hospital because of hypertrophy of cervical and malar lymph nodes. In the case of lymphomas, hypertrophy of lymph nodes is systemically observed. Because Canine Patient 9 had only two swollen lymph nodes, this patient was clinically diagnosed as probable metastatic lymphoma. The diagnosis according to the present invention also revealed that it was a tumor which had metastasized from the tumor previously existed in this patient as the absorbance at 450 nm greatly increased to 0.27.

Canine Patient 10 (Shiba Inu) underwent extirpation of oral malignant melanoma of the right lip on Mar. 11, 2006. This patient has a history of anticancer drug treatment (cyclophosphamide) from Jun. 10 to Sep. 26 in 2006, and has received BIREMO S, which contains organic germanium as a main ingredient, since May 23, 2006. On Mar. 20, 2007, this patient underwent extirpation of a tumor which was considered to be metastasis from the tumor mentioned above, and the serodiagnosis was carried out. As a result, the absorbance at 450 nm was approximately 0, hardly detected. Based on the pathological diagnosis using the tissue extirpated at that time, Canine Patient 10 was diagnosed as metastatic malignant melanoma. On Jun. 27, 2007, three months after the extirpation of metastatic melanoma, metastasis occurred in this patient again. The tumor which was extirpated on Mar. 20, 2007 existed in the right cervical part, and the tumor which occurred on Jun. 27, 2007 was on the opposite side. As for the shape of the tumor, a black mass was formed similarly to the previous tumor. The tumor, having the size of 3.1×3.2×0.8 cm, was also clinically diagnosed as metastasis. The serodiagnosis was carried out again to find that the absorbance at 450 nm increased to 0.02, which indicated that it was metastatic tumor from the previous one.

(2)-7 Therapy Monitoring

Canine Patient 12 (Miniature Dachshund) underwent tumor extirpation on Apr. 19, 2007. According to the pathological diagnosis using the extirpated tumor, the patient was suffering from moderately-malignant combined mammary adenocarcinoma with a high probability of invasive and metastatic development. The serodiagnosis was carried out at that time, and the absorbance at 450 nm was 0.03. On Jun. 3, 2008, about one year after the extirpation, the serodiagnosis was carried out to find that the absorbance at 450 nm was 0, not detected at all. Although any recurrent tumors were not found with the naked eye, an anticancer drug (INTERCAT) was administered once-weekly for 2 months to prevent recurrence. The serodiagnosis was carried out 2, 4, and 6 weeks after the administration of the anticancer drug started. As a result, the absorbance at 450 nm was 0, not detected at all, in all trials. These results obtained in Canine Patient 12 confirmed that the value becomes lower than that detected in a cancer-bearing state if tumors can be completely removed, as well as that the value does not increase if anticancer drug treatment successfully prevents cancer metastasis, and thus change in treated patients can be followed. In addition, the diagnosis of recurrence can also be carried out as shown by Canine Patient 8, which confirms that the therapy monitoring can also be made possible.

(2)-8 Diagnosis of Malignancy of Recurrent Tumor

Canine Patient 13 (Golden Retriever) underwent tumor extirpation on May 1, 2005. The pathological diagnosis using the extirpated tumor revealed that the tumor in this patient was malignant neoplastic lesion originated from mammary ductal epithelium, i.e., malignant mammary ductal carcinoma and malignant papillary carcinoma continuously growing through the mammary ducts. On Jun. 28, 2008, about 3 years thereafter, tumor was found again and thus extirpation was carried out. The pathological diagnosis using the extirpated tumor revealed that nothing but severe infiltration of inflammatory cells such as neutrophils, macrophages, plasma cells and the like could be observed around surgical sutures under the skin which was considered to be the previous surgical wound, and thus the patient was diagnosed as having no neoplastic lesions. According to the serodiagnosis carried out at that time, the absorbance at 450 nm was 0, not detected at all. The results observed in Canine Patients 8 and 13 indicated that the value of the serodiagnosis does not decrease or is sustained in cases where the recurrent tumor is malignant, and is not detected in cases where the tumor is benign.

(3) Diagnosis in Cats

Next, cancer-bearing cats and healthy cats were diagnosed. Using the above-described partial polypeptide of canine TRIP11 and anti-cat IgG antibody, the IgG antibody titer of feline serum which specifically reacts with the polypeptide was measured in the same manner as described above. As a secondary antibody, HRP-conjugated anti-cat IgG antibody (PEROXIDASE-CONJUGATED GOAT IgG FRACTION TO CAT IgG (WHOLE MOLECULE): manufactured by CAPPEL RESERCH REAGENTS) 8,000-fold diluted with the blocking solution was used.

Feline Patient 1 (Chinchilla) underwent tumor extirpation of mammary adenocarcinoma on Aug. 17, 2005. The absorbance at 450 nm was 0.05. In Feline Patient 2 (Himalayan), which underwent extirpation of ductal carcinoma on Oct. 17, 2006, the absorbance at 450 nm was 0.34. On the other hand, the absorbance was not detected in healthy cats at all.

Thus, similarly to dogs, the absorbance value was detected in samples from cats suffering from cancer, while the absorbance value was not detected at all in samples from healthy cats. Hence, similarly to dogs, cancers in cats can also be detected by this method.

(4) Diagnosis in Healthy Human

Using the above-described partial polypeptide of canine TRIP11 and anti-human IgG antibody above, the IgG antibody titer of healthy human serum which specifically reacts with the polypeptide was measured in the same manner as described above. As a secondary antibody, HRP-conjugated anti-human IgG antibody (HRP-Goat Anti-Human IgG(H+L) Conjugate: manufactured by Zymed Laboratories) 10000-fold diluted with the blocking solution was used. As a positive control, an immobilized ovalbumin antigen prepared by immobilizing 50 µg/ml ovalbumin in phosphate buffered saline on a solid phase was used. As a result, in Healthy Human 1, the absorbance at 450 nm observed on an ovalbumin antigen was 0.25, while the absorbance at 450 nm observed on the recombinant protein was 0, not detected at all. Similarly, in Healthy Human 2, the absorbance at 450 nm observed on an ovalbumin antigen was 0.18, while the absorbance at 450 nm observed on the recombinant protein was 0, not detected at all.

Further, the diagnosis was carried out in the same manner as described above using a full-length canine TRIP11 having the sequence shown in SEQ ID NO:45 prepared in Example D-2. As a result, it was revealed that the diagnosis can be similarly attained in humans, dogs and cats.

Example D-4

Cancer Diagnosis Using Polypeptide Derived from Human TRIP11

Using the partial polypeptide of human TRIP11 (SEQ ID NO:55; 236th to 1023rd amino acid region of SEQ ID NO:47)

prepared in Example D-2, the IgG antibody titer of human, canine and feline sera which react with the polypeptide was measured in the same manner as in Example D-3.

The diagnosis was carried out using healthy human serum. In the same manner as in Example D-3 (4), ovalbumin antigen was used as a positive control. As a result, the absorbance value was detected in the case where ovalbumin was immobilized on a solid phase, while the absorbance value was hardly detected in the case where the partial polypeptide of human TRIP11 was immobilized on a solid phase.

Similarly, in healthy dogs and cats, the absorbance at 450 nm was hardly detected in the case where the polypeptide was immobilized on a solid phase.

On the other hand, Canine Patient 11 (Shih Tzu) underwent extirpation of mammary adenocarcinoma on Jun. 21, 2007. According to the pathological diagnosis using the extirpated tissue, the mammary gland tissue contained highly atypical, invasive cells, and grew to form adenomatous hyperplasia showing large and small massive structures. Hence, this patient was diagnosed as malignant tumor. In Canine Patient 11, the absorbance at 450 nm was 0.19. The malignancy diagnosis was carried out using additional 310 serum samples which had been diagnosed as malignant by pathological diagnosis. As a result, by diagnosing a sample showing twice the average value of healthy canine samples as malignant, 74 samples i.e. 23.8% of the malignant cases could be successfully diagnosed as malignant. Moreover, in Feline Patient 3 (Mixed Breed), which underwent extirpation of mammary adenocarcinoma on Apr. 3, 2007, the absorbance at 450 nm was 0.06.

The above described results indicated that the diagnosis can also be similarly attained in humans, dogs and cats by using a polypeptide derived from human TRIP11.

Furthermore, pleural effusion and ascites samples collected from terminal cancer dogs were subjected to the diagnosis using the recombinant human protein in the same manner as the recombinant canine protein. As a result, values similar to those detected in serum samples could be detected, and hence cancer diagnosis could be successfully attained.

In addition, the diagnosis was carried out in the same manner as described above using a full-length human TRIP11 having the sequence shown in SEQ ID NO:47 prepared in Example D-2. As a result, it was revealed that the diagnosis can also be similarly attained in humans, dogs and cats.

Example D-5

Cancer Diagnosis by Measuring Antigen Polypeptide (1)

Mice and rabbits were immunized with the recombinant canine protein having the sequence shown in SEQ ID NO:54 prepared in Example D-2 to obtain an antibody specific to this antigen. Using this polyclonal antibody, detection of the antigen polypeptide per se contained in the serum from cancer bearing living body was carried out by sandwich ELISA. Using anti-mouse IgG antibody, the amount of the protein in the serum which specifically reacts with the prepared polyclonal antibody specific to the prepared protein was measured by sandwich ELISA.

As for immobilization of a primary antibody on a solid phase, 100 µL/well of the rabbit antiserum 20-fold diluted with phosphate buffered saline was added to a 96-well Immobilizer Amino plate (manufactured by Nunc), and the plate was shaken at room temperature for 2 hours. As for blocking, 100 µL/well of 50 mM sodium bicarbonate buffer (pH 8.3) containing 0.5% BSA (bovine serum albumin, manufactured by Sigma Aldrich Japan) (hereinafter referred to as blocking solution) was added to the plate, and the plate was shaken at room temperature for 1 hour. To the plate, 100 µL/well of the serum from cancer-bearing body diluted with the blocking solution was added, and the plate was shaken at room temperature for 3 hours to allow the reaction to proceed. As for the diluted serum, a 10-fold serial dilution ranging 10 to 1,000-fold was prepared. After washing the wells 3 times with phosphate buffered saline containing 0.05% Tween20 (manufactured by Wako Pure Chemicals) (hereinafter referred to as PBS-T), 100 µL/well of mouse antiserum 200-fold diluted with the blocking solution was added thereto, and the plate was shaken at room temperature for 1 hour to allow the reaction to proceed. After washing the wells 3 times with PBS-T, 100 of HRP-conjugated mouse IgG antibody (Stabilized Goat Anti Mouse HRP conjugated: manufactured by PIERCE) 2000-fold diluted with the blocking solution was added thereto as a tertiary antibody, and the plate was shaken at room temperature for 1 hour to allow the reaction to proceed. After washing the wells 3 times with PBS-T, 100 µl/well of a HRP substrate, TMB (1-Step Turbo TMB (tetramethylbenzidine), manufactured by PIERCE), was added thereto, and the enzyme-substrate reaction was allowed to proceed at room temperature for 30 minutes. Thereafter, the reaction was stopped by adding 100 µl/well of 0.5 M sulfuric acid solution (manufactured by Sigma Aldrich Japan), and then the absorbance was measured at 450 nm with a microplate reader. As a control, a plate on which the rabbit antiserum was not immobilized and a plate with which serum from a cancer-bearing body was not reacted were measured in the same manner as described above.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody which was prepared by using the recombinant canine polypeptide as an immunogen.

In addition, the diagnosis was carried out in the same manner as described above using an antibody which was prepared by using as an immunogen the full-length canine TRIP11 having the sequence shown in SEQ ID NO:45 prepared in Example D-2.

As a result, cancers could also be diagnosed in dogs and cats by this method in which the antigen polypeptide was detected with an antibody which was prepared by using a full-length canine TRIP11 as an immunogen.

Example D-6

Cancer Diagnosis by Measuring Antigen Polypeptide (2)

Mice and rabbits were immunized with the recombinant human protein having the sequence shown in SEQ ID NO:55 prepared in Example D-2 to obtain an antibody specific to this antigen. In the same manner as in Example D-5, detection of the antigen polypeptide per se contained in the serum from cancer-bearing body was carried out by sandwich ELISA using this polyclonal antibody.

As a result, the polypeptide was detected in cancer-bearing dogs and cats suffering from cutaneous leiomyosarcoma, breast cancer, malignant melanoma or the like, while the polypeptide was not detected in healthy dogs, healthy cats and healthy humans. Hence, cancers could also be diagnosed by this method in which the antigen polypeptide was detected with an antibody prepared by using the recombinant human polypeptide as an immunogen.

In addition, the diagnosis was carried out in the same manner as described above using an antibody which was prepared by using as an immunogen the full-length human TRIP11 having the sequence shown in SEQ ID NO:47 prepared in Example D-2.

As a result, cancers could also be diagnosed in dogs and cats by this method in which the antigen polypeptide was detected with an antibody which was prepared by using a full-length human TRIP11 as an immunogen.

Example E-1

Combined Diagnosis of Cancer Using Four Antigen Polypeptides (1)

(1) Cancer Diagnosis in Dogs

Using the recombinant canine polypeptide (SEQ ID NO:2) prepared in Example A-2, the canine calmegin protein (SEQ ID NO:16) prepared in Example B-2, the full-length (SEQ ID NO:26 or 42) or partial (SEQ ID NO:35; 1514th to 2339th amino acid region of SEQ ID NO:26) polypeptide of canine CEP prepared in Example C-2, the full-length (SEQ ID NO:45) or partial (SEQ ID NO:54; 237th to 1023rd amino acid region of SEQ ID NO:45) polypeptide of canine TRIP11 prepared in Example D-2 and anti-dog IgG antibody, the IgG antibody titer of the serum which specifically reacts with any of the proteins or polypeptides mentioned above was measured.

By diagnosing a sample showing twice the average value of healthy canine samples as malignant, 272 samples i.e. 87.5% of the malignant cases could be successfully diagnosed as malignant. The subject living body was diagnosed as malignant when any one of 4 proteins and polypeptides indicated malignancy (the same shall apply hereinafter). The details of these 272 cancer samples are as follows. It is noted that the following number of each cancer case is a cumulative total, as some samples contained multiple primaries.

Malignant melanoma, 10 cases; lymphoma, 13 cases; pheochromocytoma, 1 case; suppurative inflammation, 1 case; granulosa cell tumor, 1 case; hepatocellular carcinoma, 5 cases; angioma, 1 case; malignant testicular tumor, 8 cases; intraoral tumor, 4 cases; perianal adenocarcinoma, 14 cases; osteosarcoma, 5 cases; fibrosarcoma, 9 cases; ductal carcinoma, 10 cases; chondrosarcoma, 2 cases; mammary adenocarcinoma, 56 cases; combined mammary adenocarcinoma, 26 cases; lung cancer, 2 cases; sebaceous carcinoma, 2 cases; nasal adenocarcinoma, 2 cases; mastocytoma, 37 cases; adrenomedullary tumor, 1 case; leiomyosarcoma, 2 cases; squamous cell carcinoma, 11 cases; chronic lymphocytic leukemia, 1 case; undifferentiated sarcoma, 2 cases; malignant mixed tumor, 2 cases; tumor in the posterior segment of the left lobe of the lung, 1 case; tumor in the right infra-axillary region, 1 case; tumor in the elbow of the right forelimb, 1 case; bladder cancer (transitional cell carcinoma), 1 case; metastatic malignant melanoma, 3 cases; amelanotic malignant melanoma, 1 case; adenocarcinoma of the large intestine, 1 case; plasmacytoma, 1 case; histiocytic sarcoma, 1 case; liposarcoma, 1 case; poorly differentiated sarcoma, 1 case; synovial sarcoma, 1 case; malignant hemangiopericytoma, 1 case; apocrine sweat gland carcinoma, 3 cases; bronchial adenocarcinoma, 1 case; germinoma, 1 case; malignant fibrous histiocytoma, 1 case; metastatic malignant epithelioma, 1 case; mammary ductal carcinoma, 1 case; angiosarcoma, 1 case; tubular mammary adenocarcinoma, 1 case; invasive trichoepithelioma, 1 case; prostate cancer, 1 case; soft part sarcoma (spindle cell tumor), 1 case; ceruminous adenocarcinoma, 1 case; multicentric lymphoma, 2 cases; invasive trichoepithelioma, 1 case; anal sac adenocarcinoma, 1 case; apocrine carcinoma, 1 case; gastric adenocarcinoma, 1 case; seminoma, 1 case; basal cell carcinoma, 1 case; hemangiopericytoma, 4 cases; myxosarcoma, 1 case; sebaceous epithelioma, 1 case; splenic tumor, 1 case.

(2) Cancer Diagnosis in Cats

Next, cancer-bearing cats and healthy cats were diagnosed. Using 4 kinds of canine antigen polypeptides described above and anti-cat IgG antibody, the IgG antibody titer of feline serum which specifically reacts with any of the polypeptides was measured in the same manner as described above. As a secondary antibody, HRP-conjugated anti-cat IgG antibody (PEROXIDASE-CONJUGATED GOAT IgG FRACTION TO CAT IgG (WHOLE MOLECULE): manufactured by CAPPEL RESERCH REAGENTS) 8,000-fold diluted with the blocking solution was used.

Among a total of 17 samples used in the cancer diagnosis, 11 samples were definitely diagnosed as malignant by the pathological diagnosis using the extirpated tumor tissue. By diagnosing a sample showing twice the average value of healthy feline samples as malignant, 9 samples i.e. 81.8% of the malignant cases could be successfully diagnosed as malignant.

Example E-2

Combined Diagnosis of Cancer Using Four Antigen Polypeptides (2)

(1) Cancer Diagnosis in Dogs

Using the recombinant human polypeptide (SEQ ID NO:4) prepared in Example A-2, the human calmegin protein (SEQ ID NO:18) prepared in Example B-2, the full-length (SEQ ID NO:28) or partial (SEQ ID NO:36; 1513rd to 2325th amino acid region of SEQ ID NO:28) polypeptide of human CEP prepared in Example C-2, the full-length (SEQ ID NO:47) or partial (SEQ ID NO:55; 236th to 1023rd amino acid region of SEQ ID NO:47) polypeptide of human TRIP11 prepared in Example D-2 and anti-dog IgG antibody, the IgG antibody titer of the serum which specifically reacts with any of the proteins or polypeptides mentioned above was measured in the same manner as described above.

By diagnosing a sample showing twice the average value of healthy canine samples as malignant, 268 samples i.e. 86.2% of the malignant cases could be successfully diagnosed as malignant.

(2) Cancer Diagnosis in Cats

Next, cancer-bearing cats and healthy cats were diagnosed. Using 4 kinds of canine antigen polypeptides described above and anti-cat IgG antibody, the IgG antibody titer of feline serum which specifically reacts with any of the polypeptides was measured in the same manner as described above. As a secondary antibody, HRP-conjugated anti-cat IgG antibody (PEROXIDASE-CONJUGATED GOAT IgG FRACTION TO CAT IgG (WHOLE MOLECULE): manufactured by CAPPEL RESERCH REAGENTS) 8,000-fold diluted with the blocking solution was used.

Among a total of 17 samples used in the cancer diagnosis, 11 samples were definitely diagnosed as malignant by the pathological diagnosis using the extirpated tumor tissue. By diagnosing a sample showing twice the average value of healthy feline samples as malignant, 7 samples i.e. 63.6% of the malignant cases could be successfully diagnosed as malignant.

Example E-3

Combined Diagnosis of Cancer by Measuring Four Antigen Polypeptides (1)

Mice and rabbits were immunized with the recombinant canine polypeptide (SEQ ID NO:2) prepared in Example A-2, the canine calmegin protein (SEQ ID NO:16) prepared in Example B-2, the full-length (SEQ ID NO:26 or 42) or partial (SEQ ID NO:35; 1514th to 2339th amino acid region of SEQ ID NO:26) polypeptide of canine CEP prepared in Example C-2, or the full-length (SEQ ID NO:45) or partial (SEQ ID NO:54; 237th to 1023rd amino acid region of SEQ ID NO:45) polypeptide of canine TRIP11 prepared in Example D-2 to obtain specific antibodies against these antigens. In the same manner as in Examples A, B, C, D-5, the antigen polypeptides per se contained in serum from cancer-bearing living body were detected by sandwich ELISA using the prepared polyclonal antibodies.

As a result, this method in which antigen polypeptides were detected using antibodies prepared by using canine antigen polypeptides as an immunogen could successfully diagnose 252 samples i.e. 81.0% of the malignant cases as malignant by diagnosing a sample showing twice the average value of healthy canine samples as malignant. Similarly, also in cats, 8 samples i.e. 72.7% of the malignant cases could be successfully diagnosed as malignant by diagnosing a sample showing twice the average value of healthy feline samples as malignant.

Example E-4

Combined Diagnosis of Cancer by Measuring Four Antigen Polypeptides (2)

Mice and rabbits were immunized with the recombinant human polypeptide (SEQ ID NO:4) prepared in Example A-2, the human calmegin protein (SEQ ID NO:18) prepared in Example B-2, the full-length (SEQ ID NO:28) or partial (SEQ ID NO:36; 1513rd to 2325th amino acid region of SEQ ID NO:28) polypeptide of human CEP prepared in Example C-2, or the full-length (SEQ ID NO:47) or partial (SEQ ID NO:55; 236th to 1023rd amino acid region of SEQ ID NO:47) polypeptide of human TRIP11 prepared in Example D-2 to obtain specific antibodies against these antigens. In the same manner in Examples A, B, C, D-5, the antigen polypeptides per se contained in serum from cancer-bearing living body were detected by sandwich ELISA using the prepared polyclonal antibodies.

As a result, this method in which antigen polypeptides were detected using antibodies prepared by using human antigen polypeptides as an immunogen could successfully diagnose 248 samples i.e. 79.7% of the malignant cases as malignant by diagnosing a sample showing twice the average value of healthy canine samples as malignant. Similarly, also in cats, 7 samples i.e. 63.6% of the malignant cases could be successfully diagnosed as malignant by diagnosing a sample showing twice the average value of healthy feline samples as malignant.

---

The invention claimed is:

1. A method for detecting a cancer(s), which is applied to a sample separated from a living body and comprises measuring in the sample an antibody that binds any one of the polypeptides (g) to (h) below raised in the living body by immunoassay using as an antigen any one of the polypeptides (g) to (h) below:
  (g) a polypeptide consisting of not less than 500 and not more than 1000 consecutive amino acids of the amino acid sequence shown in SEQ ID NO: 26 and comprising not less than 500 consecutive amino acids located in the region of 1514th to 2339th amino acids of SEQ ID NO: 26, or a polypeptide consisting of not less than 500 and not more than 1000 consecutive amino acids of the amino acid sequence shown in SEQ ID NO: 28 and comprising not less than 500 consecutive amino acids located in the region of 1513th to 2325th amino acids of SEQ ID NO: 28;
  (h) a polypeptide consisting of not less than 500 and not more than 1000 consecutive amino acids of the amino acid sequence shown in SEQ ID NO: 45 and comprising not less than 500 consecutive amino acids located in the region of 237th to 1023rd amino acids of SEQ ID NO: 45, or a polypeptide consisting of not less than 500 and not more than 1000 consecutive amino acids of the amino acid sequence shown in SEQ ID NO: 47 and comprising not less than 500 consecutive amino acids located in the region of 236th to 1023rd amino acids of SEQ ID NO: 47,
  wherein increase of said antibody in comparison to a control sample indicates the presence of cancer(s).

2. The method according to claim 1, wherein said living body is a dog, a human or a cat.

3. The method according to claim 2, wherein said antibody to be measured is an antibody raised in the living body against the amino acid sequence shown in any one of SEQ ID NOs: 26 and 45.

4. The method according to claim 2, wherein said antibody to be measured is an antibody raised in the living body against the amino acid sequence shown in any one of SEQ ID NOs: 28 and 47.

5. The method according to claim 1, wherein the polypeptide (g) comprises the 1514th to 2339th amino acids of the amino acid sequence shown in SEQ ID NO: 26, or comprises the 1513th to 2325th amino acids of the amino acid sequence shown in SEQ ID NO: 28, and wherein the polypeptide (h) comprises the 237th to 1023rd amino acids of the amino acid sequence shown in SEQ ID NO: 45, or comprises the 236th to 1023rd amino acids of the amino acid sequence shown in SEQ ID NO: 47.

6. The method according to claim 5, wherein the polypeptide (g) has the amino acid sequence shown in SEQ ID NO: 35 or 36, and wherein the polypeptide (h) has the amino acid sequence shown in SEQ ID NO: 54 or 55.

7. The method according to claim 1, wherein said sample is a serum, plasma, ascites or a pleural effusion.

8. The method according to claim 1, further comprising detecting stage of cancer progression based on the expression level of any one of the polypeptides (g) to (h), wherein the measured expression level is compared with an expression level from a sample taken from the living body at an earlier time, and where a higher expression level of said polypeptide indicates a more advanced stage.

9. The method according to claim 1, further comprising monitoring an effect of treatment of said cancer(s) based on whether the expression level of any one of the polypeptides (g) to (h) decreases or not.

10. The method according to claim 1, wherein the control sample is serum from a healthy body.

11. The method according to claim 1, further comprising detecting the antibody raised in the living body in a control sample, wherein the control sample is a sample separated from a living healthy body.

12. The method according to claim 1, wherein said cancer is at least one selected from the group consisting of brain tumor; squamous cell carcinomas of head, neck, lung, uterus and esophagus; melanoma; adenocarcinomas of lung and uterus; renal cancer; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer; suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma; poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; and leiomyosarcoma.

\* \* \* \* \*

SEQUENCE LISTING

```
<160> NUMBER OF SEQ ID NOS: 59

<210> SEQ ID NO 1
<211> LENGTH: 1508
<212> TYPE: DNA
<213> ORGANISM: Canis familiaris
<220> FEATURE:
<221> NAME/KEY: CDS
<222> LOCATION: (17)..(937)

<400> SEQUENCE: 1
gcggcccggg cgggac atg gcg gcg ctc tac gcc tgc acc aag tgc cac cag      52
                  Met Ala Ala Leu Tyr Ala Cys Thr Lys Cys His Gln
                   1               5                  10 cgc ttc ccc ttc gag gcg ctg tct cag ggg cag cag ctg tgc aag gaa       100
Arg Phe Pro Phe Glu Ala Leu Ser Gln Gly Gln Gln Leu Cys Lys Glu
         15                  20                  25 tgt cgg att gca cac cct gtt gtg aag tgc acc tac tgt aga act gag       148
Cys Arg Ile Ala His Pro Val Val Lys Cys Thr Tyr Cys Arg Thr Glu
 30                  35                  40 tac cag caa gag agt aaa acc aat aca ata tgc aaa aaa tgt gct cag       196
Tyr Gln Gln Glu Ser Lys Thr Asn Thr Ile Cys Lys Lys Cys Ala Gln
 45                  50                  55                  60 aat gtg cag tta tat gga acg ccc aaa cct tgt cag tac tgc aac ata       244
Asn Val Gln Leu Tyr Gly Thr Pro Lys Pro Cys Gln Tyr Cys Asn Ile
                 65                  70                  75 att gca gca ttt att ggc aac aaa tgc cag cga tgc acg aat tca gag       292
Ile Ala Ala Phe Ile Gly Asn Lys Cys Gln Arg Cys Thr Asn Ser Glu
             80                  85                  90 aag aag tat gga cca cca tat tca tgt gaa cag tgt aaa caa cag tgt       340
Lys Lys Tyr Gly Pro Pro Tyr Ser Cys Glu Gln Cys Lys Gln Gln Cys
         95                  100                 105
```

```
gca ttt gac agg aaa gat gat aga aag aag gta gat ggg aaa ttg ctg      388
Ala Phe Asp Arg Lys Asp Asp Arg Lys Lys Val Asp Gly Lys Leu Leu
    110                 115                 120 tgt tgg ctg tgc aca ctt tca tac aaa cgg gtc ctt caa aag acc aaa      436
Cys Trp Leu Cys Thr Leu Ser Tyr Lys Arg Val Leu Gln Lys Thr Lys
125                 130                 135                 140 gag cag agg aaa cat ctg agc agc tct tcc cgt gcc agc cac cag gag      484
Glu Gln Arg Lys His Leu Ser Ser Ser Ser Arg Ala Ser His Gln Glu
                145                 150                 155 aag gaa cag tat cga ctg agt ggt ggc agc cat tat aac agc cag aaa      532
Lys Glu Gln Tyr Arg Leu Ser Gly Gly Ser His Tyr Asn Ser Gln Lys
                160                 165                 170 aca ctt tct acg tct tca att caa aat gaa atc cca aag aaa aaa tcc      580
Thr Leu Ser Thr Ser Ser Ile Gln Asn Glu Ile Pro Lys Lys Lys Ser
            175                 180                 185 aag ttt gag tca atc aca act aat gga gac agc ttt tcc cca gac ctg      628
Lys Phe Glu Ser Ile Thr Thr Asn Gly Asp Ser Phe Ser Pro Asp Leu
        190                 195                 200 gct ctg gac tca cca ggc act gac cac ttt gtc atc att gcc cag ctg      676
Ala Leu Asp Ser Pro Gly Thr Asp His Phe Val Ile Ile Ala Gln Leu
205                 210                 215                 220 aag gaa gaa gtg gcc act ttg aag aag atg ctg cat caa aag gat caa      724
Lys Glu Glu Val Ala Thr Leu Lys Lys Met Leu His Gln Lys Asp Gln
                225                 230                 235 atg att tta gag aaa gag aag aag atc aca gag ttg aag gct gat ttt      772
Met Ile Leu Glu Lys Glu Lys Lys Ile Thr Glu Leu Lys Ala Asp Phe
                240                 245                 250 caa tac caa gaa tct cag atg aga gcc aaa atg aac cag atg gag aaa      820
Gln Tyr Gln Glu Ser Gln Met Arg Ala Lys Met Asn Gln Met Glu Lys
            255                 260                 265 act cac aaa gaa gtc aca gag caa ttg cag gcc aaa aac cga gaa ctc      868
Thr His Lys Glu Val Thr Glu Gln Leu Gln Ala Lys Asn Arg Glu Leu
        270                 275                 280 ctg aag cag gca gct gcc ttg tcc aag agc aag aag tca gag aag tca      916
Leu Lys Gln Ala Ala Ala Leu Ser Lys Ser Lys Lys Ser Glu Lys Ser
285                 290                 295                 300 gga gct ata act tct cca tga gagaccataa ggaggcttcc agccacagca         967
Gly Ala Ile Thr Ser Pro
                305 aaggggtttc ctgggttagg gttggtggcc tggctgttat ctgggaattg cccacgctcc    1027 cgggaagggc ctgtcccagt cggctctgcc ctaccgccgc agcgtcccca cctggctgaa    1087 gctgacgtcc gacgacgtga aggagcagat ctacaaactg gccaagaagg gtctgactcc    1147 ctcgcagatc ggtgtgatcc tgagagactc ccatggtgtt gcacaagtac gttttgtgac    1207 aggcaataaa atcttgagaa ttcttaagtc aagggactt gcacctgatc tccctgagga    1267 tctgtaccat ttgattaaga aagctgttgc tgttcgaaag catcttgaga ggaacagaaa    1327 ggataaggat gccaaattcc gactgattct gattgagagc cgtattcacc gattggctcg    1387 atattataag accaaaagag ttctccctcc caattggaaa tacgagtcat ccacagcctc    1447 tgccctggtc gcataaattt ggctatgtac tcaagcaata aaatcattgt ctactagaaa    1507 a                                                                    1508

<210> SEQ ID NO 2
<211> LENGTH: 306
<212> TYPE: PRT
<213> ORGANISM: Canis familiaris
```

<400> SEQUENCE: 2

```
Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
            20                  25                  30

His Pro Val Val Lys Cys Thr Tyr Cys Arg Thr Glu Tyr Gln Gln Glu
        35                  40                  45

Ser Lys Thr Asn Thr Ile Cys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Cys Ala Phe Asp Arg
            100                 105                 110

Lys Asp Asp Arg Lys Lys Val Asp Gly Lys Leu Leu Cys Trp Leu Cys
            115                 120                 125

Thr Leu Ser Tyr Lys Arg Val Leu Gln Lys Thr Lys Glu Gln Arg Lys
130                 135                 140

His Leu Ser Ser Ser Arg Ala Ser His Gln Lys Glu Gln Tyr
145                 150                 155                 160

Arg Leu Ser Gly Gly Ser His Tyr Asn Ser Gln Lys Thr Leu Ser Thr
                165                 170                 175

Ser Ser Ile Gln Asn Glu Ile Pro Lys Lys Ser Lys Phe Glu Ser
            180                 185                 190

Ile Thr Thr Asn Gly Asp Ser Phe Ser Pro Asp Leu Ala Leu Asp Ser
            195                 200                 205

Pro Gly Thr Asp His Phe Val Ile Ile Ala Gln Leu Lys Glu Glu Val
210                 215                 220

Ala Thr Leu Lys Lys Met Leu His Gln Lys Asp Gln Met Ile Leu Glu
225                 230                 235                 240

Lys Glu Lys Lys Ile Thr Glu Leu Lys Ala Asp Phe Gln Tyr Gln Glu
                245                 250                 255

Ser Gln Met Arg Ala Lys Met Asn Gln Met Glu Lys Thr His Lys Glu
            260                 265                 270

Val Thr Glu Gln Leu Gln Ala Lys Asn Arg Glu Leu Leu Lys Gln Ala
            275                 280                 285

Ala Ala Leu Ser Lys Ser Lys Ser Glu Lys Ser Gly Ala Ile Thr
290                 295                 300

Ser Pro
305
```

<210> SEQ ID NO 3
<211> LENGTH: 2161
<212> TYPE: DNA
<213> ORGANISM: Homo sapiens
<220> FEATURE:
<221> NAME/KEY: CDS
<222> LOCATION: (103)..(1026)

<400> SEQUENCE: 3

```
gccgcagcca gcagcctgca gccgccgccg ggttgtgcct cagactgtca gataaatcgg      60
cgggccgggc cggcgggtcg gtgagcgcgg cccgggccgg ac atg gcg gcg ctc       114
                                              Met Ala Ala Leu
                                              1
```

```
tac gcc tgc acc aag tgc cac cag cgc ttc ccc ttc gag gcg ctg tct    162
Tyr Ala Cys Thr Lys Cys His Gln Arg Phe Pro Phe Glu Ala Leu Ser
 5               10                  15                  20 cag ggg cag cag ctg tgc aag gaa tgt cgg att gca cac cct gtt gtg    210
Gln Gly Gln Gln Leu Cys Lys Glu Cys Arg Ile Ala His Pro Val Val
             25                  30                  35 aag tgc acc tac tgc agg act gag tac cag cag gag agt aaa acc aat    258
Lys Cys Thr Tyr Cys Arg Thr Glu Tyr Gln Gln Glu Ser Lys Thr Asn
                 40                  45                  50 aca ata tgc aag aaa tgt gct cag aac gtg cag ttg tat gga acg ccc    306
Thr Ile Cys Lys Lys Cys Ala Gln Asn Val Gln Leu Tyr Gly Thr Pro
             55                  60                  65 aaa cct tgt cag tat tgc aac ata att gca gca ttt att ggg aat aaa    354
Lys Pro Cys Gln Tyr Cys Asn Ile Ile Ala Ala Phe Ile Gly Asn Lys
 70                  75                  80 tgc cag cgc tgc aca aat tca gaa aag aag tat gga cca ccc tat tct    402
Cys Gln Arg Cys Thr Asn Ser Glu Lys Lys Tyr Gly Pro Pro Tyr Ser
 85                  90                  95                 100 tgt gaa cag tgc aag cag cag tgt gca ttt gac agg aaa gat gat aga    450
Cys Glu Gln Cys Lys Gln Gln Cys Ala Phe Asp Arg Lys Asp Asp Arg
                105                 110                 115 aag aag gta gat ggg aaa ttg ctg tgc tgg ctg tgc aca ctt tca tac    498
Lys Lys Val Asp Gly Lys Leu Leu Cys Trp Leu Cys Thr Leu Ser Tyr
            120                 125                 130 aaa cgg gtc ctt cag aag acc aaa gag cag agg aaa cac ctg agt agc    546
Lys Arg Val Leu Gln Lys Thr Lys Glu Gln Arg Lys His Leu Ser Ser
            135                 140                 145 tct tct cgt gct ggc cac cag gag aag gag cag tat agt cgc ctg agt    594
Ser Ser Arg Ala Gly His Gln Glu Lys Glu Gln Tyr Ser Arg Leu Ser
    150                 155                 160 ggt ggt ggc cat tat aac agc cag aaa aca ctt tct aca tct tca att    642
Gly Gly Gly His Tyr Asn Ser Gln Lys Thr Leu Ser Thr Ser Ser Ile
165                 170                 175                 180 caa aat gaa atc cca aag aaa aag tcc aag ttt gag tca atc aca act    690
Gln Asn Glu Ile Pro Lys Lys Lys Ser Lys Phe Glu Ser Ile Thr Thr
                185                 190                 195 aat gga gac agc ttc tcc cca gac ctg gct ctg gac tca cca ggc act    738
Asn Gly Asp Ser Phe Ser Pro Asp Leu Ala Leu Asp Ser Pro Gly Thr
            200                 205                 210 gac cac ttt gtc atc att gcc caa ctg aag gaa gaa gtg gct acc ctg    786
Asp His Phe Val Ile Ile Ala Gln Leu Lys Glu Glu Val Ala Thr Leu
            215                 220                 225 aag aag atg ttg cat caa aag gat caa atg att tta gag aaa gag aag    834
Lys Lys Met Leu His Gln Lys Asp Gln Met Ile Leu Glu Lys Glu Lys
            230                 235                 240 aag att aca gag ttg aag gct gat ttt cag tac cag gaa tcg cag atg    882
Lys Ile Thr Glu Leu Lys Ala Asp Phe Gln Tyr Gln Glu Ser Gln Met
245                 250                 255                 260 aga gcc aaa atg aac cag atg gag aaa acc cac aaa gaa gtc aca gaa    930
Arg Ala Lys Met Asn Gln Met Glu Lys Thr His Lys Glu Val Thr Glu
                265                 270                 275 caa ctg cag gcc aaa aac cga gag ctc ctg aag cag gca gct gct ttg    978
Gln Leu Gln Ala Lys Asn Arg Glu Leu Leu Lys Gln Ala Ala Ala Leu
            280                 285                 290 tcc aag agc aag aag tca gag aag tca gga gct ata acc tct cca tga   1026
Ser Lys Ser Lys Lys Ser Glu Lys Ser Gly Ala Ile Thr Ser Pro
            295                 300                 305 cagacctcaa ggaggctccc tagcaacagc aaatggagtt gtccagggtt agggttggag  1086
acctggctgt tctgtgggaa ttgcaagctt tcttaagaaa tctctatttt attacagtta  1146
```

-continued

```
tccttctttg tgcgattgca gtgggctgaa tggaaacacc tggtttgtgc tgtgttagac      1206
tgcatgcttg agtgtttggg atttcaagct cgctctcttt ctctcactat taggactttt      1266 cttttcttc ttcctcttct ctctattttg gttctattct ttttttttct tttttctttt       1326
tttttttttt ttttttttg tggtggtcac tgctcagtgt aatgtgcaga atgatttgtt       1386
ttttgttttt tttttttttt tttggtcctt cattgcatcc tgccataccc atgagcaaac      1446
agtttggcat taattatata tcactgccac cctctgaact ttgaaaactg ccatcttcag      1506
acttggtata atggaagagg ctttctctct ccaataaacc ttttgcttca gggtatactc      1566
ttcggttttt ttccagatgt attatgtatg aactttgtac tatgtatagc cagagtttta      1626
tttatttttt aaaaaagaaa ctttttcttg ataaggaat aatggtggtc tagctagttc       1686
ttgtaaaagt gatgcctctt gaaaaaaaac agtcctattc actagctttt agtaaaagaa      1746
tcagatcttt tctttcttgt taccttggag tcttaaaaac tgattgctaa ggtgaaacaa      1806
ttcaatgcat aagtatggag ctaagtgcct tttggaggat ttcttggaag agcatttatg      1866
gagatactta agggaggtag caaagatttg aaccgtctgt cttttaagt aagggcagaa       1926 agcaaggttg tccaggttgt actggacact tctctcccca ccctttcct gattgtttta       1986 tgtgattgat tttaaattct cacactgcca cttctttaaa aaataaaatc ctttatttgc      2046
ttaaaaaaaa aaaaaaaaa aaaaaaaaaa aaaaaaaaa aaaaaaaaaa aaaaaaaaaa        2106
aaaaaaaaaa aaaaaaaaaa aaaaaaaaaa aaaaaaaaa aaaaaaaaaa aaaaa            2161
```

<210> SEQ ID NO 4
<211> LENGTH: 307
<212> TYPE: PRT
<213> ORGANISM: Homo sapiens

<400> SEQUENCE: 4

```
Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
            20                  25                  30

His Pro Val Val Lys Cys Thr Tyr Cys Arg Thr Glu Tyr Gln Gln Glu
        35                  40                  45

Ser Lys Thr Asn Thr Ile Cys Lys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Gln Cys Ala Phe Asp Arg
            100                 105                 110

Lys Asp Asp Arg Lys Lys Val Asp Gly Lys Leu Leu Cys Trp Leu Cys
        115                 120                 125

Thr Leu Ser Tyr Lys Arg Val Leu Gln Lys Thr Lys Glu Gln Arg Lys
    130                 135                 140

His Leu Ser Ser Ser Arg Ala Gly His Gln Glu Lys Glu Gln Tyr
145                 150                 155                 160

Ser Arg Leu Ser Gly Gly Gly His Tyr Asn Ser Gln Lys Thr Leu Ser
                165                 170                 175

Thr Ser Ser Ile Gln Asn Glu Ile Pro Lys Lys Ser Lys Phe Glu
            180                 185                 190
```

```
Ser Ile Thr Thr Asn Gly Asp Ser Phe Ser Pro Asp Leu Ala Leu Asp
    195                 200                 205
Ser Pro Gly Thr Asp His Phe Val Ile Ile Ala Gln Leu Lys Glu Glu
    210                 215                 220
Val Ala Thr Leu Lys Lys Met Leu His Gln Lys Asp Gln Met Ile Leu
225                 230                 235                 240
Glu Lys Glu Lys Lys Ile Thr Glu Leu Lys Ala Asp Phe Gln Tyr Gln
                245                 250                 255
Glu Ser Gln Met Arg Ala Lys Met Asn Gln Met Glu Lys Thr His Lys
            260                 265                 270
Glu Val Thr Glu Gln Leu Gln Ala Lys Asn Arg Glu Leu Leu Lys Gln
        275                 280                 285
Ala Ala Ala Leu Ser Lys Ser Lys Lys Ser Glu Lys Ser Gly Ala Ile
    290                 295                 300
Thr Ser Pro
305
```

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
aattaaccct cactaaaggg                                                   20

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
taatacgact cactatagg                                                    19

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
agctgtgcaa ggaatgtc                                                     18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
ccattagttg tgattgac                                                     18

<210> SEQ ID NO 9
<211> LENGTH: 18
<212> TYPE: DNA
<213> ORGANISM: Artificial Sequence
<220> FEATURE:
<223> OTHER INFORMATION: GAPDH primer

<400> SEQUENCE: 9 gggctgctttt taactctg                                                    18

<210> SEQ ID NO 10
<211> LENGTH: 18
<212> TYPE: DNA
<213> ORGANISM: Artificial Sequence
<220> FEATURE:
<223> OTHER INFORMATION: GAPDH primer

<400> SEQUENCE: 10
ccaggaaatg agcttgac                                                     18

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
atcatatggc ggcgctctac gc                                                22

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
cgctcgagtg gagaagttat agctc                                             25

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gatatcatgg cggcgctcta cgc                                               23

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
gaattctcat ggagaggtta tagc                                              24

<210> SEQ ID NO 15
<211> LENGTH: 2326
<212> TYPE: DNA
<213> ORGANISM: Canis familiaris
<220> FEATURE:
<221> NAME/KEY: CDS
<222> LOCATION: (62)..(1894)

<400> SEQUENCE: 15
cagcgcctcg gacatcggag ctgccgctgc cgaacacggg cccgcaacac aggtaatcag        60 t atg cat ttc caa agc ttt tgg cta tgt ctg gga ctt ctg ttc atc tca      109

```
      Met His Phe Gln Ser Phe Trp Leu Cys Leu Gly Leu Leu Phe Ile Ser
        1           5              10              15 gtt aat gca gaa ttt atg gat gat gat gtt gag atg gaa gat ttt gat           157
Val Asn Ala Glu Phe Met Asp Asp Asp Val Glu Met Glu Asp Phe Asp
             20              25              30 gaa aat tca gaa gag att gat gtt aat gaa ggt gaa ctc ccc tca gag           205
Glu Asn Ser Glu Glu Ile Asp Val Asn Glu Gly Glu Leu Pro Ser Glu
         35              40              45 att aat tat aag aca cct cag cct atg gga gaa gta tat ttt aca gaa           253
Ile Asn Tyr Lys Thr Pro Gln Pro Met Gly Glu Val Tyr Phe Thr Glu
     50              55              60 act ttt gat agt gga agg ttg gct ggg tgg gtc tta tca aaa gca aag           301
Thr Phe Asp Ser Gly Arg Leu Ala Gly Trp Val Leu Ser Lys Ala Lys
 65              70              75              80 aaa gat gat aca gat gca gag att tcc ata tat gat gga aga tgg gaa           349
Lys Asp Asp Thr Asp Ala Glu Ile Ser Ile Tyr Asp Gly Arg Trp Glu
             85              90              95 ata gaa gaa ttg aaa gaa aac cga gtg cct ggt gac aga ggg ctg gta           397
Ile Glu Glu Leu Lys Glu Asn Arg Val Pro Gly Asp Arg Gly Leu Val
         100             105             110 ctg aaa tct aga gca aag cat cat gca ata gct gct gta tta gca aaa           445
Leu Lys Ser Arg Ala Lys His His Ala Ile Ala Ala Val Leu Ala Lys
         115             120             125 ccc ttc att ttt gct gac aaa ccc ttg atc gtt caa tat gaa gta aat           493
Pro Phe Ile Phe Ala Asp Lys Pro Leu Ile Val Gln Tyr Glu Val Asn
 130             135             140 ttt caa gat ggt att gat tgt gga ggt gca tac att aaa ctc cta gca           541
Phe Gln Asp Gly Ile Asp Cys Gly Gly Ala Tyr Ile Lys Leu Leu Ala
145             150             155             160 gac act gat ggt ttg aat ctg gaa aac ttt tat gat aaa aca tcc tat           589
Asp Thr Asp Gly Leu Asn Leu Glu Asn Phe Tyr Asp Lys Thr Ser Tyr
             165             170             175 acc att atg ttt gga cca gat aaa tgt gga gaa gat tat aaa ctt cat           637
Thr Ile Met Phe Gly Pro Asp Lys Cys Gly Glu Asp Tyr Lys Leu His
         180             185             190 ttc atc ttc aga cac aaa cat cct aaa act gga gtt ttt gaa gag aaa           685
Phe Ile Phe Arg His Lys His Pro Lys Thr Gly Val Phe Glu Glu Lys
         195             200             205 cat gcc aaa cct cca gat gta gac ctt aaa aag ttc ttt aca gac agg           733
His Ala Lys Pro Pro Asp Val Asp Leu Lys Lys Phe Phe Thr Asp Arg
 210             215             220 aag act cat ctt tat acc ctt gtg atg aat cca gat gac aca ttt gaa           781
Lys Thr His Leu Tyr Thr Leu Val Met Asn Pro Asp Asp Thr Phe Glu
225             230             235             240 gta cta att gat caa gta gtt gta aac caa gga agc ctc cta gaa gat           829
Val Leu Ile Asp Gln Val Val Val Asn Gln Gly Ser Leu Leu Glu Asp
             245             250             255 gtg gtt cct cct atc aat cct ccc aaa gaa att gaa gac ccc agt gat           877
Val Val Pro Pro Ile Asn Pro Pro Lys Glu Ile Glu Asp Pro Ser Asp
         260             265             270 aaa aag cct gat gaa tgg gat gaa aga gca aaa atc cct gat cct tct           925
Lys Lys Pro Asp Glu Trp Asp Glu Arg Ala Lys Ile Pro Asp Pro Ser
         275             280             285 gct gtc aaa cca gaa gac tgg gat gaa agt gaa cct gcc caa ata gaa           973
Ala Val Lys Pro Glu Asp Trp Asp Glu Ser Glu Pro Ala Gln Ile Glu
         290             295             300 gat tta agt gtt gtt aaa cct gat ggc tgg ctt gat gat gaa cca aaa          1021
Asp Leu Ser Val Val Lys Pro Asp Gly Trp Leu Asp Asp Glu Pro Lys
305             310             315             320
```

```
ttt att cca gat cca aat gct gaa aaa cct gat gac tgg aat gaa gac      1069
Phe Ile Pro Asp Pro Asn Ala Glu Lys Pro Asp Asp Trp Asn Glu Asp
                325                 330                 335 atg gat gga gaa tgg gag gca cct cgt att tct aat cca gca tgt cga      1117
Met Asp Gly Glu Trp Glu Ala Pro Arg Ile Ser Asn Pro Ala Cys Arg
            340                 345                 350 att ggg tgt ggt gag tgg tca cct ccc atg ata gat aat ccc aaa tac      1165
Ile Gly Cys Gly Glu Trp Ser Pro Pro Met Ile Asp Asn Pro Lys Tyr
        355                 360                 365 aaa gga gta tgg aga cct cca atg ata gat aat cct aac tac cag gga      1213
Lys Gly Val Trp Arg Pro Pro Met Ile Asp Asn Pro Asn Tyr Gln Gly
    370                 375                 380 atc tgg agt cct cga aaa atc ccg aat cca gat tat ttt gaa gat gat      1261
Ile Trp Ser Pro Arg Lys Ile Pro Asn Pro Asp Tyr Phe Glu Asp Asp
385                 390                 395                 400 cat cca ttt ctt ctg act tct ttc cgt gct ctt ggt tta gag ctt tgg      1309
His Pro Phe Leu Leu Thr Ser Phe Arg Ala Leu Gly Leu Glu Leu Trp
                405                 410                 415 tct atg acc tct aat att tac ttt gat aat ttt att atc tgc tcg gaa      1357
Ser Met Thr Ser Asn Ile Tyr Phe Asp Asn Phe Ile Ile Cys Ser Glu
            420                 425                 430 aag gaa aca gca gat cgc tgg gct gca gat ggg tgg gga gtg aag ata      1405
Lys Glu Thr Ala Asp Arg Trp Ala Ala Asp Gly Trp Gly Val Lys Ile
        435                 440                 445 ctg gta gca aat gct aac gag cct ggt ata ttt aaa cag tta atg gca      1453
Leu Val Ala Asn Ala Asn Glu Pro Gly Ile Phe Lys Gln Leu Met Ala
    450                 455                 460 gct gct gaa gag cgc cca tgg ctt tgg ctc att tat ttt gtg aca gca      1501
Ala Ala Glu Glu Arg Pro Trp Leu Trp Leu Ile Tyr Phe Val Thr Ala
465                 470                 475                 480 ggg ctt cca ata gca tta att gct tca ttt tgt tgg cca aga aaa gtc      1549
Gly Leu Pro Ile Ala Leu Ile Ala Ser Phe Cys Trp Pro Arg Lys Val
                485                 490                 495 aag aaa aaa tat gaa gat tca gag tat aaa aag act gac ata tgc aag      1597
Lys Lys Lys Tyr Glu Asp Ser Glu Tyr Lys Lys Thr Asp Ile Cys Lys
            500                 505                 510 cca caa aca aag gga gca cta gag caa gaa gtg aag gaa aag aaa gct      1645
Pro Gln Thr Lys Gly Ala Leu Glu Gln Glu Val Lys Glu Lys Lys Ala
        515                 520                 525 gcc ctg gag aaa cca gta gac ttg gaa gaa gaa aaa aag caa agt gat      1693
Ala Leu Glu Lys Pro Val Asp Leu Glu Glu Glu Lys Lys Gln Ser Asp
    530                 535                 540 ggt gaa act gtt gaa aaa gaa gag gaa gct gaa cct gag gaa aag agt      1741
Gly Glu Thr Val Glu Lys Glu Glu Glu Ala Glu Pro Glu Glu Lys Ser
545                 550                 555                 560 gaa gaa gaa att gaa atc ata gaa gga caa gaa gaa ggt aat aaa tca      1789
Glu Glu Glu Ile Glu Ile Ile Glu Gly Gln Glu Glu Gly Asn Lys Ser
                565                 570                 575 aat aag tct gga tca gag gat gag atg aag gaa gcg gat gag agc aca      1837
Asn Lys Ser Gly Ser Glu Asp Glu Met Lys Glu Ala Asp Glu Ser Thr
            580                 585                 590 gga tct gga gat ggg cca gtg aag tca gtg cgc aaa aga aga gta cga      1885
Gly Ser Gly Asp Gly Pro Val Lys Ser Val Arg Lys Arg Arg Val Arg
        595                 600                 605 aag gaa taa actatattca agtattttta attcctgagc gagatatttg              1934
Lys Glu
    610 gcattctaaa atcagtgtgc cagagctgaa cttgagtcag tctgcacatg tttctaatat    1994 ctagcaatgt tattctttca gacacttatt ttagtctttc ttttcaggaa aaaaaaaact   2054
```

```
ttcaagttac ctggtctttg gatttagagt aaaaaagagg ggcatgttac gtatcagatt    2114
taagagacta ataccattag aagttaccaa gttttaatag ttggagaaag ttttggtttg    2174
tacagagaaa aataatatgc agcagctttg ctgctgttgg aaaatcagtt attggaattt    2234 cccttaaac agctatacaa caatattact ggtagttcta taataaaat gagagtgtgt      2294 tctgttgtac agagctaact gcaaaaaaaa aa    2326

<210> SEQ ID NO 16
<211> LENGTH: 610
<212> TYPE: PRT
<213> ORGANISM: Canis familiaris

<400> SEQUENCE: 16
```

| | | | | | | | | | | | | | | |
|---|---|---|---|---|---|---|---|---|---|---|---|---|---|---|
| Met | His | Phe | Gln | Ser | Phe | Trp | Leu | Cys | Leu | Gly | Leu | Leu | Phe | Ile | Ser |
| 1 | | | | 5 | | | | | 10 | | | | | 15 | |
| Val | Asn | Ala | Glu | Phe | Met | Asp | Asp | Val | Glu | Met | Glu | Asp | Phe | Asp |
| | | | 20 | | | | | 25 | | | | | 30 | |
| Glu | Asn | Ser | Glu | Glu | Ile | Asp | Val | Asn | Glu | Gly | Glu | Leu | Pro | Ser | Glu |
| | | | | 35 | | | | | 40 | | | | | 45 | |
| Ile | Asn | Tyr | Lys | Thr | Pro | Gln | Pro | Met | Gly | Glu | Val | Tyr | Phe | Thr | Glu |
| | 50 | | | | | 55 | | | | | 60 | | | | |
| Thr | Phe | Asp | Ser | Gly | Arg | Leu | Ala | Gly | Trp | Val | Leu | Ser | Lys | Ala | Lys |
| 65 | | | | | 70 | | | | | 75 | | | | | 80 |
| Lys | Asp | Asp | Thr | Asp | Ala | Glu | Ile | Ser | Ile | Tyr | Asp | Gly | Arg | Trp | Glu |
| | | | | 85 | | | | | 90 | | | | | 95 | |
| Ile | Glu | Glu | Leu | Lys | Glu | Asn | Arg | Val | Pro | Gly | Asp | Arg | Gly | Leu | Val |
| | | | 100 | | | | | 105 | | | | | 110 | | |
| Leu | Lys | Ser | Arg | Ala | Lys | His | His | Ala | Ile | Ala | Ala | Val | Leu | Ala | Lys |
| | | | 115 | | | | | 120 | | | | | 125 | | |
| Pro | Phe | Ile | Phe | Ala | Asp | Lys | Pro | Leu | Ile | Val | Gln | Tyr | Glu | Val | Asn |
| | 130 | | | | | 135 | | | | | 140 | | | | |
| Phe | Gln | Asp | Gly | Ile | Asp | Cys | Gly | Gly | Ala | Tyr | Ile | Lys | Leu | Leu | Ala |
| 145 | | | | | 150 | | | | | 155 | | | | | 160 |
| Asp | Thr | Asp | Gly | Leu | Asn | Leu | Glu | Asn | Phe | Tyr | Asp | Lys | Thr | Ser | Tyr |
| | | | | 165 | | | | | 170 | | | | | 175 | |
| Thr | Ile | Met | Phe | Gly | Pro | Asp | Lys | Cys | Gly | Glu | Asp | Tyr | Lys | Leu | His |
| | | | 180 | | | | | 185 | | | | | 190 | | |
| Phe | Ile | Phe | Arg | His | Lys | His | Pro | Lys | Thr | Gly | Val | Phe | Glu | Glu | Lys |
| | | | 195 | | | | | 200 | | | | | 205 | | |
| His | Ala | Lys | Pro | Pro | Asp | Val | Asp | Leu | Lys | Lys | Phe | Phe | Thr | Asp | Arg |
| | 210 | | | | | 215 | | | | | 220 | | | | |
| Lys | Thr | His | Leu | Tyr | Thr | Leu | Val | Met | Asn | Pro | Asp | Asp | Thr | Phe | Glu |
| 225 | | | | | 230 | | | | | 235 | | | | | 240 |
| Val | Leu | Ile | Asp | Gln | Val | Val | Asn | Gln | Gly | Ser | Leu | Leu | Glu | Asp |
| | | | | 245 | | | | | 250 | | | | | 255 | |
| Val | Val | Pro | Pro | Ile | Asn | Pro | Pro | Lys | Glu | Ile | Glu | Asp | Pro | Ser | Asp |
| | | | 260 | | | | | 265 | | | | | 270 | | |
| Lys | Lys | Pro | Asp | Glu | Trp | Asp | Glu | Arg | Ala | Lys | Ile | Pro | Asp | Pro | Ser |
| | | | 275 | | | | | 280 | | | | | 285 | | |
| Ala | Val | Lys | Pro | Glu | Asp | Trp | Asp | Glu | Ser | Glu | Pro | Ala | Gln | Ile | Glu |
| | 290 | | | | | 295 | | | | | 300 | | | | |
| Asp | Leu | Ser | Val | Val | Lys | Pro | Asp | Gly | Trp | Leu | Asp | Asp | Glu | Pro | Lys |
| 305 | | | | | 310 | | | | | 315 | | | | | 320 |

-continued

```
Phe Ile Pro Asp Pro Asn Ala Glu Lys Pro Asp Trp Asn Glu Asp
                325                 330                 335
Met Asp Gly Glu Trp Glu Ala Pro Arg Ile Ser Asn Pro Ala Cys Arg
    340                 345                 350
Ile Gly Cys Gly Glu Trp Ser Pro Pro Met Ile Asp Asn Pro Lys Tyr
            355                 360                 365
Lys Gly Val Trp Arg Pro Pro Met Ile Asp Asn Pro Asn Tyr Gln Gly
        370                 375                 380
Ile Trp Ser Pro Arg Lys Ile Pro Asn Pro Asp Tyr Phe Glu Asp Asp
385                 390                 395                 400
His Pro Phe Leu Leu Thr Ser Phe Arg Ala Leu Gly Leu Glu Leu Trp
                405                 410                 415
Ser Met Thr Ser Asn Ile Tyr Phe Asp Asn Phe Ile Ile Cys Ser Glu
            420                 425                 430
Lys Glu Thr Ala Asp Arg Trp Ala Ala Asp Gly Trp Gly Val Lys Ile
        435                 440                 445
Leu Val Ala Asn Ala Asn Glu Pro Gly Ile Phe Lys Gln Leu Met Ala
    450                 455                 460
Ala Ala Glu Glu Arg Pro Trp Leu Trp Leu Ile Tyr Phe Val Thr Ala
465                 470                 475                 480
Gly Leu Pro Ile Ala Leu Ile Ala Ser Phe Cys Trp Pro Arg Lys Val
                485                 490                 495
Lys Lys Lys Tyr Glu Asp Ser Glu Tyr Lys Lys Thr Asp Ile Cys Lys
            500                 505                 510
Pro Gln Thr Lys Gly Ala Leu Glu Gln Glu Val Lys Glu Lys Lys Ala
        515                 520                 525
Ala Leu Glu Lys Pro Val Asp Leu Glu Glu Lys Lys Gln Ser Asp
    530                 535                 540
Gly Glu Thr Val Glu Lys Glu Glu Ala Glu Pro Glu Glu Lys Ser
545                 550                 555                 560
Glu Glu Glu Ile Glu Ile Ile Glu Gly Gln Glu Gly Asn Lys Ser
                565                 570                 575
Asn Lys Ser Gly Ser Glu Asp Glu Met Lys Glu Ala Asp Glu Ser Thr
            580                 585                 590
Gly Ser Gly Asp Gly Pro Val Lys Ser Val Arg Lys Arg Val Arg
        595                 600                 605
Lys Glu
    610

<210> SEQ ID NO 17
<211> LENGTH: 2710
<212> TYPE: DNA
<213> ORGANISM: Homo sapiens
<220> FEATURE:
<221> NAME/KEY: CDS
<222> LOCATION: (102)..(1934)

<400> SEQUENCE: 17
cgccggcggg actggtctga agagacgcgg ggacaaagtg gcaacgactt ggacatctga      60
gctgtcactg ccgaaaacag gccgcaagag agataatcaa t atg cat ttc caa gcc     116
                                              Met His Phe Gln Ala
                                                1               5 ttt tgg cta tgt ttg ggt ctt ctg ttc atc tca att aat gca gaa ttt       164
Phe Trp Leu Cys Leu Gly Leu Leu Phe Ile Ser Ile Asn Ala Glu Phe
            10                  15                  20 atg gat gat gat gtt gag acg gaa gac ttt gaa gaa aat tca gaa gaa       212
```

```
                    Met Asp Asp Val Glu Thr Glu Asp Phe Glu Asn Ser Glu Glu
                         25                  30                  35 att gat gtt aat gaa agt gaa ctt tcc tca gag att aaa tat aag aca          260
Ile Asp Val Asn Glu Ser Glu Leu Ser Ser Glu Ile Lys Tyr Lys Thr
         40                  45                  50 cct caa cct ata gga gaa gta tat ttt gca gaa act ttt gat agt gga          308
Pro Gln Pro Ile Gly Glu Val Tyr Phe Ala Glu Thr Phe Asp Ser Gly
 55                  60                  65 agg ttg gct gga tgg gtc tta tca aaa gca aag aaa gat gac atg gat          356
Arg Leu Ala Gly Trp Val Leu Ser Lys Ala Lys Lys Asp Asp Met Asp
 70                  75                  80                  85 gag gaa att tca ata tac gat gga aga tgg gaa att gaa gag ttg aaa          404
Glu Glu Ile Ser Ile Tyr Asp Gly Arg Trp Glu Ile Glu Glu Leu Lys
                 90                  95                 100 gaa aac cag gta cct ggt gac aga gga ctg gta tta aaa tct aga gca          452
Glu Asn Gln Val Pro Gly Asp Arg Gly Leu Val Leu Lys Ser Arg Ala
             105                 110                 115 aag cat cat gca ata tct gct gta tta gca aaa cca ttc att ttt gct          500
Lys His His Ala Ile Ser Ala Val Leu Ala Lys Pro Phe Ile Phe Ala
         120                 125                 130 gat aaa ccc ttg ata gtt caa tat gaa gta aat ttt caa gat ggt att          548
Asp Lys Pro Leu Ile Val Gln Tyr Glu Val Asn Phe Gln Asp Gly Ile
 135                 140                 145 gat tgt gga ggt gca tac att aaa ctc cta gca gac act gat gat ttg          596
Asp Cys Gly Gly Ala Tyr Ile Lys Leu Leu Ala Asp Thr Asp Asp Leu
150                 155                 160                 165 att ctg gaa aac ttt tat gat aaa aca tcc tat atc att atg ttt gga          644
Ile Leu Glu Asn Phe Tyr Asp Lys Thr Ser Tyr Ile Ile Met Phe Gly
                 170                 175                 180 cca gat aaa tgt gga gaa gat tat aaa ctt cat ttt atc ttc aga cat          692
Pro Asp Lys Cys Gly Glu Asp Tyr Lys Leu His Phe Ile Phe Arg His
             185                 190                 195 aaa cat ccc aaa act gga gtt ttc gaa gag aaa cat gcc aaa cct cca          740
Lys His Pro Lys Thr Gly Val Phe Glu Glu Lys His Ala Lys Pro Pro
         200                 205                 210 gat gta gac ctt aaa aag ttc ttt aca gac agg aag act cat ctt tat          788
Asp Val Asp Leu Lys Lys Phe Phe Thr Asp Arg Lys Thr His Leu Tyr
 215                 220                 225 acc ctt gtg atg aat cca gat gac aca ttt gag gtg tta gtt gat caa          836
Thr Leu Val Met Asn Pro Asp Asp Thr Phe Glu Val Leu Val Asp Gln
230                 235                 240                 245 aca gtt gta aac aaa gga agc ctc cta gag gat gtg gtt cct cct atc          884
Thr Val Val Asn Lys Gly Ser Leu Leu Glu Asp Val Val Pro Pro Ile
                 250                 255                 260 aaa cct ccc aaa gaa att gaa gat ccc aat gat aaa aaa cct gag gaa          932
Lys Pro Pro Lys Glu Ile Glu Asp Pro Asn Asp Lys Lys Pro Glu Glu
             265                 270                 275 tgg gat gaa aga gca aaa att cct gat cct tct gcc gtc aaa cca gaa          980
Trp Asp Glu Arg Ala Lys Ile Pro Asp Pro Ser Ala Val Lys Pro Glu
         280                 285                 290 gac tgg gat gaa agt gaa cct gcc caa ata gaa gat tca agt gtt gtt         1028
Asp Trp Asp Glu Ser Glu Pro Ala Gln Ile Glu Asp Ser Ser Val Val
 295                 300                 305 aaa cct gct ggc tgg ctt gat gat gaa cca aaa ttt atc cct gat cct         1076
Lys Pro Ala Gly Trp Leu Asp Asp Glu Pro Lys Phe Ile Pro Asp Pro
310                 315                 320                 325 aat gct gaa aaa cct gat gac tgg aat gaa gac acg gat gga gaa tgg         1124
Asn Ala Glu Lys Pro Asp Asp Trp Asn Glu Asp Thr Asp Gly Glu Trp
                 330                 335                 340
```

```
gag gca cct cag att ctt aat cca gca tgt cgg att ggg tgt ggt gag    1172
Glu Ala Pro Gln Ile Leu Asn Pro Ala Cys Arg Ile Gly Cys Gly Glu
            345                 350                 355 tgg aaa cct ccc atg ata gat aac cca aaa tac aaa gga gta tgg aga    1220
Trp Lys Pro Pro Met Ile Asp Asn Pro Lys Tyr Lys Gly Val Trp Arg
            360                 365                 370 cct cca ctg gtc gat aat cct aac tat cag gga atc tgg agt cct cga    1268
Pro Pro Leu Val Asp Asn Pro Asn Tyr Gln Gly Ile Trp Ser Pro Arg
    375                 380                 385 aaa att cct aat cca gat tat ttc gaa gat gat cat cca ttt ctt ctg    1316
Lys Ile Pro Asn Pro Asp Tyr Phe Glu Asp Asp His Pro Phe Leu Leu
390                 395                 400                 405 act tct ttc agt gct ctt ggt tta gag ctt tgg tct atg acc tct gat    1364
Thr Ser Phe Ser Ala Leu Gly Leu Glu Leu Trp Ser Met Thr Ser Asp
                410                 415                 420 atc tac ttt gat aat ttt att atc tgt tcg gaa aag gaa gta gca gat    1412
Ile Tyr Phe Asp Asn Phe Ile Ile Cys Ser Glu Lys Glu Val Ala Asp
                425                 430                 435 cac tgg gct gca gat ggt tgg aga tgg aaa ata atg ata gca aat gct    1460
His Trp Ala Ala Asp Gly Trp Arg Trp Lys Ile Met Ile Ala Asn Ala
            440                 445                 450 aat aag cct ggt gta tta aaa cag tta atg gca gct gct gaa ggg cac    1508
Asn Lys Pro Gly Val Leu Lys Gln Leu Met Ala Ala Ala Glu Gly His
455                 460                 465 cca tgg ctt tgg ttg att tat ctt gtg aca gca gga gtg cca ata gca    1556
Pro Trp Leu Trp Leu Ile Tyr Leu Val Thr Ala Gly Val Pro Ile Ala
470                 475                 480                 485 tta att act tca ttt tgt tgg cca aga aaa gta aag aaa aaa cat aaa    1604
Leu Ile Thr Ser Phe Cys Trp Pro Arg Lys Val Lys Lys Lys His Lys
                490                 495                 500 gat aca gag tat aaa aaa acc gac ata tgt ata cca caa aca aaa gga    1652
Asp Thr Glu Tyr Lys Lys Thr Asp Ile Cys Ile Pro Gln Thr Lys Gly
            505                 510                 515 gta cta gag caa gaa gaa aag gaa gag aaa gca gcc ctg gaa aaa cca    1700
Val Leu Glu Gln Glu Glu Lys Glu Glu Lys Ala Ala Leu Glu Lys Pro
        520                 525                 530 atg gac ctg gaa gag gaa aaa aag caa aat gat ggt gaa atg ctt gaa    1748
Met Asp Leu Glu Glu Glu Lys Lys Gln Asn Asp Gly Glu Met Leu Glu
535                 540                 545 aaa gaa gag gaa agt gaa cct gag gaa aag agt gaa gaa gaa att gaa    1796
Lys Glu Glu Glu Ser Glu Pro Glu Glu Lys Ser Glu Glu Glu Ile Glu
550                 555                 560                 565 atc ata gaa ggg caa gaa gaa agt aat caa tca aat aag tct ggg tca    1844
Ile Ile Glu Gly Gln Glu Glu Ser Asn Gln Ser Asn Lys Ser Gly Ser
                570                 575                 580 gag gat gag atg aaa gaa gca gat gag agc aca gga tct gga gat ggg    1892
Glu Asp Glu Met Lys Glu Ala Asp Glu Ser Thr Gly Ser Gly Asp Gly
            585                 590                 595 ccg ata aag tca gta cgc aaa aga aga gta cga aag gac taa             1934
Pro Ile Lys Ser Val Arg Lys Arg Arg Val Arg Lys Asp
        600                 605                 610 actagattga aatattttta attcccgaga ggatgtttgg cattgtaaaa atcagcatgc   1994
cagacctgaa ctttaatcag tctgcacatc ctgtttctaa tatctagcaa cattatattc   2054
tttcagacat ttattttagt ccttcatttc cgaggaaaaa gaagcaactt tgaagttacc   2114
tcatctttga atttagaata aaagtggcac attacatatc ggatctaaga gattaatacc   2174
attagaagtt acacagtttt agttgtttgg agatagtttt ggtttgtaca gaacaaaata   2234
atatgtagca gcttcattgc tattggaaaa atcagttatt ggaatttcca cttaaatggc   2294
```

```
tatacaacaa tataactggt agttctataa taaaaatgag catatgttct gttgtgaaga    2354
gctaaatgca ataaagtttc tgtatggttg tttgattcta tcaacaattg aaagtgttgt    2414
atatgaccca catttaccta gtttgtgtca aattatagtt acagtgagtt gtttgcttaa    2474
attatagatt cctttaagga catgccttgt tcataaaatc actggattat attgcagcat    2534
attttacatt tgaatacaag gataatgggt tttatcaaaa caaaatgatg tacagatttt    2594
ttttcaagtt tttatagttg ctttatgcca gagtggttta ccccattcac aaaatttctt    2654
atgcatacat tgctattgaa aataaaattt aaatattttt tcatcctgaa aaaaaa       2710
```

<210> SEQ ID NO 18
<211> LENGTH: 610
<212> TYPE: PRT
<213> ORGANISM: Homo sapiens

<400> SEQUENCE: 18

```
Met His Phe Gln Ala Phe Trp Leu Cys Leu Gly Leu Leu Phe Ile Ser
1               5                   10                  15

Ile Asn Ala Glu Phe Met Asp Asp Val Glu Thr Glu Asp Phe Glu
            20                  25                  30

Glu Asn Ser Glu Glu Ile Asp Val Asn Glu Ser Glu Leu Ser Ser Glu
        35                  40                  45

Ile Lys Tyr Lys Thr Pro Gln Pro Ile Gly Glu Val Tyr Phe Ala Glu
    50                  55                  60

Thr Phe Asp Ser Gly Arg Leu Ala Gly Trp Val Leu Ser Lys Ala Lys
65                  70                  75                  80

Lys Asp Asp Met Asp Glu Glu Ile Ser Ile Tyr Asp Gly Arg Trp Glu
                85                  90                  95

Ile Glu Glu Leu Lys Glu Asn Gln Val Pro Gly Asp Arg Gly Leu Val
            100                 105                 110

Leu Lys Ser Arg Ala Lys His His Ala Ile Ser Ala Val Leu Ala Lys
        115                 120                 125

Pro Phe Ile Phe Ala Asp Lys Pro Leu Ile Val Gln Tyr Glu Val Asn
    130                 135                 140

Phe Gln Asp Gly Ile Asp Cys Gly Gly Ala Tyr Ile Lys Leu Leu Ala
145                 150                 155                 160

Asp Thr Asp Asp Leu Ile Leu Glu Asn Phe Tyr Asp Lys Thr Ser Tyr
                165                 170                 175

Ile Ile Met Phe Gly Pro Asp Lys Cys Gly Glu Asp Tyr Lys Leu His
            180                 185                 190

Phe Ile Phe Arg His Lys His Pro Lys Thr Gly Val Phe Glu Glu Lys
        195                 200                 205

His Ala Lys Pro Pro Asp Val Asp Leu Lys Lys Phe Phe Thr Asp Arg
    210                 215                 220

Lys Thr His Leu Tyr Thr Leu Val Met Asn Pro Asp Asp Thr Phe Glu
225                 230                 235                 240

Val Leu Val Asp Gln Thr Val Val Asn Lys Gly Ser Leu Leu Glu Asp
                245                 250                 255

Val Val Pro Pro Ile Lys Pro Pro Lys Glu Ile Glu Asp Pro Asn Asp
            260                 265                 270

Lys Lys Pro Glu Glu Trp Asp Glu Arg Ala Lys Ile Pro Asp Pro Ser
        275                 280                 285

Ala Val Lys Pro Glu Asp Trp Asp Glu Ser Glu Pro Ala Gln Ile Glu
    290                 295                 300
```

-continued

```
Asp Ser Ser Val Val Lys Pro Ala Gly Trp Leu Asp Asp Glu Pro Lys
305                 310                 315                 320

Phe Ile Pro Asp Pro Asn Ala Glu Lys Pro Asp Trp Asn Glu Asp
            325                 330                 335

Thr Asp Gly Glu Trp Glu Ala Pro Gln Ile Leu Asn Pro Ala Cys Arg
            340                 345                 350

Ile Gly Cys Gly Glu Trp Lys Pro Pro Met Ile Asp Asn Pro Lys Tyr
            355                 360                 365

Lys Gly Val Trp Arg Pro Pro Leu Val Asp Asn Pro Asn Tyr Gln Gly
    370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Ser Ala Leu Gly Leu Glu Leu Trp
            405                 410                 415

Ser Met Thr Ser Asp Ile Tyr Phe Asp Asn Phe Ile Ile Cys Ser Glu
            420                 425                 430

Lys Glu Val Ala Asp His Trp Ala Ala Asp Gly Trp Arg Trp Lys Ile
            435                 440                 445

Met Ile Ala Asn Ala Asn Lys Pro Gly Val Leu Lys Gln Leu Met Ala
    450                 455                 460

Ala Ala Glu Gly His Pro Trp Leu Trp Leu Ile Tyr Leu Val Thr Ala
465                 470                 475                 480

Gly Val Pro Ile Ala Leu Ile Thr Ser Phe Cys Trp Pro Arg Lys Val
            485                 490                 495

Lys Lys Lys His Lys Asp Thr Glu Tyr Lys Lys Thr Asp Ile Cys Ile
            500                 505                 510

Pro Gln Thr Lys Gly Val Leu Glu Gln Glu Lys Glu Lys Ala
    515                 520                 525

Ala Leu Glu Lys Pro Met Asp Leu Glu Glu Lys Lys Gln Asn Asp
    530                 535                 540

Gly Glu Met Leu Glu Lys Glu Glu Ser Glu Pro Glu Glu Lys Ser
545                 550                 555                 560

Glu Glu Glu Ile Glu Ile Ile Glu Gly Gln Glu Ser Asn Gln Ser
            565                 570                 575

Asn Lys Ser Gly Ser Glu Asp Glu Met Lys Glu Ala Asp Glu Ser Thr
    580                 585                 590

Gly Ser Gly Asp Gly Pro Ile Lys Ser Val Arg Lys Arg Val Arg
            595                 600                 605

Lys Asp
    610
```

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gtgatgaatc cagatgac                                                  18

<210> SEQ ID NO 20
<211> LENGTH: 18
<212> TYPE: DNA
<213> ORGANISM: Artificial Sequence
<220> FEATURE:

<223> OTHER INFORMATION: Synthetic primer

<400> SEQUENCE: 20
ggtcatagac caaagctc                                                      18

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
aaggatccat gcatttccaa agc                                                23

<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22
ccgaattctt attcctttcg tactc                                              25

<210> SEQ ID NO 23
<211> LENGTH: 26
<212> TYPE: DNA
<213> ORGANISM: Artificial Sequence
<220> FEATURE:
<223> OTHER INFORMATION: Synthetic primer

<400> SEQUENCE: 23
gaattcatgc atttccaagc cttttg                                             26

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
ctcgagttag tcctttcgta ctc                                                23

<210> SEQ ID NO 25
<211> LENGTH: 7353
<212> TYPE: DNA
<213> ORGANISM: Canis familiaris
<220> FEATURE:
<221> NAME/KEY: CDS
<222> LOCATION: (1)..(7020)

<400> SEQUENCE: 25

```
atg aag aaa ggt tct cag caa aag ttt ttg aaa gca aag atg cca cca        48
Met Lys Lys Gly Ser Gln Gln Lys Phe Leu Lys Ala Lys Met Pro Pro
1               5                   10                  15 tca tct cac tct cct agt cca cca tcc ctt acg tcc aat atg aga tct        96
Ser Ser His Ser Pro Ser Pro Pro Ser Leu Thr Ser Asn Met Arg Ser
            20                  25                  30 agg tca ctt tcg cct cta agt gga tct gag act ctg cct ttt cat ttt       144
Arg Ser Leu Ser Pro Leu Ser Gly Ser Glu Thr Leu Pro Phe His Phe
        35                  40                  45 gga gga ccg tgg cat gag caa gtt gag att aca gat gaa agc aca gtg       192
Gly Gly Pro Trp His Glu Gln Val Glu Ile Thr Asp Glu Ser Thr Val
```

```
              50                  55                  60
gtt tta gac tac caa gac cat aaa gaa gct gat tca cat gca gga gtc     240
Val Leu Asp Tyr Gln Asp His Lys Glu Ala Asp Ser His Ala Gly Val
 65                  70                  75                  80 cga tat att aca gag gcc ctt gtt aga aaa ctt act aaa cag gac aat     288
Arg Tyr Ile Thr Glu Ala Leu Val Arg Lys Leu Thr Lys Gln Asp Asn
                     85                  90                  95 ttg gcc ttg gta aaa tct ctg aac ctt tca ctt gct aaa ggt ggt ggc     336
Leu Ala Leu Val Lys Ser Leu Asn Leu Ser Leu Ala Lys Gly Gly Gly
                100                 105                 110 aag aaa ttc agg tgt atc gaa aat ttg gaa aaa tgt gtt aaa ctt gaa     384
Lys Lys Phe Arg Cys Ile Glu Asn Leu Glu Lys Cys Val Lys Leu Glu
            115                 120                 125 gta ctg aat ctc agc tat aat cta ata gga aag att gag aaa gtg gac     432
Val Leu Asn Leu Ser Tyr Asn Leu Ile Gly Lys Ile Glu Lys Val Asp
        130                 135                 140 aaa ctg tta aaa tta cgt gaa ctc aac tta tcg tat aac aaa atc cgc     480
Lys Leu Leu Lys Leu Arg Glu Leu Asn Leu Ser Tyr Asn Lys Ile Arg
145                 150                 155                 160 aaa att gaa ggc ata gaa aat tta tat aat ctg caa aag ctg aac ctt     528
Lys Ile Glu Gly Ile Glu Asn Leu Tyr Asn Leu Gln Lys Leu Asn Leu
                165                 170                 175 gca gga aat gaa atc gaa cat atc cca gta tgg tta ggg aag aag tta     576
Ala Gly Asn Glu Ile Glu His Ile Pro Val Trp Leu Gly Lys Lys Leu
                180                 185                 190 aaa tct ttg cga atc ctg aat ctg aaa ggc aac aag ata tca tcg ctc     624
Lys Ser Leu Arg Ile Leu Asn Leu Lys Gly Asn Lys Ile Ser Ser Leu
            195                 200                 205 caa gat gta agc aag ttg aaa cca ctt caa gat ttg act tct ctg atc     672
Gln Asp Val Ser Lys Leu Lys Pro Leu Gln Asp Leu Thr Ser Leu Ile
        210                 215                 220 cta ctt gaa aat cca gtt gcg acc ctt cct cat tat atc cag ttt acc     720
Leu Leu Glu Asn Pro Val Ala Thr Leu Pro His Tyr Ile Gln Phe Thr
225                 230                 235                 240 att ttt cac ctt cgc tca ttg gaa agt ttg gaa ggt cag cca gta act     768
Ile Phe His Leu Arg Ser Leu Glu Ser Leu Glu Gly Gln Pro Val Thr
                245                 250                 255 agt cag gac aga caa gaa gct ttt gcg aga ttc agt tta gat gag gta     816
Ser Gln Asp Arg Gln Glu Ala Phe Ala Arg Phe Ser Leu Asp Glu Val
                260                 265                 270 gaa aga ctg gaa aga gac ctg gag aag aag aca atg gaa act gaa gag     864
Glu Arg Leu Glu Arg Asp Leu Glu Lys Lys Thr Met Glu Thr Glu Glu
            275                 280                 285 ctt agg agt gag cag aca agg ttc ctt gag gaa att aaa agt cag gat     912
Leu Arg Ser Glu Gln Thr Arg Phe Leu Glu Glu Ile Lys Ser Gln Asp
        290                 295                 300 aaa ttg aac aaa tca ctg aaa gag gag gcc aga cta caa aaa cag agc     960
Lys Leu Asn Lys Ser Leu Lys Glu Glu Ala Arg Leu Gln Lys Gln Ser
305                 310                 315                 320 tat gag gag ctg gag agt aac cta aac acc aaa aat gaa ttg cta aaa    1008
Tyr Glu Glu Leu Glu Ser Asn Leu Asn Thr Lys Asn Glu Leu Leu Lys
                325                 330                 335 cag aag acc atg gaa cta atg cga gca tgt cag aaa cag tat gag atg    1056
Gln Lys Thr Met Glu Leu Met Arg Ala Cys Gln Lys Gln Tyr Glu Met
                340                 345                 350 gaa cag gag ttg gcc ttt tat aaa att gat gcc aaa ttt gaa cca cta    1104
Glu Gln Glu Leu Ala Phe Tyr Lys Ile Asp Ala Lys Phe Glu Pro Leu
            355                 360                 365 aat tat tac cca tca gag tat gtc gaa att gat aaa acc cca gat gaa    1152
Asn Tyr Tyr Pro Ser Glu Tyr Val Glu Ile Asp Lys Thr Pro Asp Glu
```

-continued

```
            Asn Tyr Tyr Pro Ser Glu Tyr Val Glu Ile Asp Lys Thr Pro Asp Glu
                370                 375                 380 agc cct tac att ggc aaa tcc aga tac aag aga aat atg ttc act aca     1200
Ser Pro Tyr Ile Gly Lys Ser Arg Tyr Lys Arg Asn Met Phe Thr Thr
385                 390                 395                 400 gag agt tat att att gca aat gcc cag aca gta aag atc aag aag atg     1248
Glu Ser Tyr Ile Ile Ala Asn Ala Gln Thr Val Lys Ile Lys Lys Met
                405                 410                 415 gag cta gat gaa ggg gaa caa ctc aga aat gag cac gtg aac ttg gga     1296
Glu Leu Asp Glu Gly Glu Gln Leu Arg Asn Glu His Val Asn Leu Gly
            420                 425                 430 gca tcg cca aca gac ata caa ctg gaa gac aaa gaa aaa aaa ata agt     1344
Ala Ser Pro Thr Asp Ile Gln Leu Glu Asp Lys Glu Lys Lys Ile Ser
        435                 440                 445 gca gca caa act cga cta tca gaa cta cat gat gaa ata gaa aag gca     1392
Ala Ala Gln Thr Arg Leu Ser Glu Leu His Asp Glu Ile Glu Lys Ala
    450                 455                 460 gaa caa caa att tta aga gcc act gaa gaa ttt aaa caa ctg gaa gaa     1440
Glu Gln Gln Ile Leu Arg Ala Thr Glu Glu Phe Lys Gln Leu Glu Glu
465                 470                 475                 480 gct ata caa ctt aaa aaa att tca gaa gcg gag aaa gac ctt ctt ttc     1488
Ala Ile Gln Leu Lys Lys Ile Ser Glu Ala Glu Lys Asp Leu Leu Phe
                485                 490                 495 aag cag ttg agt ggt agg ata cag ctt ctc aat aaa tta cgc caa gaa     1536
Lys Gln Leu Ser Gly Arg Ile Gln Leu Leu Asn Lys Leu Arg Gln Glu
            500                 505                 510 gct gtg gat cta gaa aca cag atg gaa aag caa agg caa gaa att ggt     1584
Ala Val Asp Leu Glu Thr Gln Met Glu Lys Gln Arg Gln Glu Ile Gly
        515                 520                 525 gaa aag cag aat gag atc aag gac ctg gaa ata gtc aca gat agc ctg     1632
Glu Lys Gln Asn Glu Ile Lys Asp Leu Glu Ile Val Thr Asp Ser Leu
    530                 535                 540 gat tcc aga gac cca aaa cat tgc cat atg aag gct cag aaa aga ggt     1680
Asp Ser Arg Asp Pro Lys His Cys His Met Lys Ala Gln Lys Arg Gly
545                 550                 555                 560 aaa gaa caa caa ctt gac att atg aac aag cag tac aaa cag ctt gaa     1728
Lys Glu Gln Gln Leu Asp Ile Met Asn Lys Gln Tyr Lys Gln Leu Glu
                565                 570                 575 agc cgt ttg gat gag ata ctt tct aga att gcc aaa gaa act gaa gag     1776
Ser Arg Leu Asp Glu Ile Leu Ser Arg Ile Ala Lys Glu Thr Glu Glu
            580                 585                 590 att aag gac ctt gaa gaa cag ctt act gaa gga caa ata gcc gca aac     1824
Ile Lys Asp Leu Glu Glu Gln Leu Thr Glu Gly Gln Ile Ala Ala Asn
        595                 600                 605 gaa gcc ctg aag aag gac tta gaa agt gtc atc agt ggg ttg caa gaa     1872
Glu Ala Leu Lys Lys Asp Leu Glu Ser Val Ile Ser Gly Leu Gln Glu
    610                 615                 620 tac ctg gag act gtc aaa ggt cag gcc cgt cag gcc cag aat gag tgc     1920
Tyr Leu Glu Thr Val Lys Gly Gln Ala Arg Gln Ala Gln Asn Glu Cys
625                 630                 635                 640 aga aag cta cag gat gag aag gag aca ttg ctg cag aga ttg agt gag     1968
Arg Lys Leu Gln Asp Glu Lys Glu Thr Leu Leu Gln Arg Leu Ser Glu
                645                 650                 655 gtc gag cag gag agg gac caa ctg gaa ata gtg gcc ata gat gca gaa     2016
Val Glu Gln Glu Arg Asp Gln Leu Glu Ile Val Ala Ile Asp Ala Glu
            660                 665                 670 aat atg agg aag gag ctc gca gaa ctg gag aat gcc ctc cag gag cag     2064
Asn Met Arg Lys Glu Leu Ala Glu Leu Glu Asn Ala Leu Gln Glu Gln
        675                 680                 685
```

| | |
|---|---|
| cat gag gtg aat ata tct ctg cag cag acc cag gga gat ctc agt gcc<br>His Glu Val Asn Ile Ser Leu Gln Gln Thr Gln Gly Asp Leu Ser Ala<br>690     695     700 | 2112 |
| tat gag gct gag cta gag gct cag ctg aaa ata cgg gat gct gaa gcc<br>Tyr Glu Ala Glu Leu Glu Ala Gln Leu Lys Ile Arg Asp Ala Glu Ala<br>705    710     715     720 | 2160 |
| aac cag ctc aag gag gag ttg gaa aaa ctt aga agg ttg agc cag tta<br>Asn Gln Leu Lys Glu Glu Leu Glu Lys Leu Arg Arg Leu Ser Gln Leu<br>    725     730     735 | 2208 |
| gaa caa tcg gcc ctt caa gca gag ctt gag aag gaa aag caa gcc ttc<br>Glu Gln Ser Ala Leu Gln Ala Glu Leu Glu Lys Glu Lys Gln Ala Phe<br>740     745     750 | 2256 |
| aag act gct gtc aaa aaa gcc cag ctc tca gaa gga aag gac caa gaa<br>Lys Thr Ala Val Lys Lys Ala Gln Leu Ser Glu Gly Lys Asp Gln Glu<br>755     760     765 | 2304 |
| aat agt gag ctc cgc aca caa ctc caa cag ctg cag gat gac aat gac<br>Asn Ser Glu Leu Arg Thr Gln Leu Gln Gln Leu Gln Asp Asp Asn Asp<br>770     775     780 | 2352 |
| cta ttg aaa cag caa ctt aaa gat ttc cag agt cac ctt aac cat gtg<br>Leu Leu Lys Gln Gln Leu Lys Asp Phe Gln Ser His Leu Asn His Val<br>785     790     795     800 | 2400 |
| gtt gat ggt ttg att cgt cca gaa gaa gtg gca gct tgt gtg gat gag<br>Val Asp Gly Leu Ile Arg Pro Glu Glu Val Ala Ala Cys Val Asp Glu<br>    805     810     815 | 2448 |
| cta agg aaa aaa ctg aag tca gga gct ggg gaa atg aga atc cat act<br>Leu Arg Lys Lys Leu Lys Ser Gly Ala Gly Glu Met Arg Ile His Thr<br>820     825     830 | 2496 |
| cct tca gat gtc tta ggg aaa agt ctt gct gac ttg cag aag caa ttc<br>Pro Ser Asp Val Leu Gly Lys Ser Leu Ala Asp Leu Gln Lys Gln Phe<br>835     840     845 | 2544 |
| agt gag atc ctg gca cgc tcc cag tgg gaa aga cag gaa gca caa gtg<br>Ser Glu Ile Leu Ala Arg Ser Gln Trp Glu Arg Gln Glu Ala Gln Val<br>850     855     860 | 2592 |
| aga gag aga aaa ctc cag gag gaa atg gct ctg caa caa gag aaa ctg<br>Arg Glu Arg Lys Leu Gln Glu Glu Met Ala Leu Gln Gln Glu Lys Leu<br>865     870     880 | 2640 |
| gcg agc gga caa gag gag ttc agg cac gcc tgc gag agg gcc ctg gaa<br>Ala Ser Gly Gln Glu Glu Phe Arg His Ala Cys Glu Arg Ala Leu Glu<br>    885     890     895 | 2688 |
| gcc cga att agt ttt gat aag agg cag cac gaa gca aga atc cag cag<br>Ala Arg Ile Ser Phe Asp Lys Arg Gln His Glu Ala Arg Ile Gln Gln<br>900     905     910 | 2736 |
| ttg gag aat gaa att cac tat ttg caa gaa aat cta aaa agt atg gag<br>Leu Glu Asn Glu Ile His Tyr Leu Gln Glu Asn Leu Lys Ser Met Glu<br>915     920     925 | 2784 |
| gaa atc caa ggt ctc aca gac ctc caa ctt cag gaa gct gat gaa gag<br>Glu Ile Gln Gly Leu Thr Asp Leu Gln Leu Gln Glu Ala Asp Glu Glu<br>930     935     940 | 2832 |
| aag gag aga att ctg gcc caa ctc cgg gag tta gag aaa aag aag aaa<br>Lys Glu Arg Ile Leu Ala Gln Leu Arg Glu Leu Glu Lys Lys Lys Lys<br>945     950     955     960 | 2880 |
| ctt gag gat gcc aag tct cag gag cag ttt ctt gga tta gat aga gaa<br>Leu Glu Asp Ala Lys Ser Gln Glu Gln Phe Leu Gly Leu Asp Arg Glu<br>    965     970     975 | 2928 |
| ttg aag aag cta aag aaa gct gtg gct gcc tct gat aag ctg gcc aca<br>Leu Lys Lys Leu Lys Lys Ala Val Ala Ala Ser Asp Lys Leu Ala Thr<br>980     985     990 | 2976 |
| gct gag ctc acc att gcc aaa gac cag ctc aag tcc ctt cat gga act<br>Ala Glu Leu Thr Ile Ala Lys Asp Gln Leu Lys Ser Leu His Gly Thr<br>995     1000     1005 | 3024 |

```
gtg atg aaa att aac cag gag cga gca gag gag ctg cag gag acg      3069
Val Met Lys Ile Asn Gln Glu Arg Ala Glu Glu Leu Gln Glu Thr
    1010                1015                1020 gag agg ttc agc aga aag gca gca caa gca gct agg gat ctg atc      3114
Glu Arg Phe Ser Arg Lys Ala Ala Gln Ala Ala Arg Asp Leu Ile
1025                1030                1035 cga gca gaa gcg gag att gaa ctc ctg cag aag ctt ctc aga gat      3159
Arg Ala Glu Ala Glu Ile Glu Leu Leu Gln Lys Leu Leu Arg Asp
    1040                1045                1050 aaa gag gag cag ttt cga aat gag att gag aaa gta gat gtc ggc      3204
Lys Glu Glu Gln Phe Arg Asn Glu Ile Glu Lys Val Asp Val Gly
1055                1060                1065 tct gga gga gca aag tca cag atg ctg gag atg gag aaa cta aat      3249
Ser Gly Gly Ala Lys Ser Gln Met Leu Glu Met Glu Lys Leu Asn
    1070                1075                1080 gag aca atg gag agg caa aga aca gag att gct agg ctg agg aat      3294
Glu Thr Met Glu Arg Gln Arg Thr Glu Ile Ala Arg Leu Arg Asn
1085                1090                1095 tta cta gac ctc acc ggg gct gat aac aaa gga aac ttt gaa aat      3339
Leu Leu Asp Leu Thr Gly Ala Asp Asn Lys Gly Asn Phe Glu Asn
    1100                1105                1110 gtt ttg gaa gaa att gct gaa ctt cga cgt gaa gtt tct cat cag      3384
Val Leu Glu Glu Ile Ala Glu Leu Arg Arg Glu Val Ser His Gln
1115                1120                1125 aat gat tac atc agc agc atg aca gat cct ttc aaa aga cga ggc      3429
Asn Asp Tyr Ile Ser Ser Met Thr Asp Pro Phe Lys Arg Arg Gly
    1130                1135                1140 tat tgg tac ttt atg cca cca cca tca tca tca aaa gtt tcc agc      3474
Tyr Trp Tyr Phe Met Pro Pro Pro Ser Ser Ser Lys Val Ser Ser
1145                1150                1155 cac agt tcc cag gcc acc aag gac tct ggt gtt ggc cta aag tac      3519
His Ser Ser Gln Ala Thr Lys Asp Ser Gly Val Gly Leu Lys Tyr
    1160                1165                1170 aca gcc tcc act ccg gtt aga aaa cca cat cgt gga cgg cag gat      3564
Thr Ala Ser Thr Pro Val Arg Lys Pro His Arg Gly Arg Gln Asp
1175                1180                1185 gga aag gag aac agt ggg cct cca cct gcc tca gga tac tgg gtg      3609
Gly Lys Glu Asn Ser Gly Pro Pro Pro Ala Ser Gly Tyr Trp Val
    1190                1195                1200 tat tct cct atc agg agt ggg tta cat aaa tcg ttc tca aat aga      3654
Tyr Ser Pro Ile Arg Ser Gly Leu His Lys Ser Phe Ser Asn Arg
1205                1210                1215 gac gca gac agt gga gga gat agc cag gaa gag agc gag cta gat      3699
Asp Ala Asp Ser Gly Gly Asp Ser Gln Glu Glu Ser Glu Leu Asp
    1220                1225                1230 gac caa gaa gac cac cca ttt gta cct cct cct gga tac atg atg      3744
Asp Gln Glu Asp His Pro Phe Val Pro Pro Pro Gly Tyr Met Met
1235                1240                1245 tac act gtg ttt cct gat ggt tct cct gta ccc cag ggc atg gcc      3789
Tyr Thr Val Phe Pro Asp Gly Ser Pro Val Pro Gln Gly Met Ala
    1250                1255                1260 ctg tat gca ccc cct cct ccc ttg ccc aac aat agc cag cct ctt      3834
Leu Tyr Ala Pro Pro Pro Pro Leu Pro Asn Asn Ser Gln Pro Leu
1265                1270                1275 gac ctt ggc act gtt gtt tat ggc cca cct cct gtt ggg gct ccc      3879
Asp Leu Gly Thr Val Val Tyr Gly Pro Pro Pro Val Gly Ala Pro
    1280                1285                1290 atc gtg tat ggg cct cca cct ccc aac ttc tcc gta ccc ctc atc      3924
Ile Val Tyr Gly Pro Pro Pro Pro Asn Phe Ser Val Pro Leu Ile
```

-continued

| | | | | | | | | | | | | |
|---|---|---|---|---|---|---|---|---|---|---|---|---|
| | | 1295 | | | 1300 | | | | 1305 | | | |
| ccc | gtg | ggt | gtg | ctg | cac | tgc | aat | gtc | cca | gaa | cac | cat aac ttg | 3969 |
| Pro | Val | Gly | Val | Leu | His | Cys | Asn | Val | Pro | Glu | His | His Asn Leu |
| | 1310 | | | | 1315 | | | | 1320 | | | |
| gag | aat | gaa | gtt | tct | aga | tta | gaa | gac | ata | atg | cag | cat tta aaa | 4014 |
| Glu | Asn | Glu | Val | Ser | Arg | Leu | Glu | Asp | Ile | Met | Gln | His Leu Lys |
| | 1325 | | | | 1330 | | | | 1335 | | | |
| tct | ggg | aaa | cgg | gaa | cag | tgc | atg | aaa | aca | ccc | aag | ctg cag tcg | 4059 |
| Ser | Gly | Lys | Arg | Glu | Gln | Cys | Met | Lys | Thr | Pro | Lys | Leu Gln Ser |
| | 1340 | | | | 1345 | | | | 1350 | | | |
| gag | aaa | gaa | ctc | gca | gag | ctg | cag | cat | aac | att | gat | ggt ctt ttg | 4104 |
| Glu | Lys | Glu | Leu | Ala | Glu | Leu | Gln | His | Asn | Ile | Asp | Gly Leu Leu |
| | 1355 | | | | 1360 | | | | 1365 | | | |
| caa | gag | aag | aaa | gac | tta | gag | cat | gaa | gta | gaa | gaa | tta cat aga | 4149 |
| Gln | Glu | Lys | Lys | Asp | Leu | Glu | His | Glu | Val | Glu | Glu | Leu His Arg |
| | 1370 | | | | 1375 | | | | 1380 | | | |
| acc | atc | caa | aaa | cat | caa | cag | cga | aaa | gat | ttc | att | gat gga aac | 4194 |
| Thr | Ile | Gln | Lys | His | Gln | Gln | Arg | Lys | Asp | Phe | Ile | Asp Gly Asn |
| | 1385 | | | | 1390 | | | | 1395 | | | |
| gtt | gag | agt | ctt | gtg | aat | gat | cta | gaa | ata | gag | aag | tca ctc aaa | 4239 |
| Val | Glu | Ser | Leu | Val | Asn | Asp | Leu | Glu | Ile | Glu | Lys | Ser Leu Lys |
| | 1400 | | | | 1405 | | | | 1410 | | | |
| cac | cat | gaa | gat | att | gtt | gat | gaa | att | gaa | tgt | att | gag agg acc | 4284 |
| His | His | Glu | Asp | Ile | Val | Asp | Glu | Ile | Glu | Cys | Ile | Glu Arg Thr |
| | 1415 | | | | 1420 | | | | 1425 | | | |
| ctt | ctg | aag | cgc | cgt | gca | gag | ctc | agg | gaa | gcc | gac | cgg ctg ctg | 4329 |
| Leu | Leu | Lys | Arg | Arg | Ala | Glu | Leu | Arg | Glu | Ala | Asp | Arg Leu Leu |
| | 1430 | | | | 1435 | | | | 1440 | | | |
| acg | gag | gct | gaa | agt | gaa | ctt | tca | tgc | acg | aaa | gag | aaa aca aaa | 4374 |
| Thr | Glu | Ala | Glu | Ser | Glu | Leu | Ser | Cys | Thr | Lys | Glu | Lys Thr Lys |
| | 1445 | | | | 1450 | | | | 1455 | | | |
| cat | gct | gtt | gag | aag | ttc | act | gat | gcc | aag | aga | aat | tta ttg caa | 4419 |
| His | Ala | Val | Glu | Lys | Phe | Thr | Asp | Ala | Lys | Arg | Asn | Leu Leu Gln |
| | 1460 | | | | 1465 | | | | 1470 | | | |
| act | gag | aaa | gat | gct | gag | gag | tta | gaa | agg | aga | gcc | cag gaa act | 4464 |
| Thr | Glu | Lys | Asp | Ala | Glu | Glu | Leu | Glu | Arg | Arg | Ala | Gln Glu Thr |
| | 1475 | | | | 1480 | | | | 1485 | | | |
| gcc | att | aac | ctc | gtc | aaa | gcc | gac | cag | cag | ctg | aga | ttg ctc cag | 4509 |
| Ala | Ile | Asn | Leu | Val | Lys | Ala | Asp | Gln | Gln | Leu | Arg | Leu Leu Gln |
| | 1490 | | | | 1495 | | | | 1500 | | | |
| gct | gac | acg | aag | gat | ttg | gag | cag | cac | aaa | atg | gag | caa gag gaa | 4554 |
| Ala | Asp | Thr | Lys | Asp | Leu | Glu | Gln | His | Lys | Met | Glu | Gln Glu Glu |
| | 1505 | | | | 1510 | | | | 1515 | | | |
| atc | ttg | aaa | gaa | ata | aac | aaa | gtt | gtt | gca | gca | aaa | gac tca gac | 4599 |
| Ile | Leu | Lys | Glu | Ile | Asn | Lys | Val | Val | Ala | Ala | Lys | Asp Ser Asp |
| | 1520 | | | | 1525 | | | | 1530 | | | |
| ttc | cag | agc | cta | aac | aag | aag | aag | gaa | gta | ctg | aca | gga gag ctg | 4644 |
| Phe | Gln | Ser | Leu | Asn | Lys | Lys | Lys | Glu | Val | Leu | Thr | Gly Glu Leu |
| | 1535 | | | | 1540 | | | | 1545 | | | |
| cag | aaa | ctc | cag | aag | gac | att | gag | act | gca | cgg | cac | aat gag gat | 4689 |
| Gln | Lys | Leu | Gln | Lys | Asp | Ile | Glu | Thr | Ala | Arg | His | Asn Glu Asp |
| | 1550 | | | | 1555 | | | | 1560 | | | |
| cag | cac | ctg | cag | gtc | ctt | aaa | gag | tcg | gag | acc | ctc | ctg cag gcc | 4734 |
| Gln | His | Leu | Gln | Val | Leu | Lys | Glu | Ser | Glu | Thr | Leu | Leu Gln Ala |
| | 1565 | | | | 1570 | | | | 1575 | | | |
| aag | aaa | gct | gag | ctg | gaa | aat | ctg | aaa | agc | cag | gtg | tca gga cag | 4779 |
| Lys | Lys | Ala | Glu | Leu | Glu | Asn | Leu | Lys | Ser | Gln | Val | Ser Gly Gln |
| | 1580 | | | | 1585 | | | | 1590 | | | |
| cag | cag | gag | atg | gcc | gtc | ttg | gac | agg | gag | tta | gga | cac aag aag | 4824 |

```
               Gln Gln Glu Met Ala Val Leu Asp Arg Glu Leu Gly His Lys Lys
                   1595                1600                1605 gaa gag ctg cat ctc ctc cag gaa agc atg gtc cag gcc aaa gct            4869
Glu Glu Leu His Leu Leu Gln Glu Ser Met Val Gln Ala Lys Ala
        1610                1615                1620 gac ctc cag gaa gca ctg aga cta gga gaa agc gaa gta act gag            4914
Asp Leu Gln Glu Ala Leu Arg Leu Gly Glu Ser Glu Val Thr Glu
        1625                1630                1635 aag tgc aat cac att agg gaa gta aaa tct ctt ctg gaa gaa ctc            4959
Lys Cys Asn His Ile Arg Glu Val Lys Ser Leu Leu Glu Glu Leu
        1640                1645                1650 agt ttt cag aaa gga gaa ctg aat gtc cag atc agt gaa aaa aaa            5004
Ser Phe Gln Lys Gly Glu Leu Asn Val Gln Ile Ser Glu Lys Lys
        1655                1660                1665 act caa ctt gca ctc ata aag cag gaa att gaa aaa gag gaa gac            5049
Thr Gln Leu Ala Leu Ile Lys Gln Glu Ile Glu Lys Glu Glu Asp
        1670                1675                1680 aat ctt cag gta gtt tta ggg caa atg tct aaa cat aaa act gaa            5094
Asn Leu Gln Val Val Leu Gly Gln Met Ser Lys His Lys Thr Glu
        1685                1690                1695 cta aag aat att ctg gac atg ttg caa ctt gaa aat aat gag ctg            5139
Leu Lys Asn Ile Leu Asp Met Leu Gln Leu Glu Asn Asn Glu Leu
        1700                1705                1710 caa ggt ttg aag ctc caa cat gac caa aag atg tct gaa tta gag            5184
Gln Gly Leu Lys Leu Gln His Asp Gln Lys Met Ser Glu Leu Glu
        1715                1720                1725 aag act cgg gtt gaa gtg ctc gag gag aaa ctg gag tta gag agt            5229
Lys Thr Arg Val Glu Val Leu Glu Glu Lys Leu Glu Leu Glu Ser
        1730                1735                1740 ctg cag cag gca gcc ctg cga cag aga ggg gag ata gag tgg cag            5274
Leu Gln Gln Ala Ala Leu Arg Gln Arg Gly Glu Ile Glu Trp Gln
        1745                1750                1755 aag cag ctc ctc cag agg aac aca cag gaa gta gag cgg atg act            5319
Lys Gln Leu Leu Gln Arg Asn Thr Gln Glu Val Glu Arg Met Thr
        1760                1765                1770 gct gag acc cga gca tta cag tcg tgt gtt gag tct ttg tgc aaa            5364
Ala Glu Thr Arg Ala Leu Gln Ser Cys Val Glu Ser Leu Cys Lys
        1775                1780                1785 gaa aag caa gat ctc gaa gaa aaa cag gac agc tgg gaa aag aag            5409
Glu Lys Gln Asp Leu Glu Glu Lys Gln Asp Ser Trp Glu Lys Lys
        1790                1795                1800 ttg gca cag acc aaa cgg gtt cta gca gct gca gaa gag gac agc            5454
Leu Ala Gln Thr Lys Arg Val Leu Ala Ala Ala Glu Glu Asp Ser
        1805                1810                1815 gag atg gag cgg gca cgc tta gaa aag ttg gaa ctg gac gcc agg            5499
Glu Met Glu Arg Ala Arg Leu Glu Lys Leu Glu Leu Asp Ala Arg
        1820                1825                1830 aag ctg cag cag gag ttg gac caa cga aac agg gag aag ctc tcc            5544
Lys Leu Gln Gln Glu Leu Asp Gln Arg Asn Arg Glu Lys Leu Ser
        1835                1840                1845 ctg cat caa gac ctg gca gtg gtg cag cag cag cta caa gaa aaa            5589
Leu His Gln Asp Leu Ala Val Val Gln Gln Gln Leu Gln Glu Lys
        1850                1855                1860 cag gaa gca gta aac tca tta cag aag gaa cta act gat gtc cag            5634
Gln Glu Ala Val Asn Ser Leu Gln Lys Glu Leu Thr Asp Val Gln
        1865                1870                1875 gag cat ttg gac cta gca gaa cag gag gtg ctc tgc acc acc aag            5679
Glu His Leu Asp Leu Ala Glu Gln Glu Val Leu Cys Thr Thr Lys
        1880                1885                1890
```

```
cgc aag gac gca ctg ctc agc gaa cag acc agg ctc gag aag gac      5724
Arg Lys Asp Ala Leu Leu Ser Glu Gln Thr Arg Leu Glu Lys Asp
    1895                1900                1905 gtg ggt gaa tgg acg aag aag ttt gaa gac tgc cag aaa gaa ggg      5769
Val Gly Glu Trp Thr Lys Lys Phe Glu Asp Cys Gln Lys Glu Gly
1910                1915                1920 gag aca aag cag caa cag ctt caa ggg ctt cag aag gag att gaa      5814
Glu Thr Lys Gln Gln Gln Leu Gln Gly Leu Gln Lys Glu Ile Glu
    1925                1930                1935 gga aac gag gcg aag cta gcc caa caa gaa atg atg ttt cag aga      5859
Gly Asn Glu Ala Lys Leu Ala Gln Gln Glu Met Met Phe Gln Arg
1940                1945                1950 ctc cag aaa gag cga gaa tgt gaa gaa aaa aag tta gaa gct agt      5904
Leu Gln Lys Glu Arg Glu Cys Glu Glu Lys Lys Leu Glu Ala Ser
    1955                1960                1965 aaa gtg act ctg aag gag cag cag caa cag ctg gaa aag gaa ttg      5949
Lys Val Thr Leu Lys Glu Gln Gln Gln Gln Leu Glu Lys Glu Leu
1970                1975                1980 atg gag cag aaa ggc aag ctg gac cag gtg ctc gct aag ctc ttg      5994
Met Glu Gln Lys Gly Lys Leu Asp Gln Val Leu Ala Lys Leu Leu
    1985                1990                1995 gtg gct gag gag cgt gtc agg acc ttg cag gag gag gga agg tgg      6039
Val Ala Glu Glu Arg Val Arg Thr Leu Gln Glu Glu Gly Arg Trp
2000                2005                2010 agc gag acc ctg gag aag acg ctc tcc cag acc aag cga cag ctt      6084
Ser Glu Thr Leu Glu Lys Thr Leu Ser Gln Thr Lys Arg Gln Leu
    2015                2020                2025 tca gaa cgg gag cag cag tta ctg gcc aag tca gac gag ctg ctg      6129
Ser Glu Arg Glu Gln Gln Leu Leu Ala Lys Ser Asp Glu Leu Leu
2030                2035                2040 gcc ctg cag aag gag acg gac tcc atg agg gcg gac ttc agc ctc      6174
Ala Leu Gln Lys Glu Thr Asp Ser Met Arg Ala Asp Phe Ser Leu
    2045                2050                2055 ttg cgc aac cag ttc ctg aca gaa aga aag aaa gcc gag aag cag      6219
Leu Arg Asn Gln Phe Leu Thr Glu Arg Lys Lys Ala Glu Lys Gln
2060                2065                2070 gtg gcc agc ctg aag gaa gcc ctt aag atc cag cgg agc caa ctg      6264
Val Ala Ser Leu Lys Glu Ala Leu Lys Ile Gln Arg Ser Gln Leu
    2075                2080                2085 gag aag aac ctt ctg gag caa aag cag gag aac agc tgc atg cag      6309
Glu Lys Asn Leu Leu Glu Gln Lys Gln Glu Asn Ser Cys Met Gln
2090                2095                2100 agg gag atg gca acc atc gaa cag gtg gcc cag gac aac cac gag      6354
Arg Glu Met Ala Thr Ile Glu Gln Val Ala Gln Asp Asn His Glu
    2105                2110                2115 cgg gcc cgg cgc cta atg agg gag ctc aac cag atg cag cgc gag      6399
Arg Ala Arg Arg Leu Met Arg Glu Leu Asn Gln Met Gln Arg Glu
2120                2125                2130 tac gtg gag ctc agg aaa cag atg aca aac caa aag gat ttg gaa      6444
Tyr Val Glu Leu Arg Lys Gln Met Thr Asn Gln Lys Asp Leu Glu
    2135                2140                2145 aga aga cag atg gaa atc agt gat gcg atg caa gca ctt aaa tgt      6489
Arg Arg Gln Met Glu Ile Ser Asp Ala Met Gln Ala Leu Lys Cys
2150                2155                2160 gag gtg aaa gat gaa atc cga acc agc ctg aag aat ctc aac cag      6534
Glu Val Lys Asp Glu Ile Arg Thr Ser Leu Lys Asn Leu Asn Gln
    2165                2170                2175 ttt ctt cca gaa ctg cca gcg gac ctg gag gcc ctt ctg gaa agg      6579
Phe Leu Pro Glu Leu Pro Ala Asp Leu Glu Ala Leu Leu Glu Arg
2180                2185                2190
```

```
aat gag aac ctt gga gga ggc ttg gag agc ttg aaa gag aat ttc      6624
Asn Glu Asn Leu Gly Gly Gly Leu Glu Ser Leu Lys Glu Asn Phe
    2195                2200                2205 ccg ttt acc gtg agc gac aga cca tca tct tgc gaa gag aaa ctg      6669
Pro Phe Thr Val Ser Asp Arg Pro Ser Ser Cys Glu Glu Lys Leu
2210                2215                2220 aat ttt ggc cag gct cac gtg gcg gat gaa cag tgg cgg gga gag      6714
Asn Phe Gly Gln Ala His Val Ala Asp Glu Gln Trp Arg Gly Glu
    2225                2230                2235 gca ctc cgg gag aag ctg cgc cac cgc gag gac cgg ctc aag gcc      6759
Ala Leu Arg Glu Lys Leu Arg His Arg Glu Asp Arg Leu Lys Ala
2240                2245                2250 cag ctg cgc cgc tgc atg tcc aag cag gcc gag gtg ctg agc gag      6804
Gln Leu Arg Arg Cys Met Ser Lys Gln Ala Glu Val Leu Ser Glu
    2255                2260                2265 ggc cgg cgg cgc acg gag ggg acc ctg cac agc ctg cgg cgg cag      6849
Gly Arg Arg Arg Thr Glu Gly Thr Leu His Ser Leu Arg Arg Gln
2270                2275                2280 gtg gac gcc ctg ggc gag ctg gtc acc agc act tcc ggg gac tcc      6894
Val Asp Ala Leu Gly Glu Leu Val Thr Ser Thr Ser Gly Asp Ser
    2285                2290                2295 gcg tcc acc cgc agt ctg tcg cgc acc gag ggc tcg ctc gcc gag      6939
Ala Ser Thr Arg Ser Leu Ser Arg Thr Glu Gly Ser Leu Ala Glu
2300                2305                2310 gac gaa ccg ccg ggg ccc agc cag agc tcc cgg cgg ctc ccc cga      6984
Asp Glu Pro Pro Gly Pro Ser Gln Ser Ser Arg Arg Leu Pro Arg
    2315                2320                2325 ggc ccg tcg ccg cgg ctg gac gcg cac cga ccc tga ggacccggag       7030
Gly Pro Ser Pro Arg Leu Asp Ala His Arg Pro
2330                2335 gacccggagg cccggcgtcc cctcggaacg cttcctccgc gtccgcggac accaggctca 7090
cgggaaggcg cgtccatgcg ggaagagccg cgagcgaaac ccggatgccc gggctggtct  7150
ctgggccttg gaaacgtgtt gccgtaaaag cagcgcccgc ggctgcggac ttgaagcccc  7210
gaactggtaa actcggcggc tgccgggcga actgtactca ggacttttt cacggacacc   7270 gtcagatttt attttggaa atctatttc atatgaaaat aaaagataaa agcgcctgaa   7330
aaaaaaaaaa aaaaaaaact agt                                         7353
```

<210> SEQ ID NO 26
<211> LENGTH: 2339
<212> TYPE: PRT
<213> ORGANISM: Canis familiaris

<400> SEQUENCE: 26

```
Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45

Gly Gly Pro Trp His Glu Gln Val Glu Ile Thr Asp Glu Ser Thr Val
    50                  55                  60

Val Leu Asp Tyr Gln Asp His Lys Glu Ala Asp Ser His Ala Gly Val
65                  70                  75                  80

Arg Tyr Ile Thr Glu Ala Leu Val Arg Lys Leu Thr Lys Gln Asp Asn
                85                  90                  95
```

```
Leu Ala Leu Val Lys Ser Leu Asn Leu Ser Leu Ala Lys Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220

Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
                245                 250                 255

Ser Gln Asp Arg Gln Glu Ala Phe Ala Arg Phe Ser Leu Asp Glu Val
            260                 265                 270

Glu Arg Leu Glu Arg Asp Leu Glu Lys Lys Thr Met Glu Thr Glu Glu
        275                 280                 285

Leu Arg Ser Glu Gln Thr Arg Phe Leu Glu Glu Ile Lys Ser Gln Asp
    290                 295                 300

Lys Leu Asn Lys Ser Leu Lys Glu Glu Ala Arg Leu Gln Lys Gln Ser
305                 310                 315                 320

Tyr Glu Glu Leu Glu Ser Asn Leu Asn Thr Lys Asn Glu Leu Leu Lys
                325                 330                 335

Gln Lys Thr Met Glu Leu Met Arg Ala Cys Gln Lys Gln Tyr Glu Met
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Val Glu Ile Asp Lys Thr Pro Asp Glu
    370                 375                 380

Ser Pro Tyr Ile Gly Lys Ser Arg Tyr Lys Arg Asn Met Phe Thr Thr
385                 390                 395                 400

Glu Ser Tyr Ile Ile Ala Asn Ala Gln Thr Val Lys Ile Lys Lys Met
                405                 410                 415

Glu Leu Asp Glu Gly Glu Gln Leu Arg Asn Glu His Val Asn Leu Gly
            420                 425                 430

Ala Ser Pro Thr Asp Ile Gln Leu Glu Asp Lys Glu Lys Lys Ile Ser
        435                 440                 445

Ala Ala Gln Thr Arg Leu Ser Glu Leu His Asp Glu Ile Glu Lys Ala
    450                 455                 460

Glu Gln Gln Ile Leu Arg Ala Thr Glu Glu Phe Lys Gln Leu Glu Glu
465                 470                 475                 480

Ala Ile Gln Leu Lys Lys Ile Ser Glu Ala Glu Lys Asp Leu Leu Phe
                485                 490                 495

Lys Gln Leu Ser Gly Arg Ile Gln Leu Leu Asn Lys Leu Arg Gln Glu
            500                 505                 510

Ala Val Asp Leu Glu Thr Gln Met Glu Lys Gln Arg Gln Glu Ile Gly
```

```
            515                 520                 525
Glu Lys Gln Asn Glu Ile Lys Asp Leu Glu Ile Val Thr Asp Ser Leu
    530                 535                 540

Asp Ser Arg Asp Pro Lys His Cys His Met Lys Ala Gln Lys Arg Gly
545                 550                 555                 560

Lys Glu Gln Gln Leu Asp Ile Met Asn Lys Gln Tyr Lys Gln Leu Glu
                565                 570                 575

Ser Arg Leu Asp Glu Ile Leu Ser Arg Ile Ala Lys Glu Thr Glu Glu
                580                 585                 590

Ile Lys Asp Leu Glu Glu Gln Leu Thr Glu Gly Gln Ile Ala Ala Asn
        595                 600                 605

Glu Ala Leu Lys Lys Asp Leu Glu Ser Val Ile Ser Gly Leu Gln Glu
    610                 615                 620

Tyr Leu Glu Thr Val Lys Gly Gln Ala Arg Gln Ala Gln Asn Glu Cys
625                 630                 635                 640

Arg Lys Leu Gln Asp Glu Lys Glu Thr Leu Leu Gln Arg Leu Ser Glu
                645                 650                 655

Val Glu Gln Glu Arg Asp Gln Leu Glu Ile Val Ala Ile Asp Ala Glu
                660                 665                 670

Asn Met Arg Lys Glu Leu Ala Glu Leu Glu Asn Ala Leu Gln Glu Gln
        675                 680                 685

His Glu Val Asn Ile Ser Leu Gln Gln Thr Gln Gly Asp Leu Ser Ala
    690                 695                 700

Tyr Glu Ala Glu Leu Glu Ala Gln Leu Lys Ile Arg Asp Ala Glu Ala
705                 710                 715                 720

Asn Gln Leu Lys Glu Glu Leu Glu Lys Leu Arg Arg Leu Ser Gln Leu
                725                 730                 735

Glu Gln Ser Ala Leu Gln Ala Glu Leu Glu Lys Glu Lys Gln Ala Phe
                740                 745                 750

Lys Thr Ala Val Lys Lys Ala Gln Leu Ser Glu Gly Lys Asp Gln Glu
        755                 760                 765

Asn Ser Glu Leu Arg Thr Gln Leu Gln Gln Leu Gln Asp Asp Asn Asp
    770                 775                 780

Leu Leu Lys Gln Gln Leu Lys Asp Phe Gln Ser His Leu Asn His Val
785                 790                 795                 800

Val Asp Gly Leu Ile Arg Pro Glu Glu Val Ala Ala Cys Val Asp Glu
                805                 810                 815

Leu Arg Lys Lys Leu Lys Ser Gly Ala Gly Glu Met Arg Ile His Thr
                820                 825                 830

Pro Ser Asp Val Leu Gly Lys Ser Leu Ala Asp Leu Gln Lys Gln Phe
        835                 840                 845

Ser Glu Ile Leu Ala Arg Ser Gln Trp Glu Arg Gln Glu Ala Gln Val
    850                 855                 860

Arg Glu Arg Lys Leu Gln Glu Glu Met Ala Leu Gln Gln Glu Lys Leu
865                 870                 875                 880

Ala Ser Gly Gln Glu Glu Phe Arg His Ala Cys Glu Arg Ala Leu Glu
                885                 890                 895

Ala Arg Ile Ser Phe Asp Lys Arg Gln His Glu Ala Arg Ile Gln Gln
                900                 905                 910

Leu Glu Asn Glu Ile His Tyr Leu Gln Glu Asn Leu Lys Ser Met Glu
        915                 920                 925

Glu Ile Gln Gly Leu Thr Asp Leu Gln Leu Gln Glu Ala Asp Glu Glu
    930                 935                 940
```

```
Lys Glu Arg Ile Leu Ala Gln Leu Arg Glu Leu Glu Lys Lys Lys
945                 950                 955                 960

Leu Glu Asp Ala Lys Ser Gln Glu Gln Phe Leu Gly Leu Asp Arg Glu
                965                 970                 975

Leu Lys Lys Leu Lys Lys Ala Val Ala Ala Ser Asp Lys Leu Ala Thr
                980                 985                 990

Ala Glu Leu Thr Ile Ala Lys Asp  Gln Leu Lys Ser Leu  His Gly Thr
            995                 1000                1005

Val Met  Lys Ile Asn Gln Glu  Arg Ala Glu Glu Leu  Gln Glu Thr
    1010                1015                1020

Glu Arg  Phe Ser Arg Lys Ala  Ala Gln Ala Ala Arg  Asp Leu Ile
    1025                1030                1035

Arg Ala  Glu Ala Glu Ile Glu  Leu Leu Gln Lys Leu  Leu Arg Asp
    1040                1045                1050

Lys Glu  Glu Gln Phe Arg Asn  Glu Ile Glu Lys Val  Asp Val Gly
    1055                1060                1065

Ser Gly  Gly Ala Lys Ser Gln  Met Leu Glu Met Glu  Lys Leu Asn
    1070                1075                1080

Glu Thr  Met Glu Arg Gln Arg  Thr Glu Ile Ala Arg  Leu Arg Asn
    1085                1090                1095

Leu Leu  Asp Leu Thr Gly Ala  Asp Asn Lys Gly Asn  Phe Glu Asn
    1100                1105                1110

Val Leu  Glu Glu Ile Ala Glu  Leu Arg Arg Glu Val  Ser His Gln
    1115                1120                1125

Asn Asp  Tyr Ile Ser Ser Met  Thr Asp Pro Phe Lys  Arg Arg Gly
    1130                1135                1140

Tyr Trp  Tyr Phe Met Pro Pro  Pro Ser Ser Ser Lys  Val Ser Ser
    1145                1150                1155

His Ser  Ser Gln Ala Thr Lys  Asp Ser Gly Val Gly  Leu Lys Tyr
    1160                1165                1170

Thr Ala  Ser Thr Pro Val Arg  Lys Pro His Arg Gly  Arg Gln Asp
    1175                1180                1185

Gly Lys  Glu Asn Ser Gly Pro  Pro Pro Ala Ser Gly  Tyr Trp Val
    1190                1195                1200

Tyr Ser  Pro Ile Arg Ser Gly  Leu His Lys Ser Phe  Ser Asn Arg
    1205                1210                1215

Asp Ala  Asp Ser Gly Gly Asp  Ser Gln Glu Glu Ser  Glu Leu Asp
    1220                1225                1230

Asp Gln  Glu Asp His Pro Phe  Val Pro Pro Pro Gly  Tyr Met Met
    1235                1240                1245

Tyr Thr  Val Phe Pro Asp Gly  Ser Pro Val Pro Gln  Gly Met Ala
    1250                1255                1260

Leu Tyr  Ala Pro Pro Pro Pro  Leu Pro Asn Asn Ser  Gln Pro Leu
    1265                1270                1275

Asp Leu  Gly Thr Val Val Tyr  Gly Pro Pro Val Gly  Gly Ala Pro
    1280                1285                1290

Ile Val  Tyr Gly Pro Pro Pro  Pro Asn Phe Ser Val  Pro Leu Ile
    1295                1300                1305

Pro Val  Gly Val Leu His Cys  Asn Val Pro Glu His  His Asn Leu
    1310                1315                1320

Glu Asn  Glu Val Ser Arg Leu  Glu Asp Ile Met Gln  His Leu Lys
    1325                1330                1335
```

```
Ser Gly Lys Arg Glu Gln Cys Met Lys Thr Pro Lys Leu Gln Ser
    1340                1345                1350

Glu Lys Glu Leu Ala Glu Leu Gln His Asn Ile Asp Gly Leu Leu
    1355                1360                1365

Gln Glu Lys Lys Asp Leu Glu His Glu Val Glu Leu His Arg
    1370                1375                1380

Thr Ile Gln Lys His Gln Gln Arg Lys Asp Phe Ile Asp Gly Asn
    1385                1390                1395

Val Glu Ser Leu Val Asn Asp Leu Glu Ile Glu Lys Ser Leu Lys
    1400                1405                1410

His His Glu Asp Ile Val Asp Glu Ile Glu Cys Ile Glu Arg Thr
    1415                1420                1425

Leu Leu Lys Arg Arg Ala Glu Leu Arg Glu Ala Asp Arg Leu Leu
    1430                1435                1440

Thr Glu Ala Glu Ser Glu Leu Ser Cys Thr Lys Glu Lys Thr Lys
    1445                1450                1455

His Ala Val Glu Lys Phe Thr Asp Ala Lys Arg Asn Leu Leu Gln
    1460                1465                1470

Thr Glu Lys Asp Ala Glu Glu Leu Glu Arg Arg Ala Gln Glu Thr
    1475                1480                1485

Ala Ile Asn Leu Val Lys Ala Asp Gln Gln Leu Arg Leu Leu Gln
    1490                1495                1500

Ala Asp Thr Lys Asp Leu Glu Gln His Lys Met Glu Gln Glu Glu
    1505                1510                1515

Ile Leu Lys Glu Ile Asn Lys Val Val Ala Ala Lys Asp Ser Asp
    1520                1525                1530

Phe Gln Ser Leu Asn Lys Lys Lys Glu Val Leu Thr Gly Glu Leu
    1535                1540                1545

Gln Lys Leu Gln Lys Asp Ile Glu Thr Ala Arg His Asn Glu Asp
    1550                1555                1560

Gln His Leu Gln Val Leu Lys Glu Ser Glu Thr Leu Leu Gln Ala
    1565                1570                1575

Lys Lys Ala Glu Leu Glu Asn Leu Lys Ser Gln Val Ser Gly Gln
    1580                1585                1590

Gln Gln Glu Met Ala Val Leu Asp Arg Glu Leu Gly His Lys Lys
    1595                1600                1605

Glu Glu Leu His Leu Leu Gln Glu Ser Met Val Gln Ala Lys Ala
    1610                1615                1620

Asp Leu Gln Glu Ala Leu Arg Leu Gly Glu Ser Glu Val Thr Glu
    1625                1630                1635

Lys Cys Asn His Ile Arg Glu Val Lys Ser Leu Leu Glu Glu Leu
    1640                1645                1650

Ser Phe Gln Lys Gly Glu Leu Asn Val Gln Ile Ser Glu Lys Lys
    1655                1660                1665

Thr Gln Leu Ala Leu Ile Lys Gln Glu Ile Glu Lys Glu Glu Asp
    1670                1675                1680

Asn Leu Gln Val Val Leu Gly Gln Met Ser Lys His Lys Thr Glu
    1685                1690                1695

Leu Lys Asn Ile Leu Asp Met Leu Gln Leu Glu Asn Asn Glu Leu
    1700                1705                1710

Gln Gly Leu Lys Leu Gln His Asp Gln Lys Met Ser Glu Leu Glu
    1715                1720                1725

Lys Thr Arg Val Glu Val Leu Glu Glu Lys Leu Glu Leu Glu Ser
```

```
              1730                1735                1740

Leu Gln Gln Ala Ala Leu Arg Gln Arg Gly Glu Ile Glu Trp Gln
              1745                1750                1755

Lys Gln Leu Leu Gln Arg Asn Thr Gln Glu Val Glu Arg Met Thr
              1760                1765                1770

Ala Glu Thr Arg Ala Leu Gln Ser Cys Val Glu Ser Leu Cys Lys
              1775                1780                1785

Glu Lys Gln Asp Leu Glu Glu Lys Gln Asp Ser Trp Glu Lys Lys
              1790                1795                1800

Leu Ala Gln Thr Lys Arg Val Leu Ala Ala Glu Glu Asp Ser
              1805                1810                1815

Glu Met Glu Arg Ala Arg Leu Glu Lys Leu Glu Leu Asp Ala Arg
              1820                1825                1830

Lys Leu Gln Gln Glu Leu Asp Gln Arg Asn Arg Glu Lys Leu Ser
              1835                1840                1845

Leu His Gln Asp Leu Ala Val Val Gln Gln Gln Leu Gln Glu Lys
              1850                1855                1860

Gln Glu Ala Val Asn Ser Leu Gln Lys Glu Leu Thr Asp Val Gln
              1865                1870                1875

Glu His Leu Asp Leu Ala Glu Gln Glu Val Leu Cys Thr Thr Lys
              1880                1885                1890

Arg Lys Asp Ala Leu Leu Ser Glu Gln Thr Arg Leu Glu Lys Asp
              1895                1900                1905

Val Gly Glu Trp Thr Lys Lys Phe Glu Asp Cys Gln Lys Glu Gly
              1910                1915                1920

Glu Thr Lys Gln Gln Gln Leu Gln Gly Leu Gln Lys Glu Ile Glu
              1925                1930                1935

Gly Asn Glu Ala Lys Leu Ala Gln Gln Glu Met Met Phe Gln Arg
              1940                1945                1950

Leu Gln Lys Glu Arg Glu Cys Glu Glu Lys Lys Leu Glu Ala Ser
              1955                1960                1965

Lys Val Thr Leu Lys Glu Gln Gln Gln Gln Leu Glu Lys Glu Leu
              1970                1975                1980

Met Glu Gln Lys Gly Lys Leu Asp Gln Val Leu Ala Lys Leu Leu
              1985                1990                1995

Val Ala Glu Glu Arg Val Arg Thr Leu Gln Glu Glu Gly Arg Trp
              2000                2005                2010

Ser Glu Thr Leu Glu Lys Thr Leu Ser Gln Thr Lys Arg Gln Leu
              2015                2020                2025

Ser Glu Arg Glu Gln Gln Leu Leu Ala Lys Ser Asp Glu Leu Leu
              2030                2035                2040

Ala Leu Gln Lys Glu Thr Asp Ser Met Arg Ala Asp Phe Ser Leu
              2045                2050                2055

Leu Arg Asn Gln Phe Leu Thr Glu Arg Lys Lys Ala Glu Lys Gln
              2060                2065                2070

Val Ala Ser Leu Lys Glu Ala Leu Lys Ile Gln Arg Ser Gln Leu
              2075                2080                2085

Glu Lys Asn Leu Leu Glu Gln Lys Gln Glu Asn Ser Cys Met Gln
              2090                2095                2100

Arg Glu Met Ala Thr Ile Glu Gln Val Ala Gln Asp Asn His Glu
              2105                2110                2115

Arg Ala Arg Arg Leu Met Arg Glu Leu Asn Gln Met Gln Arg Glu
              2120                2125                2130
```

```
Tyr Val Glu Leu Arg Lys Gln Met Thr Asn Lys Asp Leu Glu
    2135                2140                2145

Arg Arg Gln Met Glu Ile Ser Asp Ala Met Gln Ala Leu Lys Cys
2150                2155                2160

Glu Val Lys Asp Glu Ile Arg Thr Ser Leu Lys Asn Leu Asn Gln
    2165                2170                2175

Phe Leu Pro Glu Leu Pro Ala Asp Leu Glu Ala Leu Leu Glu Arg
    2180                2185                2190

Asn Glu Asn Leu Gly Gly Gly Leu Glu Ser Leu Lys Glu Asn Phe
    2195                2200                2205

Pro Phe Thr Val Ser Asp Arg Pro Ser Ser Cys Glu Glu Lys Leu
    2210                2215                2220

Asn Phe Gly Gln Ala His Val Ala Asp Glu Gln Trp Arg Gly Glu
    2225                2230                2235

Ala Leu Arg Glu Lys Leu Arg His Arg Glu Asp Arg Leu Lys Ala
    2240                2245                2250

Gln Leu Arg Arg Cys Met Ser Lys Gln Ala Glu Val Leu Ser Glu
    2255                2260                2265

Gly Arg Arg Arg Thr Glu Gly Thr Leu His Ser Leu Arg Arg Gln
    2270                2275                2280

Val Asp Ala Leu Gly Glu Leu Val Thr Ser Thr Gly Asp Ser
    2285                2290                2295

Ala Ser Thr Arg Ser Leu Ser Arg Thr Glu Gly Ser Leu Ala Glu
    2300                2305                2310

Asp Glu Pro Pro Gly Pro Ser Gln Ser Ser Arg Arg Leu Pro Arg
    2315                2320                2325

Gly Pro Ser Pro Arg Leu Asp Ala His Arg Pro
    2330                2335

<210> SEQ ID NO 27
<211> LENGTH: 7431
<212> TYPE: DNA
<213> ORGANISM: Homo sapiens
<220> FEATURE:
<221> NAME/KEY: CDS
<222> LOCATION: (32)..(7009)

<400> SEQUENCE: 27
gttttgatga acacctggct ttattcttgc a atg aag aaa ggt tct caa caa        52
                                   Met Lys Lys Gly Ser Gln Gln
                                     1               5 aaa ata ttc tcc aaa gca aag ata cca tca tca tct cac tct cct atc     100
Lys Ile Phe Ser Lys Ala Lys Ile Pro Ser Ser Ser His Ser Pro Ile
        10                  15                  20 cca tca tct atg tcc aat atg aga tct agg tca ctt tca cct ttg att     148
Pro Ser Ser Met Ser Asn Met Arg Ser Arg Ser Leu Ser Pro Leu Ile
    25                  30                  35 gga tca gag act cta cct ttt cat tct gga gga cag tgg tgt gag caa     196
Gly Ser Glu Thr Leu Pro Phe His Ser Gly Gly Gln Trp Cys Glu Gln
40                  45                  50                  55 gtt gag att gca gat gaa aac aat atg ctt ttg gac tat caa gac cat     244
Val Glu Ile Ala Asp Glu Asn Asn Met Leu Leu Asp Tyr Gln Asp His
                60                  65                  70 aaa gga gct gat tca cat gca gga gtt aga tat att aca gag gcc ctc     292
Lys Gly Ala Asp Ser His Ala Gly Val Arg Tyr Ile Thr Glu Ala Leu
            75                  80                  85 att aaa aaa ctt act aaa cag gat aat ttg gct ttg ata aaa tct ctg     340
```

```
            Ile Lys Lys Leu Thr Lys Gln Asp Asn Leu Ala Leu Ile Lys Ser Leu
                         90                  95                 100 aac ctt tca ctt tct aaa gac ggt ggc aag aaa ttt aag tat att gag      388
Asn Leu Ser Leu Ser Lys Asp Gly Gly Lys Lys Phe Lys Tyr Ile Glu
            105                 110                 115 aat ttg gaa aaa tgt gtt aaa ctt gaa gta ctg aat ctc agc tat aat      436
Asn Leu Glu Lys Cys Val Lys Leu Glu Val Leu Asn Leu Ser Tyr Asn
120                 125                 130                 135 cta ata ggg aag att gaa aag ttg gac aag ctg tta aaa tta cgt gaa      484
Leu Ile Gly Lys Ile Glu Lys Leu Asp Lys Leu Leu Lys Leu Arg Glu
                140                 145                 150 ctc aac tta tca tat aac aaa atc agc aaa att gaa ggc ata gaa aat      532
Leu Asn Leu Ser Tyr Asn Lys Ile Ser Lys Ile Glu Gly Ile Glu Asn
            155                 160                 165 atg tgt aat ctg caa aag ctt aac ctt gca gga aat gaa att gag cat      580
Met Cys Asn Leu Gln Lys Leu Asn Leu Ala Gly Asn Glu Ile Glu His
        170                 175                 180 att cca gta tgg tta ggg aag aag tta aaa tct ttg cga gtc ctc aat      628
Ile Pro Val Trp Leu Gly Lys Lys Leu Lys Ser Leu Arg Val Leu Asn
185                 190                 195 ttg aaa ggc aac aag ata tca tcg ctc caa gat ata agc aag ttg aaa      676
Leu Lys Gly Asn Lys Ile Ser Ser Leu Gln Asp Ile Ser Lys Leu Lys
200                 205                 210                 215 ccg ctt caa gat ttg att tct ctg atc cta gtt gaa aat cca gtt gtg      724
Pro Leu Gln Asp Leu Ile Ser Leu Ile Leu Val Glu Asn Pro Val Val
                220                 225                 230 acc ctt cct cat tac ctc cag ttt acc att ttc cac ctc cgt tca ttg      772
Thr Leu Pro His Tyr Leu Gln Phe Thr Ile Phe His Leu Arg Ser Leu
            235                 240                 245 gaa agt ttg gaa ggt cag cca gta acc act cag gat aga cag gag gct      820
Glu Ser Leu Glu Gly Gln Pro Val Thr Thr Gln Asp Arg Gln Glu Ala
        250                 255                 260 ttt gag aga ttc agt tta gaa gag gta gaa aga ctg gaa aga gac cta      868
Phe Glu Arg Phe Ser Leu Glu Glu Val Glu Arg Leu Glu Arg Asp Leu
265                 270                 275 gaa aaa aag atg ata gaa act gaa gag ctt aag agc aaa caa aca agg      916
Glu Lys Lys Met Ile Glu Thr Glu Glu Leu Lys Ser Lys Gln Thr Arg
280                 285                 290                 295 ttc ctt gag gaa att aaa aat caa gat aaa ttg aat aaa tca tta aaa      964
Phe Leu Glu Glu Ile Lys Asn Gln Asp Lys Leu Asn Lys Ser Leu Lys
                300                 305                 310 gag gag gcc atg tta cag aaa cag agc tgt gag gaa ctc aag agt gac     1012
Glu Glu Ala Met Leu Gln Lys Gln Ser Cys Glu Glu Leu Lys Ser Asp
            315                 320                 325 tta aac aca aaa aat gaa ttg cta aaa cag aag acc ata gaa tta aca     1060
Leu Asn Thr Lys Asn Glu Leu Leu Lys Gln Lys Thr Ile Glu Leu Thr
        330                 335                 340 cga gca tgt cag aag caa tat gag ctg gaa cag gaa ttg gcc ttt tat     1108
Arg Ala Cys Gln Lys Gln Tyr Glu Leu Glu Gln Glu Leu Ala Phe Tyr
345                 350                 355 aaa att gat gct aaa ttt gag cca cta aat tat tat cca tca gag tat     1156
Lys Ile Asp Ala Lys Phe Glu Pro Leu Asn Tyr Tyr Pro Ser Glu Tyr
360                 365                 370                 375 gct gaa att gat aaa gcc cca gat gaa agc cct tac att ggc aaa tcc     1204
Ala Glu Ile Asp Lys Ala Pro Asp Glu Ser Pro Tyr Ile Gly Lys Ser
                380                 385                 390 aga tac aag aga aat atg ttt gcc aca gag agt tat att att gac agt     1252
Arg Tyr Lys Arg Asn Met Phe Ala Thr Glu Ser Tyr Ile Ile Asp Ser
            395                 400                 405
```

| | |
|---|---|
| gct cag gca gta cag atc aag aag atg gag cca gat gaa caa ctt aga<br>Ala Gln Ala Val Gln Ile Lys Lys Met Glu Pro Asp Glu Gln Leu Arg<br>410 415 420 | 1300 |
| aat gat cac atg aac ttg aga ggc cac aca cca ctg gac acg caa ctg<br>Asn Asp His Met Asn Leu Arg Gly His Thr Pro Leu Asp Thr Gln Leu<br>425 430 435 | 1348 |
| gaa gac aaa gaa aaa aaa ata agt gca gca caa act cga cta tca gaa<br>Glu Asp Lys Glu Lys Lys Ile Ser Ala Ala Gln Thr Arg Leu Ser Glu<br>440 445 450 455 | 1396 |
| ctg cat gat gaa ata gaa aag gca gaa caa caa att ttg aga gct act<br>Leu His Asp Glu Ile Glu Lys Ala Glu Gln Gln Ile Leu Arg Ala Thr<br>460 465 470 | 1444 |
| gaa gaa ttt aaa caa ctg gaa gaa gct ata caa cta aaa aag att tca<br>Glu Glu Phe Lys Gln Leu Glu Glu Ala Ile Gln Leu Lys Lys Ile Ser<br>475 480 485 | 1492 |
| gaa gca ggg aaa gac ctt ctt tac aag cag ttg agt ggt aga cta caa<br>Glu Ala Gly Lys Asp Leu Leu Tyr Lys Gln Leu Ser Gly Arg Leu Gln<br>490 495 500 | 1540 |
| ctt gta aat aaa tta cgc cag gaa gct ctg gat cta gaa ctg cag atg<br>Leu Val Asn Lys Leu Arg Gln Glu Ala Leu Asp Leu Glu Leu Gln Met<br>505 510 515 | 1588 |
| gaa aag caa aag cag gaa att gcc gga aag cag aag gag att aag gac<br>Glu Lys Gln Lys Gln Glu Ile Ala Gly Lys Gln Lys Glu Ile Lys Asp<br>520 525 530 535 | 1636 |
| ctg caa ata gcc ata gat agc ctg gat tcc aaa gac cca aaa cat tcc<br>Leu Gln Ile Ala Ile Asp Ser Leu Asp Ser Lys Asp Pro Lys His Ser<br>540 545 550 | 1684 |
| cat atg aag gct caa aag agc ggt aaa gaa caa cag ctt gac att atg<br>His Met Lys Ala Gln Lys Ser Gly Lys Glu Gln Gln Leu Asp Ile Met<br>555 560 565 | 1732 |
| aac aag cag tac caa caa ctt gaa agt cgt ttg gat gag ata ctt tct<br>Asn Lys Gln Tyr Gln Gln Leu Glu Ser Arg Leu Asp Glu Ile Leu Ser<br>570 575 580 | 1780 |
| aga att gct aag gaa acg gaa gag att aag gac ctt gaa gaa cag ctt<br>Arg Ile Ala Lys Glu Thr Glu Glu Ile Lys Asp Leu Glu Glu Gln Leu<br>585 590 595 | 1828 |
| act gaa ggc cag ata gca gca aat gaa gcc ctg aag aag gat tta gaa<br>Thr Glu Gly Gln Ile Ala Ala Asn Glu Ala Leu Lys Lys Asp Leu Glu<br>600 605 610 615 | 1876 |
| ggt gtt atc agt ggg ttg caa gaa tac ctg ggg acc att aaa ggc cag<br>Gly Val Ile Ser Gly Leu Gln Glu Tyr Leu Gly Thr Ile Lys Gly Gln<br>620 625 630 | 1924 |
| gca act cag gcc cag aat gag tgc agg aag ctg cgg gat gag aaa gag<br>Ala Thr Gln Ala Gln Asn Glu Cys Arg Lys Leu Arg Asp Glu Lys Glu<br>635 640 645 | 1972 |
| aca ttg ttg cag aga ttg aca gaa gtc gag cag gag aga gac cag ctg<br>Thr Leu Leu Gln Arg Leu Thr Glu Val Glu Gln Glu Arg Asp Gln Leu<br>650 655 660 | 2020 |
| gaa ata gtt gcc atg gat gca gaa aat atg agg aag gag ctt gca gag<br>Glu Ile Val Ala Met Asp Ala Glu Asn Met Arg Lys Glu Leu Ala Glu<br>665 670 675 | 2068 |
| cta gaa agt gcc ctc caa gag cag cat gag gtg aat gca tct ttg cag<br>Leu Glu Ser Ala Leu Gln Glu Gln His Glu Val Asn Ala Ser Leu Gln<br>680 685 690 695 | 2116 |
| cag acc cag gga gat ctc agt gcc tat gaa gct gag cta gag gct cgg<br>Gln Thr Gln Gly Asp Leu Ser Ala Tyr Glu Ala Glu Leu Glu Ala Arg<br>700 705 710 | 2164 |
| cta aac cta agg gat gct gaa gcc aac cag ctc aag gaa gag ttg gaa<br>Leu Asn Leu Arg Asp Ala Glu Ala Asn Gln Leu Lys Glu Glu Leu Glu<br>715 720 725 | 2212 |

```
aaa gta aca aga ctt acc cag tta gaa caa tca gcc ctt caa gca gaa    2260
Lys Val Thr Arg Leu Thr Gln Leu Glu Gln Ser Ala Leu Gln Ala Glu
        730                 735                 740 ctt gag aag gaa agg caa gcc ctc aag aat gcc ctt gga aaa gcc cag    2308
Leu Glu Lys Glu Arg Gln Ala Leu Lys Asn Ala Leu Gly Lys Ala Gln
745                 750                 755 ttc tca gaa gaa aag gag caa gag aac agt gag ctc cat gca aaa ctt    2356
Phe Ser Glu Glu Lys Glu Gln Glu Asn Ser Glu Leu His Ala Lys Leu
760                 765                 770                 775 aaa cac ttg cag gat gac aat aat ctg tta aaa cag caa ctt aaa gat    2404
Lys His Leu Gln Asp Asp Asn Asn Leu Leu Lys Gln Gln Leu Lys Asp
                780                 785                 790 ttc cag aat cac ctt aac cat gtg gtt gat ggt ttg gtt cgt cca gaa    2452
Phe Gln Asn His Leu Asn His Val Val Asp Gly Leu Val Arg Pro Glu
            795                 800                 805 gaa gtg gca gct cgt gtg gat gag cta aga aga aaa ctg aaa tta gga    2500
Glu Val Ala Ala Arg Val Asp Glu Leu Arg Arg Lys Leu Lys Leu Gly
        810                 815                 820 act ggg gaa atg aac atc cat agt cct tca gat gtc tta ggg aaa agt    2548
Thr Gly Glu Met Asn Ile His Ser Pro Ser Asp Val Leu Gly Lys Ser
825                 830                 835 ctt gct gat tta cag aaa caa ttc agt gaa att ctt gca cgc tcc aag    2596
Leu Ala Asp Leu Gln Lys Gln Phe Ser Glu Ile Leu Ala Arg Ser Lys
840                 845                 850                 855 tgg gaa aga gat gaa gca caa gtt aga gag aga aaa ctc caa gaa gaa    2644
Trp Glu Arg Asp Glu Ala Gln Val Arg Glu Arg Lys Leu Gln Glu Glu
                860                 865                 870 atg gct ctg cag caa gag aaa ctg gca act gga caa gaa gag ttc agg    2692
Met Ala Leu Gln Gln Glu Lys Leu Ala Thr Gly Gln Glu Glu Phe Arg
            875                 880                 885 cag gcc tgt gag aga gcc ctg gaa gca aga atg aat ttt gat aag agg    2740
Gln Ala Cys Glu Arg Ala Leu Glu Ala Arg Met Asn Phe Asp Lys Arg
        890                 895                 900 caa cat gaa gca aga atc cag caa atg gag aat gaa att cac tat ttg    2788
Gln His Glu Ala Arg Ile Gln Gln Met Glu Asn Glu Ile His Tyr Leu
905                 910                 915 caa gaa aat cta aaa agt atg gag gaa atc caa ggc ctt aca gat ctc    2836
Gln Glu Asn Leu Lys Ser Met Glu Glu Ile Gln Gly Leu Thr Asp Leu
920                 925                 930                 935 caa ctt cag gaa gct gat gaa gag aag gag aga att ctg gcc caa ctc    2884
Gln Leu Gln Glu Ala Asp Glu Glu Lys Glu Arg Ile Leu Ala Gln Leu
                940                 945                 950 cga gag tta gag aaa aag aag aaa ctt gaa gat gcc aaa tct cag gag    2932
Arg Glu Leu Glu Lys Lys Lys Lys Leu Glu Asp Ala Lys Ser Gln Glu
            955                 960                 965 caa gtt ttt ggt tta gat aaa gaa ctg aag aaa cta aag aaa gcc gtg    2980
Gln Val Phe Gly Leu Asp Lys Glu Leu Lys Lys Leu Lys Lys Ala Val
        970                 975                 980 gcc acc tct gat aag cta gcc aca gct gag ctc acc att gcc aaa gac    3028
Ala Thr Ser Asp Lys Leu Ala Thr Ala Glu Leu Thr Ile Ala Lys Asp
985                 990                 995 cag ctg aag tcc ctt cat gga act gtt atg aaa att aac cag gag        3073
Gln Leu Lys Ser Leu His Gly Thr Val Met Lys Ile Asn Gln Glu
    1000                1005                1010 cga gca gag gag ttg cag gaa gca gag agg ttc agc aga aag gca        3118
Arg Ala Glu Glu Leu Gln Glu Ala Glu Arg Phe Ser Arg Lys Ala
1015                1020                1025 gca caa gca gcc aga gat ctc acc cga gca gaa gct gag atc gaa        3163
Ala Gln Ala Ala Arg Asp Leu Thr Arg Ala Glu Ala Glu Ile Glu
```

```
                                                   -continued 1030                     1035                     1040 ctc ctg cag aat ctc ctc agg cag aag ggg gag cag ttt cga ctt     3208
Leu Leu Gln Asn Leu Leu Arg Gln Lys Gly Glu Gln Phe Arg Leu
1045                     1050                    1055 gag atg gag aaa aca ggt gta ggt act gga gca aac tca cag gtc     3253
Glu Met Glu Lys Thr Gly Val Gly Thr Gly Ala Asn Ser Gln Val
1060                     1065                    1070 cta gaa att gag aaa ctg aat gag aca atg gaa cga caa agg aca     3298
Leu Glu Ile Glu Lys Leu Asn Glu Thr Met Glu Arg Gln Arg Thr
1075                     1080                    1085 gag att gca agg ctg cag aat gta cta gac ctc act gga agt gac     3343
Glu Ile Ala Arg Leu Gln Asn Val Leu Asp Leu Thr Gly Ser Asp
1090                     1095                    1100 aac aaa gga ggc ttt gaa aat gtt tta gaa gaa att gct gaa ctt     3388
Asn Lys Gly Gly Phe Glu Asn Val Leu Glu Glu Ile Ala Glu Leu
1105                     1110                    1115 cga cgt gaa gtt tct tat cag aat gat tac ata agc agc atg gca     3433
Arg Arg Glu Val Ser Tyr Gln Asn Asp Tyr Ile Ser Ser Met Ala
1120                     1125                    1130 gat cct ttc aaa aga cga ggc tat tgg tac ttt atg cca cca cca     3478
Asp Pro Phe Lys Arg Arg Gly Tyr Trp Tyr Phe Met Pro Pro Pro
1135                     1140                    1145 cca tca tca aaa gtt tcc agc cat agt tcc cag gcc acc aag gac     3523
Pro Ser Ser Lys Val Ser Ser His Ser Ser Gln Ala Thr Lys Asp
1150                     1155                    1160 tct ggt gtt ggc ctt aag tac tca gcc tca act cct gtt aga aaa     3568
Ser Gly Val Gly Leu Lys Tyr Ser Ala Ser Thr Pro Val Arg Lys
1165                     1170                    1175 cca cgc cct ggg cag cag gat ggg aag gaa ggc agt caa cct ccc     3613
Pro Arg Pro Gly Gln Gln Asp Gly Lys Glu Gly Ser Gln Pro Pro
1180                     1185                    1190 cct gcc tca gga tac tgg gtt tat tct ccc atc agg agt ggg tta     3658
Pro Ala Ser Gly Tyr Trp Val Tyr Ser Pro Ile Arg Ser Gly Leu
1195                     1200                    1205 cat aaa ctg ttt cca agt aga gat gca gac agt gga gga gat agt     3703
His Lys Leu Phe Pro Ser Arg Asp Ala Asp Ser Gly Gly Asp Ser
1210                     1215                    1220 cag gaa gag agt gag ctg gat gac caa gaa gaa ccc cca ttt gtg     3748
Gln Glu Glu Ser Glu Leu Asp Asp Gln Glu Glu Pro Pro Phe Val
1225                     1230                    1235 cct cct cct gga tac atg atg tat act gtg ctt cct gat ggt tct     3793
Pro Pro Pro Gly Tyr Met Met Tyr Thr Val Leu Pro Asp Gly Ser
1240                     1245                    1250 cct gta ccc cag ggc atg gcc ctg tat gca cca cct cct ccc ttg     3838
Pro Val Pro Gln Gly Met Ala Leu Tyr Ala Pro Pro Pro Pro Leu
1255                     1260                    1265 cca aac aat agc cga cct ctc acc cct ggc act gtt gtt tat ggc     3883
Pro Asn Asn Ser Arg Pro Leu Thr Pro Gly Thr Val Val Tyr Gly
1270                     1275                    1280 cca cct cct gct ggg gcc ccc atg gtg tat ggg cct cca ccc ccc     3928
Pro Pro Pro Ala Gly Ala Pro Met Val Tyr Gly Pro Pro Pro Pro
1285                     1290                    1295 aac ttc tcc atc ccc ttc atc cct atg ggt gtg ctg cat tgc aac     3973
Asn Phe Ser Ile Pro Phe Ile Pro Met Gly Val Leu His Cys Asn
1300                     1305                    1310 gtc cct gaa cac cat aac tta gag aat gaa gtt tct aga tta gaa     4018
Val Pro Glu His His Asn Leu Glu Asn Glu Val Ser Arg Leu Glu
1315                     1320                    1325 gac ata atg cag cat tta aaa tca aag aag cgg gaa gaa agg tgg     4063
```

```
                Asp Ile Met Gln His Leu Lys Ser Lys Lys Arg Glu Glu Arg Trp
                1330                1335                1340 atg aga gca tcc aag cgg cag tcg gag aaa gaa atg gaa gaa ctg       4108
Met Arg Ala Ser Lys Arg Gln Ser Glu Lys Glu Met Glu Glu Leu
1345                1350                1355 cat cat aat att gat gat ctt ttg caa gag aag aaa agc tta gag       4153
His His Asn Ile Asp Asp Leu Leu Gln Glu Lys Lys Ser Leu Glu
    1360                1365                1370 tgt gaa gta gaa gaa tta cat aga act gtc cag aaa cgt caa cag       4198
Cys Glu Val Glu Glu Leu His Arg Thr Val Gln Lys Arg Gln Gln
1375                1380                1385 caa aag gac ttc att gat gga aat gtt gag agt ctt atg act gaa       4243
Gln Lys Asp Phe Ile Asp Gly Asn Val Glu Ser Leu Met Thr Glu
    1390                1395                1400 cta gaa ata gaa aaa tca ctc aaa cat cat gaa gat att gta gat       4288
Leu Glu Ile Glu Lys Ser Leu Lys His His Glu Asp Ile Val Asp
1405                1410                1415 gaa att gag tgc att gag aag act ctt ctg aaa cgt cgc tca gag       4333
Glu Ile Glu Cys Ile Glu Lys Thr Leu Leu Lys Arg Arg Ser Glu
1420                1425                1430 ctc agg gaa gct gac cga ctc ctg gca gag gct gag agt gaa ctt       4378
Leu Arg Glu Ala Asp Arg Leu Leu Ala Glu Ala Glu Ser Glu Leu
1435                1440                1445 tca tgc act aaa gaa aag aca aaa aat gct gtt gaa aag ttc act       4423
Ser Cys Thr Lys Glu Lys Thr Lys Asn Ala Val Glu Lys Phe Thr
1450                1455                1460 gat gcc aag aga agt tta ttg caa act gag tca gat gct gag gaa       4468
Asp Ala Lys Arg Ser Leu Leu Gln Thr Glu Ser Asp Ala Glu Glu
1465                1470                1475 tta gaa agg aga gct cag gaa act gct gtt aac ctc gtc aaa gct       4513
Leu Glu Arg Arg Ala Gln Glu Thr Ala Val Asn Leu Val Lys Ala
    1480                1485                1490 gat cag cag cta aga tcg ctc cag gct gat gca aag gat ttg gag       4558
Asp Gln Gln Leu Arg Ser Leu Gln Ala Asp Ala Lys Asp Leu Glu
1495                1500                1505 cag cac aaa atc aag caa gaa gaa atc ttg aaa gaa ata aac aaa       4603
Gln His Lys Ile Lys Gln Glu Glu Ile Leu Lys Glu Ile Asn Lys
1510                1515                1520 att gta gca gca aaa gac tca gac ttc caa tgt tta agc aag aag       4648
Ile Val Ala Ala Lys Asp Ser Asp Phe Gln Cys Leu Ser Lys Lys
1525                1530                1535 aag gaa aaa ctg aca gaa gag ctt cag aaa cta cag aaa gac ata       4693
Lys Glu Lys Leu Thr Glu Glu Leu Gln Lys Leu Gln Lys Asp Ile
1540                1545                1550 gag atg gca gaa cgc aat gag gat cac cac ctg cag gtc ctt aaa       4738
Glu Met Ala Glu Arg Asn Glu Asp His His Leu Gln Val Leu Lys
1555                1560                1565 gaa tct gag gtg ctt ctt cag gcc aaa aga gcc gag ctg gaa aag       4783
Glu Ser Glu Val Leu Leu Gln Ala Lys Arg Ala Glu Leu Glu Lys
1570                1575                1580 ctg aaa agc cag gtg aca agt cag cag cag gag atg gct gtc ttg       4828
Leu Lys Ser Gln Val Thr Ser Gln Gln Gln Glu Met Ala Val Leu
1585                1590                1595 gac agg cag tta ggg cat aaa aag gag gag ctg cat cta ctc caa       4873
Asp Arg Gln Leu Gly His Lys Lys Glu Glu Leu His Leu Leu Gln
1600                1605                1610 gga agc atg gtc cag gca aaa gct gac ctc cag gaa gct ctg aga       4918
Gly Ser Met Val Gln Ala Lys Ala Asp Leu Gln Glu Ala Leu Arg
1615                1620                1625
```

```
ctg gga gag act gaa gta act gag aag tgc aat cac att agg gaa      4963
Leu Gly Glu Thr Glu Val Thr Glu Lys Cys Asn His Ile Arg Glu
1630                1635                1640 gta aaa tct ctt ctg gaa gaa ctg agt ttt cag aaa gga gaa cta      5008
Val Lys Ser Leu Leu Glu Glu Leu Ser Phe Gln Lys Gly Glu Leu
1645                1650                1655 aat gtt cag att agt gaa aga aaa act caa ctt aca ctt ata aag      5053
Asn Val Gln Ile Ser Glu Arg Lys Thr Gln Leu Thr Leu Ile Lys
1660                1665                1670 cag gaa att gaa aaa gag gaa gaa aat ctt cag gtt gtt tta agg      5098
Gln Glu Ile Glu Lys Glu Glu Glu Asn Leu Gln Val Val Leu Arg
1675                1680                1685 cag atg tct aaa cat aaa acc gaa cta aag aat att ctg gac atg      5143
Gln Met Ser Lys His Lys Thr Glu Leu Lys Asn Ile Leu Asp Met
1690                1695                1700 ttg caa ctt gaa aac cat gag cta caa ggt ttg aag cta caa cat      5188
Leu Gln Leu Glu Asn His Glu Leu Gln Gly Leu Lys Leu Gln His
1705                1710                1715 gac caa agg gta tct gaa tta gag aag act cag gtg gca gtg cta      5233
Asp Gln Arg Val Ser Glu Leu Glu Lys Thr Gln Val Ala Val Leu
1720                1725                1730 gag gag aaa ctg gag tta gag aat ttg cag cag ata tcc cag cag      5278
Glu Glu Lys Leu Glu Leu Glu Asn Leu Gln Gln Ile Ser Gln Gln
1735                1740                1745 cag aaa ggg gaa ata gag tgg cag aag cag ctc ctt gag agg gat      5323
Gln Lys Gly Glu Ile Glu Trp Gln Lys Gln Leu Leu Glu Arg Asp
1750                1755                1760 aaa cga gaa ata gaa cga atg act gct gag tcc cga gct tta caa      5368
Lys Arg Glu Ile Glu Arg Met Thr Ala Glu Ser Arg Ala Leu Gln
1765                1770                1775 tcg tgt gtt gag tgt ttg agc aaa gaa aag gaa gat ctc caa gag      5413
Ser Cys Val Glu Cys Leu Ser Lys Glu Lys Glu Asp Leu Gln Glu
1780                1785                1790 aaa tgt gac att tgg gaa aaa aag ttg gca caa acc aaa agg gtt      5458
Lys Cys Asp Ile Trp Glu Lys Lys Leu Ala Gln Thr Lys Arg Val
1795                1800                1805 tta gca gca gca gaa gaa aat agc aaa atg gag caa tca aac tta      5503
Leu Ala Ala Ala Glu Glu Asn Ser Lys Met Glu Gln Ser Asn Leu
1810                1815                1820 gaa aag ttg gaa ttg aat gtc aga aaa ctg cag cag gaa cta gac      5548
Glu Lys Leu Glu Leu Asn Val Arg Lys Leu Gln Gln Glu Leu Asp
1825                1830                1835 caa cta aac aga gac aag ttg tca ctg cat aac gac att tca gca      5593
Gln Leu Asn Arg Asp Lys Leu Ser Leu His Asn Asp Ile Ser Ala
1840                1845                1850 atg caa cag cag ctc caa gaa aaa cga gaa gca gta aac tca ctg      5638
Met Gln Gln Gln Leu Gln Glu Lys Arg Glu Ala Val Asn Ser Leu
1855                1860                1865 cag gag gaa cta gct aat gtc caa gac cat ttg aac cta gca aaa      5683
Gln Glu Glu Leu Ala Asn Val Gln Asp His Leu Asn Leu Ala Lys
1870                1875                1880 cag gac ctg ctt cac acc acc aag cat cag gat gtg ttg ctc agt      5728
Gln Asp Leu Leu His Thr Thr Lys His Gln Asp Val Leu Leu Ser
1885                1890                1895 gag cag acc cga ctc cag aag gac atc agt gaa tgg gca aat agg      5773
Glu Gln Thr Arg Leu Gln Lys Asp Ile Ser Glu Trp Ala Asn Arg
1900                1905                1910 ttt gaa gac tgt cag aaa gaa gag gag aca aaa caa caa caa ctt      5818
Phe Glu Asp Cys Gln Lys Glu Glu Glu Thr Lys Gln Gln Gln Leu
1915                1920                1925
```

-continued

```
caa gtg ctt cag aat gag att gaa gaa aac aag ctc aaa cta gtc      5863
Gln Val Leu Gln Asn Glu Ile Glu Glu Asn Lys Leu Lys Leu Val
1930                1935                1940 caa caa gaa atg atg ttt cag aga ctc cag aaa gag aga gaa agt      5908
Gln Gln Glu Met Met Phe Gln Arg Leu Gln Lys Glu Arg Glu Ser
1945                1950                1955 gaa gaa agc aaa tta gaa acc agt aaa gtg aca ctg aag gag caa      5953
Glu Glu Ser Lys Leu Glu Thr Ser Lys Val Thr Leu Lys Glu Gln
1960                1965                1970 cag cac cag ctg gaa aag gaa tta aca gac cag aaa agc aaa ctg      5998
Gln His Gln Leu Glu Lys Glu Leu Thr Asp Gln Lys Ser Lys Leu
1975                1980                1985 gac caa gtg ctc tca aag gtg ctg gca gct gaa gag cgt gtt agg      6043
Asp Gln Val Leu Ser Lys Val Leu Ala Ala Glu Glu Arg Val Arg
1990                1995                2000 act ctg cag gaa gag gag agg tgg tgt gag agc ctg gag aag aca      6088
Thr Leu Gln Glu Glu Glu Arg Trp Cys Glu Ser Leu Glu Lys Thr
2005                2010                2015 ctc tcc caa act aaa cgg cag ctt tca gaa agg gag cag caa ttg      6133
Leu Ser Gln Thr Lys Arg Gln Leu Ser Glu Arg Glu Gln Gln Leu
2020                2025                2030 gtg gag aaa tca ggt gag ctg ttg gcc ctc cag aaa gag gca gat      6178
Val Glu Lys Ser Gly Glu Leu Leu Ala Leu Gln Lys Glu Ala Asp
2035                2040                2045 tct atg agg gca gac ttc agc ctt ctg cgg aac cag ttc ttg aca      6223
Ser Met Arg Ala Asp Phe Ser Leu Leu Arg Asn Gln Phe Leu Thr
2050                2055                2060 gaa aga aag aaa gct gag aag cag gtg gcc agc ctg aag gaa gca      6268
Glu Arg Lys Lys Ala Glu Lys Gln Val Ala Ser Leu Lys Glu Ala
2065                2070                2075 ctt aag atc cag cgg agc cag ctg gag aaa aac ctt ctt gag caa      6313
Leu Lys Ile Gln Arg Ser Gln Leu Glu Lys Asn Leu Leu Glu Gln
2080                2085                2090 aaa cag gag aac agc tgc ata caa aag gaa atg gca aca att gaa      6358
Lys Gln Glu Asn Ser Cys Ile Gln Lys Glu Met Ala Thr Ile Glu
2095                2100                2105 ctg gta gcc cag gac aac cat gag cgg gcc agg cgc ctg atg aag      6403
Leu Val Ala Gln Asp Asn His Glu Arg Ala Arg Arg Leu Met Lys
2110                2115                2120 gag ctc aac cag atg cag tat gag tac acg gag ctc aag aaa cag      6448
Glu Leu Asn Gln Met Gln Tyr Glu Tyr Thr Glu Leu Lys Lys Gln
2125                2130                2135 atg gca aac caa aaa gat ttg gag aga aga caa atg gaa atc agt      6493
Met Ala Asn Gln Lys Asp Leu Glu Arg Arg Gln Met Glu Ile Ser
2140                2145                2150 gat gca atg agg aca ctt aaa tct gag gtg aag gat gaa atc aga      6538
Asp Ala Met Arg Thr Leu Lys Ser Glu Val Lys Asp Glu Ile Arg
2155                2160                2165 acc agc ttg aag aat ctt aat cag ttt ctt cca gaa cta cca gca      6583
Thr Ser Leu Lys Asn Leu Asn Gln Phe Leu Pro Glu Leu Pro Ala
2170                2175                2180 gat cta gaa gct att ttg gaa aga aac gaa aac cta gaa gga gaa      6628
Asp Leu Glu Ala Ile Leu Glu Arg Asn Glu Asn Leu Glu Gly Glu
2185                2190                2195 ttg gaa agc ttg aaa gag aac ctt cca ttt acc atg aat gag gga      6673
Leu Glu Ser Leu Lys Glu Asn Leu Pro Phe Thr Met Asn Glu Gly
2200                2205                2210 cct ttt gaa gaa aaa ctg aac ttt tcc caa gtt cac ata atg gat      6718
Pro Phe Glu Glu Lys Leu Asn Phe Ser Gln Val His Ile Met Asp
```

```
gaa cac tgg cgt gga gaa gca ctc cgg gag aaa ctg cgt cac cgg      6763
Glu His Trp Arg Gly Glu Ala Leu Arg Glu Lys Leu Arg His Arg
2230            2235                2240 gaa gac cga ctc aag gcc caa ctc cga cac tgt atg tcc aag caa      6808
Glu Asp Arg Leu Lys Ala Gln Leu Arg His Cys Met Ser Lys Gln
2245            2250                2255 gca gaa gta tta att aaa gga aag cgg cag aca gag ggc act tta      6853
Ala Glu Val Leu Ile Lys Gly Lys Arg Gln Thr Glu Gly Thr Leu
2260            2265                2270 cac agt ttg agg aga caa gta gat gct tta ggg gaa ttg gtc acc      6898
His Ser Leu Arg Arg Gln Val Asp Ala Leu Gly Glu Leu Val Thr
2275            2280                2285 agc acc tct gca gat tca gcg tca tca ccc agt ctg tct cag ctg      6943
Ser Thr Ser Ala Asp Ser Ala Ser Ser Pro Ser Leu Ser Gln Leu
2290            2295                2300 gag tct tcc ctc aca gag gac tct caa ctt gga caa aat cag gaa      6988
Glu Ser Ser Leu Thr Glu Asp Ser Gln Leu Gly Gln Asn Gln Glu
2305            2310                2315 aag aat gcc tca gcc aga tga ggaatactgt cttgtgtaaa tatattcaag     7039
Lys Asn Ala Ser Ala Arg
2320            2325 gaaacacct ccactacctc actgacttca taattggaat gtcacatggt ttttttaatc  7099
aagatgcagt gaactgagat tctgaaactc cactgtagtt tactttgcct gtaccattaa  7159
tgccaatgtt tttataaatc acttgtacat agtacatatg ggaatagttg catatgggaa  7219
tttaaaccaa catgtggctg agcctttttt tttttaatct tcgtaacatg tttaaaaaaa  7279
aacagtgatt ttaactgcat atttgaacct acaaactggt aaatcttatt aacaaaaaga  7339
atgtacttaa ggccctcttt atttatagtg tcgagttatt tttgaatttt gcttaaaatc  7399 tattttcat atgaaaataa aagataacaa tc                                7431
```

<210> SEQ ID NO 28
<211> LENGTH: 2325
<212> TYPE: PRT
<213> ORGANISM: Homo sapiens

<400> SEQUENCE: 28

```
Met Lys Lys Gly Ser Gln Gln Lys Ile Phe Ser Lys Ala Lys Ile Pro
1               5                   10                  15

Ser Ser Ser His Ser Pro Ile Pro Ser Ser Met Ser Asn Met Arg Ser
            20                  25                  30

Arg Ser Leu Ser Pro Leu Ile Gly Ser Glu Thr Leu Pro Phe His Ser
        35                  40                  45

Gly Gly Gln Trp Cys Glu Gln Val Glu Ile Ala Asp Glu Asn Asn Met
    50                  55                  60

Leu Leu Asp Tyr Gln Asp His Lys Gly Ala Asp Ser His Ala Gly Val
65                  70                  75                  80

Arg Tyr Ile Thr Glu Ala Leu Ile Lys Lys Leu Thr Lys Gln Asp Asn
                85                  90                  95

Leu Ala Leu Ile Lys Ser Leu Asn Leu Ser Leu Ser Lys Asp Gly Gly
            100                 105                 110

Lys Lys Phe Lys Tyr Ile Glu Asn Leu Glu Lys Cys Val Lys Leu Glu
        115                 120                 125

Val Leu Asn Leu Ser Tyr Asn Leu Ile Gly Lys Ile Glu Lys Leu Asp
    130                 135                 140
```

```
Lys Leu Leu Lys Leu Arg Glu Leu Asn Leu Ser Tyr Asn Lys Ile Ser
145                 150                 155                 160

Lys Ile Glu Gly Ile Glu Asn Met Cys Asn Leu Gln Lys Leu Asn Leu
            165                 170                 175

Ala Gly Asn Glu Ile Glu His Ile Pro Val Trp Leu Gly Lys Lys Leu
            180                 185                 190

Lys Ser Leu Arg Val Leu Asn Leu Lys Gly Asn Lys Ile Ser Ser Leu
        195                 200                 205

Gln Asp Ile Ser Lys Leu Lys Pro Leu Gln Asp Leu Ile Ser Leu Ile
    210                 215                 220

Leu Val Glu Asn Pro Val Val Thr Leu Pro His Tyr Leu Gln Phe Thr
225                 230                 235                 240

Ile Phe His Leu Arg Ser Leu Glu Ser Leu Glu Gly Gln Pro Val Thr
                245                 250                 255

Thr Gln Asp Arg Gln Glu Ala Phe Glu Arg Phe Ser Leu Glu Glu Val
            260                 265                 270

Glu Arg Leu Glu Arg Asp Leu Glu Lys Lys Met Ile Glu Thr Glu Glu
        275                 280                 285

Leu Lys Ser Lys Gln Thr Arg Phe Leu Glu Glu Ile Lys Asn Gln Asp
290                 295                 300

Lys Leu Asn Lys Ser Leu Lys Glu Ala Met Leu Gln Lys Gln Ser
305                 310                 315                 320

Cys Glu Glu Leu Lys Ser Asp Leu Asn Thr Lys Asn Glu Leu Leu Lys
                325                 330                 335

Gln Lys Thr Ile Glu Leu Thr Arg Ala Cys Gln Lys Gln Tyr Glu Leu
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Ala Glu Ile Asp Lys Ala Pro Asp Glu
    370                 375                 380

Ser Pro Tyr Ile Gly Lys Ser Arg Tyr Lys Arg Asn Met Phe Ala Thr
385                 390                 395                 400

Glu Ser Tyr Ile Ile Asp Ser Ala Gln Ala Val Gln Ile Lys Lys Met
                405                 410                 415

Glu Pro Asp Glu Gln Leu Arg Asn Asp His Met Asn Leu Arg Gly His
            420                 425                 430

Thr Pro Leu Asp Thr Gln Leu Glu Asp Lys Glu Lys Lys Ile Ser Ala
        435                 440                 445

Ala Gln Thr Arg Leu Ser Glu Leu His Asp Glu Ile Glu Lys Ala Glu
450                 455                 460

Gln Gln Ile Leu Arg Ala Thr Glu Glu Phe Lys Gln Leu Glu Glu Ala
465                 470                 475                 480

Ile Gln Leu Lys Lys Ile Ser Glu Ala Gly Lys Asp Leu Leu Tyr Lys
                485                 490                 495

Gln Leu Ser Gly Arg Leu Gln Leu Val Asn Lys Leu Arg Gln Glu Ala
            500                 505                 510

Leu Asp Leu Glu Leu Gln Met Glu Lys Gln Lys Gln Glu Ile Ala Gly
        515                 520                 525

Lys Gln Lys Glu Ile Lys Asp Leu Gln Ile Ala Ile Asp Ser Leu Asp
    530                 535                 540

Ser Lys Asp Pro Lys His Ser His Met Lys Ala Gln Lys Ser Gly Lys
545                 550                 555                 560

Glu Gln Gln Leu Asp Ile Met Asn Lys Gln Tyr Gln Gln Leu Glu Ser
```

```
                565                 570                 575
Arg Leu Asp Glu Ile Leu Ser Arg Ile Ala Lys Glu Thr Glu Glu Ile
                580                 585                 590

Lys Asp Leu Glu Glu Gln Leu Thr Glu Gly Gln Ile Ala Ala Asn Glu
                595                 600                 605

Ala Leu Lys Lys Asp Leu Glu Gly Val Ile Ser Gly Leu Gln Glu Tyr
                610                 615                 620

Leu Gly Thr Ile Lys Gly Gln Ala Thr Gln Ala Gln Asn Glu Cys Arg
625                 630                 635                 640

Lys Leu Arg Asp Glu Lys Glu Thr Leu Leu Gln Arg Leu Thr Glu Val
                645                 650                 655

Glu Gln Glu Arg Asp Gln Leu Glu Ile Val Ala Met Asp Ala Glu Asn
                660                 665                 670

Met Arg Lys Glu Leu Ala Glu Leu Glu Ser Ala Leu Gln Glu Gln His
                675                 680                 685

Glu Val Asn Ala Ser Leu Gln Gln Thr Gln Gly Asp Leu Ser Ala Tyr
                690                 695                 700

Glu Ala Glu Leu Glu Ala Arg Leu Asn Leu Arg Asp Ala Glu Ala Asn
705                 710                 715                 720

Gln Leu Lys Glu Glu Leu Glu Lys Val Thr Arg Leu Thr Gln Leu Glu
                725                 730                 735

Gln Ser Ala Leu Gln Ala Glu Leu Glu Lys Glu Arg Gln Ala Leu Lys
                740                 745                 750

Asn Ala Leu Gly Lys Ala Gln Phe Ser Glu Glu Lys Glu Gln Glu Asn
                755                 760                 765

Ser Glu Leu His Ala Lys Leu Lys His Leu Gln Asp Asn Asn Leu
770                 775                 780

Leu Lys Gln Gln Leu Lys Asp Phe Gln Asn His Leu Asn His Val Val
785                 790                 795                 800

Asp Gly Leu Val Arg Pro Glu Val Ala Ala Arg Val Asp Glu Leu
                805                 810                 815

Arg Arg Lys Leu Lys Leu Gly Thr Gly Glu Met Asn Ile His Ser Pro
                820                 825                 830

Ser Asp Val Leu Gly Lys Ser Leu Ala Asp Leu Gln Lys Gln Phe Ser
                835                 840                 845

Glu Ile Leu Ala Arg Ser Lys Trp Glu Arg Asp Glu Ala Gln Val Arg
                850                 855                 860

Glu Arg Lys Leu Gln Glu Glu Met Ala Leu Gln Gln Glu Lys Leu Ala
865                 870                 875                 880

Thr Gly Gln Glu Glu Phe Arg Gln Ala Cys Glu Arg Ala Leu Glu Ala
                885                 890                 895

Arg Met Asn Phe Asp Lys Arg Gln His Glu Ala Arg Ile Gln Gln Met
                900                 905                 910

Glu Asn Glu Ile His Tyr Leu Gln Glu Asn Leu Lys Ser Met Glu Glu
                915                 920                 925

Ile Gln Gly Leu Thr Asp Leu Gln Leu Gln Glu Ala Asp Glu Glu Lys
                930                 935                 940

Glu Arg Ile Leu Ala Gln Leu Arg Glu Leu Glu Lys Lys Lys Lys Leu
945                 950                 955                 960

Glu Asp Ala Lys Ser Gln Glu Gln Val Phe Gly Leu Asp Lys Glu Leu
                965                 970                 975

Lys Lys Leu Lys Lys Ala Val Ala Thr Ser Asp Lys Leu Ala Thr Ala
                980                 985                 990
```

```
Glu Leu Thr Ile Ala Lys Asp Gln Leu Lys Ser Leu His Gly Thr Val
        995                 1000                1005

Met Lys Ile Asn Gln Glu Arg Ala Glu Leu Gln Glu Ala Glu
    1010                1015                1020

Arg Phe Ser Arg Lys Ala Ala Gln Ala Ala Arg Asp Leu Thr Arg
    1025                1030                1035

Ala Glu Ala Glu Ile Glu Leu Leu Gln Asn Leu Leu Arg Gln Lys
    1040                1045                1050

Gly Glu Gln Phe Arg Leu Glu Met Glu Lys Thr Gly Val Gly Thr
    1055                1060                1065

Gly Ala Asn Ser Gln Val Leu Glu Ile Glu Lys Leu Asn Glu Thr
    1070                1075                1080

Met Glu Arg Gln Arg Thr Glu Ile Ala Arg Leu Gln Asn Val Leu
    1085                1090                1095

Asp Leu Thr Gly Ser Asp Asn Lys Gly Gly Phe Glu Asn Val Leu
    1100                1105                1110

Glu Glu Ile Ala Glu Leu Arg Arg Glu Val Ser Tyr Gln Asn Asp
    1115                1120                1125

Tyr Ile Ser Ser Met Ala Asp Pro Phe Lys Arg Arg Gly Tyr Trp
    1130                1135                1140

Tyr Phe Met Pro Pro Pro Ser Ser Lys Val Ser Ser His Ser
    1145                1150                1155

Ser Gln Ala Thr Lys Asp Ser Gly Val Gly Leu Lys Tyr Ser Ala
    1160                1165                1170

Ser Thr Pro Val Arg Lys Pro Arg Pro Gly Gln Gln Asp Gly Lys
    1175                1180                1185

Glu Gly Ser Gln Pro Pro Pro Ala Ser Gly Tyr Trp Val Tyr Ser
    1190                1195                1200

Pro Ile Arg Ser Gly Leu His Lys Leu Phe Pro Ser Arg Asp Ala
    1205                1210                1215

Asp Ser Gly Gly Asp Ser Gln Glu Glu Ser Glu Leu Asp Asp Gln
    1220                1225                1230

Glu Glu Pro Pro Phe Val Pro Pro Pro Gly Tyr Met Met Tyr Thr
    1235                1240                1245

Val Leu Pro Asp Gly Ser Pro Val Pro Gln Gly Met Ala Leu Tyr
    1250                1255                1260

Ala Pro Pro Pro Pro Leu Pro Asn Asn Ser Arg Pro Leu Thr Pro
    1265                1270                1275

Gly Thr Val Val Tyr Gly Pro Pro Pro Ala Gly Ala Pro Met Val
    1280                1285                1290

Tyr Gly Pro Pro Pro Pro Asn Phe Ser Ile Pro Phe Ile Pro Met
    1295                1300                1305

Gly Val Leu His Cys Asn Val Pro Glu His His Asn Leu Glu Asn
    1310                1315                1320

Glu Val Ser Arg Leu Glu Asp Ile Met Gln His Leu Lys Ser Lys
    1325                1330                1335

Lys Arg Glu Glu Arg Trp Met Arg Ala Ser Lys Arg Gln Ser Glu
    1340                1345                1350

Lys Glu Met Glu Glu Leu His His Asn Ile Asp Asp Leu Leu Gln
    1355                1360                1365

Glu Lys Lys Ser Leu Glu Cys Glu Val Glu Glu Leu His Arg Thr
    1370                1375                1380
```

```
Val Gln Lys Arg Gln Gln Gln  Lys Asp Phe Ile Asp  Gly Asn Val
1385             1390              1395

Glu Ser Leu Met Thr Glu Leu  Glu Ile Glu Lys Ser  Leu Lys His
1400             1405              1410

His Glu Asp Ile Val Asp Glu  Ile Glu Cys Ile Glu  Lys Thr Leu
1415             1420              1425

Leu Lys Arg Arg Ser Glu Leu  Arg Glu Ala Asp Arg  Leu Leu Ala
1430             1435              1440

Glu Ala Glu Ser Glu Leu Ser  Cys Thr Lys Glu Lys  Thr Lys Asn
1445             1450              1455

Ala Val Glu Lys Phe Thr Asp  Ala Lys Arg Ser Leu  Leu Gln Thr
1460             1465              1470

Glu Ser Asp Ala Glu Glu Leu  Glu Arg Arg Ala Gln  Glu Thr Ala
1475             1480              1485

Val Asn Leu Val Lys Ala Asp  Gln Gln Leu Arg Ser  Leu Gln Ala
1490             1495              1500

Asp Ala Lys Asp Leu Glu Gln  His Lys Ile Lys Gln  Glu Glu Ile
1505             1510              1515

Leu Lys Glu Ile Asn Lys Ile  Val Ala Ala Lys Asp  Ser Asp Phe
1520             1525              1530

Gln Cys Leu Ser Lys Lys Lys  Glu Lys Leu Thr Glu  Glu Leu Gln
1535             1540              1545

Lys Leu Gln Lys Asp Ile Glu  Met Ala Glu Arg Asn  Glu Asp His
1550             1555              1560

His Leu Gln Val Leu Lys Glu  Ser Glu Val Leu Leu  Gln Ala Lys
1565             1570              1575

Arg Ala Glu Leu Glu Lys Leu  Lys Ser Gln Val Thr  Ser Gln Gln
1580             1585              1590

Gln Glu Met Ala Val Leu Asp  Arg Gln Leu Gly His  Lys Lys Glu
1595             1600              1605

Glu Leu His Leu Leu Gln Gly  Ser Met Val Gln Ala  Lys Ala Asp
1610             1615              1620

Leu Gln Glu Ala Leu Arg Leu  Gly Glu Thr Glu Val  Thr Glu Lys
1625             1630              1635

Cys Asn His Ile Arg Glu Val  Lys Ser Leu Leu Glu  Glu Leu Ser
1640             1645              1650

Phe Gln Lys Gly Glu Leu Asn  Val Gln Ile Ser Glu  Arg Lys Thr
1655             1660              1665

Gln Leu Thr Leu Ile Lys Gln  Glu Ile Glu Lys Glu  Glu Glu Asn
1670             1675              1680

Leu Gln Val Val Leu Arg Gln  Met Ser Lys His Lys  Thr Glu Leu
1685             1690              1695

Lys Asn Ile Leu Asp Met Leu  Gln Leu Glu Asn His  Glu Leu Gln
1700             1705              1710

Gly Leu Lys Leu Gln His Asp  Gln Arg Val Ser Glu  Leu Glu Lys
1715             1720              1725

Thr Gln Val Ala Val Leu Glu  Glu Lys Leu Glu Leu  Glu Asn Leu
1730             1735              1740

Gln Gln Ile Ser Gln Gln Lys  Gly Glu Ile Glu Trp  Gln Lys
1745             1750              1755

Gln Leu Leu Glu Arg Asp Lys  Arg Glu Ile Glu Arg  Met Thr Ala
1760             1765              1770

Glu Ser Arg Ala Leu Gln Ser  Cys Val Glu Cys Leu  Ser Lys Glu
```

-continued

```
           1775                1780               1785
Lys Glu  Asp Leu Gln Glu Lys  Cys Asp Ile Trp Glu  Lys Lys Leu
         1790                1795               1800

Ala Gln  Thr Lys Arg Val Leu  Ala Ala Ala Glu Glu  Asn Ser Lys
         1805                1810               1815

Met Glu  Gln Ser Asn Leu Glu  Lys Leu Glu Leu Asn  Val Arg Lys
         1820                1825               1830

Leu Gln  Gln Glu Leu Asp Gln  Leu Asn Arg Asp Lys  Leu Ser Leu
         1835                1840               1845

His Asn  Asp Ile Ser Ala Met  Gln Gln Gln Leu Gln  Glu Lys Arg
         1850                1855               1860

Glu Ala  Val Asn Ser Leu Gln  Glu Glu Leu Ala Asn  Val Gln Asp
         1865                1870               1875

His Leu  Asn Leu Ala Lys Gln  Asp Leu Leu His Thr  Thr Lys His
         1880                1885               1890

Gln Asp  Val Leu Leu Ser Glu  Gln Thr Arg Leu Gln  Lys Asp Ile
         1895                1900               1905

Ser Glu  Trp Ala Asn Arg Phe  Glu Asp Cys Gln Lys  Glu Glu Glu
         1910                1915               1920

Thr Lys  Gln Gln Gln Leu Gln  Val Leu Gln Asn Glu  Ile Glu Glu
         1925                1930               1935

Asn Lys  Leu Lys Leu Val Gln  Gln Glu Met Met Phe  Gln Arg Leu
         1940                1945               1950

Gln Lys  Glu Arg Glu Ser Glu  Glu Ser Lys Leu Glu  Thr Ser Lys
         1955                1960               1965

Val Thr  Leu Lys Glu Gln Gln  His Gln Leu Glu Lys  Glu Leu Thr
         1970                1975               1980

Asp Gln  Lys Ser Lys Leu Asp  Gln Val Leu Ser Lys  Val Leu Ala
         1985                1990               1995

Ala Glu  Glu Arg Val Arg Thr  Leu Gln Glu Glu Glu  Arg Trp Cys
         2000                2005               2010

Glu Ser  Leu Glu Lys Thr Leu  Ser Gln Thr Lys Arg  Gln Leu Ser
         2015                2020               2025

Glu Arg  Glu Gln Gln Leu Val  Glu Lys Ser Gly Glu  Leu Leu Ala
         2030                2035               2040

Leu Gln  Lys Glu Ala Asp Ser  Met Arg Ala Asp Phe  Ser Leu Leu
         2045                2050               2055

Arg Asn  Gln Phe Leu Thr Glu  Arg Lys Lys Ala Glu  Lys Gln Val
         2060                2065               2070

Ala Ser  Leu Lys Glu Ala Leu  Lys Ile Gln Arg Ser  Gln Leu Glu
         2075                2080               2085

Lys Asn  Leu Leu Glu Gln Lys  Gln Glu Asn Ser Cys  Ile Gln Lys
         2090                2095               2100

Glu Met  Ala Thr Ile Glu Leu  Val Ala Gln Asp Asn  His Glu Arg
         2105                2110               2115

Ala Arg  Arg Leu Met Lys Glu  Leu Asn Gln Met Gln  Tyr Glu Tyr
         2120                2125               2130

Thr Glu  Leu Lys Lys Gln Met  Ala Asn Gln Lys Asp  Leu Glu Arg
         2135                2140               2145

Arg Gln  Met Glu Ile Ser Asp  Ala Met Arg Thr Leu  Lys Ser Glu
         2150                2155               2160

Val Lys  Asp Glu Ile Arg Thr  Ser Leu Lys Asn Leu  Asn Gln Phe
         2165                2170               2175
```

-continued

Leu Pro Glu Leu Pro Ala Asp Leu Glu Ala Ile Leu Glu Arg Asn
    2180            2185                2190

Glu Asn Leu Glu Gly Glu Leu Glu Ser Leu Lys Glu Asn Leu Pro
    2195            2200                2205

Phe Thr Met Asn Glu Gly Pro Phe Glu Lys Leu Asn Phe Ser
    2210            2215                2220

Gln Val His Ile Met Asp Glu His Trp Arg Gly Glu Ala Leu Arg
    2225            2230                2235

Glu Lys Leu Arg His Arg Glu Asp Arg Leu Lys Ala Gln Leu Arg
    2240            2245                2250

His Cys Met Ser Lys Gln Ala Glu Val Leu Ile Lys Gly Lys Arg
    2255            2260                2265

Gln Thr Glu Gly Thr Leu His Ser Leu Arg Arg Gln Val Asp Ala
    2270            2275                2280

Leu Gly Glu Leu Val Thr Ser Thr Ser Ala Asp Ser Ala Ser Ser
    2285            2290                2295

Pro Ser Leu Ser Gln Leu Glu Ser Ser Leu Thr Glu Asp Ser Gln
    2300            2305                2310

Leu Gly Gln Asn Gln Glu Lys Asn Ala Ser Ala Arg
    2315            2320                2325

<210> SEQ ID NO 29
<211> LENGTH: 18
<212> TYPE: DNA
<213> ORGANISM: Artificial Sequence
<220> FEATURE:
<223> OTHER INFORMATION: Synthetic primer

<400> SEQUENCE: 29
gcagcaaaag actcagac                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic primer

<400> SEQUENCE: 30
aagttgcaac atgtccag                                                 18

<210> SEQ ID NO 31
<211> LENGTH: 28
<212> TYPE: DNA
<213> ORGANISM: Artificial Sequence
<220> FEATURE:
<223> OTHER INFORMATION: Synthetic primer

<400> SEQUENCE: 31
catatggagc aagaggaaat cttgaaag                                      28

<210> SEQ ID NO 32
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
ggtaccgggt cggtgcgcgt c                                             21

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
ggatccatca agcaagaaga aatc                    24

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
gtcgactcat ctggctgagg cattc                   25

<210> SEQ ID NO 35
<211> LENGTH: 826
<212> TYPE: PRT
<213> ORGANISM: Canis familiaris

<400> SEQUENCE: 35

Met Glu Gln Glu Glu Ile Leu Lys Glu Ile Asn Lys Val Ala Ala
1               5                   10                  15

Lys Asp Ser Asp Phe Gln Ser Leu Asn Lys Lys Glu Val Leu Thr
                20                  25                  30

Gly Glu Leu Gln Lys Leu Gln Lys Asp Ile Glu Thr Ala Arg His Asn
            35                  40                  45

Glu Asp Gln His Leu Gln Val Leu Lys Glu Ser Glu Thr Leu Leu Gln
        50                  55                  60

Ala Lys Lys Ala Glu Leu Glu Asn Leu Lys Ser Gln Val Ser Gly Gln
65                  70                  75                  80

Gln Gln Glu Met Ala Val Leu Asp Arg Glu Leu Gly His Lys Lys Glu
                85                  90                  95

Glu Leu His Leu Leu Gln Glu Ser Met Val Gln Ala Lys Ala Asp Leu
            100                 105                 110

Gln Glu Ala Leu Arg Leu Gly Glu Ser Glu Val Thr Glu Lys Cys Asn
        115                 120                 125

His Ile Arg Glu Val Lys Ser Leu Leu Glu Glu Leu Ser Phe Gln Lys
    130                 135                 140

Gly Glu Leu Asn Val Gln Ile Ser Glu Lys Lys Thr Gln Leu Ala Leu
145                 150                 155                 160

Ile Lys Gln Glu Ile Glu Lys Glu Glu Asp Asn Leu Gln Val Val Leu
                165                 170                 175

Gly Gln Met Ser Lys His Lys Thr Glu Leu Lys Asn Ile Leu Asp Met
            180                 185                 190

Leu Gln Leu Glu Asn Asn Glu Leu Gln Gly Leu Lys Leu Gln His Asp
        195                 200                 205

Gln Lys Met Ser Glu Leu Glu Lys Thr Arg Val Glu Val Leu Glu Glu
    210                 215                 220

Lys Leu Glu Leu Glu Ser Leu Gln Gln Ala Ala Leu Arg Gln Arg Gly
225                 230                 235                 240

Glu Ile Glu Trp Gln Lys Gln Leu Leu Gln Arg Asn Thr Gln Glu Val
                245                 250                 255

```
Glu Arg Met Thr Ala Glu Thr Arg Ala Leu Gln Ser Cys Val Glu Ser
            260                 265                 270

Leu Cys Lys Glu Lys Gln Asp Leu Glu Lys Gln Asp Ser Trp Glu
        275                 280                 285

Lys Lys Leu Ala Gln Thr Lys Arg Val Leu Ala Ala Glu Glu Asp
            290                 295                 300

Ser Glu Met Glu Arg Ala Arg Leu Glu Lys Leu Glu Leu Asp Ala Arg
305                 310                 315                 320

Lys Leu Gln Gln Glu Leu Asp Gln Arg Asn Arg Glu Lys Leu Ser Leu
                325                 330                 335

His Gln Asp Leu Ala Val Val Gln Gln Leu Gln Glu Lys Gln Glu
            340                 345                 350

Ala Val Asn Ser Leu Gln Lys Glu Leu Thr Asp Val Gln Glu His Leu
        355                 360                 365

Asp Leu Ala Glu Gln Glu Val Leu Cys Thr Thr Lys Arg Lys Asp Ala
    370                 375                 380

Leu Leu Ser Glu Gln Thr Arg Leu Glu Lys Asp Val Gly Glu Trp Thr
385                 390                 395                 400

Lys Lys Phe Glu Asp Cys Gln Lys Glu Gly Thr Lys Gln Gln
            405                 410                 415

Leu Gln Gly Leu Gln Lys Glu Ile Glu Gly Asn Glu Ala Lys Leu Ala
                420                 425                 430

Gln Gln Glu Met Met Phe Gln Arg Leu Gln Lys Glu Arg Glu Cys Glu
            435                 440                 445

Glu Lys Lys Leu Glu Ala Ser Lys Val Thr Leu Lys Glu Gln Gln Gln
        450                 455                 460

Gln Leu Glu Lys Glu Leu Met Glu Gln Lys Gly Lys Leu Asp Gln Val
465                 470                 475                 480

Leu Ala Lys Leu Leu Val Ala Glu Glu Arg Val Arg Thr Leu Gln Glu
                485                 490                 495

Glu Gly Arg Trp Ser Glu Thr Leu Glu Lys Thr Leu Ser Gln Thr Lys
            500                 505                 510

Arg Gln Leu Ser Glu Arg Glu Gln Gln Leu Leu Ala Lys Ser Asp Glu
        515                 520                 525

Leu Leu Ala Leu Gln Lys Glu Thr Asp Ser Met Arg Ala Asp Phe Ser
530                 535                 540

Leu Leu Arg Asn Gln Phe Leu Thr Glu Arg Lys Lys Ala Glu Lys Gln
545                 550                 555                 560

Val Ala Ser Leu Lys Glu Ala Leu Lys Ile Gln Arg Ser Gln Leu Glu
                565                 570                 575

Lys Asn Leu Leu Glu Gln Lys Gln Glu Asn Ser Cys Met Gln Arg Glu
            580                 585                 590

Met Ala Thr Ile Glu Gln Val Ala Gln Asp Asn His Glu Arg Ala Arg
        595                 600                 605

Arg Leu Met Arg Glu Leu Asn Gln Met Gln Arg Glu Tyr Val Glu Leu
    610                 615                 620

Arg Lys Gln Met Thr Asn Gln Lys Asp Leu Glu Arg Arg Gln Met Glu
625                 630                 635                 640

Ile Ser Asp Ala Met Gln Ala Leu Lys Cys Glu Val Lys Asp Glu Ile
                645                 650                 655

Arg Thr Ser Leu Lys Asn Leu Asn Gln Phe Leu Pro Glu Leu Pro Ala
            660                 665                 670
```

```
Asp Leu Glu Ala Leu Leu Glu Arg Asn Glu Asn Leu Gly Gly Leu
            675                 680                 685

Glu Ser Leu Lys Glu Asn Phe Pro Phe Thr Val Ser Asp Arg Pro Ser
690                 695                 700

Ser Cys Glu Glu Lys Leu Asn Phe Gly Gln Ala His Val Ala Asp Glu
705                 710                 715                 720

Gln Trp Arg Gly Glu Ala Leu Arg Glu Lys Leu Arg His Arg Glu Asp
            725                 730                 735

Arg Leu Lys Ala Gln Leu Arg Arg Cys Met Ser Lys Gln Ala Glu Val
            740                 745                 750

Leu Ser Glu Gly Arg Arg Thr Glu Gly Thr Leu His Ser Leu Arg
            755                 760                 765

Arg Gln Val Asp Ala Leu Gly Glu Leu Val Thr Ser Thr Ser Gly Asp
            770                 775                 780

Ser Ala Ser Thr Arg Ser Leu Ser Arg Thr Glu Gly Ser Leu Ala Glu
785                 790                 795                 800

Asp Glu Pro Pro Gly Pro Ser Gln Ser Ser Arg Arg Leu Pro Arg Gly
            805                 810                 815

Pro Ser Pro Arg Leu Asp Ala His Arg Pro
            820                 825

<210> SEQ ID NO 36
<211> LENGTH: 813
<212> TYPE: PRT
<213> ORGANISM: Homo sapiens

<400> SEQUENCE: 36

Ile Lys Gln Glu Glu Ile Leu Lys Glu Ile Asn Lys Ile Val Ala Ala
1               5                   10                  15

Lys Asp Ser Asp Phe Gln Cys Leu Ser Lys Lys Glu Lys Leu Thr
            20                  25                  30

Glu Glu Leu Gln Lys Leu Gln Lys Asp Ile Glu Met Ala Glu Arg Asn
            35                  40                  45

Glu Asp His His Leu Gln Val Leu Lys Glu Ser Glu Val Leu Leu Gln
50                  55                  60

Ala Lys Arg Ala Glu Leu Gly Lys Leu Lys Ser Gln Val Thr Ser Gln
65                  70                  75                  80

Gln Gln Glu Met Ala Val Leu Asp Arg Gln Leu Gly His Lys Lys Glu
            85                  90                  95

Glu Leu His Leu Leu Gln Gly Ser Met Val Gln Ala Lys Ala Asp Leu
            100                 105                 110

Gln Glu Ala Leu Arg Leu Gly Glu Thr Glu Val Thr Glu Lys Cys Asn
            115                 120                 125

His Ile Arg Glu Val Lys Ser Leu Leu Glu Glu Leu Ser Phe Gln Lys
            130                 135                 140

Gly Glu Leu Asn Val Gln Ile Ser Glu Arg Lys Thr Gln Leu Thr Leu
145                 150                 155                 160

Ile Lys Gln Glu Ile Glu Lys Glu Glu Asn Leu Gln Val Val Leu
            165                 170                 175

Arg Gln Met Ser Lys His Lys Thr Glu Leu Lys Asn Ile Leu Asp Met
            180                 185                 190

Leu Gln Leu Glu Asn His Glu Leu Gln Gly Leu Lys Leu Gln His Asp
            195                 200                 205

Gln Arg Val Ser Glu Leu Glu Lys Thr Gln Val Ala Val Leu Glu Glu
            210                 215                 220
```

-continued

```
Lys Leu Glu Leu Glu Asn Leu Gln Gln Ile Ser Gln Gln Lys Gly
225                 230                 235                 240

Glu Ile Glu Trp Gln Lys Gln Leu Leu Glu Arg Asp Lys Arg Glu Ile
            245                 250                 255

Glu Arg Met Thr Ala Glu Ser Arg Ala Leu Gln Ser Cys Val Glu Cys
            260                 265                 270

Leu Ser Lys Glu Lys Glu Asp Leu Gln Glu Lys Cys Asp Ile Trp Glu
            275                 280                 285

Lys Lys Leu Ala Gln Thr Lys Arg Val Leu Ala Ala Glu Glu Asn
290                 295                 300

Ser Lys Met Glu Gln Ser Asn Leu Glu Lys Leu Glu Leu Asn Val Arg
305                 310                 315                 320

Lys Leu Gln Gln Glu Leu Asp Gln Leu Asn Arg Asp Lys Leu Ser Leu
                325                 330                 335

His Asn Asp Ile Ser Ala Met Gln Gln Leu Gln Glu Lys Arg Glu
            340                 345                 350

Ala Val Asn Ser Leu Gln Glu Glu Leu Ala Asn Val Gln Asp His Leu
            355                 360                 365

Asn Leu Ala Lys Gln Asp Leu Leu His Thr Thr Lys His Gln Asp Val
370                 375                 380

Leu Leu Ser Glu Gln Thr Arg Leu Gln Lys Asp Ile Ser Glu Trp Ala
385                 390                 395                 400

Asn Arg Phe Glu Asp Cys Gln Lys Glu Glu Thr Lys Gln Gln Gln
            405                 410                 415

Leu Gln Val Leu Gln Asn Glu Ile Glu Glu Asn Lys Leu Lys Leu Val
            420                 425                 430

Gln Gln Glu Met Met Phe Gln Arg Leu Gln Lys Glu Arg Glu Ser Glu
            435                 440                 445

Glu Ser Lys Leu Glu Thr Ser Lys Val Thr Leu Lys Glu Gln His
            450                 455                 460

Gln Leu Glu Lys Glu Leu Thr Asp Gln Lys Ser Lys Leu Asp Gln Val
465                 470                 475                 480

Leu Ser Lys Val Leu Ala Ala Glu Glu Arg Val Arg Thr Leu Gln Glu
            485                 490                 495

Glu Glu Arg Trp Cys Glu Ser Leu Glu Lys Thr Leu Ser Gln Thr Lys
            500                 505                 510

Arg Gln Leu Ser Glu Arg Glu Gln Gln Leu Val Glu Lys Ser Gly Glu
            515                 520                 525

Leu Leu Ala Leu Gln Lys Glu Ala Asp Ser Met Arg Ala Asp Phe Ser
            530                 535                 540

Leu Leu Arg Asn Gln Phe Leu Thr Glu Arg Lys Lys Ala Glu Lys Gln
545                 550                 555                 560

Val Ala Ser Leu Lys Glu Ala Leu Lys Ile Gln Arg Ser Gln Leu Glu
            565                 570                 575

Lys Asn Leu Leu Glu Gln Lys Gln Glu Asn Ser Cys Ile Gln Lys Glu
            580                 585                 590

Met Ala Thr Ile Glu Leu Val Ala Gln Asp Asn His Glu Arg Ala Arg
            595                 600                 605

Arg Leu Met Lys Glu Leu Asn Gln Met Gln Tyr Glu Tyr Thr Glu Leu
            610                 615                 620

Lys Lys Gln Met Ala Asn Gln Lys Asp Leu Glu Arg Arg Gln Met Glu
625                 630                 635                 640
```

```
Ile Ser Asp Ala Met Arg Thr Leu Lys Ser Glu Val Lys Asp Glu Ile
            645                 650                 655

Arg Thr Ser Leu Lys Asn Leu Asn Gln Phe Leu Pro Glu Leu Pro Ala
        660                 665                 670

Asp Leu Glu Ala Ile Leu Glu Arg Asn Glu Asn Leu Glu Gly Glu Leu
    675                 680                 685

Glu Ser Leu Lys Glu Asn Leu Pro Phe Thr Met Asn Glu Gly Pro Phe
690                 695                 700

Glu Glu Lys Leu Asn Phe Ser Gln Val His Ile Met Asp Glu His Trp
705                 710                 715                 720

Arg Gly Glu Ala Leu Arg Glu Lys Leu Arg His Arg Glu Asp Arg Leu
                725                 730                 735

Lys Ala Gln Leu Arg His Cys Met Ser Lys Gln Ala Glu Val Leu Ile
            740                 745                 750

Lys Gly Lys Arg Gln Thr Glu Gly Thr Leu His Ser Leu Arg Arg Gln
        755                 760                 765

Val Asp Ala Leu Gly Glu Leu Val Thr Ser Thr Ser Ala Asp Ser Ala
    770                 775                 780

Ser Ser Pro Ser Leu Ser Gln Leu Glu Ser Ser Leu Thr Glu Asp Ser
785                 790                 795                 800

Gln Leu Gly Gln Asn Gln Glu Lys Asn Ala Ser Ala Arg
                805                 810
```

<210> SEQ ID NO 37
<211> LENGTH: 24
<212> TYPE: DNA
<213> ORGANISM: Artificial Sequence
<220> FEATURE:
<223> OTHER INFORMATION: Synthetic primer

<400> SEQUENCE: 37
ggatccatga agaaaggttc tcag         24

<210> SEQ ID NO 38
<211> LENGTH: 24
<212> TYPE: DNA
<213> ORGANISM: Artificial Sequence
<220> FEATURE:
<223> OTHER INFORMATION: Synthetic primer

<400> SEQUENCE: 38
gtcgactcag ggtcggtgcg cgtc         24

<210> SEQ ID NO 39
<211> LENGTH: 25
<212> TYPE: DNA
<213> ORGANISM: Artificial Sequence
<220> FEATURE:
<223> OTHER INFORMATION: Synthetic primer

<400> SEQUENCE: 39
ggatccatga agaaaggttc tcaac        25

<210> SEQ ID NO 40
<211> LENGTH: 25
<212> TYPE: DNA
<213> ORGANISM: Artificial Sequence
<220> FEATURE:
<223> OTHER INFORMATION: Synthetic primer

<400> SEQUENCE: 40

```
gtcgactcat ctggctgagg cattc                                             25
```

```
<210> SEQ ID NO 41
<211> LENGTH: 7770
<212> TYPE: DNA
<213> ORGANISM: Canis familiaris
<220> FEATURE:
<221> NAME/KEY: CDS
<222> LOCATION: (1)..(7770)

<400> SEQUENCE: 41
```

| | | | | | | | | | | | | | | | | |
|---|---|---|---|---|---|---|---|---|---|---|---|---|---|---|---|---|
| atg | aag | aaa | ggt | tct | cag | caa | aag | ttt | ttg | aaa | gca | aag | atg | cca | cca | 48 |
| Met | Lys | Lys | Gly | Ser | Gln | Gln | Lys | Phe | Leu | Lys | Ala | Lys | Met | Pro | Pro | |
| 1 | | | | 5 | | | | | 10 | | | | | 15 | | |

| tca | tct | cac | tct | cct | agt | cca | cca | tcc | ctt | acg | tcc | aat | atg | aga | tct | 96 |
|---|---|---|---|---|---|---|---|---|---|---|---|---|---|---|---|---|
| Ser | Ser | His | Ser | Pro | Ser | Pro | Pro | Ser | Leu | Thr | Ser | Asn | Met | Arg | Ser | |
| | | | 20 | | | | | 25 | | | | | 30 | | | |

| agg | tca | ctt | tcg | cct | cta | agt | gga | tct | gag | act | ctg | cct | ttt | cat | ttt | 144 |
|---|---|---|---|---|---|---|---|---|---|---|---|---|---|---|---|---|
| Arg | Ser | Leu | Ser | Pro | Leu | Ser | Gly | Ser | Glu | Thr | Leu | Pro | Phe | His | Phe | |
| | | 35 | | | | | 40 | | | | | 45 | | | | |

| gga | gga | ccg | tgg | cat | gag | caa | gtt | gag | att | aca | gat | gaa | agc | aca | gtg | 192 |
|---|---|---|---|---|---|---|---|---|---|---|---|---|---|---|---|---|
| Gly | Gly | Pro | Trp | His | Glu | Gln | Val | Glu | Ile | Thr | Asp | Glu | Ser | Thr | Val | |
| 50 | | | | | 55 | | | | | 60 | | | | | | |

| gtt | tta | gac | tac | caa | gac | cat | aaa | gaa | gct | gat | tca | cat | gca | gga | gtc | 240 |
|---|---|---|---|---|---|---|---|---|---|---|---|---|---|---|---|---|
| Val | Leu | Asp | Tyr | Gln | Asp | His | Lys | Glu | Ala | Asp | Ser | His | Ala | Gly | Val | |
| 65 | | | | | 70 | | | | | 75 | | | | | 80 | |

| cga | tat | att | aca | gag | gcc | ctt | gtt | aga | aaa | ctt | act | aaa | cag | gac | aat | 288 |
|---|---|---|---|---|---|---|---|---|---|---|---|---|---|---|---|---|
| Arg | Tyr | Ile | Thr | Glu | Ala | Leu | Val | Arg | Lys | Leu | Thr | Lys | Gln | Asp | Asn | |
| | | | | 85 | | | | | 90 | | | | | 95 | | |

| ttg | gcc | ttg | gta | aaa | tct | ctg | aac | ctt | tca | ctt | gct | aaa | ggt | ggt | ggc | 336 |
|---|---|---|---|---|---|---|---|---|---|---|---|---|---|---|---|---|
| Leu | Ala | Leu | Val | Lys | Ser | Leu | Asn | Leu | Ser | Leu | Ala | Lys | Gly | Gly | Gly | |
| | | | 100 | | | | | 105 | | | | | 110 | | | |

| aag | aaa | ttc | agg | tgt | atc | gaa | aat | ttg | gaa | aaa | tgt | gtt | aaa | ctt | gaa | 384 |
|---|---|---|---|---|---|---|---|---|---|---|---|---|---|---|---|---|
| Lys | Lys | Phe | Arg | Cys | Ile | Glu | Asn | Leu | Glu | Lys | Cys | Val | Lys | Leu | Glu | |
| | 115 | | | | | 120 | | | | | 125 | | | | | |

| gta | ctg | aat | ctc | agc | tat | aat | cta | ata | gga | aag | att | gag | aaa | gtg | gac | 432 |
|---|---|---|---|---|---|---|---|---|---|---|---|---|---|---|---|---|
| Val | Leu | Asn | Leu | Ser | Tyr | Asn | Leu | Ile | Gly | Lys | Ile | Glu | Lys | Val | Asp | |
| 130 | | | | | 135 | | | | | 140 | | | | | | |

| aaa | ctg | tta | aaa | tta | cgt | gaa | ctc | aac | tta | tcg | tat | aac | aaa | atc | cgc | 480 |
|---|---|---|---|---|---|---|---|---|---|---|---|---|---|---|---|---|
| Lys | Leu | Leu | Lys | Leu | Arg | Glu | Leu | Asn | Leu | Ser | Tyr | Asn | Lys | Ile | Arg | |
| 145 | | | | | 150 | | | | | 155 | | | | | 160 | |

| aaa | att | gaa | ggc | ata | gaa | aat | tta | tat | aat | ctg | caa | aag | ctg | aac | ctt | 528 |
|---|---|---|---|---|---|---|---|---|---|---|---|---|---|---|---|---|
| Lys | Ile | Glu | Gly | Ile | Glu | Asn | Leu | Tyr | Asn | Leu | Gln | Lys | Leu | Asn | Leu | |
| | | | | 165 | | | | | 170 | | | | | 175 | | |

| gca | gga | aat | gaa | atc | gaa | cat | atc | cca | gta | tgg | tta | ggg | aag | aag | tta | 576 |
|---|---|---|---|---|---|---|---|---|---|---|---|---|---|---|---|---|
| Ala | Gly | Asn | Glu | Ile | Glu | His | Ile | Pro | Val | Trp | Leu | Gly | Lys | Lys | Leu | |
| | | | 180 | | | | | 185 | | | | | 190 | | | |

| aaa | tct | ttg | cga | atc | ctg | aat | ctg | aaa | ggc | aac | aag | ata | tca | tcg | ctc | 624 |
|---|---|---|---|---|---|---|---|---|---|---|---|---|---|---|---|---|
| Lys | Ser | Leu | Arg | Ile | Leu | Asn | Leu | Lys | Gly | Asn | Lys | Ile | Ser | Ser | Leu | |
| | | 195 | | | | | 200 | | | | | 205 | | | | |

| caa | gat | gta | agc | aag | ttg | aaa | cca | ctt | caa | gat | ttg | act | tct | ctg | atc | 672 |
|---|---|---|---|---|---|---|---|---|---|---|---|---|---|---|---|---|
| Gln | Asp | Val | Ser | Lys | Leu | Lys | Pro | Leu | Gln | Asp | Leu | Thr | Ser | Leu | Ile | |
| 210 | | | | | 215 | | | | | 220 | | | | | | |

| cta | ctt | gaa | aat | cca | gtt | gcg | acc | ctt | cct | cat | tat | atc | cag | ttt | acc | 720 |
|---|---|---|---|---|---|---|---|---|---|---|---|---|---|---|---|---|
| Leu | Leu | Glu | Asn | Pro | Val | Ala | Thr | Leu | Pro | His | Tyr | Ile | Gln | Phe | Thr | |
| 225 | | | | | 230 | | | | | 235 | | | | | 240 | |

| att | ttt | cac | ctt | cgc | tca | ttg | gaa | agt | ttg | gaa | ggt | cag | cca | gta | act | 768 |
|---|---|---|---|---|---|---|---|---|---|---|---|---|---|---|---|---|
| Ile | Phe | His | Leu | Arg | Ser | Leu | Glu | Ser | Leu | Glu | Gly | Gln | Pro | Val | Thr | |
| | | | | 245 | | | | | 250 | | | | | 255 | | |

| agt | cag | gac | aga | caa | gaa | gct | ttt | gcg | aga | ttc | agt | tta | gat | gag | gta | 816 |
|---|---|---|---|---|---|---|---|---|---|---|---|---|---|---|---|---|
| Ser | Gln | Asp | Arg | Gln | Glu | Ala | Phe | Ala | Arg | Phe | Ser | Leu | Asp | Glu | Val | |

-continued

```
              260              265              270
gaa aga ctg gaa aga gac ctg gag aag aag aca atg gaa act gaa gag    864
Glu Arg Leu Glu Arg Asp Leu Glu Lys Lys Thr Met Glu Thr Glu Glu
        275              280              285 ctt agg agt gag cag aca agg ttc ctt gag gaa att aaa agt cag gat    912
Leu Arg Ser Glu Gln Thr Arg Phe Leu Glu Glu Ile Lys Ser Gln Asp
    290              295              300 aaa ttg aac aaa tca ctg aaa gag gag gcc aga cta caa aaa cag agc    960
Lys Leu Asn Lys Ser Leu Lys Glu Glu Ala Arg Leu Gln Lys Gln Ser
305              310              315              320 tat gag gag ctg gag agt aac cta aac acc aaa aat gaa ttg cta aaa   1008
Tyr Glu Glu Leu Glu Ser Asn Leu Asn Thr Lys Asn Glu Leu Leu Lys
            325              330              335 cag aag acc atg gaa cta atg cga gca tgt cag aaa cag tat gag atg   1056
Gln Lys Thr Met Glu Leu Met Arg Ala Cys Gln Lys Gln Tyr Glu Met
        340              345              350 gaa cag gag ttg gcc ttt tat aaa att gat gcc aaa ttt gaa cca cta   1104
Glu Gln Glu Leu Ala Phe Tyr Lys Ile Asp Ala Lys Phe Glu Pro Leu
    355              360              365 aat tat tac cca tca gag tat gtc gaa att gat aaa acc cca gat gaa   1152
Asn Tyr Tyr Pro Ser Glu Tyr Val Glu Ile Asp Lys Thr Pro Asp Glu
370              375              380 agc cct tac att ggc aaa tcc aga tac aag aga aat atg ttc act aca   1200
Ser Pro Tyr Ile Gly Lys Ser Arg Tyr Lys Arg Asn Met Phe Thr Thr
385              390              395              400 gag agt tat att att gca aat gcc cag aca gta aag atc aag aag atg   1248
Glu Ser Tyr Ile Ile Ala Asn Ala Gln Thr Val Lys Ile Lys Lys Met
            405              410              415 gag cta gat gaa ggg gaa caa ctc aga aat gag cac gtg aac ttg gga   1296
Glu Leu Asp Glu Gly Glu Gln Leu Arg Asn Glu His Val Asn Leu Gly
        420              425              430 gca tcg cca aca gac ata caa ctg gaa gac aaa gaa aaa aaa ata agt   1344
Ala Ser Pro Thr Asp Ile Gln Leu Glu Asp Lys Glu Lys Lys Ile Ser
    435              440              445 gca gca caa act cga cta tca gaa cta cat gat gaa ata gaa aag gca   1392
Ala Ala Gln Thr Arg Leu Ser Glu Leu His Asp Glu Ile Glu Lys Ala
450              455              460 gaa caa caa att tta aga gcc act gaa gaa ttt aaa caa ctg gaa gaa   1440
Glu Gln Gln Ile Leu Arg Ala Thr Glu Glu Phe Lys Gln Leu Glu Glu
465              470              475              480 gct ata caa ctt aaa aaa att tca gaa gcg gag aaa gac ctt ctt ttc   1488
Ala Ile Gln Leu Lys Lys Ile Ser Glu Ala Glu Lys Asp Leu Leu Phe
            485              490              495 aag cag ttg agt ggt agg ata cag ctt ctc aat aaa tta cgc caa gaa   1536
Lys Gln Leu Ser Gly Arg Ile Gln Leu Leu Asn Lys Leu Arg Gln Glu
        500              505              510 gct gtg gat cta gaa aca cag atg gaa aag caa agg caa gaa att ggt   1584
Ala Val Asp Leu Glu Thr Gln Met Glu Lys Gln Arg Gln Glu Ile Gly
    515              520              525 gaa aag cag aat gag atc aag gac ctg gaa ata gtc aca gat agc ctg   1632
Glu Lys Gln Asn Glu Ile Lys Asp Leu Glu Ile Val Thr Asp Ser Leu
530              535              540 gat tcc aga gac cca aaa cat tgc cat atg aag gct cag aaa aga ggt   1680
Asp Ser Arg Asp Pro Lys His Cys His Met Lys Ala Gln Lys Arg Gly
545              550              555              560 aaa gaa caa caa ctt gac att atg aac aag cag tac aaa cag ctt gaa   1728
Lys Glu Gln Gln Leu Asp Ile Met Asn Lys Gln Tyr Lys Gln Leu Glu
            565              570              575 agc cgt ttg gat gag ata ctt tct aga att gcc aaa gaa act gaa gag   1776
```

```
                Ser Arg Leu Asp Glu Ile Leu Ser Arg Ile Ala Lys Glu Thr Glu Glu
                            580                 585                 590 att aag gac ctt gaa gaa cag ctt act gaa gga caa ata gcc gca aac         1824
Ile Lys Asp Leu Glu Glu Gln Leu Thr Glu Gly Gln Ile Ala Ala Asn
            595                 600                 605 gaa gcc ctg aag aag gac tta gaa agt gtc atc agt ggg ttg caa gaa         1872
Glu Ala Leu Lys Lys Asp Leu Glu Ser Val Ile Ser Gly Leu Gln Glu
610                 615                 620 tac ctg gag act gtc aaa ggt cag gcc cgt cag gcc cag aat gag tgc         1920
Tyr Leu Glu Thr Val Lys Gly Gln Ala Arg Gln Ala Gln Asn Glu Cys
625                 630                 635                 640 aga aag cta cag gat gag aag gag aca ttg ctg cag aga ttg agt gag         1968
Arg Lys Leu Gln Asp Glu Lys Glu Thr Leu Leu Gln Arg Leu Ser Glu
                645                 650                 655 gtc gag cag gag agg gac caa ctg gaa ata gtg gcc ata gat gca gaa         2016
Val Glu Gln Glu Arg Asp Gln Leu Glu Ile Val Ala Ile Asp Ala Glu
            660                 665                 670 aat atg agg aag gag ctc gca gaa ctg gag aat gcc ctc cag gag cag         2064
Asn Met Arg Lys Glu Leu Ala Glu Leu Glu Asn Ala Leu Gln Glu Gln
675                 680                 685 cat gag gtg aat ata tct ctg cag cag acc cag gga gat ctc agt gcc         2112
His Glu Val Asn Ile Ser Leu Gln Gln Thr Gln Gly Asp Leu Ser Ala
            690                 695                 700 tat gag gct gag cta gag gct cag ctg aaa ata cgg gat gct gaa gcc         2160
Tyr Glu Ala Glu Leu Glu Ala Gln Leu Lys Ile Arg Asp Ala Glu Ala
705                 710                 715                 720 aac cag ctc aag gag gag ttg gaa aaa ctt aga agg ttg agc cag tta         2208
Asn Gln Leu Lys Glu Glu Leu Glu Lys Leu Arg Arg Leu Ser Gln Leu
                725                 730                 735 gaa caa tcg gcc ctt caa gca gag ctt gag aag gaa aag caa gcc ttc         2256
Glu Gln Ser Ala Leu Gln Ala Glu Leu Glu Lys Glu Lys Gln Ala Phe
            740                 745                 750 aag act gct gtc aaa aaa gcc cag ctc tca gaa gga aag gac caa gaa         2304
Lys Thr Ala Val Lys Lys Ala Gln Leu Ser Glu Gly Lys Asp Gln Glu
755                 760                 765 aat agt gag ctc cgc aca caa ctc caa cag ctg cag gat gac aat gac         2352
Asn Ser Glu Leu Arg Thr Gln Leu Gln Gln Leu Gln Asp Asp Asn Asp
            770                 775                 780 cta ttg aaa cag caa ctt aaa gat ttc cag agt cac ctt aac cat gtg         2400
Leu Leu Lys Gln Gln Leu Lys Asp Phe Gln Ser His Leu Asn His Val
785                 790                 795                 800 gtt gat ggt ttg att cgt cca gaa gaa gtg gca gct tgt gtg gat gag         2448
Val Asp Gly Leu Ile Arg Pro Glu Glu Val Ala Ala Cys Val Asp Glu
                805                 810                 815 cta agg aaa aaa ctg aag tca gga gct ggg gaa atg aga atc cat act         2496
Leu Arg Lys Lys Leu Lys Ser Gly Ala Gly Glu Met Arg Ile His Thr
            820                 825                 830 cct tca gat gtc tta ggg aaa agt ctt gct gac ttg cag aag caa ttc         2544
Pro Ser Asp Val Leu Gly Lys Ser Leu Ala Asp Leu Gln Lys Gln Phe
835                 840                 845 agt gag atc ctg gca cgc tcc cag tgg gaa aga cag gaa gca caa gtg         2592
Ser Glu Ile Leu Ala Arg Ser Gln Trp Glu Arg Gln Glu Ala Gln Val
            850                 855                 860 aga gag aga aaa ctc cag gag gaa atg gct ctg caa caa gag aaa ctg         2640
Arg Glu Arg Lys Leu Gln Glu Glu Met Ala Leu Gln Gln Glu Lys Leu
865                 870                 875                 880 gcg agc gga caa gag gag ttc agg cac gcc tgc gag agg gcc ctg gaa         2688
Ala Ser Gly Gln Glu Glu Phe Arg His Ala Cys Glu Arg Ala Leu Glu
                885                 890                 895
```

```
                                                  -continued gcc cga att agt ttt gat aag agg cag cac gaa gca aga atc cag cag    2736
Ala Arg Ile Ser Phe Asp Lys Arg Gln His Glu Ala Arg Ile Gln Gln
                900                 905                 910 ttg gag aat gaa att cac tat ttg caa gaa aat cta aaa agt atg gag    2784
Leu Glu Asn Glu Ile His Tyr Leu Gln Glu Asn Leu Lys Ser Met Glu
        915                 920                 925 gaa atc caa ggt ctc aca gac ctc caa ctt cag gaa gct gat gaa gag    2832
Glu Ile Gln Gly Leu Thr Asp Leu Gln Leu Gln Glu Ala Asp Glu Glu
    930                 935                 940 aag gag aga att ctg gcc caa ctc cgg gag tta gag aaa aag aag aaa    2880
Lys Glu Arg Ile Leu Ala Gln Leu Arg Glu Leu Glu Lys Lys Lys Lys
945                 950                 955                 960 ctt gag gat gcc aag tct cag gag cag ttt ctt gga tta gat aga gaa    2928
Leu Glu Asp Ala Lys Ser Gln Glu Gln Phe Leu Gly Leu Asp Arg Glu
                965                 970                 975 ttg aag aag cta aag aaa gct gtg gct gcc tct gat aag ctg gcc aca    2976
Leu Lys Lys Leu Lys Lys Ala Val Ala Ala Ser Asp Lys Leu Ala Thr
            980                 985                 990 gct gag ctc acc att gcc aaa gac cag ctc aag tcc ctt cat gga act    3024
Ala Glu Leu Thr Ile Ala Lys Asp Gln Leu Lys Ser Leu His Gly Thr
        995                 1000                1005 gtg atg aaa att aac cag gag cga gca gag gag ctg cag gag acg       3069
Val Met Lys Ile Asn Gln Glu Arg Ala Glu Glu Leu Gln Glu Thr
1010                1015                1020 gag agg ttc agc aga aag gca gca caa gca gct agg gat ctg atc       3114
Glu Arg Phe Ser Arg Lys Ala Ala Gln Ala Ala Arg Asp Leu Ile
1025                1030                1035 cga gca gaa gcg gag att gaa ctc ctg cag aag ctt ctc aga gat       3159
Arg Ala Glu Ala Glu Ile Glu Leu Leu Gln Lys Leu Leu Arg Asp
1040                1045                1050 aaa gag gag cag ttt cga aat gag att gag aaa gta gat gtc ggc       3204
Lys Glu Glu Gln Phe Arg Asn Glu Ile Glu Lys Val Asp Val Gly
1055                1060                1065 tct gga gga gca aag tca cag atg ctg gag atg gag aaa cta aat       3249
Ser Gly Gly Ala Lys Ser Gln Met Leu Glu Met Glu Lys Leu Asn
1070                1075                1080 gag aca atg gag agg caa aga aca gag att gct agg ctg agg aat       3294
Glu Thr Met Glu Arg Gln Arg Thr Glu Ile Ala Arg Leu Arg Asn
1085                1090                1095 tta cta gac ctc acc ggg gct gat aac aaa gga aac ttt gaa aat       3339
Leu Leu Asp Leu Thr Gly Ala Asp Asn Lys Gly Asn Phe Glu Asn
1100                1105                1110 gtt ttg gaa gaa att gct gaa ctt cga cgt gaa gtt tct cat cag       3384
Val Leu Glu Glu Ile Ala Glu Leu Arg Arg Glu Val Ser His Gln
1115                1120                1125 aat gat tac atc agc agc atg aca gat cct ttc aaa aga cga ggc       3429
Asn Asp Tyr Ile Ser Ser Met Thr Asp Pro Phe Lys Arg Arg Gly
1130                1135                1140 tat tgg tac ttt atg cca cca cca tca tca tca aaa gtt tcc agc       3474
Tyr Trp Tyr Phe Met Pro Pro Pro Ser Ser Ser Lys Val Ser Ser
1145                1150                1155 cac agt tcc cag gcc acc aag gac tct ggt gtt ggc cta aag tac       3519
His Ser Ser Gln Ala Thr Lys Asp Ser Gly Val Gly Leu Lys Tyr
1160                1165                1170 aca gcc tcc act ccg gtt aga aaa cca cat cgt gga cgg cag gat       3564
Thr Ala Ser Thr Pro Val Arg Lys Pro His Arg Gly Arg Gln Asp
1175                1180                1185 gga aag gag aac agt ggg cct cca cct gcc tca gga tac tgg gtg       3609
Gly Lys Glu Asn Ser Gly Pro Pro Pro Ala Ser Gly Tyr Trp Val
1190                1195                1200
```

| | |
|---|---|
| tat tct cct atc agg agt ggg tta cat aaa tcg ttc tca aat aga<br>Tyr Ser Pro Ile Arg Ser Gly Leu His Lys Ser Phe Ser Asn Arg<br>1205              1210                   1215 | 3654 |
| gac gca gac agt gga gga gat agc cag gaa gag agc gag cta gat<br>Asp Ala Asp Ser Gly Gly Asp Ser Gln Glu Glu Ser Glu Leu Asp<br>1220              1225                   1230 | 3699 |
| gac caa gaa gac cac cca ttt gta cct cct cct gga tac atg atg<br>Asp Gln Glu Asp His Pro Phe Val Pro Pro Pro Gly Tyr Met Met<br>1235              1240                   1245 | 3744 |
| tac act gtg ttt cct gat ggt tct cct gta ccc cag ggc atg gcc<br>Tyr Thr Val Phe Pro Asp Gly Ser Pro Val Pro Gln Gly Met Ala<br>1250              1255                   1260 | 3789 |
| ctg tat gca ccc cct cct ccc ttg ccc aac aat agc cag cct ctt<br>Leu Tyr Ala Pro Pro Pro Pro Leu Pro Asn Asn Ser Gln Pro Leu<br>1265              1270                   1275 | 3834 |
| gac ctt ggc act gtt gtt tat ggc cca cct cct gtt ggg gct ccc<br>Asp Leu Gly Thr Val Val Tyr Gly Pro Pro Pro Val Gly Ala Pro<br>1280              1285                   1290 | 3879 |
| atc gtg tat ggg cct cca cct ccc aac ttc tcc gta ccc ctc atc<br>Ile Val Tyr Gly Pro Pro Pro Pro Asn Phe Ser Val Pro Leu Ile<br>1295              1300                   1305 | 3924 |
| ccc gtg ggt gtg ctg cac tgc aat gtc cca gaa cac cat aac ttg<br>Pro Val Gly Val Leu His Cys Asn Val Pro Glu His His Asn Leu<br>1310              1315                   1320 | 3969 |
| gag aat gaa gtt tct aga tta gaa gac ata atg cag cat tta aaa<br>Glu Asn Glu Val Ser Arg Leu Glu Asp Ile Met Gln His Leu Lys<br>1325              1330                   1335 | 4014 |
| tct ggg aaa cgg gaa cag tgc atg aaa aca ccc aag ctg cag tcg<br>Ser Gly Lys Arg Glu Gln Cys Met Lys Thr Pro Lys Leu Gln Ser<br>1340              1345                   1350 | 4059 |
| gag aaa gaa ctc gca gag ctg cag cat aac att gat ggt ctt ttg<br>Glu Lys Glu Leu Ala Glu Leu Gln His Asn Ile Asp Gly Leu Leu<br>1355              1360                   1365 | 4104 |
| caa gag aag aaa gac tta gag cat gaa gta gaa gaa tta cat aga<br>Gln Glu Lys Lys Asp Leu Glu His Glu Val Glu Glu Leu His Arg<br>1370              1375                   1380 | 4149 |
| acc atc caa aaa cat caa cag cga aaa gat ttc att gat gga aac<br>Thr Ile Gln Lys His Gln Gln Arg Lys Asp Phe Ile Asp Gly Asn<br>1385              1390                   1395 | 4194 |
| gtt gag agt ctt gtg aat gat cta gaa ata gag aag tca ctc aaa<br>Val Glu Ser Leu Val Asn Asp Leu Glu Ile Glu Lys Ser Leu Lys<br>1400              1405                   1410 | 4239 |
| cac cat gaa gat att gtt gat gaa att gaa tgt att gag agg acc<br>His His Glu Asp Ile Val Asp Glu Ile Glu Cys Ile Glu Arg Thr<br>1415              1420                   1425 | 4284 |
| ctt ctg aag cgc cgt gca gag ctc agg gaa gcc gac cgg ctg ctg<br>Leu Leu Lys Arg Arg Ala Glu Leu Arg Glu Ala Asp Arg Leu Leu<br>1430              1435                   1440 | 4329 |
| acg gag gct gaa agt gaa ctt tca tgc acg aaa gag aaa aca aaa<br>Thr Glu Ala Glu Ser Glu Leu Ser Cys Thr Lys Glu Lys Thr Lys<br>1445              1450                   1455 | 4374 |
| cat gct gtt gag aag ttc act gat gcc aag aga aat tta ttg caa<br>His Ala Val Glu Lys Phe Thr Asp Ala Lys Arg Asn Leu Leu Gln<br>1460              1465                   1470 | 4419 |
| act gag aaa gat gct gag gag tta gaa agg aga gcc cag gaa act<br>Thr Glu Lys Asp Ala Glu Glu Leu Glu Arg Arg Ala Gln Glu Thr<br>1475              1480                   1485 | 4464 |
| gcc att aac ctc gtc aaa gcc gac cag cag ctg aga ttg ctc cag<br>Ala Ile Asn Leu Val Lys Ala Asp Gln Gln Leu Arg Leu Leu Gln | 4509 |

-continued

| | | |
|---|---|---|
| gct gac acg aag gat ttg gag cag cac aaa atg gag caa gag gaa<br>Ala Asp Thr Lys Asp Leu Glu Gln His Lys Met Glu Gln Glu Glu<br>1505                       1510                     1515 | | 4554 |
| atc ttg aaa gaa ata aac aaa gtt gtt gca gca aaa gac tca gac<br>Ile Leu Lys Glu Ile Asn Lys Val Val Ala Ala Lys Asp Ser Asp<br>1520                       1525                     1530 | | 4599 |
| ttc cag agc cta aac aag aag aag gaa gta ctg aca gga gag ctg<br>Phe Gln Ser Leu Asn Lys Lys Lys Glu Val Leu Thr Gly Glu Leu<br>1535                       1540                     1545 | | 4644 |
| cag aaa ctc cag aag gac att gag act gca cgg cac aat gag gat<br>Gln Lys Leu Gln Lys Asp Ile Glu Thr Ala Arg His Asn Glu Asp<br>1550                       1555                     1560 | | 4689 |
| cag cac ctg cag gtc ctt aaa gag tcg gag acc ctc ctg cag gcc<br>Gln His Leu Gln Val Leu Lys Glu Ser Glu Thr Leu Leu Gln Ala<br>1565                       1570                     1575 | | 4734 |
| aag aaa gct gag ctg gaa aat ctg aaa agc cag gtg tca gga cag<br>Lys Lys Ala Glu Leu Glu Asn Leu Lys Ser Gln Val Ser Gly Gln<br>1580                       1585                     1590 | | 4779 |
| cag cag gag atg gcc gtc ttg gac agg gag tta gga cac aag aag<br>Gln Gln Glu Met Ala Val Leu Asp Arg Glu Leu Gly His Lys Lys<br>1595                       1600                     1605 | | 4824 |
| gaa gag ctg cat ctc ctc cag gaa agc atg gtc cag gcc aaa gct<br>Glu Glu Leu His Leu Leu Gln Glu Ser Met Val Gln Ala Lys Ala<br>1610                       1615                     1620 | | 4869 |
| gac ctc cag gaa gca ctg aga cta gga gaa agt gaa gta act gag<br>Asp Leu Gln Glu Ala Leu Arg Leu Gly Glu Ser Glu Val Thr Glu<br>1625                       1630                     1635 | | 4914 |
| aag tgc aat cac att agg gaa gta aaa tct ctt ctg gaa gaa ctc<br>Lys Cys Asn His Ile Arg Glu Val Lys Ser Leu Leu Glu Glu Leu<br>1640                       1645                     1650 | | 4959 |
| agt ttt cag aaa gga gaa ctg aat gtc cag atc agt gaa aaa aaa<br>Ser Phe Gln Lys Gly Glu Leu Asn Val Gln Ile Ser Glu Lys Lys<br>1655                       1660                     1665 | | 5004 |
| act caa ctt gca ctc ata aag cag gaa att gaa aaa gag gaa gac<br>Thr Gln Leu Ala Leu Ile Lys Gln Glu Ile Glu Lys Glu Glu Asp<br>1670                       1675                     1680 | | 5049 |
| aat ctt cag gta gtt tta ggg caa atg tct aaa cat aaa act gaa<br>Asn Leu Gln Val Val Leu Gly Gln Met Ser Lys His Lys Thr Glu<br>1685                       1690                     1695 | | 5094 |
| cta aag aat att ctg gac atg ttg caa ctt gaa aat aat gag ctg<br>Leu Lys Asn Ile Leu Asp Met Leu Gln Leu Glu Asn Asn Glu Leu<br>1700                       1705                     1710 | | 5139 |
| caa ggt ttg aag ctc caa cat gac caa aag atg tct gaa tta gag<br>Gln Gly Leu Lys Leu Gln His Asp Gln Lys Met Ser Glu Leu Glu<br>1715                       1720                     1725 | | 5184 |
| aag act cgg gtt gaa gtg ctg gag gag aaa ctg gag tta gag agt<br>Lys Thr Arg Val Glu Val Leu Glu Glu Lys Leu Glu Leu Glu Ser<br>1730                       1735                     1740 | | 5229 |
| ctg cag cag gca gcc ctg cga cag aga ggg gag ata gag tgg cag<br>Leu Gln Gln Ala Ala Leu Arg Gln Arg Gly Glu Ile Glu Trp Gln<br>1745                       1750                     1755 | | 5274 |
| aag cag ctc ctc cag agg aac aca cag gaa gta gag cgg atg act<br>Lys Gln Leu Leu Gln Arg Asn Thr Gln Glu Val Glu Arg Met Thr<br>1760                       1765                     1770 | | 5319 |
| gct gag acc cga gca tta cag tca tgt gtt gag tct ttg tgc aaa<br>Ala Glu Thr Arg Ala Leu Gln Ser Cys Val Glu Ser Leu Cys Lys<br>1775                       1780                     1785 | | 5364 |
| gaa aag caa gat ctc gaa gaa aaa cag gac agc tgg gaa aag aag | | 5409 |

-continued

| | | |
|---|---|---|
| Glu Lys Gln Asp Leu Glu Glu Lys Gln Asp Ser Trp Glu Lys Lys<br>1790                            1795                          1800 | | |
| ttg gca cag acc aaa cgg gtt cta gca gct gca gaa gag gac agc<br>Leu Ala Gln Thr Lys Arg Val Leu Ala Ala Ala Glu Glu Asp Ser<br>1805                            1810                          1815 | | 5454 |
| gag atg gag cgg gca cgc tta gaa aag ttg gaa ctg gac gcc agg<br>Glu Met Glu Arg Ala Arg Leu Glu Lys Leu Glu Leu Asp Ala Arg<br>1820                            1825                          1830 | | 5499 |
| aag ctg cag cag gag ttg gac caa cga aac agg gag aag ctc tcc<br>Lys Leu Gln Gln Glu Leu Asp Gln Arg Asn Arg Glu Lys Leu Ser<br>1835                            1840                          1845 | | 5544 |
| ctg cat caa gac ctg gca gtg gtg cag cag cag cta caa gaa aaa<br>Leu His Gln Asp Leu Ala Val Val Gln Gln Gln Leu Gln Glu Lys<br>1850                            1855                          1860 | | 5589 |
| cag gaa gca gta aac tca tta cag aag gaa cta gct gat gtc cag<br>Gln Glu Ala Val Asn Ser Leu Gln Lys Glu Leu Ala Asp Val Gln<br>1865                            1870                          1875 | | 5634 |
| gag cat ttg gac cta gca gaa cag gag gtg ctc tgc acc acc aag<br>Glu His Leu Asp Leu Ala Glu Gln Glu Val Leu Cys Thr Thr Lys<br>1880                            1885                          1890 | | 5679 |
| cgc aag gac gca ctg ctc agc gaa cag acc agg ctc gag aag gac<br>Arg Lys Asp Ala Leu Leu Ser Glu Gln Thr Arg Leu Glu Lys Asp<br>1895                            1900                          1905 | | 5724 |
| gtg ggt gaa tgg acg aag aag ttt gaa gac tgc cag aaa gaa ggg<br>Val Gly Glu Trp Thr Lys Lys Phe Glu Asp Cys Gln Lys Glu Gly<br>1910                            1915                          1920 | | 5769 |
| gag aca aag cag caa cag ctt caa ggg ctt cag aag gag att gaa<br>Glu Thr Lys Gln Gln Gln Leu Gln Gly Leu Gln Lys Glu Ile Glu<br>1925                            1930                          1935 | | 5814 |
| gga aac gag gcg aag cta gcc caa caa gaa atg atg ttt cag aga<br>Gly Asn Glu Ala Lys Leu Ala Gln Gln Glu Met Met Phe Gln Arg<br>1940                            1945                          1950 | | 5859 |
| ctc cag aaa gag cga gaa tgt gaa gaa aaa aag tta gaa gct agt<br>Leu Gln Lys Glu Arg Glu Cys Glu Glu Lys Lys Leu Glu Ala Ser<br>1955                            1960                          1965 | | 5904 |
| aaa gtg act ctg aag gag cag cag caa cag ctg gaa aag gaa ttg<br>Lys Val Thr Leu Lys Glu Gln Gln Gln Gln Leu Glu Lys Glu Leu<br>1970                            1975                          1980 | | 5949 |
| atg gag cag aaa ggc aag ctg gac cag gtg ctc gct aag ctc ttg<br>Met Glu Gln Lys Gly Lys Leu Asp Gln Val Leu Ala Lys Leu Leu<br>1985                            1990                          1995 | | 5994 |
| gtg gct gag gag cgt gtc agg acc ttg cag gag gag gga agg tgg<br>Val Ala Glu Glu Arg Val Arg Thr Leu Gln Glu Glu Gly Arg Trp<br>2000                            2005                          2010 | | 6039 |
| agc gag acc ctg gag aag acg ctc tcc cag acc aag cga cag ctt<br>Ser Glu Thr Leu Glu Lys Thr Leu Ser Gln Thr Lys Arg Gln Leu<br>2015                            2020                          2025 | | 6084 |
| tca gaa cgg gag cag cag tta ctg gcc aag tca gac gag ctg ctg<br>Ser Glu Arg Glu Gln Gln Leu Leu Ala Lys Ser Asp Glu Leu Leu<br>2030                            2035                          2040 | | 6129 |
| gcc ctg cag aag gag acg gac tcc atg agg gcg gac ttc agc ctc<br>Ala Leu Gln Lys Glu Thr Asp Ser Met Arg Ala Asp Phe Ser Leu<br>2045                            2050                          2055 | | 6174 |
| ttg cgc aac cag ttc ctg aca gaa aga aag aaa gcc gag aag cag<br>Leu Arg Asn Gln Phe Leu Thr Glu Arg Lys Lys Ala Glu Lys Gln<br>2060                            2065                          2070 | | 6219 |
| gtg gcc agc ctg aag gaa gcc ctt aag atc cag cgg agc caa ctg<br>Val Ala Ser Leu Lys Glu Ala Leu Lys Ile Gln Arg Ser Gln Leu<br>2075                            2080                          2085 | | 6264 |

| | | | | | | | | | | | | |
|---|---|---|---|---|---|---|---|---|---|---|---|---|
| gag | aag | aac | ctt | ctg | gag | caa | aag | cag | gag | aac | agc | tgc atg cag | 6309 |
| Glu | Lys | Asn | Leu | Leu | Glu | Gln | Lys | Gln | Glu | Asn | Ser | Cys Met Gln |
| | 2090 | | | | 2095 | | | | 2100 | | | |

| | | | | | | | | | | | | |
|---|---|---|---|---|---|---|---|---|---|---|---|---|
| agg | gag | atg | gca | acc | atc | gaa | cag | gtg | gcc | cag | gac | aac cac gag | 6354 |
| Arg | Glu | Met | Ala | Thr | Ile | Glu | Gln | Val | Ala | Gln | Asp | Asn His Glu |
| | 2105 | | | | 2110 | | | | 2115 | | | |

| | | | | | | | | | | | | |
|---|---|---|---|---|---|---|---|---|---|---|---|---|
| cgg | gcc | cgg | cgc | ctg | atg | agg | gag | ctc | aac | cag | atg | cag cgc gag | 6399 |
| Arg | Ala | Arg | Arg | Leu | Met | Arg | Glu | Leu | Asn | Gln | Met | Gln Arg Glu |
| | 2120 | | | | 2125 | | | | 2130 | | | |

| | | | | | | | | | | | | |
|---|---|---|---|---|---|---|---|---|---|---|---|---|
| tac | gtg | gag | ctc | agg | aaa | cag | atg | aca | aac | caa | aag | gat ttg gaa | 6444 |
| Tyr | Val | Glu | Leu | Arg | Lys | Gln | Met | Thr | Asn | Gln | Lys | Asp Leu Glu |
| | 2135 | | | | 2140 | | | | 2145 | | | |

| | | | | | | | | | | | | |
|---|---|---|---|---|---|---|---|---|---|---|---|---|
| aga | aga | cag | atg | gaa | atc | agt | gat | gcg | atg | caa | gca | ctt aaa tgt | 6489 |
| Arg | Arg | Gln | Met | Glu | Ile | Ser | Asp | Ala | Met | Gln | Ala | Leu Lys Cys |
| | 2150 | | | | 2155 | | | | 2160 | | | |

| | | | | | | | | | | | | |
|---|---|---|---|---|---|---|---|---|---|---|---|---|
| gag | gtg | aaa | gat | gaa | atc | cga | acc | agc | ctg | aag | aat | ctc aac cag | 6534 |
| Glu | Val | Lys | Asp | Glu | Ile | Arg | Thr | Ser | Leu | Lys | Asn | Leu Asn Gln |
| | 2165 | | | | 2170 | | | | 2175 | | | |

| | | | | | | | | | | | | |
|---|---|---|---|---|---|---|---|---|---|---|---|---|
| ttt | ctt | cca | gag | ctg | cca | gcg | gac | ctg | gag | gcc | ctt | ctg gaa agg | 6579 |
| Phe | Leu | Pro | Glu | Leu | Pro | Ala | Asp | Leu | Glu | Ala | Leu | Leu Glu Arg |
| | 2180 | | | | 2185 | | | | 2190 | | | |

| | | | | | | | | | | | | |
|---|---|---|---|---|---|---|---|---|---|---|---|---|
| aat | gag | aac | ctt | gga | gga | ggc | ttg | gag | agc | ttg | aaa | gag aat ttc | 6624 |
| Asn | Glu | Asn | Leu | Gly | Gly | Gly | Leu | Glu | Ser | Leu | Lys | Glu Asn Phe |
| | 2195 | | | | 2200 | | | | 2205 | | | |

| | | | | | | | | | | | | |
|---|---|---|---|---|---|---|---|---|---|---|---|---|
| ccg | ttt | acc | gtg | agc | gac | aga | cca | tca | tct | tgc | gaa | gag aaa ctg | 6669 |
| Pro | Phe | Thr | Val | Ser | Asp | Arg | Pro | Ser | Ser | Cys | Glu | Glu Lys Leu |
| | 2210 | | | | 2215 | | | | 2220 | | | |

| | | | | | | | | | | | | |
|---|---|---|---|---|---|---|---|---|---|---|---|---|
| aat | ttt | ggc | cag | gct | cac | gtg | gcg | gat | gaa | cag | tgg | cgg gga gag | 6714 |
| Asn | Phe | Gly | Gln | Ala | His | Val | Ala | Asp | Glu | Gln | Trp | Arg Gly Glu |
| | 2225 | | | | 2230 | | | | 2235 | | | |

| | | | | | | | | | | | | |
|---|---|---|---|---|---|---|---|---|---|---|---|---|
| gca | ctc | cgg | gag | aag | ctg | cgc | cac | cgc | gag | gac | cgg | ctc aag gcc | 6759 |
| Ala | Leu | Arg | Glu | Lys | Leu | Arg | His | Arg | Glu | Asp | Arg | Leu Lys Ala |
| | 2240 | | | | 2245 | | | | 2250 | | | |

| | | | | | | | | | | | | |
|---|---|---|---|---|---|---|---|---|---|---|---|---|
| cag | ctg | cgc | cgc | tgc | atg | tcc | aag | cag | gcc | gag | gtg | ctg agc gag | 6804 |
| Gln | Leu | Arg | Arg | Cys | Met | Ser | Lys | Gln | Ala | Glu | Val | Leu Ser Glu |
| | 2255 | | | | 2260 | | | | 2265 | | | |

| | | | | | | | | | | | | |
|---|---|---|---|---|---|---|---|---|---|---|---|---|
| ggc | cgg | cgg | cgc | acg | gag | ggg | acc | ctg | cac | agc | ctg | cgg cgg cag | 6849 |
| Gly | Arg | Arg | Arg | Thr | Glu | Gly | Thr | Leu | His | Ser | Leu | Arg Arg Gln |
| | 2270 | | | | 2275 | | | | 2280 | | | |

| | | | | | | | | | | | | |
|---|---|---|---|---|---|---|---|---|---|---|---|---|
| gtg | gac | gcc | ctg | ggc | gag | ctg | gtc | acc | agc | act | tcc | ggg gac tcc | 6894 |
| Val | Asp | Ala | Leu | Gly | Glu | Leu | Val | Thr | Ser | Thr | Ser | Gly Asp Ser |
| | 2285 | | | | 2290 | | | | 2295 | | | |

| | | | | | | | | | | | | |
|---|---|---|---|---|---|---|---|---|---|---|---|---|
| gcg | tcc | acc | cgc | agt | ctg | tcg | cgc | acc | gag | ggc | tcg | ctc gcc gag | 6939 |
| Ala | Ser | Thr | Arg | Ser | Leu | Ser | Arg | Thr | Glu | Gly | Ser | Leu Ala Glu |
| | 2300 | | | | 2305 | | | | 2310 | | | |

| | | | | | | | | | | | | |
|---|---|---|---|---|---|---|---|---|---|---|---|---|
| gac | gaa | ccg | ccg | ggg | ccc | agc | cag | gag | ctg | cac | gtg | ctg ggg tcg | 6984 |
| Asp | Glu | Pro | Pro | Gly | Pro | Ser | Gln | Glu | Leu | His | Val | Leu Gly Ser |
| | 2315 | | | | 2320 | | | | 2325 | | | |

| | | | | | | | | | | | | |
|---|---|---|---|---|---|---|---|---|---|---|---|---|
| ggc | ggc | agc | gac | cga | ggt | gga | gga | cgg | ggc | ggg | agg | aag ggc | 7029 |
| Gly | Gly | Ser | Asp | Arg | Gly | Gly | Gly | Arg | Gly | Gly | Arg | Lys Gly |
| | 2330 | | | | 2335 | | | | 2340 | | | |

| | | | | | | | | | | | | |
|---|---|---|---|---|---|---|---|---|---|---|---|---|
| ctt | tcc | cga | cgc | cgc | cgc | tgg | aac | cac | gga | gaa | gcg | cgc ctc ggc | 7074 |
| Leu | Ser | Arg | Arg | Arg | Arg | Trp | Asn | His | Gly | Glu | Ala | Arg Leu Gly |
| | 2345 | | | | 2350 | | | | 2355 | | | |

| | | | | | | | | | | | | |
|---|---|---|---|---|---|---|---|---|---|---|---|---|
| ccg | cgg | agg | ccc | cca | cgg | gag | ggg | gca | ggg | cgg | ggc | gcg gcc ttc | 7119 |
| Pro | Arg | Arg | Pro | Pro | Arg | Glu | Gly | Ala | Gly | Arg | Gly | Ala Ala Phe |
| | 2360 | | | | 2365 | | | | 2370 | | | |

| | | | | | | | | | | | | |
|---|---|---|---|---|---|---|---|---|---|---|---|---|
| cga | gcc | ttg | gtc | tcc | tgc | tcc | cgc | cct | gca | gag | ctc | ccg gcg gct | 7164 |
| Arg | Ala | Leu | Val | Ser | Cys | Ser | Arg | Pro | Ala | Glu | Leu | Pro Ala Ala |
| | 2375 | | | | 2380 | | | | 2385 | | | |

```
ccc ccg agg ccc gtc gcc gcg gct gga cgc gca ccg acc ctg agg      7209
Pro Pro Arg Pro Val Ala Ala Ala Gly Arg Ala Pro Thr Leu Arg
    2390            2395                2400 acc cgg agg acc cgg agg ccc ggc gtc ccc tcg gaa cgc ttc ctc      7254
Thr Arg Arg Thr Arg Arg Pro Gly Val Pro Ser Glu Arg Phe Leu
    2405            2410                2415 cgc gtc cgc gga cac cag gct cac ggg aag gcg cgt cca tgc ggg      7299
Arg Val Arg Gly His Gln Ala His Gly Lys Ala Arg Pro Cys Gly
    2420            2425                2430 aag agc cgc gag cgg aac ccg gat gcc cgg gct ggt ctc tgg gcc      7344
Lys Ser Arg Glu Arg Asn Pro Asp Ala Arg Ala Gly Leu Trp Ala
    2435            2440                2445 ttg gaa acg tgt tgc cgt aaa agc agc gcc cgc ggc tgc gga ctt      7389
Leu Glu Thr Cys Cys Arg Lys Ser Ser Ala Arg Gly Cys Gly Leu
    2450            2455                2460 gaa gcc ccg aac tgc cgc cgt gcc cgg tgc gga gcg agc gtg cgg      7434
Glu Ala Pro Asn Cys Arg Arg Ala Arg Cys Gly Ala Ser Val Arg
    2465            2470                2475 tac cct ctc gtg cct cgg ggc cgg act gga cga ggg gcc gtg acc      7479
Tyr Pro Leu Val Pro Arg Gly Arg Thr Gly Arg Gly Ala Val Thr
    2480            2485                2490 ccg tgg ggc cgc ctg cag tcc cga ggg acg cgg acc acc ccc cgg      7524
Pro Trp Gly Arg Leu Gln Ser Arg Gly Thr Arg Thr Thr Pro Arg
    2495            2500                2505 ccg gtg cga cgg gag cat ccc cag cac cag gaa agg ccc cca ggg      7569
Pro Val Arg Arg Glu His Pro Gln His Gln Glu Arg Pro Pro Gly
    2510            2515                2520 cgc gtt acc gcg gcc cac act gag acc gcc cct ccc cgc cgg gtg      7614
Arg Val Thr Ala Ala His Thr Glu Thr Ala Pro Pro Arg Arg Val
    2525            2530                2535 ttc cac gcg cga gta gca gtc ggg gag gtc agc ctc ggg ccc ggc      7659
Phe His Ala Arg Val Ala Val Gly Glu Val Ser Leu Gly Pro Gly
    2540            2545                2550 cgc ggt ctc gag cga aca cgg ggc ggg ggc ggg ggg gcg ggg gcg      7704
Arg Gly Leu Glu Arg Thr Arg Gly Gly Gly Gly Gly Ala Gly Ala
    2555            2560                2565 gga ctc ctc gca gag gcc gcg gcc acg gcc cgg tgc gca gac ccc      7749
Gly Leu Leu Ala Glu Ala Ala Ala Thr Ala Arg Cys Ala Asp Pro
    2570            2575                2580 tcc aca gac ccc tcc gca tag                                      7770
Ser Thr Asp Pro Ser Ala
    2585

<210> SEQ ID NO 42
<211> LENGTH: 2589
<212> TYPE: PRT
<213> ORGANISM: Canis familiaris

<400> SEQUENCE: 42

Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
                20                  25                  30

Arg Ser Leu Ser Pro Leu Ser Gly Ser Glu Thr Leu Pro Phe His Phe
            35                  40                  45

Gly Gly Pro Trp His Glu Gln Val Glu Ile Thr Asp Glu Ser Thr Val
        50                  55                  60

Val Leu Asp Tyr Gln Asp His Lys Glu Ala Asp Ser His Ala Gly Val
65                  70                  75                  80
```

```
Arg Tyr Ile Thr Glu Ala Leu Val Arg Lys Leu Thr Lys Gln Asp Asn
                85                  90                  95

Leu Ala Leu Val Lys Ser Leu Asn Leu Ser Leu Ala Lys Gly Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220

Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
                245                 250                 255

Ser Gln Asp Arg Gln Glu Ala Phe Ala Arg Phe Ser Leu Asp Glu Val
            260                 265                 270

Glu Arg Leu Glu Arg Asp Leu Glu Lys Lys Thr Met Glu Thr Glu Glu
        275                 280                 285

Leu Arg Ser Glu Gln Thr Arg Phe Leu Glu Glu Ile Lys Ser Gln Asp
    290                 295                 300

Lys Leu Asn Lys Ser Leu Lys Glu Glu Ala Arg Leu Gln Lys Gln Ser
305                 310                 315                 320

Tyr Glu Glu Leu Glu Ser Asn Leu Asn Thr Lys Asn Glu Leu Leu Lys
                325                 330                 335

Gln Lys Thr Met Glu Leu Met Arg Ala Cys Gln Lys Gln Tyr Glu Met
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Val Glu Ile Asp Lys Thr Pro Asp Glu
    370                 375                 380

Ser Pro Tyr Ile Gly Lys Ser Arg Tyr Lys Arg Asn Met Phe Thr Thr
385                 390                 395                 400

Glu Ser Tyr Ile Ile Ala Asn Ala Gln Thr Val Lys Ile Lys Lys Met
                405                 410                 415

Glu Leu Asp Glu Gly Glu Gln Leu Arg Asn Glu His Val Asn Leu Gly
            420                 425                 430

Ala Ser Pro Thr Asp Ile Gln Leu Glu Asp Lys Glu Lys Ile Ser
        435                 440                 445

Ala Ala Gln Thr Arg Leu Ser Glu Leu His Asp Glu Ile Glu Lys Ala
    450                 455                 460

Glu Gln Gln Ile Leu Arg Ala Thr Glu Glu Phe Lys Gln Leu Glu Glu
465                 470                 475                 480

Ala Ile Gln Leu Lys Lys Ile Ser Glu Ala Glu Lys Asp Leu Leu Phe
                485                 490                 495
```

```
Lys Gln Leu Ser Gly Arg Ile Gln Leu Leu Asn Lys Leu Arg Gln Glu
            500                 505                 510

Ala Val Asp Leu Glu Thr Gln Met Glu Lys Gln Arg Gln Glu Ile Gly
            515                 520                 525

Glu Lys Gln Asn Glu Ile Lys Asp Leu Glu Ile Val Thr Asp Ser Leu
        530                 535                 540

Asp Ser Arg Asp Pro Lys His Cys His Met Lys Ala Gln Lys Arg Gly
545                 550                 555                 560

Lys Glu Gln Gln Leu Asp Ile Met Asn Lys Gln Tyr Lys Gln Leu Glu
                565                 570                 575

Ser Arg Leu Asp Glu Ile Leu Ser Arg Ile Ala Lys Glu Thr Glu Glu
            580                 585                 590

Ile Lys Asp Leu Glu Glu Gln Leu Thr Glu Gly Gln Ile Ala Ala Asn
        595                 600                 605

Glu Ala Leu Lys Lys Asp Leu Glu Ser Val Ile Ser Gly Leu Gln Glu
610                 615                 620

Tyr Leu Glu Thr Val Lys Gly Gln Ala Arg Gln Ala Gln Asn Glu Cys
625                 630                 635                 640

Arg Lys Leu Gln Asp Glu Lys Glu Thr Leu Leu Gln Arg Leu Ser Glu
                645                 650                 655

Val Glu Gln Glu Arg Asp Gln Leu Glu Ile Val Ala Ile Asp Ala Glu
            660                 665                 670

Asn Met Arg Lys Glu Leu Ala Glu Leu Glu Asn Ala Leu Gln Glu Gln
        675                 680                 685

His Glu Val Asn Ile Ser Leu Gln Gln Thr Gln Gly Asp Leu Ser Ala
690                 695                 700

Tyr Glu Ala Glu Leu Glu Ala Gln Leu Lys Ile Arg Asp Ala Glu Ala
705                 710                 715                 720

Asn Gln Leu Lys Glu Glu Leu Glu Lys Leu Arg Arg Leu Ser Gln Leu
                725                 730                 735

Glu Gln Ser Ala Leu Gln Ala Glu Glu Lys Glu Lys Gln Ala Phe
            740                 745                 750

Lys Thr Ala Val Lys Lys Ala Gln Leu Ser Glu Gly Lys Asp Gln Glu
        755                 760                 765

Asn Ser Glu Leu Arg Thr Gln Leu Gln Gln Leu Gln Asp Asp Asn Asp
770                 775                 780

Leu Leu Lys Gln Gln Leu Lys Asp Phe Gln Ser His Leu Asn His Val
785                 790                 795                 800

Val Asp Gly Leu Ile Arg Pro Glu Glu Val Ala Ala Cys Val Asp Glu
                805                 810                 815

Leu Arg Lys Lys Leu Lys Ser Gly Ala Gly Glu Met Arg Ile His Thr
            820                 825                 830

Pro Ser Asp Val Leu Gly Lys Ser Leu Ala Asp Leu Gln Lys Gln Phe
        835                 840                 845

Ser Glu Ile Leu Ala Arg Ser Gln Trp Glu Arg Gln Glu Ala Gln Val
        850                 855                 860

Arg Glu Arg Lys Leu Gln Glu Glu Met Ala Leu Gln Gln Glu Lys Leu
865                 870                 875                 880

Ala Ser Gly Gln Glu Glu Phe Arg His Ala Cys Glu Arg Ala Leu Glu
                885                 890                 895

Ala Arg Ile Ser Phe Asp Lys Arg Gln His Glu Ala Arg Ile Gln Gln
            900                 905                 910

Leu Glu Asn Glu Ile His Tyr Leu Gln Glu Asn Leu Lys Ser Met Glu
```

-continued

```
            915                 920                 925
Glu Ile Gln Gly Leu Thr Asp Leu Gln Leu Gln Glu Ala Asp Glu Glu
            930                 935                 940
Lys Glu Arg Ile Leu Ala Gln Leu Arg Glu Leu Glu Lys Lys Lys Lys
945                 950                 955                 960
Leu Glu Asp Ala Lys Ser Gln Glu Gln Phe Leu Gly Leu Asp Arg Glu
                965                 970                 975
Leu Lys Lys Leu Lys Lys Ala Val Ala Ala Ser Asp Lys Leu Ala Thr
                980                 985                 990
Ala Glu Leu Thr Ile Ala Lys Asp Gln Leu Lys Ser Leu His Gly Thr
                995                 1000                1005
Val Met Lys Ile Asn Gln Glu Arg Ala Glu Glu Leu Gln Glu Thr
        1010                1015                1020
Glu Arg Phe Ser Arg Lys Ala Ala Gln Ala Ala Arg Asp Leu Ile
        1025                1030                1035
Arg Ala Glu Ala Glu Ile Glu Leu Leu Gln Lys Leu Leu Arg Asp
        1040                1045                1050
Lys Glu Glu Gln Phe Arg Asn Glu Ile Glu Lys Val Asp Val Gly
        1055                1060                1065
Ser Gly Gly Ala Lys Ser Gln Met Leu Glu Met Glu Lys Leu Asn
        1070                1075                1080
Glu Thr Met Glu Arg Gln Arg Thr Glu Ile Ala Arg Leu Arg Asn
        1085                1090                1095
Leu Leu Asp Leu Thr Gly Ala Asp Asn Lys Gly Asn Phe Glu Asn
        1100                1105                1110
Val Leu Glu Glu Ile Ala Glu Leu Arg Arg Glu Val Ser His Gln
        1115                1120                1125
Asn Asp Tyr Ile Ser Ser Met Thr Asp Pro Phe Lys Arg Arg Gly
        1130                1135                1140
Tyr Trp Tyr Phe Met Pro Pro Pro Ser Ser Ser Lys Val Ser Ser
        1145                1150                1155
His Ser Ser Gln Ala Thr Lys Asp Ser Gly Val Gly Leu Lys Tyr
        1160                1165                1170
Thr Ala Ser Thr Pro Val Arg Lys Pro His Arg Gly Arg Gln Asp
        1175                1180                1185
Gly Lys Glu Asn Ser Gly Pro Pro Ala Ser Gly Tyr Trp Val
        1190                1195                1200
Tyr Ser Pro Ile Arg Ser Gly Leu His Lys Ser Phe Ser Asn Arg
        1205                1210                1215
Asp Ala Asp Ser Gly Gly Asp Ser Gln Glu Glu Ser Glu Leu Asp
        1220                1225                1230
Asp Gln Glu Asp His Pro Phe Val Pro Pro Pro Gly Tyr Met Met
        1235                1240                1245
Tyr Thr Val Phe Pro Asp Gly Ser Pro Val Pro Gln Gly Met Ala
        1250                1255                1260
Leu Tyr Ala Pro Pro Pro Pro Leu Pro Asn Asn Ser Gln Pro Leu
        1265                1270                1275
Asp Leu Gly Thr Val Val Tyr Gly Pro Pro Val Gly Ala Pro
        1280                1285                1290
Ile Val Tyr Gly Pro Pro Pro Asn Phe Ser Val Pro Leu Ile
        1295                1300                1305
Pro Val Gly Val Leu His Cys Asn Val Pro Glu His His Asn Leu
        1310                1315                1320
```

```
Glu Asn Glu Val Ser Arg Leu Glu Asp Ile Met Gln His Leu Lys
    1325            1330            1335

Ser Gly Lys Arg Glu Gln Cys Met Lys Thr Pro Lys Leu Gln Ser
    1340            1345            1350

Glu Lys Glu Leu Ala Glu Leu Gln His Asn Ile Asp Gly Leu Leu
    1355            1360            1365

Gln Glu Lys Lys Asp Leu Glu His Glu Val Glu Glu Leu His Arg
    1370            1375            1380

Thr Ile Gln Lys His Gln Gln Arg Lys Asp Phe Ile Asp Gly Asn
    1385            1390            1395

Val Glu Ser Leu Val Asn Asp Leu Glu Ile Glu Lys Ser Leu Lys
    1400            1405            1410

His His Glu Asp Ile Val Asp Glu Ile Glu Cys Ile Glu Arg Thr
    1415            1420            1425

Leu Leu Lys Arg Arg Ala Glu Leu Arg Glu Ala Asp Arg Leu Leu
    1430            1435            1440

Thr Glu Ala Glu Ser Glu Leu Ser Cys Thr Lys Glu Lys Thr Lys
    1445            1450            1455

His Ala Val Glu Lys Phe Thr Asp Ala Lys Arg Asn Leu Leu Gln
    1460            1465            1470

Thr Glu Lys Asp Ala Glu Glu Leu Glu Arg Arg Ala Gln Glu Thr
    1475            1480            1485

Ala Ile Asn Leu Val Lys Ala Asp Gln Gln Leu Arg Leu Leu Gln
    1490            1495            1500

Ala Asp Thr Lys Asp Leu Glu Gln His Lys Met Glu Gln Glu Glu
    1505            1510            1515

Ile Leu Lys Glu Ile Asn Lys Val Val Ala Ala Lys Asp Ser Asp
    1520            1525            1530

Phe Gln Ser Leu Asn Lys Lys Lys Glu Val Leu Thr Gly Glu Leu
    1535            1540            1545

Gln Lys Leu Gln Lys Asp Ile Glu Thr Ala Arg His Asn Glu Asp
    1550            1555            1560

Gln His Leu Gln Val Leu Lys Glu Ser Glu Thr Leu Leu Gln Ala
    1565            1570            1575

Lys Lys Ala Glu Leu Glu Asn Leu Lys Ser Gln Val Ser Gly Gln
    1580            1585            1590

Gln Gln Glu Met Ala Val Leu Asp Arg Glu Leu Gly His Lys Lys
    1595            1600            1605

Glu Glu Leu His Leu Leu Gln Glu Ser Met Val Gln Ala Lys Ala
    1610            1615            1620

Asp Leu Gln Glu Ala Leu Arg Leu Gly Glu Ser Glu Val Thr Glu
    1625            1630            1635

Lys Cys Asn His Ile Arg Glu Val Lys Ser Leu Leu Glu Glu Leu
    1640            1645            1650

Ser Phe Gln Lys Gly Glu Leu Asn Val Gln Ile Ser Glu Lys Lys
    1655            1660            1665

Thr Gln Leu Ala Leu Ile Lys Gln Glu Ile Glu Lys Glu Glu Asp
    1670            1675            1680

Asn Leu Gln Val Val Leu Gly Gln Met Ser Lys His Lys Thr Glu
    1685            1690            1695

Leu Lys Asn Ile Leu Asp Met Leu Gln Leu Glu Asn Asn Glu Leu
    1700            1705            1710
```

-continued

Gln Gly Leu Lys Leu Gln His Asp Gln Lys Met Ser Glu Leu Glu
1715                1720                1725

Lys Thr Arg Val Glu Val Leu Glu Glu Lys Leu Glu Leu Glu Ser
1730                1735                1740

Leu Gln Gln Ala Ala Leu Arg Gln Arg Gly Glu Ile Glu Trp Gln
1745                1750                1755

Lys Gln Leu Leu Gln Arg Asn Thr Gln Glu Val Glu Arg Met Thr
1760                1765                1770

Ala Glu Thr Arg Ala Leu Gln Ser Cys Val Glu Ser Leu Cys Lys
1775                1780                1785

Glu Lys Gln Asp Leu Glu Glu Lys Gln Asp Ser Trp Glu Lys Lys
1790                1795                1800

Leu Ala Gln Thr Lys Arg Val Leu Ala Ala Glu Glu Asp Ser
1805                1810                1815

Glu Met Glu Arg Ala Arg Leu Glu Lys Leu Glu Leu Asp Ala Arg
1820                1825                1830

Lys Leu Gln Gln Glu Leu Asp Gln Arg Asn Arg Glu Lys Leu Ser
1835                1840                1845

Leu His Gln Asp Leu Ala Val Val Gln Gln Gln Leu Gln Glu Lys
1850                1855                1860

Gln Glu Ala Val Asn Ser Leu Gln Lys Glu Leu Ala Asp Val Gln
1865                1870                1875

Glu His Leu Asp Leu Ala Glu Gln Glu Val Leu Cys Thr Thr Lys
1880                1885                1890

Arg Lys Asp Ala Leu Leu Ser Glu Gln Thr Arg Leu Glu Lys Asp
1895                1900                1905

Val Gly Glu Trp Thr Lys Lys Phe Glu Asp Cys Gln Lys Glu Gly
1910                1915                1920

Glu Thr Lys Gln Gln Gln Leu Gln Gly Leu Gln Lys Glu Ile Glu
1925                1930                1935

Gly Asn Glu Ala Lys Leu Ala Gln Gln Glu Met Met Phe Gln Arg
1940                1945                1950

Leu Gln Lys Glu Arg Glu Cys Glu Glu Lys Lys Leu Glu Ala Ser
1955                1960                1965

Lys Val Thr Leu Lys Glu Gln Gln Gln Leu Glu Lys Glu Leu
1970                1975                1980

Met Glu Gln Lys Gly Lys Leu Asp Gln Val Leu Ala Lys Leu Leu
1985                1990                1995

Val Ala Glu Glu Arg Val Arg Thr Leu Gln Glu Glu Gly Arg Trp
2000                2005                2010

Ser Glu Thr Leu Glu Lys Thr Leu Ser Gln Thr Lys Arg Gln Leu
2015                2020                2025

Ser Glu Arg Glu Gln Gln Leu Leu Ala Lys Ser Asp Glu Leu Leu
2030                2035                2040

Ala Leu Gln Lys Glu Thr Asp Ser Met Arg Ala Asp Phe Ser Leu
2045                2050                2055

Leu Arg Asn Gln Phe Leu Thr Glu Arg Lys Lys Ala Glu Lys Gln
2060                2065                2070

Val Ala Ser Leu Lys Glu Ala Leu Lys Ile Gln Arg Ser Gln Leu
2075                2080                2085

Glu Lys Asn Leu Leu Glu Gln Lys Gln Glu Asn Ser Cys Met Gln
2090                2095                2100

Arg Glu Met Ala Thr Ile Glu Gln Val Ala Gln Asp Asn His Glu

-continued

```
            2105                2110                2115
Arg Ala Arg Arg Leu Met Arg Glu Leu Asn Gln Met Gln Arg Glu
        2120                2125                2130
Tyr Val Glu Leu Arg Lys Gln Met Thr Asn Gln Lys Asp Leu Glu
        2135                2140                2145
Arg Arg Gln Met Glu Ile Ser Asp Ala Met Gln Ala Leu Lys Cys
        2150                2155                2160
Glu Val Lys Asp Glu Ile Arg Thr Ser Leu Lys Asn Leu Asn Gln
        2165                2170                2175
Phe Leu Pro Glu Leu Pro Ala Asp Leu Glu Ala Leu Leu Glu Arg
        2180                2185                2190
Asn Glu Asn Leu Gly Gly Gly Leu Glu Ser Leu Lys Glu Asn Phe
        2195                2200                2205
Pro Phe Thr Val Ser Asp Arg Pro Ser Ser Cys Glu Glu Lys Leu
        2210                2215                2220
Asn Phe Gly Gln Ala His Val Ala Asp Glu Gln Trp Arg Gly Glu
        2225                2230                2235
Ala Leu Arg Glu Lys Leu Arg His Arg Glu Asp Arg Leu Lys Ala
        2240                2245                2250
Gln Leu Arg Arg Cys Met Ser Lys Gln Ala Glu Val Leu Ser Glu
        2255                2260                2265
Gly Arg Arg Arg Thr Glu Gly Thr Leu His Ser Leu Arg Arg Gln
        2270                2275                2280
Val Asp Ala Leu Gly Glu Leu Val Thr Ser Thr Ser Gly Asp Ser
        2285                2290                2295
Ala Ser Thr Arg Ser Leu Ser Arg Thr Glu Gly Ser Leu Ala Glu
        2300                2305                2310
Asp Glu Pro Pro Gly Pro Ser Gln Glu Leu His Val Leu Gly Ser
        2315                2320                2325
Gly Gly Ser Asp Arg Gly Gly Gly Arg Gly Gly Arg Lys Gly
        2330                2335                2340
Leu Ser Arg Arg Arg Arg Trp Asn His Gly Glu Ala Arg Leu Gly
        2345                2350                2355
Pro Arg Arg Pro Arg Glu Gly Ala Gly Arg Gly Ala Ala Phe
        2360                2365                2370
Arg Ala Leu Val Ser Cys Ser Arg Pro Ala Glu Leu Pro Ala Ala
        2375                2380                2385
Pro Pro Arg Pro Val Ala Ala Gly Arg Ala Pro Thr Leu Arg
        2390                2395                2400
Thr Arg Arg Thr Arg Arg Pro Gly Val Pro Ser Glu Arg Phe Leu
        2405                2410                2415
Arg Val Arg Gly His Gln Ala His Gly Lys Ala Arg Pro Cys Gly
        2420                2425                2430
Lys Ser Arg Glu Arg Asn Pro Asp Ala Arg Ala Gly Leu Trp Ala
        2435                2440                2445
Leu Glu Thr Cys Cys Arg Lys Ser Ser Ala Arg Gly Cys Gly Leu
        2450                2455                2460
Glu Ala Pro Asn Cys Arg Arg Ala Arg Cys Gly Ala Ser Val Arg
        2465                2470                2475
Tyr Pro Leu Val Pro Arg Gly Arg Thr Gly Arg Gly Ala Val Thr
        2480                2485                2490
Pro Trp Gly Arg Leu Gln Ser Arg Gly Thr Arg Thr Thr Pro Arg
        2495                2500                2505
```

```
Pro Val Arg Arg Glu His Pro Gln His Gln Glu Arg Pro Pro Gly
    2510                2515                2520

Arg Val Thr Ala Ala His Thr Glu Thr Ala Pro Pro Arg Arg Val
    2525                2530                2535

Phe His Ala Arg Val Ala Val Gly Glu Val Ser Leu Gly Pro Gly
    2540                2545                2550

Arg Gly Leu Glu Arg Thr Arg Gly Gly Gly Gly Ala Gly Ala
    2555                2560                2565

Gly Leu Leu Ala Glu Ala Ala Ala Thr Ala Arg Cys Ala Asp Pro
    2570                2575                2580

Ser Thr Asp Pro Ser Ala
    2585

<210> SEQ ID NO 43
<211> LENGTH: 23
<212> TYPE: DNA
<213> ORGANISM: Artificial Sequence
<220> FEATURE:
<223> OTHER INFORMATION: Synthetic primer

<400> SEQUENCE: 43
gtcgacctat gcggaggggt ctg                                            23

<210> SEQ ID NO 44
<211> LENGTH: 6046
<212> TYPE: DNA
<213> ORGANISM: Canis familiaris
<220> FEATURE:
<221> NAME/KEY: CDS
<222> LOCATION: (1)..(5934)

<400> SEQUENCE: 44 atg tcg tcc tgg ctc ggg ggc ctg ggc tcc ggc ctg gca cag tcg ctg        48
Met Ser Ser Trp Leu Gly Gly Leu Gly Ser Gly Leu Ala Gln Ser Leu
1               5                   10                  15 ggg caa gtc gga ggc agc ctg gcc tcc ctc act ggc cag att tca aac        96
Gly Gln Val Gly Gly Ser Leu Ala Ser Leu Thr Gly Gln Ile Ser Asn
            20                  25                  30 ttt acg aag gac atg ctg atg gag ggc acg gag gag gtg gaa gca gaa       144
Phe Thr Lys Asp Met Leu Met Glu Gly Thr Glu Glu Val Glu Ala Glu
        35                  40                  45 tta cct aat tct agg aga aag gaa gtt gaa gcc att cat gca atc tta       192
Leu Pro Asn Ser Arg Arg Lys Glu Val Glu Ala Ile His Ala Ile Leu
    50                  55                  60 aga tca gag aat gag aga ctc aaa gaa ctt tgt act gat tta gaa gag       240
Arg Ser Glu Asn Glu Arg Leu Lys Glu Leu Cys Thr Asp Leu Glu Glu
65                  70                  75                  80 aag cat gaa gca tca gag ctt caa ata aag caa caa tct aca aat tac       288
Lys His Glu Ala Ser Glu Leu Gln Ile Lys Gln Gln Ser Thr Asn Tyr
                85                  90                  95 cga aat caa cta caa cag aaa gag gta gaa atc agc cat ctt aaa gca       336
Arg Asn Gln Leu Gln Gln Lys Glu Val Glu Ile Ser His Leu Lys Ala
            100                 105                 110 aga cag att gca ctg cag gat cag ttg ctg aag ctg cag tca gct gct       384
Arg Gln Ile Ala Leu Gln Asp Gln Leu Leu Lys Leu Gln Ser Ala Ala
        115                 120                 125 cag tct gca cat tca gga gct agc agc gta cca gca gcc ctg gca tca       432
Gln Ser Ala His Ser Gly Ala Ser Ser Val Pro Ala Ala Leu Ala Ser
    130                 135                 140 tct ccg ttc agc tat tct gtc agt cat cat gct tca gct ttc cat gac       480
```

```
Ser Pro Phe Ser Tyr Ser Val Ser His His Ala Ser Ala Phe His Asp
145             150                 155                 160 gat gac atg gac ttc agt gac ata att tca tca caa caa gaa ata aac       528
Asp Asp Met Asp Phe Ser Asp Ile Ile Ser Ser Gln Gln Glu Ile Asn
                165                 170                 175 aga tta tca aat gaa gtt tca aga ctt gag tct gag gtt ggc cat tgg       576
Arg Leu Ser Asn Glu Val Ser Arg Leu Glu Ser Glu Val Gly His Trp
            180                 185                 190 agg cat att gct cag act tct aaa gca caa gga tca aat agc tct gat       624
Arg His Ile Ala Gln Thr Ser Lys Ala Gln Gly Ser Asn Ser Ser Asp
                195                 200                 205 caa agt gaa atc tgt aaa cta caa agt atc att aag gaa ctc aaa cag       672
Gln Ser Glu Ile Cys Lys Leu Gln Ser Ile Ile Lys Glu Leu Lys Gln
210                 215                 220 att cga agt cag gaa atc gat gac cat caa cat gaa atg tca gtg ttg       720
Ile Arg Ser Gln Glu Ile Asp Asp His Gln His Glu Met Ser Val Leu
225                 230                 235                 240 cag aat gca cat caa cag aag ttg aca gat ata agt cgt cgg cat cga       768
Gln Asn Ala His Gln Gln Lys Leu Thr Asp Ile Ser Arg Arg His Arg
                245                 250                 255 gaa gaa tta cgt gac tat gaa gaa cga att gaa gaa ctg gaa aat ctg       816
Glu Glu Leu Arg Asp Tyr Glu Glu Arg Ile Glu Glu Leu Glu Asn Leu
            260                 265                 270 tta gaa caa ggt ggc tca gga att gta ata cct gat cac tca aaa atc       864
Leu Glu Gln Gly Gly Ser Gly Ile Val Ile Pro Asp His Ser Lys Ile
                275                 280                 285 cat gag atg caa aaa act att cag aat cta caa act gaa aaa gta gca       912
His Glu Met Gln Lys Thr Ile Gln Asn Leu Gln Thr Glu Lys Val Ala
                290                 295                 300 tct ata aaa aaa att gaa gaa ctt gag gat aaa ata aaa gac ata gat       960
Ser Ile Lys Lys Ile Glu Glu Leu Glu Asp Lys Ile Lys Asp Ile Asp
305                 310                 315                 320 aaa aaa ttg tct tct gca gaa aat gac aga gat gtt ttg agg aag gag      1008
Lys Lys Leu Ser Ser Ala Glu Asn Asp Arg Asp Val Leu Arg Lys Glu
                325                 330                 335 aaa gaa tgc cta aat gtt gaa aac aga caa ata aca gaa caa tgt gaa      1056
Lys Glu Cys Leu Asn Val Glu Asn Arg Gln Ile Thr Glu Gln Cys Glu
            340                 345                 350 agc ttg aaa ctg gaa tgt aaa ttg cag cat gat gct gag aag caa ggt      1104
Ser Leu Lys Leu Glu Cys Lys Leu Gln His Asp Ala Glu Lys Gln Gly
                355                 360                 365 gat act gtg aca gaa aaa gaa aga atc ctt cca cag agt aca tca gtg      1152
Asp Thr Val Thr Glu Lys Glu Arg Ile Leu Pro Gln Ser Thr Ser Val
                370                 375                 380 gaa gag gaa gtg ctc aaa ctg cag caa gca ctg tct gat gcg gaa aat      1200
Glu Glu Glu Val Leu Lys Leu Gln Gln Ala Leu Ser Asp Ala Glu Asn
385                 390                 395                 400 gaa att atg aga ctg agt aat tta tac cag gat aac agt ctc act gaa      1248
Glu Ile Met Arg Leu Ser Asn Leu Tyr Gln Asp Asn Ser Leu Thr Glu
                405                 410                 415 gat aat ttg aaa ctt aaa atg cat gtc gaa ttt tta gaa aaa cag aag      1296
Asp Asn Leu Lys Leu Lys Met His Val Glu Phe Leu Glu Lys Gln Lys
                420                 425                 430 tcc tta ttg agt caa gaa aag gaa gag ctt caa cta tca ctt tta aag      1344
Ser Leu Leu Ser Gln Glu Lys Glu Glu Leu Gln Leu Ser Leu Leu Lys
            435                 440                 445 ttg aac aat gaa tat gaa gtg att aaa agt aca gct gtg aga gac atg      1392
Leu Asn Asn Glu Tyr Glu Val Ile Lys Ser Thr Ala Val Arg Asp Met
                450                 455                 460
```

| | | |
|---|---|---|
| gat atg gat tca aca tta tgt gat tta aga ctg acc ttg gag gca aag<br>Asp Met Asp Ser Thr Leu Cys Asp Leu Arg Leu Thr Leu Glu Ala Lys<br>465                             470                         475                   480 | 1440 |
| gac cag gaa ctc aat cag agt ctc act gag aag gaa ata ttg gtt gct<br>Asp Gln Glu Leu Asn Gln Ser Leu Thr Glu Lys Glu Ile Leu Val Ala<br>                   485                         490                      495 | 1488 |
| gag tta gag gaa ttg gac aga caa aac caa gaa gct aca aag cac atg<br>Glu Leu Glu Glu Leu Asp Arg Gln Asn Gln Glu Ala Thr Lys His Met<br>    500                         505                      510 | 1536 |
| att ctg ata aaa gat cag cta tca aaa caa caa agt gag gga gaa act<br>Ile Leu Ile Lys Asp Gln Leu Ser Lys Gln Gln Ser Glu Gly Glu Thr<br>             515                      520                      525 | 1584 |
| atc att agt aaa ctg aga aaa gat cta aat gat gaa aac aag aga gtc<br>Ile Ile Ser Lys Leu Arg Lys Asp Leu Asn Asp Glu Asn Lys Arg Val<br>530                             535                        540 | 1632 |
| cat caa ctt gaa gat gat aaa aag aat atg act aaa gaa cta aat gtg<br>His Gln Leu Glu Asp Asp Lys Lys Asn Met Thr Lys Glu Leu Asn Val<br>545                             550                        555                   560 | 1680 |
| cag aaa gag aag tta gtt caa agt gaa ctc gtc cta aat ggc ttg cat<br>Gln Lys Glu Lys Leu Val Gln Ser Glu Leu Val Leu Asn Gly Leu His<br>                  565                         570                      575 | 1728 |
| tta gcc aag cag aag ctt gag gag aaa gta gaa gat tta gtg gat cag<br>Leu Ala Lys Gln Lys Leu Glu Glu Lys Val Glu Asp Leu Val Asp Gln<br>             580                      585                      590 | 1776 |
| cta aat aaa tca caa aaa agt aat tta aac atg cag aag gag aac ttt<br>Leu Asn Lys Ser Gln Lys Ser Asn Leu Asn Met Gln Lys Glu Asn Phe<br>         595                      600                      605 | 1824 |
| gga ctt aag gaa cat att aaa caa aat gag gaa gag ctt tct aga gtc<br>Gly Leu Lys Glu His Ile Lys Gln Asn Glu Glu Glu Leu Ser Arg Val<br>610                             615                      620 | 1872 |
| agg gat gag tta act cag tct cta agt cga gac tct ggc agt gat ttt<br>Arg Asp Glu Leu Thr Gln Ser Leu Ser Arg Asp Ser Gly Ser Asp Phe<br>625                             630                      635                   640 | 1920 |
| aag gat gac tta ctt aaa gaa agg gaa gct gaa gtc aga aac tta aaa<br>Lys Asp Asp Leu Leu Lys Glu Arg Glu Ala Glu Val Arg Asn Leu Lys<br>                  645                         650                      655 | 1968 |
| caa aat ctt tca gaa ata gaa cag ctc aat gac agt tta aac aaa gtt<br>Gln Asn Leu Ser Glu Ile Glu Gln Leu Asn Asp Ser Leu Asn Lys Val<br>             660                      665                      670 | 2016 |
| gcc ttt gat ctc aaa atg gaa aat gaa aag ttg gtc tta gcg tgt gaa<br>Ala Phe Asp Leu Lys Met Glu Asn Glu Lys Leu Val Leu Ala Cys Glu<br>         675                      680                      685 | 2064 |
| gat ata aga cat cag ttg gaa gaa tca att gtt ggc agc aat cag atg<br>Asp Ile Arg His Gln Leu Glu Glu Ser Ile Val Gly Ser Asn Gln Met<br>690                           695                      700 | 2112 |
| tct ctg gaa aga aac act att gtg gag gct cta aaa atg gaa aaa gga<br>Ser Leu Glu Arg Asn Thr Ile Val Glu Ala Leu Lys Met Glu Lys Gly<br>705                             710                        715                   720 | 2160 |
| cag tta gaa gca gaa ttg agt cga gct gac caa agg ctg tta gaa gaa<br>Gln Leu Glu Ala Glu Leu Ser Arg Ala Asp Gln Arg Leu Leu Glu Glu<br>                  725                         730                      735 | 2208 |
| gcc agt aag tat gaa cag acg att caa gag cta tca aag gca cgt gat<br>Ala Ser Lys Tyr Glu Gln Thr Ile Gln Glu Leu Ser Lys Ala Arg Asp<br>             740                      745                      750 | 2256 |
| ttg agg acc tct gct tta cag ctg gag cag cag cat tta atg aaa ctc<br>Leu Arg Thr Ser Ala Leu Gln Leu Glu Gln Gln His Leu Met Lys Leu<br>         755                      760                      765 | 2304 |
| agt caa gag aag gac ttc gaa ata gca gaa ctt aaa aag aac att gaa<br>Ser Gln Glu Lys Asp Phe Glu Ile Ala Glu Leu Lys Lys Asn Ile Glu<br>770                           775                      780 | 2352 |

```
cag atg gat act gat cat aaa gaa act aag gca att ttg tca tct att    2400
Gln Met Asp Thr Asp His Lys Glu Thr Lys Ala Ile Leu Ser Ser Ile
785             790                 795                 800 tta gaa gag cag aag caa ttg acg caa ctt ata agt gag aag gaa att    2448
Leu Glu Glu Gln Lys Gln Leu Thr Gln Leu Ile Ser Glu Lys Glu Ile
                805                 810                 815 ttt att gag aaa ctt aaa gaa aga agt tca gag ctt cag gag gaa tta    2496
Phe Ile Glu Lys Leu Lys Glu Arg Ser Ser Glu Leu Gln Glu Glu Leu
        820                 825                 830 gag aaa tct act cag gcc tca agg aaa att gaa att tta aag caa acc    2544
Glu Lys Ser Thr Gln Ala Ser Arg Lys Ile Glu Ile Leu Lys Gln Thr
835                 840                 845 att gag gag aaa gac aga agt ctt ggg tcc atg aaa gaa gaa aac aat    2592
Ile Glu Glu Lys Asp Arg Ser Leu Gly Ser Met Lys Glu Glu Asn Asn
    850                 855                 860 cat ctg aaa gaa gaa ctg gaa cgg ctc cgt gaa cag cag agt cga gcc    2640
His Leu Lys Glu Glu Leu Glu Arg Leu Arg Glu Gln Gln Ser Arg Ala
865                 870                 875                 880 gtg cct gtg gtg gag cct aaa ccc ctg gat agt gtt aca gag cta gaa    2688
Val Pro Val Val Glu Pro Lys Pro Leu Asp Ser Val Thr Glu Leu Glu
                885                 890                 895 tct gag gtg ttg cag cta aat ata gta aag agg aat ctt gag gag gaa    2736
Ser Glu Val Leu Gln Leu Asn Ile Val Lys Arg Asn Leu Glu Glu Glu
        900                 905                 910 ata aaa cgt cat cag aag att ata gaa gat caa aac cag agt aaa atg    2784
Ile Lys Arg His Gln Lys Ile Ile Glu Asp Gln Asn Gln Ser Lys Met
915                 920                 925 cag ctg ctt cag tct cta gag gag cag aag aag gaa atg gat gaa ttt    2832
Gln Leu Leu Gln Ser Leu Glu Glu Gln Lys Lys Glu Met Asp Glu Phe
    930                 935                 940 aag tgc cag cat gag caa atg aac gtc aca cac acc caa ctc ttc tta    2880
Lys Cys Gln His Glu Gln Met Asn Val Thr His Thr Gln Leu Phe Leu
945                 950                 955                 960 gag aaa gat gag gag att aag aat ttg caa aaa aca att gaa caa atc    2928
Glu Lys Asp Glu Glu Ile Lys Asn Leu Gln Lys Thr Ile Glu Gln Ile
                965                 970                 975 aaa acc caa tgg cat gaa gaa aga cag gac gtt caa atg gag aat tct    2976
Lys Thr Gln Trp His Glu Glu Arg Gln Asp Val Gln Met Glu Asn Ser
        980                 985                 990 gag ttc ttt caa gaa aca aaa gtg cag agc ctt aat cta gaa aat ggc    3024
Glu Phe Phe Gln Glu Thr Lys Val Gln Ser Leu Asn Leu Glu Asn Gly
995                 1000                1005 agt gaa aag cat gat tta tcg aaa gcc gaa act gag agg tta gta       3069
Ser Glu Lys His Asp Leu Ser Lys Ala Glu Thr Glu Arg Leu Val
    1010                1015                1020 aaa gga ata aaa gaa cga gag ctg gag att aaa ctt cta aat gaa       3114
Lys Gly Ile Lys Glu Arg Glu Leu Glu Ile Lys Leu Leu Asn Glu
1025                1030                1035 aag aat ata tct tta aca aaa caa att gat cag ctg tcc aaa gat       3159
Lys Asn Ile Ser Leu Thr Lys Gln Ile Asp Gln Leu Ser Lys Asp
    1040                1045                1050 gag gtt ggt aaa ctc act cag atc atc cag cag aaa gac tta gag       3204
Glu Val Gly Lys Leu Thr Gln Ile Ile Gln Gln Lys Asp Leu Glu
1055                1060                1065 ata caa gct ctt cat gct agg att tct tca gct tcc tac acc cag       3249
Ile Gln Ala Leu His Ala Arg Ile Ser Ser Ala Ser Tyr Thr Gln
    1070                1075                1080 gat gtt gtc tac ctt cag cag cag ctg cag gcc tat gct atg gag       3294
Asp Val Val Tyr Leu Gln Gln Gln Leu Gln Ala Tyr Ala Met Glu
```

-continued

```
        1085                1090                1095
aga gaa caa gta tta gct gtt ttg agt gag aag acc agg gaa aat    3339
Arg Glu Gln Val Leu Ala Val Leu Ser Glu Lys Thr Arg Glu Asn
    1100                1105                1110 agc cat ctg aaa aca gaa tac cac aaa atg atg gat atc gtt gct    3384
Ser His Leu Lys Thr Glu Tyr His Lys Met Met Asp Ile Val Ala
    1115                1120                1125 gct aaa gaa gca gct ctc att aag ctg caa gat gaa aat aaa aaa    3429
Ala Lys Glu Ala Ala Leu Ile Lys Leu Gln Asp Glu Asn Lys Lys
    1130                1135                1140 ttg tct gct aga tcc gaa ggt ggt ggc cag gat atg ttt aga gag    3474
Leu Ser Ala Arg Ser Glu Gly Gly Gly Gln Asp Met Phe Arg Glu
    1145                1150                1155 act gtc cag aat tta tca cgt atc att cga gaa aaa gac att gag    3519
Thr Val Gln Asn Leu Ser Arg Ile Ile Arg Glu Lys Asp Ile Glu
    1160                1165                1170 ata gat gcg tta agt cag aag tgc cag acc tta ttg aca gtt tta    3564
Ile Asp Ala Leu Ser Gln Lys Cys Gln Thr Leu Leu Thr Val Leu
    1175                1180                1185 caa aca tcg agc act ggg aat gag gtt gga ggc gtt aat agc aat    3609
Gln Thr Ser Ser Thr Gly Asn Glu Val Gly Gly Val Asn Ser Asn
    1190                1195                1200 cag ttt gag gag ctt cta cag gaa cgc gac aaa tta aaa caa caa    3654
Gln Phe Glu Glu Leu Leu Gln Glu Arg Asp Lys Leu Lys Gln Gln
    1205                1210                1215 gta aag aag atg gaa gag tgg aaa cag cag gtg atg acc aca gtt    3699
Val Lys Lys Met Glu Glu Trp Lys Gln Gln Val Met Thr Thr Val
    1220                1225                1230 cag aat atg cag cat gag tca gcc cag ctt caa gaa gaa ctt cat    3744
Gln Asn Met Gln His Glu Ser Ala Gln Leu Gln Glu Glu Leu His
    1235                1240                1245 cag ctt cag gca caa gtt ttg gtt gac agt gat aat aat tct aaa    3789
Gln Leu Gln Ala Gln Val Leu Val Asp Ser Asp Asn Asn Ser Lys
    1250                1255                1260 tta caa gtg gat tat act ggc ctg atc caa agt tat gag cag aat    3834
Leu Gln Val Asp Tyr Thr Gly Leu Ile Gln Ser Tyr Glu Gln Asn
    1265                1270                1275 gaa act aaa ctc aaa aat ttt ggg cag gag cta gca caa gtt cag    3879
Glu Thr Lys Leu Lys Asn Phe Gly Gln Glu Leu Ala Gln Val Gln
    1280                1285                1290 cac agc ata ggg cag ctg tac agt acc aaa gac ctt ctc tta gga    3924
His Ser Ile Gly Gln Leu Tyr Ser Thr Lys Asp Leu Leu Leu Gly
    1295                1300                1305 aaa ctt gat att att tct cct caa ctc ccc tcc gga tca tcg cct    3969
Lys Leu Asp Ile Ile Ser Pro Gln Leu Pro Ser Gly Ser Ser Pro
    1310                1315                1320 cct tcc cag tca gca gag tct ctt gga atg gat aag cgt gat aca    4014
Pro Ser Gln Ser Ala Glu Ser Leu Gly Met Asp Lys Arg Asp Thr
    1325                1330                1335 tca agt gag tct tca aaa cag gag cta gaa gag cta aga aag tca    4059
Ser Ser Glu Ser Ser Lys Gln Glu Leu Glu Glu Leu Arg Lys Ser
    1340                1345                1350 ctg cag gaa aaa gat gca acg att aaa aca ctc cag gaa aat aac    4104
Leu Gln Glu Lys Asp Ala Thr Ile Lys Thr Leu Gln Glu Asn Asn
    1355                1360                1365 cac aga ttg tcc gat tca att gct gcc acc tca gag cta gaa aga    4149
His Arg Leu Ser Asp Ser Ile Ala Ala Thr Ser Glu Leu Glu Arg
    1370                1375                1380 aaa gaa cac gaa cag act gat tca gaa att aag cag cta aag gag    4194
```

```
Lys Glu His Glu Gln Thr Asp Ser Glu Ile Lys Gln Leu Lys Glu
    1385                1390                1395 aaa caa gat gtt tta caa aag tca ctt aag gag aaa gac ctc tta      4239
Lys Gln Asp Val Leu Gln Lys Ser Leu Lys Glu Lys Asp Leu Leu
    1400                1405                1410 atc aaa gcc aaa agt gat cag tta ctt tct tta aat gaa aat ttc      4284
Ile Lys Ala Lys Ser Asp Gln Leu Leu Ser Leu Asn Glu Asn Phe
    1415                1420                1425 acc aac aaa gtg aat gaa aat gaa ctc ttg agg cag gca gta acc      4329
Thr Asn Lys Val Asn Glu Asn Glu Leu Leu Arg Gln Ala Val Thr
    1430                1435                1440 aac ctg aag gag cgg gta tta att tta gaa atg gac att ggt aaa      4374
Asn Leu Lys Glu Arg Val Leu Ile Leu Glu Met Asp Ile Gly Lys
    1445                1450                1455 cta aaa gaa gaa aat gaa aaa ata gtt gaa aga acc agg gaa aag      4419
Leu Lys Glu Glu Asn Glu Lys Ile Val Glu Arg Thr Arg Glu Lys
    1460                1465                1470 gaa acg gag tat caa gca tta cag gag act aat atg aag ttt tcc      4464
Glu Thr Glu Tyr Gln Ala Leu Gln Glu Thr Asn Met Lys Phe Ser
    1475                1480                1485 atg atg ctt cga gaa aaa gag ttt gag tgc cat tca atg aag gaa      4509
Met Met Leu Arg Glu Lys Glu Phe Glu Cys His Ser Met Lys Glu
    1490                1495                1500 aaa tct ctt gca ttt gag cag cta ctg aaa gaa aaa gag cag ggc      4554
Lys Ser Leu Ala Phe Glu Gln Leu Leu Lys Glu Lys Glu Gln Gly
    1505                1510                1515 aag act ggg gag tta aat caa ctt tta aat gca gtt aag tca atg      4599
Lys Thr Gly Glu Leu Asn Gln Leu Leu Asn Ala Val Lys Ser Met
    1520                1525                1530 cag gag aag aca gtt aag ttt caa caa gag aga gac cag gtc atg      4644
Gln Glu Lys Thr Val Lys Phe Gln Gln Glu Arg Asp Gln Val Met
    1535                1540                1545 ttg gcc ctg aaa cag aaa caa atg gaa aac agt gct tta cag aat      4689
Leu Ala Leu Lys Gln Lys Gln Met Glu Asn Ser Ala Leu Gln Asn
    1550                1555                1560 gag gtt caa cat tta cgc gac aaa gaa tta cgc tta aac cag gag      4734
Glu Val Gln His Leu Arg Asp Lys Glu Leu Arg Leu Asn Gln Glu
    1565                1570                1575 cta gag aga ttg cgt aac cat ctt tta gaa tca gag gat tct tac      4779
Leu Glu Arg Leu Arg Asn His Leu Leu Glu Ser Glu Asp Ser Tyr
    1580                1585                1590 acc cgt gaa gct ttg gct gca gaa gag aga gag gcc aaa ctg aga      4824
Thr Arg Glu Ala Leu Ala Ala Glu Glu Arg Glu Ala Lys Leu Arg
    1595                1600                1605 agg aaa gtc aca gta ttg gag gaa aag cta gtt tca tct tct aat      4869
Arg Lys Val Thr Val Leu Glu Glu Lys Leu Val Ser Ser Ser Asn
    1610                1615                1620 gca atg gaa aat gca agc cat cag gcc agt ttg cag gta gag tca      4914
Ala Met Glu Asn Ala Ser His Gln Ala Ser Leu Gln Val Glu Ser
    1625                1630                1635 ctg cag gag cag ctg aat gtg gtc tct aag cag agg gat gaa acc      4959
Leu Gln Glu Gln Leu Asn Val Val Ser Lys Gln Arg Asp Glu Thr
    1640                1645                1650 gcc ctg cag ctc tct gtg tct cgg gaa caa gta aag cag tat gct      5004
Ala Leu Gln Leu Ser Val Ser Arg Glu Gln Val Lys Gln Tyr Ala
    1655                1660                1665 ctc tca ctc tcc aac ctg cag atg gta cta gag cat ttc cag caa      5049
Leu Ser Leu Ser Asn Leu Gln Met Val Leu Glu His Phe Gln Gln
    1670                1675                1680
```

```
gag gaa aaa gct gtg tat tct gct gaa cta gaa aag cac aaa cag      5094
Glu Glu Lys Ala Val Tyr Ser Ala Glu Leu Glu Lys His Lys Gln
    1685                1690                1695 ctt gta gct gaa tgg aag aaa aag gca gaa aat ctg gaa gga aaa      5139
Leu Val Ala Glu Trp Lys Lys Lys Ala Glu Asn Leu Glu Gly Lys
    1700                1705                1710 ctg atg tca tta cag gag cgt ttt gat gaa gca aat gct gcg ttg      5184
Leu Met Ser Leu Gln Glu Arg Phe Asp Glu Ala Asn Ala Ala Leu
    1715                1720                1725 gat tca gca tca aga ctt aca gag cag tta gat tta aag gaa gaa      5229
Asp Ser Ala Ser Arg Leu Thr Glu Gln Leu Asp Leu Lys Glu Glu
    1730                1735                1740 caa att gaa gaa ctt aaa aaa caa aat gaa ctc cga caa gaa atg      5274
Gln Ile Glu Glu Leu Lys Lys Gln Asn Glu Leu Arg Gln Glu Met
    1745                1750                1755 ctg gat gat gta caa aag aaa ttg atg aac tta gta aac agc aca      5319
Leu Asp Asp Val Gln Lys Lys Leu Met Asn Leu Val Asn Ser Thr
    1760                1765                1770 gaa gga aaa gtg gac aaa gtc cta atg aga aac ctc ttc att gga      5364
Glu Gly Lys Val Asp Lys Val Leu Met Arg Asn Leu Phe Ile Gly
    1775                1780                1785 cat ttc cac aca cca aag cat cag cgc cac gag gtg tta cga tta      5409
His Phe His Thr Pro Lys His Gln Arg His Glu Val Leu Arg Leu
    1790                1795                1800 atg gga agc atc ctt ggt atc aag agg gag gaa atg gaa cag ttg      5454
Met Gly Ser Ile Leu Gly Ile Lys Arg Glu Glu Met Glu Gln Leu
    1805                1810                1815 ctt cat gaa gat cag ggt ggt gtt acc agg tgg atg act gga tgg      5499
Leu His Glu Asp Gln Gly Gly Val Thr Arg Trp Met Thr Gly Trp
    1820                1825                1830 ctt gga gga gga tca aaa agt gtc ccc aac aca cct ctg aga cca      5544
Leu Gly Gly Gly Ser Lys Ser Val Pro Asn Thr Pro Leu Arg Pro
    1835                1840                1845 aat caa caa tct gtg ctt aat agc tct ttt tca gaa ctt ttt gtt      5589
Asn Gln Gln Ser Val Leu Asn Ser Ser Phe Ser Glu Leu Phe Val
    1850                1855                1860 aaa ttt cta gaa aca gaa tct cat cca tct gtt cca cca cca aag      5634
Lys Phe Leu Glu Thr Glu Ser His Pro Ser Val Pro Pro Pro Lys
    1865                1870                1875 ctt tct gtt cat gat atg aaa cct ctg gat tca cca gga agg aga      5679
Leu Ser Val His Asp Met Lys Pro Leu Asp Ser Pro Gly Arg Arg
    1880                1885                1890 aaa gta gtc ata cat gta tca gaa agt ttt aaa gaa acc aca gag      5724
Lys Val Val Ile His Val Ser Glu Ser Phe Lys Glu Thr Thr Glu
    1895                1900                1905 tcc aga tgt gga agg aga aca gat gtg aat cca ttc ttg gct ccc      5769
Ser Arg Cys Gly Arg Arg Thr Asp Val Asn Pro Phe Leu Ala Pro
    1910                1915                1920 cgc tct gca gct gtg cct ctc att aac cca gct gga ctt gga cct      5814
Arg Ser Ala Ala Val Pro Leu Ile Asn Pro Ala Gly Leu Gly Pro
    1925                1930                1935 ggt ggg cct ggg cat ctt ctt ttg aag ccc atc tca gac gtg ttg      5859
Gly Gly Pro Gly His Leu Leu Leu Lys Pro Ile Ser Asp Val Leu
    1940                1945                1950 ccc aca ttt aca cct ttg ccg gtg tca cct gac aac agt gct gga      5904
Pro Thr Phe Thr Pro Leu Pro Val Ser Pro Asp Asn Ser Ala Gly
    1955                1960                1965 gtt gtg ttg aaa gac ctt tta aag caa tag atgattctca agccagagac    5954
Val Val Leu Lys Asp Leu Leu Lys Gln
    1970                1975
```

```
aacatatgta gcactttaaa gaaaccatga acactatgtg tatgtacttt atcacaaagt      6014
ggcctttcag aaaaagtcat gtgtttgttt gc                                   6046
```

<210> SEQ ID NO 45
<211> LENGTH: 1977
<212> TYPE: PRT
<213> ORGANISM: Canis familiaris

<400> SEQUENCE: 45

```
Met Ser Ser Trp Leu Gly Gly Leu Gly Ser Gly Leu Gly Gln Ser Leu
1               5                   10                  15

Gly Gln Val Gly Gly Ser Leu Ala Ser Leu Thr Gly Gln Ile Ser Asn
            20                  25                  30

Phe Thr Lys Asp Met Leu Met Glu Gly Thr Glu Glu Val Glu Ala Glu
        35                  40                  45

Leu Pro Asn Ser Arg Arg Lys Glu Val Glu Ala Ile His Ala Ile Leu
    50                  55                  60

Arg Ser Glu Asn Glu Arg Leu Lys Glu Leu Cys Thr Asp Leu Glu Glu
65                  70                  75                  80

Lys His Glu Ala Ser Glu Leu Gln Ile Lys Gln Gln Ser Thr Asn Tyr
                85                  90                  95

Arg Asn Gln Leu Gln Gln Lys Glu Val Glu Ile Ser His Leu Lys Ala
            100                 105                 110

Arg Gln Ile Ala Leu Gln Asp Gln Leu Leu Lys Leu Gln Ser Ala Ala
        115                 120                 125

Gln Ser Ala His Ser Gly Ala Ser Ser Val Pro Ala Leu Ala Ser
    130                 135                 140

Ser Pro Phe Ser Tyr Ser Val Ser His Ala Ser Ala Phe His Asp
145                 150                 155                 160

Asp Asp Met Asp Phe Ser Asp Ile Ile Ser Gln Gln Glu Ile Asn
                165                 170                 175

Arg Leu Ser Asn Glu Val Ser Arg Leu Glu Ser Glu Val Gly His Trp
            180                 185                 190

Arg His Ile Ala Gln Thr Ser Lys Ala Gln Gly Ser Asn Ser Ser Asp
        195                 200                 205

Gln Ser Glu Ile Cys Lys Leu Gln Ser Ile Ile Lys Glu Leu Lys Gln
    210                 215                 220

Ile Arg Ser Gln Glu Ile Asp Asp His Gln His Glu Met Ser Val Leu
225                 230                 235                 240

Gln Asn Ala His Gln Gln Lys Leu Thr Asp Ile Ser Arg Arg His Arg
                245                 250                 255

Glu Glu Leu Arg Asp Tyr Glu Glu Arg Ile Glu Glu Leu Glu Asn Leu
            260                 265                 270

Leu Glu Gln Gly Gly Ser Gly Ile Val Ile Pro Asp His Ser Lys Ile
        275                 280                 285

His Glu Met Gln Lys Thr Ile Gln Asn Leu Gln Thr Glu Lys Val Ala
    290                 295                 300

Ser Ile Lys Lys Ile Glu Glu Leu Glu Asp Lys Ile Lys Asp Ile Asp
305                 310                 315                 320

Lys Lys Leu Ser Ser Ala Glu Asn Asp Arg Asp Val Leu Arg Lys Glu
                325                 330                 335

Lys Glu Cys Leu Asn Val Glu Asn Arg Gln Ile Thr Glu Gln Cys Glu
            340                 345                 350
```

```
Ser Leu Lys Leu Glu Cys Lys Leu Gln His Asp Ala Glu Lys Gln Gly
        355                 360                 365

Asp Thr Val Thr Glu Lys Glu Arg Ile Leu Pro Gln Ser Thr Ser Val
370                 375                 380

Glu Glu Glu Val Leu Lys Leu Gln Gln Ala Leu Ser Asp Ala Glu Asn
385                 390                 395                 400

Glu Ile Met Arg Leu Ser Asn Leu Tyr Gln Asp Asn Ser Leu Thr Glu
                405                 410                 415

Asp Asn Leu Lys Leu Lys Met His Val Glu Phe Leu Glu Lys Gln Lys
                420                 425                 430

Ser Leu Leu Ser Gln Glu Lys Glu Glu Leu Gln Leu Ser Leu Leu Lys
            435                 440                 445

Leu Asn Asn Glu Tyr Glu Val Ile Lys Ser Thr Ala Val Arg Asp Met
        450                 455                 460

Asp Met Asp Ser Thr Leu Cys Asp Leu Arg Leu Thr Leu Glu Ala Lys
465                 470                 475                 480

Asp Gln Glu Leu Asn Gln Ser Leu Thr Glu Lys Glu Ile Leu Val Ala
                485                 490                 495

Glu Leu Glu Glu Leu Asp Arg Gln Asn Gln Glu Ala Thr Lys His Met
                500                 505                 510

Ile Leu Ile Lys Asp Gln Leu Ser Lys Gln Gln Ser Glu Gly Glu Thr
            515                 520                 525

Ile Ile Ser Lys Leu Arg Lys Asp Leu Asn Asp Glu Asn Lys Arg Val
        530                 535                 540

His Gln Leu Glu Asp Asp Lys Lys Asn Met Thr Lys Glu Leu Asn Val
545                 550                 555                 560

Gln Lys Glu Lys Leu Val Gln Ser Glu Leu Val Leu Asn Gly Leu His
                565                 570                 575

Leu Ala Lys Gln Lys Leu Glu Glu Lys Val Glu Asp Leu Val Asp Gln
                580                 585                 590

Leu Asn Lys Ser Gln Lys Ser Asn Leu Asn Met Gln Lys Glu Asn Phe
            595                 600                 605

Gly Leu Lys Glu His Ile Lys Gln Asn Glu Glu Leu Ser Arg Val
        610                 615                 620

Arg Asp Glu Leu Thr Gln Ser Leu Ser Arg Asp Ser Gly Ser Asp Phe
625                 630                 635                 640

Lys Asp Asp Leu Leu Lys Glu Arg Glu Ala Glu Val Arg Asn Leu Lys
                645                 650                 655

Gln Asn Leu Ser Glu Ile Glu Gln Leu Asn Asp Ser Leu Asn Lys Val
            660                 665                 670

Ala Phe Asp Leu Lys Met Glu Asn Glu Lys Leu Val Leu Ala Cys Glu
        675                 680                 685

Asp Ile Arg His Gln Leu Glu Glu Ser Ile Val Gly Ser Asn Gln Met
690                 695                 700

Ser Leu Glu Arg Asn Thr Ile Val Glu Ala Leu Lys Met Glu Lys Gly
705                 710                 715                 720

Gln Leu Glu Ala Glu Leu Ser Arg Ala Asp Gln Arg Leu Leu Glu Glu
                725                 730                 735

Ala Ser Lys Tyr Glu Gln Thr Ile Gln Glu Leu Ser Lys Ala Arg Asp
            740                 745                 750

Leu Arg Thr Ser Ala Leu Gln Leu Glu Gln His Leu Met Lys Leu
        755                 760                 765

Ser Gln Glu Lys Asp Phe Glu Ile Ala Glu Leu Lys Lys Asn Ile Glu
```

```
                770             775             780
Gln Met Asp Thr Asp His Lys Glu Thr Lys Ala Ile Leu Ser Ser Ile
785             790             795             800

Leu Glu Glu Gln Lys Gln Leu Thr Gln Leu Ile Ser Glu Lys Glu Ile
                805             810             815

Phe Ile Glu Lys Leu Lys Glu Arg Ser Ser Glu Leu Gln Glu Glu Leu
                820             825             830

Glu Lys Ser Thr Gln Ala Ser Arg Lys Ile Glu Ile Leu Lys Gln Thr
            835             840             845

Ile Glu Glu Lys Asp Arg Ser Leu Gly Ser Met Lys Glu Glu Asn Asn
850             855             860

His Leu Lys Glu Glu Leu Glu Arg Leu Arg Glu Gln Gln Ser Arg Ala
865             870             875             880

Val Pro Val Val Glu Pro Lys Pro Leu Asp Ser Val Thr Glu Leu Glu
                885             890             895

Ser Glu Val Leu Gln Leu Asn Ile Val Lys Arg Asn Leu Glu Glu Glu
                900             905             910

Ile Lys Arg His Gln Lys Ile Ile Glu Asp Gln Asn Gln Ser Lys Met
            915             920             925

Gln Leu Leu Gln Ser Leu Glu Glu Lys Lys Glu Met Asp Glu Phe
        930             935             940

Lys Cys Gln His Glu Gln Met Asn Val Thr His Thr Gln Leu Phe Leu
945             950             955             960

Glu Lys Asp Glu Glu Ile Lys Asn Leu Gln Lys Thr Ile Glu Gln Ile
            965             970             975

Lys Thr Gln Trp His Glu Glu Arg Gln Asp Val Gln Met Glu Asn Ser
            980             985             990

Glu Phe Phe Gln Glu Thr Lys Val  Gln Ser Leu Asn Leu  Glu Asn Gly
                995             1000            1005

Ser Glu  Lys His Asp Leu Ser  Lys Ala Glu Thr Glu  Arg Leu Val
    1010            1015            1020

Lys Gly  Ile Lys Glu Arg Glu  Leu Glu Ile Lys Leu  Leu Asn Glu
    1025            1030            1035

Lys Asn  Ile Ser Leu Thr Lys  Gln Ile Asp Gln Leu  Ser Lys Asp
    1040            1045            1050

Glu Val  Gly Lys Leu Thr Gln  Ile Ile Gln Gln Lys  Asp Leu Glu
    1055            1060            1065

Ile Gln  Ala Leu His Ala Arg  Ile Ser Ser Ala Ser  Tyr Thr Gln
    1070            1075            1080

Asp Val  Val Tyr Leu Gln Gln  Gln Leu Gln Ala Tyr  Ala Met Glu
    1085            1090            1095

Arg Glu  Gln Val Leu Ala Val  Leu Ser Glu Lys Thr  Arg Glu Asn
    1100            1105            1110

Ser His  Leu Lys Thr Glu Tyr  His Lys Met Met Asp  Ile Val Ala
    1115            1120            1125

Ala Lys  Glu Ala Ala Leu Ile  Lys Leu Gln Asp Glu  Asn Lys Lys
    1130            1135            1140

Leu Ser  Ala Arg Ser Glu Gly  Gly Gly Gln Asp Met  Phe Arg Glu
    1145            1150            1155

Thr Val  Gln Asn Leu Ser Arg  Ile Ile Arg Glu Lys  Asp Ile Glu
    1160            1165            1170

Ile Asp  Ala Leu Ser Gln Lys  Cys Gln Thr Leu Leu  Thr Val Leu
    1175            1180            1185
```

```
Gln Thr Ser Ser Thr Gly Asn Glu Val Gly Val Asn Ser Asn
    1190            1195            1200

Gln Phe Glu Glu Leu Leu Gln Glu Arg Asp Lys Leu Lys Gln Gln
    1205            1210            1215

Val Lys Lys Met Glu Glu Trp Lys Gln Gln Val Met Thr Thr Val
    1220            1225            1230

Gln Asn Met Gln His Glu Ser Ala Gln Leu Gln Glu Glu Leu His
    1235            1240            1245

Gln Leu Gln Ala Gln Val Leu Val Asp Ser Asp Asn Asn Ser Lys
    1250            1255            1260

Leu Gln Val Asp Tyr Thr Gly Leu Ile Gln Ser Tyr Glu Gln Asn
    1265            1270            1275

Glu Thr Lys Leu Lys Asn Phe Gly Gln Glu Leu Ala Gln Val Gln
    1280            1285            1290

His Ser Ile Gly Gln Leu Tyr Ser Thr Lys Asp Leu Leu Leu Gly
    1295            1300            1305

Lys Leu Asp Ile Ile Ser Pro Gln Leu Pro Ser Gly Ser Ser Pro
    1310            1315            1320

Pro Ser Gln Ser Ala Glu Ser Leu Gly Met Asp Lys Arg Asp Thr
    1325            1330            1335

Ser Ser Glu Ser Ser Lys Gln Glu Leu Glu Glu Leu Arg Lys Ser
    1340            1345            1350

Leu Gln Glu Lys Asp Ala Thr Ile Lys Thr Leu Gln Glu Asn Asn
    1355            1360            1365

His Arg Leu Ser Asp Ser Ile Ala Ala Thr Ser Glu Leu Glu Arg
    1370            1375            1380

Lys Glu His Glu Gln Thr Asp Ser Glu Ile Lys Gln Leu Lys Glu
    1385            1390            1395

Lys Gln Asp Val Leu Gln Lys Ser Leu Lys Glu Lys Asp Leu Leu
    1400            1405            1410

Ile Lys Ala Lys Ser Asp Gln Leu Leu Ser Leu Asn Glu Asn Phe
    1415            1420            1425

Thr Asn Lys Val Asn Glu Asn Glu Leu Leu Arg Gln Ala Val Thr
    1430            1435            1440

Asn Leu Lys Glu Arg Val Leu Ile Leu Glu Met Asp Ile Gly Lys
    1445            1450            1455

Leu Lys Glu Glu Asn Glu Lys Ile Val Glu Arg Thr Arg Glu Lys
    1460            1465            1470

Glu Thr Glu Tyr Gln Ala Leu Gln Glu Thr Asn Met Lys Phe Ser
    1475            1480            1485

Met Met Leu Arg Glu Lys Glu Phe Glu Cys His Ser Met Lys Glu
    1490            1495            1500

Lys Ser Leu Ala Phe Glu Gln Leu Leu Lys Glu Lys Glu Gln Gly
    1505            1510            1515

Lys Thr Gly Glu Leu Asn Gln Leu Leu Asn Ala Val Lys Ser Met
    1520            1525            1530

Gln Glu Lys Thr Val Lys Phe Gln Gln Glu Arg Asp Gln Val Met
    1535            1540            1545

Leu Ala Leu Lys Gln Lys Gln Met Glu Asn Ser Ala Leu Gln Asn
    1550            1555            1560

Glu Val Gln His Leu Arg Asp Lys Glu Leu Arg Leu Asn Gln Glu
    1565            1570            1575
```

-continued

Leu Glu Arg Leu Arg Asn His Leu Leu Glu Ser Glu Asp Ser Tyr
1580                1585                1590

Thr Arg Glu Ala Leu Ala Ala Glu Glu Arg Glu Ala Lys Leu Arg
1595                1600                1605

Arg Lys Val Thr Val Leu Glu Glu Lys Leu Val Ser Ser Ser Asn
1610                1615                1620

Ala Met Glu Asn Ala Ser His Gln Ala Ser Leu Gln Val Glu Ser
1625                1630                1635

Leu Gln Glu Gln Leu Asn Val Val Ser Lys Gln Arg Asp Glu Thr
1640                1645                1650

Ala Leu Gln Leu Ser Val Ser Arg Glu Gln Val Lys Gln Tyr Ala
1655                1660                1665

Leu Ser Leu Ser Asn Leu Gln Met Val Leu Glu His Phe Gln Gln
1670                1675                1680

Glu Glu Lys Ala Val Tyr Ser Ala Glu Leu Glu Lys His Lys Gln
1685                1690                1695

Leu Val Ala Glu Trp Lys Lys Lys Ala Glu Asn Leu Glu Gly Lys
1700                1705                1710

Leu Met Ser Leu Gln Glu Arg Phe Asp Glu Ala Asn Ala Ala Leu
1715                1720                1725

Asp Ser Ala Ser Arg Leu Thr Glu Gln Leu Asp Leu Lys Glu Glu
1730                1735                1740

Gln Ile Glu Glu Leu Lys Lys Gln Asn Glu Leu Arg Gln Glu Met
1745                1750                1755

Leu Asp Asp Val Gln Lys Lys Leu Met Asn Leu Val Asn Ser Thr
1760                1765                1770

Glu Gly Lys Val Asp Lys Val Leu Met Arg Asn Leu Phe Ile Gly
1775                1780                1785

His Phe His Thr Pro Lys His Gln Arg His Glu Val Leu Arg Leu
1790                1795                1800

Met Gly Ser Ile Leu Gly Ile Lys Arg Glu Glu Met Glu Gln Leu
1805                1810                1815

Leu His Glu Asp Gln Gly Gly Val Thr Arg Trp Met Thr Gly Trp
1820                1825                1830

Leu Gly Gly Gly Ser Lys Ser Val Pro Asn Thr Pro Leu Arg Pro
1835                1840                1845

Asn Gln Gln Ser Val Leu Asn Ser Ser Phe Ser Glu Leu Phe Val
1850                1855                1860

Lys Phe Leu Glu Thr Glu Ser His Pro Ser Val Pro Pro Pro Lys
1865                1870                1875

Leu Ser Val His Asp Met Lys Pro Leu Asp Ser Pro Gly Arg Arg
1880                1885                1890

Lys Val Val Ile His Val Ser Glu Ser Phe Lys Glu Thr Thr Glu
1895                1900                1905

Ser Arg Cys Gly Arg Arg Thr Asp Val Asn Pro Phe Leu Ala Pro
1910                1915                1920

Arg Ser Ala Ala Val Pro Leu Ile Asn Pro Ala Gly Leu Gly Pro
1925                1930                1935

Gly Gly Pro Gly His Leu Leu Lys Pro Ile Ser Asp Val Leu
1940                1945                1950

Pro Thr Phe Thr Pro Leu Pro Val Ser Pro Asp Asn Ser Ala Gly
1955                1960                1965

Val Val Leu Lys Asp Leu Leu Lys Gln

```
                   1970          1975

<210> SEQ ID NO 46
<211> LENGTH: 6452
<212> TYPE: DNA
<213> ORGANISM: Homo sapiens
<220> FEATURE:
<221> NAME/KEY: CDS
<222> LOCATION: (357)..(6296)

<400> SEQUENCE: 46
cgagcgagtg tcatggcggc cggcgtcgag ttggcaggag taacccacgg aactgaggaa    60
agtcattaga gctgagaaag aagtggccca atctggacgg tgggaattcg tgggaatgag   120
cagaaggccc tccgtagtga ctgtgtcact agaggcgggc ccctggtaaa attccaggcc   180
aggcctctgc gtttctaggc agaacctgga gtcggccttg cctgagaacc cagctttgtg   240
ttatcgtatc ctgtctcgcg aaggcaggcg ttcaaggata tttggtcgga tcgcccggcg   300
gcgctaaacg ttttcttttt tccgagcgga ccgggtcgtt ctctaaactc gccgcg atg   359
                                                              Met
                                                               1 tcg tcc tgg ctt ggg ggc ctc ggc tcc gga ttg ggc cag tct ctg ggt    407
Ser Ser Trp Leu Gly Gly Leu Gly Ser Gly Leu Gly Gln Ser Leu Gly
         5                  10                  15 caa gtc ggg ggc agc ctg gct tcc ctc act ggc cag ata tca aac ttt    455
Gln Val Gly Gly Ser Leu Ala Ser Leu Thr Gly Gln Ile Ser Asn Phe
     20                  25                  30 aca aag gat atg ctg atg gag ggc acg gag gaa gtg gaa gca gaa tta    503
Thr Lys Asp Met Leu Met Glu Gly Thr Glu Glu Val Glu Ala Glu Leu
 35                  40                  45 cct gat tct agg aca aag gaa att gaa gcc att cat gca atc ttg aga    551
Pro Asp Ser Arg Thr Lys Glu Ile Glu Ala Ile His Ala Ile Leu Arg
 50                  55                  60                  65 tca gag aat gaa agg ctt aag aaa ctt tgt act gat cta gaa gag aaa    599
Ser Glu Asn Glu Arg Leu Lys Lys Leu Cys Thr Asp Leu Glu Glu Lys
                 70                  75                  80 cat gaa gca tca gag att caa ata aag cag caa tct aca agt tac cga    647
His Glu Ala Ser Glu Ile Gln Ile Lys Gln Gln Ser Thr Ser Tyr Arg
             85                  90                  95 aat caa ctt caa caa aaa gag gta gaa atc agc cat ctt aaa gcc aga    695
Asn Gln Leu Gln Gln Lys Glu Val Glu Ile Ser His Leu Lys Ala Arg
        100                 105                 110 cag att gca ctc cag gat cag ttg ctg aaa ctg cag tca gct gct cag    743
Gln Ile Ala Leu Gln Asp Gln Leu Leu Lys Leu Gln Ser Ala Ala Gln
    115                 120                 125 tca gta cct tca gga gct ggt gta cca gca acc act gca tca tct tca    791
Ser Val Pro Ser Gly Ala Gly Val Pro Ala Thr Thr Ala Ser Ser Ser
130                 135                 140                 145 ttc gct tat ggg att agt cat cat cct tca gct ttc cat gac gat gac    839
Phe Ala Tyr Gly Ile Ser His His Pro Ser Ala Phe His Asp Asp Asp
                150                 155                 160 atg gac ttt ggt gat ata att tca tcc caa caa gaa ata aac cga ctc    887
Met Asp Phe Gly Asp Ile Ile Ser Ser Gln Gln Glu Ile Asn Arg Leu
            165                 170                 175 tca aat gaa gtt tca aga ctt gag tct gaa gtt ggc cat tgg agg cat    935
Ser Asn Glu Val Ser Arg Leu Glu Ser Glu Val Gly His Trp Arg His
        180                 185                 190 att gct cag act tcc aaa gca caa gga aca gat aac tct gat caa agt    983
Ile Ala Gln Thr Ser Lys Ala Gln Gly Thr Asp Asn Ser Asp Gln Ser
    195                 200                 205
```

```
                                                -continued gaa ata tgt aaa cta caa aat atc att aag gaa cta aaa cag aac cga    1031
Glu Ile Cys Lys Leu Gln Asn Ile Ile Lys Glu Leu Lys Gln Asn Arg
210             215                 220                 225 agt cag gaa att gat gac cat caa cat gaa atg tca gta ctg cag aat    1079
Ser Gln Glu Ile Asp Asp His Gln His Glu Met Ser Val Leu Gln Asn
                230                 235                 240 gca cac caa cag aaa ttg aca gaa ata agt cga cga cat cga gaa gaa    1127
Ala His Gln Gln Lys Leu Thr Glu Ile Ser Arg Arg His Arg Glu Glu
        245                 250                 255 tta agt gac tat gaa gaa cga att gaa gaa ctt gaa aat ctg tta caa    1175
Leu Ser Asp Tyr Glu Glu Arg Ile Glu Glu Leu Glu Asn Leu Leu Gln
            260                 265                 270 caa ggt ggc tct gga gtt ata gaa act gat ctc tct aaa atc tat gag    1223
Gln Gly Gly Ser Gly Val Ile Glu Thr Asp Leu Ser Lys Ile Tyr Glu
275                 280                 285 atg caa aaa act att caa gtt cta caa ata gaa aaa gtg gag tct acc    1271
Met Gln Lys Thr Ile Gln Val Leu Gln Ile Glu Lys Val Glu Ser Thr
290                 295                 300                 305 aaa aaa atg gaa caa ctt gag gat aaa ata aaa gat ata aat aaa aaa    1319
Lys Lys Met Glu Gln Leu Glu Asp Lys Ile Lys Asp Ile Asn Lys Lys
                310                 315                 320 tta tct tct gca gaa aat gac aga gat att ttg agg agg gaa caa gaa    1367
Leu Ser Ser Ala Glu Asn Asp Arg Asp Ile Leu Arg Arg Glu Gln Glu
            325                 330                 335 cag cta aat gtg gaa aag aga caa ata atg gaa gaa tgt gaa aac ttg    1415
Gln Leu Asn Val Glu Lys Arg Gln Ile Met Glu Glu Cys Glu Asn Leu
        340                 345                 350 aaa ttg gaa tgt agt aaa ttg cag cct tct gct gtg aag caa agt gat    1463
Lys Leu Glu Cys Ser Lys Leu Gln Pro Ser Ala Val Lys Gln Ser Asp
355                 360                 365 act atg aca gaa aag gaa aga att ctt gcc cag agt gca tca gtg gaa    1511
Thr Met Thr Glu Lys Glu Arg Ile Leu Ala Gln Ser Ala Ser Val Glu
370                 375                 380                 385 gaa gtg ttc aga cta caa caa gca ctg tct gat gcc gaa aat gaa ata    1559
Glu Val Phe Arg Leu Gln Gln Ala Leu Ser Asp Ala Glu Asn Glu Ile
                390                 395                 400 atg aga ttg agt agt tta aac cag gat aac agt ctt gct gaa gac aat    1607
Met Arg Leu Ser Ser Leu Asn Gln Asp Asn Ser Leu Ala Glu Asp Asn
            405                 410                 415 ctg aaa ctt aaa atg cgt atc gaa gtt tta gaa aaa gag aag tca tta    1655
Leu Lys Leu Lys Met Arg Ile Glu Val Leu Glu Lys Glu Lys Ser Leu
        420                 425                 430 ctg agt caa gaa aag gaa gaa ctt cag atg tca ctt tta aaa ttg aac    1703
Leu Ser Gln Glu Lys Glu Glu Leu Gln Met Ser Leu Leu Lys Leu Asn
435                 440                 445 aat gaa tat gaa gta att aaa agt aca gct aca aga gac ata agt ttg    1751
Asn Glu Tyr Glu Val Ile Lys Ser Thr Ala Thr Arg Asp Ile Ser Leu
450                 455                 460                 465 gat tca gaa tta cat gac tta aga ctt aat ttg gag gca aag gaa caa    1799
Asp Ser Glu Leu His Asp Leu Arg Leu Asn Leu Glu Ala Lys Glu Gln
                470                 475                 480 gaa ctc aat cag agt att agt gaa aag gaa aca ctg ata gct gag ata    1847
Glu Leu Asn Gln Ser Ile Ser Glu Lys Glu Thr Leu Ile Ala Glu Ile
            485                 490                 495 gaa gaa ttg gac aga cag aat caa gaa gct aca aag cac atg att ttg    1895
Glu Glu Leu Asp Arg Gln Asn Gln Glu Ala Thr Lys His Met Ile Leu
        500                 505                 510 ata aaa gat cag cta tca aaa caa caa aat gaa gga gat agc atc atc    1943
Ile Lys Asp Gln Leu Ser Lys Gln Gln Asn Glu Gly Asp Ser Ile Ile
515                 520                 525
```

-continued

```
agt aaa ctg aaa caa gat cta aat gat gaa aaa aag aga gtt cat caa   1991
Ser Lys Leu Lys Gln Asp Leu Asn Asp Glu Lys Lys Arg Val His Gln
530             535                 540                 545 ctt gaa gat gat aaa atg gac att act aaa gag tta gat gta cag aaa   2039
Leu Glu Asp Asp Lys Met Asp Ile Thr Lys Glu Leu Asp Val Gln Lys
                550                 555                 560 gaa aag cta att caa agt gaa gtg gcc cta aat gat tta cat tta acc   2087
Glu Lys Leu Ile Gln Ser Glu Val Ala Leu Asn Asp Leu His Leu Thr
            565                 570                 575 aag cag aaa ctt gag gac aaa gta gaa aat tta gta gat cag cta aat   2135
Lys Gln Lys Leu Glu Asp Lys Val Glu Asn Leu Val Asp Gln Leu Asn
        580                 585                 590 aaa tca caa gaa agt aat gta agc atc cag aag gag aat tta gaa ctt   2183
Lys Ser Gln Glu Ser Asn Val Ser Ile Gln Lys Glu Asn Leu Glu Leu
    595                 600                 605 aag gag cat att aga caa aat gag gag gag ctt tct aga ata agg aat   2231
Lys Glu His Ile Arg Gln Asn Glu Glu Glu Leu Ser Arg Ile Arg Asn
610                 615                 620                 625 gag tta atg cag tct cta aat caa gac tct aat agt aat ttt aag gat   2279
Glu Leu Met Gln Ser Leu Asn Gln Asp Ser Asn Ser Asn Phe Lys Asp
                630                 635                 640 acc tta ctt aaa gaa aga gaa gct gaa gtt aga aac tta aag caa aat   2327
Thr Leu Leu Lys Glu Arg Glu Ala Glu Val Arg Asn Leu Lys Gln Asn
            645                 650                 655 ctt tca gaa tta gaa cag ctc aat gaa aat tta aag aaa gtt gct ttt   2375
Leu Ser Glu Leu Glu Gln Leu Asn Glu Asn Leu Lys Lys Val Ala Phe
        660                 665                 670 gat gtc aaa atg gaa aat gaa aag tta gtt tta gca tgt gaa gat gtg   2423
Asp Val Lys Met Glu Asn Glu Lys Leu Val Leu Ala Cys Glu Asp Val
    675                 680                 685 agg cat cag tta gaa gaa tgt ctt gct ggt aac aat cag ctt tct ctg   2471
Arg His Gln Leu Glu Glu Cys Leu Ala Gly Asn Asn Gln Leu Ser Leu
690                 695                 700                 705 gaa aaa aac act att gtg gag act cta aaa atg gaa aaa gga gag ata   2519
Glu Lys Asn Thr Ile Val Glu Thr Leu Lys Met Glu Lys Gly Glu Ile
                710                 715                 720 gag gca gaa ttg tgt tgg gct aaa aag agg ctg ttg gaa gaa gca aac   2567
Glu Ala Glu Leu Cys Trp Ala Lys Lys Arg Leu Leu Glu Glu Ala Asn
            725                 730                 735 aag tat gag aaa acc att gaa gaa ctg tca aat gca cgt aat ttg aat   2615
Lys Tyr Glu Lys Thr Ile Glu Glu Leu Ser Asn Ala Arg Asn Leu Asn
        740                 745                 750 acc tct gcc tta cag ctg gaa cat gag cat tta att aaa ctc aat caa   2663
Thr Ser Ala Leu Gln Leu Glu His Glu His Leu Ile Lys Leu Asn Gln
    755                 760                 765 aag aaa gac atg gaa ata gca gaa ctc aaa aag aat att gaa caa atg   2711
Lys Lys Asp Met Glu Ile Ala Glu Leu Lys Lys Asn Ile Glu Gln Met
770                 775                 780                 785 gat act gac cat aaa gaa act aag gac gtt ttg tca tct agt tta gaa   2759
Asp Thr Asp His Lys Glu Thr Lys Asp Val Leu Ser Ser Ser Leu Glu
                790                 795                 800 gag cag aag cag ttg aca caa ctt ata aac aag aaa gaa att ttt att   2807
Glu Gln Lys Gln Leu Thr Gln Leu Ile Asn Lys Lys Glu Ile Phe Ile
            805                 810                 815 gaa aag ctt aaa gaa aga agt tca aag ctg cag gag gaa ttg gat aaa   2855
Glu Lys Leu Lys Glu Arg Ser Ser Lys Leu Gln Glu Glu Leu Asp Lys
        820                 825                 830 tat tct cag gcc tta aga aaa aat gaa att tta aga cag acc ata gag   2903
Tyr Ser Gln Ala Leu Arg Lys Asn Glu Ile Leu Arg Gln Thr Ile Glu
```

-continued

```
            835                 840                 845
gaa aaa gac cga agt ctt gga tcc atg aaa gag gaa aat aat cat ctg       2951
Glu Lys Asp Arg Ser Leu Gly Ser Met Lys Glu Glu Asn Asn His Leu
850                 855                 860                 865 caa gaa gaa ttg gaa cga ctc agg gaa gag cag agt cga acc gca cct       2999
Gln Glu Glu Leu Glu Arg Leu Arg Glu Glu Gln Ser Arg Thr Ala Pro
            870                 875                 880 gtg gct gac cct aaa acc ctt gat agt gtt act gaa cta gca tct gag       3047
Val Ala Asp Pro Lys Thr Leu Asp Ser Val Thr Glu Leu Ala Ser Glu
            885                 890                 895 gta tct caa ctg aac acg atc aag gaa cat ctt gaa gag gaa att aaa       3095
Val Ser Gln Leu Asn Thr Ile Lys Glu His Leu Glu Glu Glu Ile Lys
            900                 905                 910 cat cat caa aag ata att gaa gat caa aac cag agt aag atg caa cta       3143
His His Gln Lys Ile Ile Glu Asp Gln Asn Gln Ser Lys Met Gln Leu
        915                 920                 925 ctt cag tct tta caa gag caa aag aag gaa atg gat gag ttt aga tac       3191
Leu Gln Ser Leu Gln Glu Gln Lys Lys Glu Met Asp Glu Phe Arg Tyr
930                 935                 940                 945 cag cat gag caa atg aac gcc aca cac acc cag ctc ttt tta gag aag       3239
Gln His Glu Gln Met Asn Ala Thr His Thr Gln Leu Phe Leu Glu Lys
                950                 955                 960 gat gag gaa att aag agt ttg caa aaa aca att gaa caa atc aaa acc       3287
Asp Glu Glu Ile Lys Ser Leu Gln Lys Thr Ile Glu Gln Ile Lys Thr
            965                 970                 975 cag ttg cat gaa gaa aga cag gac att caa aca gat aac tct gat att       3335
Gln Leu His Glu Glu Arg Gln Asp Ile Gln Thr Asp Asn Ser Asp Ile
            980                 985                 990 ttt caa gaa aca aaa gtt cag agc ctt aat ata gaa aat gga agt gaa       3383
Phe Gln Glu Thr Lys Val Gln Ser Leu Asn Ile Glu Asn Gly Ser Glu
            995                 1000                1005 aag cat gat tta tct aaa gct gaa acg gaa aga tta gtg aaa gga            3428
Lys His Asp Leu Ser Lys Ala Glu Thr Glu Arg Leu Val Lys Gly
1010                1015                1020 ata aaa gag cga gaa ctg gag att aaa ctt cta aat gaa aag aat            3473
Ile Lys Glu Arg Glu Leu Glu Ile Lys Leu Leu Asn Glu Lys Asn
1025                1030                1035 ata tct tta act aaa cag att gat cag ttg tcc aaa gat gaa gtt            3518
Ile Ser Leu Thr Lys Gln Ile Asp Gln Leu Ser Lys Asp Glu Val
1040                1045                1050 ggt aaa cta act cag att att cag cag aaa gat ttg gag ata caa            3563
Gly Lys Leu Thr Gln Ile Ile Gln Gln Lys Asp Leu Glu Ile Gln
1055                1060                1065 gct ctt cat gct aga att tct tca act tcc cat act caa gat gtt            3608
Ala Leu His Ala Arg Ile Ser Ser Thr Ser His Thr Gln Asp Val
1070                1075                1080 gtt tac ctt caa cag caa ctg cag gct tat gct atg gaa aga gaa            3653
Val Tyr Leu Gln Gln Gln Leu Gln Ala Tyr Ala Met Glu Arg Glu
1085                1090                1095 aag gta ttt gct gtt ttg aat gag aag act agg gaa aat agc cat            3698
Lys Val Phe Ala Val Leu Asn Glu Lys Thr Arg Glu Asn Ser His
1100                1105                1110 cta aaa aca gaa tat cac aaa atg atg gat att gtt gct gcc aag            3743
Leu Lys Thr Glu Tyr His Lys Met Met Asp Ile Val Ala Ala Lys
1115                1120                1125 gaa gca gct ctt atc aaa ctg caa gat gaa aat aaa aaa ttg tcc            3788
Glu Ala Ala Leu Ile Lys Leu Gln Asp Glu Asn Lys Lys Leu Ser
1130                1135                1140 act aga ttt gaa agt agt ggc caa gat atg ttt aga gaa act att            3833
Thr Arg Phe Glu Ser Ser Gly Gln Asp Met Phe Arg Glu Thr Ile
```

```
Thr Arg Phe Glu Ser Ser Gly Gln Asp Met Phe Arg Glu Thr Ile
1145                1150                1155 cag aat tta tca cgt atc att cga gaa aaa gac atc gaa ata gat      3878
Gln Asn Leu Ser Arg Ile Ile Arg Glu Lys Asp Ile Glu Ile Asp
1160                1165                1170 gca cta agt cag aaa tgt cag act tta ttg gca gtt tta caa aca      3923
Ala Leu Ser Gln Lys Cys Gln Thr Leu Leu Ala Val Leu Gln Thr
1175                1180                1185 tcc agc act ggt aat gag gct gga ggt gtt aat agt cat caa ttt      3968
Ser Ser Thr Gly Asn Glu Ala Gly Gly Val Asn Ser His Gln Phe
1190                1195                1200 gag gag ctt cta cag gaa cgt gac aag tta aaa cag caa gta aag      4013
Glu Glu Leu Leu Gln Glu Arg Asp Lys Leu Lys Gln Gln Val Lys
1205                1210                1215 aaa atg gaa gag tgg aag cag cag gtg atg acc aca gta caa aat      4058
Lys Met Glu Glu Trp Lys Gln Gln Val Met Thr Thr Val Gln Asn
1220                1225                1230 atg caa cac gag tca gcc cag ctt cag gaa gag ctt cac caa ctt      4103
Met Gln His Glu Ser Ala Gln Leu Gln Glu Glu Leu His Gln Leu
1235                1240                1245 caa gca cag gtt ttg gtt gac agt gat aat aat tct aaa tta caa      4148
Gln Ala Gln Val Leu Val Asp Ser Asp Asn Asn Ser Lys Leu Gln
1250                1255                1260 gtg gac tat act ggc ctg atc caa agt tat gag cag aat gaa acc      4193
Val Asp Tyr Thr Gly Leu Ile Gln Ser Tyr Glu Gln Asn Glu Thr
1265                1270                1275 aaa ctc aaa aat ttt ggg cag gaa tta gca caa gtt cag cac agc      4238
Lys Leu Lys Asn Phe Gly Gln Glu Leu Ala Gln Val Gln His Ser
1280                1285                1290 att ggg cag ctt tgc aat acc aag gat ctt ctt tta gga aaa ctt      4283
Ile Gly Gln Leu Cys Asn Thr Lys Asp Leu Leu Leu Gly Lys Leu
1295                1300                1305 gat att att tca ccc cag ctg tct tct gca tca ttg ctt act ccc      4328
Asp Ile Ile Ser Pro Gln Leu Ser Ser Ala Ser Leu Leu Thr Pro
1310                1315                1320 cag tct gca gag tgt ctt aga gca agt aag tct gaa gta ttg agt      4373
Gln Ser Ala Glu Cys Leu Arg Ala Ser Lys Ser Glu Val Leu Ser
1325                1330                1335 gaa tct tct gaa ttg ctt cag caa gag tta gaa gag cta aga aaa      4418
Glu Ser Ser Glu Leu Leu Gln Gln Glu Leu Glu Glu Leu Arg Lys
1340                1345                1350 tca cta cag gaa aaa gat gca aca att aga act ctc cag gaa aat      4463
Ser Leu Gln Glu Lys Asp Ala Thr Ile Arg Thr Leu Gln Glu Asn
1355                1360                1365 aac cac aga ttg tct gat tcg att gct gcc acc tca gag cta gaa      4508
Asn His Arg Leu Ser Asp Ser Ile Ala Ala Thr Ser Glu Leu Glu
1370                1375                1380 aga aaa gaa cac gaa caa acc gat tca gaa atc aag cag cta aag      4553
Arg Lys Glu His Glu Gln Thr Asp Ser Glu Ile Lys Gln Leu Lys
1385                1390                1395 gag aaa caa gat gtt ttg caa aag tta ctt aag gaa aaa gac ctc      4598
Glu Lys Gln Asp Val Leu Gln Lys Leu Leu Lys Glu Lys Asp Leu
1400                1405                1410 tta atc aaa gcc aaa agt gat caa cta ctt tct tcc aat gaa aat      4643
Leu Ile Lys Ala Lys Ser Asp Gln Leu Leu Ser Ser Asn Glu Asn
1415                1420                1425 ttc act aac aaa gta aat gaa aac gaa ctt ttg agg cag gca gta      4688
Phe Thr Asn Lys Val Asn Glu Asn Glu Leu Leu Arg Gln Ala Val
1430                1435                1440
```

-continued

| | | |
|---|---|---|
| aca aac ctg aag gag aga ata tta att cta gag atg gac att ggc<br>Thr Asn Leu Lys Glu Arg Ile Leu Ile Leu Glu Met Asp Ile Gly<br>1445               1450                         1455 | | 4733 |
| aaa cta aaa gga gaa aat gaa aaa ata gtg gaa aca tac agg gga<br>Lys Leu Lys Gly Glu Asn Glu Lys Ile Val Glu Thr Tyr Arg Gly<br>1460               1465                         1470 | | 4778 |
| aag gaa aca gaa tat caa gcg tta caa gag act aac atg aag ttt<br>Lys Glu Thr Glu Tyr Gln Ala Leu Gln Glu Thr Asn Met Lys Phe<br>1475               1480                       1485 | | 4823 |
| tct atg atg ctg cga gaa aaa gag ttt gag tgc cac tca atg aag<br>Ser Met Met Leu Arg Glu Lys Glu Phe Glu Cys His Ser Met Lys<br>1490               1495                       1500 | | 4868 |
| gag aag gct ctt gct ttt gaa cag cta ttg aaa gag aaa gaa cag<br>Glu Lys Ala Leu Ala Phe Glu Gln Leu Leu Lys Glu Lys Glu Gln<br>1505               1510                       1515 | | 4913 |
| ggc aag act gga gag tta aat cag ctt tta aat gca gtt aaa tca<br>Gly Lys Thr Gly Glu Leu Asn Gln Leu Leu Asn Ala Val Lys Ser<br>1520               1525                       1530 | | 4958 |
| atg cag gag aag aca gtt gtg ttt caa cag gag aga gac caa gtc<br>Met Gln Glu Lys Thr Val Val Phe Gln Gln Glu Arg Asp Gln Val<br>1535               1540                       1545 | | 5003 |
| atg ttg gcc ctg aaa caa aaa caa atg gaa aat act gcc cta cag<br>Met Leu Ala Leu Lys Gln Lys Gln Met Glu Asn Thr Ala Leu Gln<br>1550               1555                       1560 | | 5048 |
| aat gag gtt caa cgt tta cgt gac aaa gaa ttt cgt tca aac caa<br>Asn Glu Val Gln Arg Leu Arg Asp Lys Glu Phe Arg Ser Asn Gln<br>1565               1570                       1575 | | 5093 |
| gag cta gag aga ttg cgt aat cat ctt tta gaa tca gaa gat tct<br>Glu Leu Glu Arg Leu Arg Asn His Leu Leu Glu Ser Glu Asp Ser<br>1580               1585                       1590 | | 5138 |
| tat acc cgt gaa gct ttg gct gca gaa gat aga gag gct aaa cta<br>Tyr Thr Arg Glu Ala Leu Ala Ala Glu Asp Arg Glu Ala Lys Leu<br>1595               1600                       1605 | | 5183 |
| aga aag aaa gtc aca gta ttg gag gaa aag cta gtt tca tcc tct<br>Arg Lys Lys Val Thr Val Leu Glu Glu Lys Leu Val Ser Ser Ser<br>1610               1615                       1620 | | 5228 |
| aat gca atg gaa aat gca agc cat caa gcc agt gtg cag gta gag<br>Asn Ala Met Glu Asn Ala Ser His Gln Ala Ser Val Gln Val Glu<br>1625               1630                       1635 | | 5273 |
| tca ttg caa gaa cag ttg aat gta gtt tcc aag caa agg gat gaa<br>Ser Leu Gln Glu Gln Leu Asn Val Val Ser Lys Gln Arg Asp Glu<br>1640               1645                       1650 | | 5318 |
| act gcg ctg cag ctt tct gtc tct cag gaa caa gta aag cag tat<br>Thr Ala Leu Gln Leu Ser Val Ser Gln Glu Gln Val Lys Gln Tyr<br>1655               1660                       1665 | | 5363 |
| gct ctg tca ctg gcc aac ctg cag atg gta cta gag cat ttc caa<br>Ala Leu Ser Leu Ala Asn Leu Gln Met Val Leu Glu His Phe Gln<br>1670               1675                       1680 | | 5408 |
| caa gag gaa aaa gct atg tat tct gct gaa ctc gaa aag caa aaa<br>Gln Glu Glu Lys Ala Met Tyr Ser Ala Glu Leu Glu Lys Gln Lys<br>1685               1690                       1695 | | 5453 |
| cag ctt ata gct gaa tgg aag aaa aac gca gaa aat ctg gaa gga<br>Gln Leu Ile Ala Glu Trp Lys Lys Asn Ala Glu Asn Leu Glu Gly<br>1700               1705                       1710 | | 5498 |
| aaa gtg ata tca tta cag gaa tgt ttg gat gaa gca aat gct gca<br>Lys Val Ile Ser Leu Gln Glu Cys Leu Asp Glu Ala Asn Ala Ala<br>1715               1720                       1725 | | 5543 |
| ttg gat tca gca tca aga ctt aca gaa cag tta gat gta aaa gaa<br>Leu Asp Ser Ala Ser Arg Leu Thr Glu Gln Leu Asp Val Lys Glu<br>1730               1735                       1740 | | 5588 |

| | | | | | | | | | | | | |
|---|---|---|---|---|---|---|---|---|---|---|---|---|
| gaa | caa | att | gaa | gaa | ctt | aaa | aga | caa | aat | gag | ctc cga caa gaa | 5633 |
| Glu | Gln | Ile | Glu | Glu | Leu | Lys | Arg | Gln | Asn | Glu | Leu Arg Gln Glu | |
| 1745 | | | | 1750 | | | | | 1755 | | | |
| atg | ctg | gat | gat | gta | caa | aag | aaa | ttg | atg | agc | tta gca aac agc | 5678 |
| Met | Leu | Asp | Asp | Val | Gln | Lys | Lys | Leu | Met | Ser | Leu Ala Asn Ser | |
| 1760 | | | | 1765 | | | | | 1770 | | | |
| tca | gaa | gga | aaa | gta | gac | aaa | gtc | cta | atg | aga | aac ctc ttc att | 5723 |
| Ser | Glu | Gly | Lys | Val | Asp | Lys | Val | Leu | Met | Arg | Asn Leu Phe Ile | |
| 1775 | | | | 1780 | | | | | 1785 | | | |
| ggt | cat | ttc | cac | aca | ccg | aaa | aat | cag | cgt | cat | gaa gtg tta cgg | 5768 |
| Gly | His | Phe | His | Thr | Pro | Lys | Asn | Gln | Arg | His | Glu Val Leu Arg | |
| 1790 | | | | 1795 | | | | | 1800 | | | |
| tta | atg | ggg | agc | atc | ctg | ggc | gtc | aga | agg | gag | gag atg gag cag | 5813 |
| Leu | Met | Gly | Ser | Ile | Leu | Gly | Val | Arg | Arg | Glu | Glu Met Glu Gln | |
| 1805 | | | | 1810 | | | | | 1815 | | | |
| ttg | ttt | cat | gac | gat | cag | ggc | agt | gtt | acc | agg | tgg atg act ggg | 5858 |
| Leu | Phe | His | Asp | Asp | Gln | Gly | Ser | Val | Thr | Arg | Trp Met Thr Gly | |
| 1820 | | | | 1825 | | | | | 1830 | | | |
| tgg | ctt | gga | gga | gga | tca | aaa | agt | gtt | ccc | aac | aca cct ttg aga | 5903 |
| Trp | Leu | Gly | Gly | Gly | Ser | Lys | Ser | Val | Pro | Asn | Thr Pro Leu Arg | |
| 1835 | | | | 1840 | | | | | 1845 | | | |
| cca | aat | cag | caa | tct | gtg | gtt | aat | agt | tct | ttt | tca gaa ctt ttt | 5948 |
| Pro | Asn | Gln | Gln | Ser | Val | Val | Asn | Ser | Ser | Phe | Ser Glu Leu Phe | |
| 1850 | | | | 1855 | | | | | 1860 | | | |
| gtt | aaa | ttt | cta | gaa | aca | gaa | tct | cat | cca | tcc | att cca cca cca | 5993 |
| Val | Lys | Phe | Leu | Glu | Thr | Glu | Ser | His | Pro | Ser | Ile Pro Pro Pro | |
| 1865 | | | | 1870 | | | | | 1875 | | | |
| aag | ctt | tct | gtt | cat | gat | atg | aaa | cct | ctg | gat | tca cca gga aga | 6038 |
| Lys | Leu | Ser | Val | His | Asp | Met | Lys | Pro | Leu | Asp | Ser Pro Gly Arg | |
| 1880 | | | | 1885 | | | | | 1890 | | | |
| aga | aaa | aga | gat | aca | aat | gca | cca | gaa | agt | ttt | aaa gat aca gca | 6083 |
| Arg | Lys | Arg | Asp | Thr | Asn | Ala | Pro | Glu | Ser | Phe | Lys Asp Thr Ala | |
| 1895 | | | | 1900 | | | | | 1905 | | | |
| gaa | tcc | agg | tct | ggt | aga | aga | aca | gat | gta | aat | ccg ttt ttg gct | 6128 |
| Glu | Ser | Arg | Ser | Gly | Arg | Arg | Thr | Asp | Val | Asn | Pro Phe Leu Ala | |
| 1910 | | | | 1915 | | | | | 1920 | | | |
| cct | cgc | tcg | gca | gct | gta | cct | ctt | att | aac | cca | gct gga ctt gga | 6173 |
| Pro | Arg | Ser | Ala | Ala | Val | Pro | Leu | Ile | Asn | Pro | Ala Gly Leu Gly | |
| 1925 | | | | 1930 | | | | | 1935 | | | |
| cct | ggt | ggg | ccc | ggg | cat | ctt | ctt | ctg | aaa | ccc | atc tca gat gtt | 6218 |
| Pro | Gly | Gly | Pro | Gly | His | Leu | Leu | Leu | Lys | Pro | Ile Ser Asp Val | |
| 1940 | | | | 1945 | | | | | 1950 | | | |
| ttg | ccc | aca | ttt | aca | cct | ttg | cca | gcg | tta | cct | gac aac agt gct | 6263 |
| Leu | Pro | Thr | Phe | Thr | Pro | Leu | Pro | Ala | Leu | Pro | Asp Asn Ser Ala | |
| 1955 | | | | 1960 | | | | | 1965 | | | |
| ggg | gtt | gtg | ctg | aaa | gac | ctt | tta | aag | caa | tag | atgattctca | 6306 |
| Gly | Val | Val | Leu | Lys | Asp | Leu | Leu | Lys | Gln | | | |
| 1970 | | | | 1975 | | | | | | | | |

| | |
|---|---|
| agccagagac aatctagcac tttaaagaaa ccatgaacac tatatgtatg tactttatca | 6366 |
| caaagtggcc tttggggaga aagtcatgta tttgttcgca attatgcttt ctctgaattt | 6426 |
| aataaaaata ttcctaatgc ttttag | 6452 |

<210> SEQ ID NO 47
<211> LENGTH: 1979
<212> TYPE: PRT
<213> ORGANISM: Homo sapiens

<400> SEQUENCE: 47

```
Met Ser Ser Trp Leu Gly Gly Leu Gly Ser Gly Leu Gly Gln Ser Leu
1               5                   10                  15
Gly Gln Val Gly Gly Ser Leu Ala Ser Leu Thr Gly Gln Ile Ser Asn
            20                  25                  30
Phe Thr Lys Asp Met Leu Met Glu Gly Thr Glu Glu Val Glu Ala Glu
        35                  40                  45
Leu Pro Asp Ser Arg Thr Lys Glu Ile Glu Ala Ile His Ala Ile Leu
    50                  55                  60
Arg Ser Glu Asn Glu Arg Leu Lys Lys Leu Cys Thr Asp Leu Glu Glu
65                  70                  75                  80
Lys His Glu Ala Ser Glu Ile Gln Ile Lys Gln Gln Ser Thr Ser Tyr
                85                  90                  95
Arg Asn Gln Leu Gln Gln Lys Glu Val Glu Ile Ser His Leu Lys Ala
            100                 105                 110
Arg Gln Ile Ala Leu Gln Asp Gln Leu Leu Lys Leu Gln Ser Ala Ala
        115                 120                 125
Gln Ser Val Pro Ser Gly Ala Gly Val Pro Ala Thr Thr Ala Ser Ser
    130                 135                 140
Ser Phe Ala Tyr Gly Ile Ser His His Pro Ser Ala Phe His Asp Asp
145                 150                 155                 160
Asp Met Asp Phe Gly Asp Ile Ile Ser Ser Gln Gln Glu Ile Asn Arg
                165                 170                 175
Leu Ser Asn Glu Val Ser Arg Leu Glu Ser Glu Val Gly His Trp Arg
            180                 185                 190
His Ile Ala Gln Thr Ser Lys Ala Gln Gly Thr Asp Asn Ser Asp Gln
        195                 200                 205
Ser Glu Ile Cys Lys Leu Gln Asn Ile Ile Lys Glu Leu Lys Gln Asn
    210                 215                 220
Arg Ser Gln Glu Ile Asp Asp His Gln His Glu Met Ser Val Leu Gln
225                 230                 235                 240
Asn Ala His Gln Gln Lys Leu Thr Glu Ile Ser Arg Arg His Arg Glu
                245                 250                 255
Glu Leu Ser Asp Tyr Glu Glu Arg Ile Glu Glu Leu Glu Asn Leu Leu
            260                 265                 270
Gln Gln Gly Gly Ser Gly Val Ile Glu Thr Asp Leu Ser Lys Ile Tyr
        275                 280                 285
Glu Met Gln Lys Thr Ile Gln Val Leu Gln Ile Glu Lys Val Glu Ser
    290                 295                 300
Thr Lys Lys Met Glu Gln Leu Glu Asp Lys Ile Lys Asp Ile Asn Lys
305                 310                 315                 320
Lys Leu Ser Ser Ala Glu Asn Asp Arg Asp Ile Leu Arg Arg Glu Gln
                325                 330                 335
Glu Gln Leu Asn Val Glu Lys Arg Gln Ile Met Glu Glu Cys Glu Asn
            340                 345                 350
Leu Lys Leu Glu Cys Ser Lys Leu Gln Pro Ser Ala Val Lys Gln Ser
        355                 360                 365
Asp Thr Met Thr Glu Lys Glu Arg Ile Leu Ala Gln Ser Ala Ser Val
    370                 375                 380
Glu Glu Val Phe Arg Leu Gln Gln Ala Leu Ser Asp Ala Glu Asn Glu
385                 390                 395                 400
Ile Met Arg Leu Ser Ser Leu Asn Gln Asp Asn Ser Leu Ala Glu Asp
                405                 410                 415
Asn Leu Lys Leu Lys Met Arg Ile Glu Val Leu Glu Lys Glu Lys Ser
```

-continued

```
            420             425             430
Leu Leu Ser Gln Glu Lys Glu Leu Gln Met Ser Leu Leu Lys Leu
            435             440             445

Asn Asn Glu Tyr Glu Val Ile Lys Ser Thr Ala Thr Arg Asp Ile Ser
450             455             460

Leu Asp Ser Glu Leu His Asp Leu Arg Leu Asn Leu Glu Ala Lys Glu
465             470             475             480

Gln Glu Leu Asn Gln Ser Ile Ser Glu Lys Glu Thr Leu Ile Ala Glu
                485             490             495

Ile Glu Glu Leu Asp Arg Gln Asn Gln Glu Ala Thr Lys His Met Ile
            500             505             510

Leu Ile Lys Asp Gln Leu Ser Lys Gln Gln Asn Glu Gly Asp Ser Ile
            515             520             525

Ile Ser Lys Leu Lys Gln Asp Leu Asn Asp Glu Lys Lys Arg Val His
            530             535             540

Gln Leu Glu Asp Asp Lys Met Asp Ile Thr Lys Glu Leu Asp Val Gln
545             550             555             560

Lys Glu Lys Leu Ile Gln Ser Glu Val Ala Leu Asn Asp Leu His Leu
                565             570             575

Thr Lys Gln Lys Leu Glu Asp Lys Val Glu Asn Leu Val Asp Gln Leu
            580             585             590

Asn Lys Ser Gln Glu Ser Asn Val Ser Ile Gln Lys Glu Asn Leu Glu
            595             600             605

Leu Lys Glu His Ile Arg Gln Asn Glu Glu Leu Ser Arg Ile Arg
            610             615             620

Asn Glu Leu Met Gln Ser Leu Asn Gln Asp Ser Asn Ser Asn Phe Lys
625             630             635             640

Asp Thr Leu Leu Lys Glu Arg Glu Ala Glu Val Arg Asn Leu Lys Gln
                645             650             655

Asn Leu Ser Glu Leu Glu Gln Leu Asn Glu Asn Leu Lys Lys Val Ala
            660             665             670

Phe Asp Val Lys Met Glu Asn Glu Lys Leu Val Leu Ala Cys Glu Asp
            675             680             685

Val Arg His Gln Leu Glu Glu Cys Leu Ala Gly Asn Asn Gln Leu Ser
690             695             700

Leu Glu Lys Asn Thr Ile Val Glu Thr Leu Lys Met Glu Lys Gly Glu
705             710             715             720

Ile Glu Ala Glu Leu Cys Trp Ala Lys Lys Arg Leu Leu Glu Glu Ala
                725             730             735

Asn Lys Tyr Glu Lys Thr Ile Glu Glu Leu Ser Asn Ala Arg Asn Leu
            740             745             750

Asn Thr Ser Ala Leu Gln Leu Glu His Glu His Leu Ile Lys Leu Asn
            755             760             765

Gln Lys Lys Asp Met Glu Ile Ala Glu Leu Lys Lys Asn Ile Glu Gln
            770             775             780

Met Asp Thr Asp His Lys Glu Thr Lys Asp Val Leu Ser Ser Ser Leu
785             790             795             800

Glu Glu Gln Lys Gln Leu Thr Gln Leu Ile Asn Lys Lys Glu Ile Phe
                805             810             815

Ile Glu Lys Leu Lys Glu Arg Ser Ser Lys Leu Gln Glu Glu Leu Asp
            820             825             830

Lys Tyr Ser Gln Ala Leu Arg Lys Asn Glu Ile Leu Arg Gln Thr Ile
            835             840             845
```

-continued

```
Glu Lys Asp Arg Ser Leu Gly Ser Met Lys Glu Asn Asn His
    850             855             860

Leu Gln Glu Glu Leu Glu Arg Leu Arg Glu Glu Gln Ser Arg Thr Ala
865             870             875             880

Pro Val Ala Asp Pro Lys Thr Leu Asp Ser Val Thr Glu Leu Ala Ser
                885             890             895

Glu Val Ser Gln Leu Asn Thr Ile Lys Glu His Leu Glu Glu Glu Ile
            900             905             910

Lys His His Gln Lys Ile Ile Glu Asp Gln Asn Gln Ser Lys Met Gln
        915             920             925

Leu Leu Gln Ser Leu Gln Glu Gln Lys Lys Glu Met Asp Glu Phe Arg
    930             935             940

Tyr Gln His Glu Gln Met Asn Ala Thr His Thr Gln Leu Phe Leu Glu
945             950             955             960

Lys Asp Glu Glu Ile Lys Ser Leu Gln Lys Thr Ile Glu Gln Ile Lys
                965             970             975

Thr Gln Leu His Glu Glu Arg Gln Asp Ile Gln Thr Asp Asn Ser Asp
            980             985             990

Ile Phe Gln Glu Thr Lys Val Gln  Ser Leu Asn Ile Glu  Asn Gly Ser
        995             1000            1005

Glu Lys  His Asp Leu Ser Lys  Ala Glu Thr Glu Arg  Leu Val Lys
    1010            1015            1020

Gly Ile  Lys Glu Arg Glu Leu  Glu Ile Lys Leu Leu  Asn Glu Lys
    1025            1030            1035

Asn Ile  Ser Leu Thr Lys Gln  Ile Asp Gln Leu Ser  Lys Asp Glu
    1040            1045            1050

Val Gly  Lys Leu Thr Gln Ile  Ile Gln Gln Lys Asp  Leu Glu Ile
    1055            1060            1065

Gln Ala  Leu His Ala Arg Ile  Ser Ser Thr Ser His  Thr Gln Asp
    1070            1075            1080

Val Val  Tyr Leu Gln Gln Gln  Leu Gln Ala Tyr Ala  Met Glu Arg
    1085            1090            1095

Glu Lys  Val Phe Ala Val Leu  Asn Glu Lys Thr Arg  Glu Asn Ser
    1100            1105            1110

His Leu  Lys Thr Glu Tyr His  Lys Met Met Asp Ile  Val Ala Ala
    1115            1120            1125

Lys Glu  Ala Ala Leu Ile Lys  Leu Gln Asp Glu Asn  Lys Lys Leu
    1130            1135            1140

Ser Thr  Arg Phe Glu Ser Ser  Gly Gln Asp Met Phe  Arg Glu Thr
    1145            1150            1155

Ile Gln  Asn Leu Ser Arg Ile  Ile Arg Glu Lys Asp  Ile Glu Ile
    1160            1165            1170

Asp Ala  Leu Ser Gln Lys Cys  Gln Thr Leu Leu Ala  Val Leu Gln
    1175            1180            1185

Thr Ser  Ser Thr Gly Asn Glu  Ala Gly Gly Val Asn  Ser His Gln
    1190            1195            1200

Phe Glu  Glu Leu Leu Gln Glu  Arg Asp Lys Leu Lys  Gln Gln Val
    1205            1210            1215

Lys Lys  Met Glu Glu Trp Lys  Gln Gln Val Met Thr  Thr Val Gln
    1220            1225            1230

Asn Met  Gln His Glu Ser Ala  Gln Leu Gln Glu Glu  Leu His Gln
    1235            1240            1245
```

-continued

Leu Gln Ala Gln Val Leu Val Asp Ser Asp Asn Asn Ser Lys Leu
1250                1255                1260

Gln Val Asp Tyr Thr Gly Leu Ile Gln Ser Tyr Glu Gln Asn Glu
1265                1270                1275

Thr Lys Leu Lys Asn Phe Gly Gln Glu Leu Ala Gln Val Gln His
1280                1285                1290

Ser Ile Gly Gln Leu Cys Asn Thr Lys Asp Leu Leu Leu Gly Lys
1295                1300                1305

Leu Asp Ile Ile Ser Pro Gln Leu Ser Ser Ala Ser Leu Leu Thr
1310                1315                1320

Pro Gln Ser Ala Glu Cys Leu Arg Ala Ser Lys Ser Glu Val Leu
1325                1330                1335

Ser Glu Ser Ser Glu Leu Leu Gln Gln Glu Leu Glu Glu Leu Arg
1340                1345                1350

Lys Ser Leu Gln Glu Lys Asp Ala Thr Ile Arg Thr Leu Gln Glu
1355                1360                1365

Asn Asn His Arg Leu Ser Asp Ser Ile Ala Ala Thr Ser Glu Leu
1370                1375                1380

Glu Arg Lys Glu His Glu Gln Thr Asp Ser Glu Ile Lys Gln Leu
1385                1390                1395

Lys Glu Lys Gln Asp Val Leu Gln Lys Leu Leu Lys Glu Lys Asp
1400                1405                1410

Leu Leu Ile Lys Ala Lys Ser Asp Gln Leu Leu Ser Ser Asn Glu
1415                1420                1425

Asn Phe Thr Asn Lys Val Asn Glu Asn Glu Leu Leu Arg Gln Ala
1430                1435                1440

Val Thr Asn Leu Lys Glu Arg Ile Leu Ile Leu Glu Met Asp Ile
1445                1450                1455

Gly Lys Leu Lys Gly Glu Asn Glu Lys Ile Val Glu Thr Tyr Arg
1460                1465                1470

Gly Lys Glu Thr Glu Tyr Gln Ala Leu Gln Glu Thr Asn Met Lys
1475                1480                1485

Phe Ser Met Met Leu Arg Glu Lys Glu Phe Glu Cys His Ser Met
1490                1495                1500

Lys Glu Lys Ala Leu Ala Phe Glu Gln Leu Leu Lys Glu Lys Glu
1505                1510                1515

Gln Gly Lys Thr Gly Glu Leu Asn Gln Leu Leu Asn Ala Val Lys
1520                1525                1530

Ser Met Gln Glu Lys Thr Val Val Phe Gln Gln Glu Arg Asp Gln
1535                1540                1545

Val Met Leu Ala Leu Lys Gln Lys Gln Met Glu Asn Thr Ala Leu
1550                1555                1560

Gln Asn Glu Val Gln Arg Leu Arg Asp Lys Glu Phe Arg Ser Asn
1565                1570                1575

Gln Glu Leu Glu Arg Leu Arg Asn His Leu Leu Glu Ser Glu Asp
1580                1585                1590

Ser Tyr Thr Arg Glu Ala Leu Ala Ala Glu Asp Arg Glu Ala Lys
1595                1600                1605

Leu Arg Lys Lys Val Thr Val Leu Glu Glu Lys Leu Val Ser Ser
1610                1615                1620

Ser Asn Ala Met Glu Asn Ala Ser His Gln Ala Ser Val Gln Val
1625                1630                1635

Glu Ser Leu Gln Glu Gln Leu Asn Val Val Ser Lys Gln Arg Asp

```
            1640                1645                1650

Glu Thr Ala Leu Gln Leu Ser Val Ser Gln Gln Val Lys Gln
            1655                1660                1665

Tyr Ala Leu Ser Leu Ala Asn Leu Gln Met Val Leu Glu His Phe
            1670                1675                1680

Gln Gln Glu Glu Lys Ala Met Tyr Ser Ala Glu Leu Glu Lys Gln
            1685                1690                1695

Lys Gln Leu Ile Ala Glu Trp Lys Lys Asn Ala Glu Asn Leu Glu
            1700                1705                1710

Gly Lys Val Ile Ser Leu Gln Glu Cys Leu Asp Glu Ala Asn Ala
            1715                1720                1725

Ala Leu Asp Ser Ala Ser Arg Leu Thr Glu Gln Leu Asp Val Lys
            1730                1735                1740

Glu Glu Gln Ile Glu Glu Leu Lys Arg Gln Asn Glu Leu Arg Gln
            1745                1750                1755

Glu Met Leu Asp Asp Val Gln Lys Lys Leu Met Ser Leu Ala Asn
            1760                1765                1770

Ser Ser Glu Gly Lys Val Asp Lys Val Leu Met Arg Asn Leu Phe
            1775                1780                1785

Ile Gly His Phe His Thr Pro Lys Asn Gln Arg His Glu Val Leu
            1790                1795                1800

Arg Leu Met Gly Ser Ile Leu Gly Val Arg Arg Glu Glu Met Glu
            1805                1810                1815

Gln Leu Phe His Asp Asp Gln Gly Ser Val Thr Arg Trp Met Thr
            1820                1825                1830

Gly Trp Leu Gly Gly Gly Ser Lys Ser Val Pro Asn Thr Pro Leu
            1835                1840                1845

Arg Pro Asn Gln Gln Ser Val Val Asn Ser Ser Phe Ser Glu Leu
            1850                1855                1860

Phe Val Lys Phe Leu Glu Thr Glu Ser His Pro Ser Ile Pro Pro
            1865                1870                1875

Pro Lys Leu Ser Val His Asp Met Lys Pro Leu Asp Ser Pro Gly
            1880                1885                1890

Arg Arg Lys Arg Asp Thr Asn Ala Pro Glu Ser Phe Lys Asp Thr
            1895                1900                1905

Ala Glu Ser Arg Ser Gly Arg Arg Thr Asp Val Asn Pro Phe Leu
            1910                1915                1920

Ala Pro Arg Ser Ala Ala Val Pro Leu Ile Asn Pro Ala Gly Leu
            1925                1930                1935

Gly Pro Gly Gly Pro Gly His Leu Leu Leu Lys Pro Ile Ser Asp
            1940                1945                1950

Val Leu Pro Thr Phe Thr Pro Leu Pro Ala Leu Pro Asp Asn Ser
            1955                1960                1965

Ala Gly Val Val Leu Lys Asp Leu Leu Lys Gln
            1970                1975

<210> SEQ ID NO 48
<211> LENGTH: 18
<212> TYPE: DNA
<213> ORGANISM: Artificial Sequence
<220> FEATURE:
<223> OTHER INFORMATION: Synthetic primer

<400> SEQUENCE: 48
gaagctacaa agcacatg                                                    18
```

<210> SEQ ID NO 49
<211> LENGTH: 18
<212> TYPE: DNA
<213> ORGANISM: Artificial Sequence
<220> FEATURE:
<223> OTHER INFORMATION: Synthetic primer

<400> SEQUENCE: 49
tcctgtcttt cttcatgc					18

<210> SEQ ID NO 50
<211> LENGTH: 23
<212> TYPE: DNA
<213> ORGANISM: Artificial Sequence
<220> FEATURE:
<223> OTHER INFORMATION: Synthetic primer

<400> SEQUENCE: 50
catatgtcag tgttgcagaa tgc				23

<210> SEQ ID NO 51
<211> LENGTH: 24
<212> TYPE: DNA
<213> ORGANISM: Artificial Sequence
<220> FEATURE:
<223> OTHER INFORMATION: Synthetic primer

<400> SEQUENCE: 51
ggtacctact aacctctcag tttc				24

<210> SEQ ID NO 52
<211> LENGTH: 23
<212> TYPE: DNA
<213> ORGANISM: Artificial Sequence
<220> FEATURE:
<223> OTHER INFORMATION: Synthetic primer

<400> SEQUENCE: 52
catatgtcag tactgcagaa tgc				23

<210> SEQ ID NO 53
<211> LENGTH: 26
<212> TYPE: DNA
<213> ORGANISM: Artificial Sequence
<220> FEATURE:
<223> OTHER INFORMATION: Synthetic primer

<400> SEQUENCE: 53
ggtacctttt attcctttca ctaatc				26

<210> SEQ ID NO 54
<211> LENGTH: 787
<212> TYPE: PRT
<213> ORGANISM: Canis familiaris

<400> SEQUENCE: 54

Met Ser Val Leu Gln Asn Ala His Gln Gln Lys Leu Thr Asp Ile Ser
1               5                   10                  15

Arg Arg His Arg Glu Glu Leu Arg Asp Tyr Glu Glu Arg Ile Glu Glu
            20                  25                  30

Leu Glu Asn Leu Leu Glu Gln Gly Gly Ser Gly Ile Val Ile Pro Asp
        35                  40                  45

His Ser Lys Ile His Glu Met Gln Lys Thr Ile Gln Asn Leu Gln Thr

```
            50                  55                  60
Glu Lys Val Ala Ser Ile Lys Lys Ile Glu Glu Leu Glu Asp Lys Ile
65                  70                  75                  80

Lys Asp Ile Asp Lys Lys Leu Ser Ser Ala Glu Asn Asp Arg Asp Val
                85                  90                  95

Leu Arg Lys Glu Lys Glu Cys Leu Asn Val Glu Asn Arg Gln Ile Thr
            100                 105                 110

Glu Gln Cys Glu Ser Leu Lys Leu Glu Cys Lys Leu Gln His Asp Ala
        115                 120                 125

Glu Lys Gln Gly Asp Thr Val Thr Glu Lys Glu Arg Ile Leu Pro Gln
    130                 135                 140

Ser Thr Ser Val Glu Glu Val Leu Lys Leu Gln Gln Ala Leu Ser
145                 150                 155                 160

Asp Ala Glu Asn Glu Ile Met Arg Leu Ser Asn Leu Tyr Gln Asp Asn
                165                 170                 175

Ser Leu Thr Glu Asp Asn Leu Lys Leu Lys Met His Val Glu Phe Leu
            180                 185                 190

Glu Lys Gln Lys Ser Leu Leu Ser Gln Glu Lys Glu Glu Leu Gln Leu
        195                 200                 205

Ser Leu Leu Lys Leu Asn Asn Glu Tyr Glu Val Ile Lys Ser Thr Ala
    210                 215                 220

Val Arg Asp Met Asp Met Asp Ser Thr Leu Cys Asp Leu Arg Leu Thr
225                 230                 235                 240

Leu Glu Ala Lys Asp Gln Glu Leu Asn Gln Ser Leu Thr Glu Lys Glu
                245                 250                 255

Ile Leu Val Ala Glu Leu Glu Leu Asp Arg Gln Asn Gln Glu Ala
            260                 265                 270

Thr Lys His Met Ile Leu Ile Lys Asp Gln Leu Ser Lys Gln Ser
        275                 280                 285

Glu Gly Glu Thr Ile Ile Ser Lys Leu Arg Lys Asp Leu Asn Asp Glu
    290                 295                 300

Asn Lys Arg Val His Gln Leu Glu Asp Lys Lys Asn Met Thr Lys
305                 310                 315                 320

Glu Leu Asn Val Gln Lys Gly Lys Leu Val Gln Ser Glu Leu Val Leu
                325                 330                 335

Asn Gly Leu His Leu Ala Lys Gln Lys Leu Glu Glu Lys Val Glu Asp
            340                 345                 350

Leu Val Asp Gln Leu Asn Lys Ser Gln Lys Ser Asn Leu Asn Met Gln
        355                 360                 365

Lys Glu Asn Phe Gly Leu Lys Glu His Ile Lys Gln Asn Glu Glu Glu
    370                 375                 380

Leu Ser Arg Val Arg Asp Glu Leu Thr Gln Ser Leu Ser Arg Asp Ser
385                 390                 395                 400

Gly Ser Asp Phe Lys Asp Asp Leu Leu Lys Glu Arg Glu Ala Glu Val
                405                 410                 415

Arg Asn Leu Lys Gln Asn Leu Ser Glu Ile Glu Gln Leu Asn Asp Ser
            420                 425                 430

Leu Asn Lys Val Ala Phe Asp Leu Lys Met Glu Asn Glu Lys Leu Val
        435                 440                 445

Leu Ala Cys Glu Asp Ile Arg His Gln Leu Glu Glu Ser Ile Val Gly
    450                 455                 460

Ser Asn Gln Met Ser Leu Glu Arg Asn Thr Ile Val Glu Ala Leu Lys
465                 470                 475                 480
```

```
Met Glu Lys Gly Gln Leu Glu Ala Glu Leu Ser Arg Ala Asp Gln Arg
            485                 490                 495

Leu Leu Glu Glu Ala Ser Lys Tyr Glu Gln Thr Ile Gln Glu Leu Ser
            500                 505                 510

Lys Ala Arg Asp Leu Arg Thr Ser Ala Leu Gln Leu Glu Gln Gln His
            515                 520                 525

Leu Met Lys Leu Ser Gln Glu Lys Asp Phe Glu Ile Ala Glu Leu Lys
            530                 535                 540

Lys Asn Ile Glu Gln Met Asp Thr Asp His Lys Glu Thr Lys Ala Ile
545                 550                 555                 560

Leu Ser Ser Ile Leu Glu Glu Gln Lys Gln Leu Thr Gln Leu Ile Ser
            565                 570                 575

Glu Lys Glu Ile Phe Ile Glu Lys Leu Lys Glu Arg Ser Ser Glu Leu
            580                 585                 590

Gln Glu Glu Leu Glu Lys Ser Thr Gln Ala Ser Arg Lys Ile Glu Ile
            595                 600                 605

Leu Lys Gln Thr Ile Glu Glu Lys Asp Arg Ser Leu Gly Ser Met Lys
            610                 615                 620

Glu Glu Asn Asn His Leu Lys Glu Glu Leu Glu Arg Leu Arg Glu Gln
625                 630                 635                 640

Gln Ser Arg Ala Val Pro Val Glu Pro Lys Pro Leu Asp Ser Val
            645                 650                 655

Thr Glu Leu Glu Ser Glu Val Leu Gln Leu Asn Ile Val Lys Arg Asn
            660                 665                 670

Leu Glu Glu Glu Ile Lys Arg His Gln Lys Ile Ile Glu Asp Gln Asn
            675                 680                 685

Gln Ser Lys Met Gln Leu Leu Gln Ser Leu Glu Glu Gln Lys Lys Glu
            690                 695                 700

Met Asp Glu Phe Lys Cys Gln His Glu Gln Met Asn Val Thr His Thr
705                 710                 715                 720

Gln Leu Phe Leu Glu Lys Asp Glu Glu Ile Lys Asn Leu Gln Lys Thr
            725                 730                 735

Ile Glu Gln Ile Lys Thr Gln Trp His Glu Glu Arg Gln Asp Val Gln
            740                 745                 750

Met Glu Asn Ser Glu Phe Phe Gln Glu Thr Lys Val Gln Ser Leu Asn
            755                 760                 765

Leu Glu Asn Gly Ser Glu Lys His Asp Leu Ser Lys Ala Glu Thr Glu
            770                 775                 780

Arg Leu Val
785

<210> SEQ ID NO 55
<211> LENGTH: 788
<212> TYPE: PRT
<213> ORGANISM: Homo sapiens

<400> SEQUENCE: 55

Met Ser Val Leu Gln Asn Ala His Gln Gln Lys Leu Thr Glu Ile Ser
1               5                   10                  15

Arg Arg His Arg Glu Glu Leu Ser Asp Tyr Glu Glu Arg Ile Glu Glu
            20                  25                  30

Leu Glu Asn Leu Leu Gln Gln Gly Gly Ser Gly Val Ile Glu Thr Asp
            35                  40                  45

Leu Ser Lys Ile Tyr Glu Met Gln Lys Thr Ile Gln Val Leu Gln Ile
```

```
                50                  55                  60
        Glu Lys Val Glu Ser Thr Lys Met Glu Gln Leu Glu Asp Lys Ile
        65                  70                  75                  80

Lys Asp Ile Asn Lys Lys Leu Ser Ser Ala Glu Asn Asp Arg Asp Ile
                            85                  90                  95

Leu Arg Arg Glu Gln Glu Gln Leu Asn Val Glu Lys Arg Gln Ile Met
                        100                 105                 110

Glu Glu Cys Glu Asn Leu Lys Leu Glu Cys Ser Lys Leu Gln Pro Ser
                    115                 120                 125

Ala Val Lys Gln Ser Asp Thr Met Thr Glu Lys Glu Arg Ile Leu Ala
                130                 135                 140

Gln Ser Ala Ser Val Glu Glu Val Phe Arg Leu Gln Gln Ala Leu Ser
        145                 150                 155                 160

Asp Ala Glu Asn Glu Ile Met Arg Leu Ser Ser Leu Asn Gln Asp Asn
                            165                 170                 175

Ser Leu Ala Glu Asp Asn Leu Lys Leu Lys Met Arg Ile Glu Val Leu
                        180                 185                 190

Glu Lys Glu Lys Ser Leu Leu Ser Gln Glu Lys Glu Glu Leu Gln Met
                    195                 200                 205

Ser Leu Leu Lys Leu Asn Asn Glu Tyr Glu Val Ile Lys Ser Thr Ala
                210                 215                 220

Thr Arg Asp Ile Ser Leu Asp Ser Glu Leu His Asp Leu Arg Leu Asn
        225                 230                 235                 240

Leu Glu Ala Lys Glu Gln Glu Leu Asn Gln Ser Ile Ser Glu Lys Glu
                            245                 250                 255

Thr Leu Ile Ala Glu Ile Glu Glu Leu Asp Arg Gln Asn Gln Glu Ala
                        260                 265                 270

Thr Lys His Met Ile Leu Ile Lys Asp Gln Leu Ser Lys Gln Gln Asn
                    275                 280                 285

Glu Gly Asp Ser Ile Ile Ser Lys Leu Lys Gln Asp Leu Asn Asp Glu
                290                 295                 300

Lys Lys Arg Val His Gln Leu Glu Asp Asp Lys Met Asp Ile Thr Lys
        305                 310                 315                 320

Glu Leu Asp Val Gln Lys Gly Lys Leu Ile Gln Ser Glu Val Ala Leu
                            325                 330                 335

Asn Asp Leu His Leu Thr Lys Gln Lys Leu Glu Asp Lys Val Glu Asn
                        340                 345                 350

Leu Val Asp Gln Leu Asn Lys Ser Gln Glu Ser Asn Val Ser Ile Gln
                    355                 360                 365

Lys Glu Asn Leu Glu Leu Lys Glu His Ile Arg Gln Asn Glu Glu Glu
                370                 375                 380

Leu Ser Arg Ile Arg Asn Glu Leu Met Gln Ser Leu Asn Gln Asp Ser
        385                 390                 395                 400

Asn Ser Asn Phe Lys Asp Thr Leu Leu Lys Glu Arg Glu Ala Glu Val
                            405                 410                 415

Arg Asn Leu Lys Gln Asn Leu Ser Glu Leu Glu Gln Leu Asn Glu Asn
                        420                 425                 430

Leu Lys Lys Val Ala Phe Asp Val Lys Met Glu Asn Glu Lys Leu Val
                    435                 440                 445

Leu Ala Cys Glu Asp Val Arg His Gln Leu Glu Glu Cys Leu Ala Gly
                450                 455                 460

Asn Asn Gln Leu Ser Leu Glu Lys Asn Thr Ile Val Glu Thr Leu Lys
        465                 470                 475                 480
```

```
Met Glu Lys Gly Glu Ile Glu Ala Glu Leu Cys Trp Ala Lys Lys Arg
            485                 490                 495
Leu Leu Glu Glu Ala Asn Lys Tyr Glu Lys Thr Ile Glu Glu Leu Ser
        500                 505                 510
Asn Ala Arg Asn Leu Asn Thr Ser Ala Leu Gln Leu Glu His Glu His
        515                 520                 525
Leu Ile Lys Leu Asn Gln Lys Lys Asp Met Glu Ile Ala Glu Leu Lys
        530                 535                 540
Lys Asn Ile Glu Gln Met Asp Thr Asp His Lys Glu Thr Lys Asp Val
545                 550                 555                 560
Leu Ser Ser Ser Leu Glu Glu Gln Lys Gln Leu Thr Gln Leu Ile Asn
                565                 570                 575
Lys Lys Glu Ile Phe Ile Glu Lys Leu Lys Glu Arg Ser Ser Lys Leu
                580                 585                 590
Gln Glu Glu Leu Asp Lys Tyr Ser Gln Ala Leu Arg Lys Asn Glu Ile
            595                 600                 605
Leu Arg Gln Thr Ile Glu Glu Lys Asp Arg Ser Leu Gly Ser Met Lys
        610                 615                 620
Glu Glu Asn Asn His Leu Gln Glu Glu Leu Glu Arg Leu Arg Glu Glu
625                 630                 635                 640
Gln Ser Arg Thr Ala Pro Val Ala Asp Pro Lys Thr Leu Asp Ser Val
                645                 650                 655
Thr Glu Leu Ala Ser Glu Val Ser Gln Leu Asn Thr Ile Lys Glu His
                660                 665                 670
Leu Glu Glu Glu Ile Lys His His Gln Lys Ile Ile Glu Asp Gln Asn
            675                 680                 685
Gln Ser Lys Met Gln Leu Leu Gln Ser Leu Gln Glu Gln Lys Lys Glu
        690                 695                 700
Met Asp Glu Phe Arg Tyr Gln His Glu Gln Met Asn Ala Thr His Thr
705                 710                 715                 720
Gln Leu Phe Leu Glu Lys Asp Glu Glu Ile Lys Ser Leu Gln Lys Thr
                725                 730                 735
Ile Glu Gln Ile Lys Thr Gln Leu His Glu Glu Arg Gly Asp Ile Gln
                740                 745                 750
Thr Asp Asn Ser Asp Ile Phe Gln Glu Thr Lys Val Gln Ser Leu Asn
            755                 760                 765
Ile Glu Asn Gly Ser Glu Lys His Asp Leu Ser Lys Ala Glu Thr Glu
        770                 775                 780
Arg Leu Val Lys
785

<210> SEQ ID NO 56
<211> LENGTH: 24
<212> TYPE: DNA
<213> ORGANISM: Artificial Sequence
<220> FEATURE:
<223> OTHER INFORMATION: Synthetic primer

<400> SEQUENCE: 56
gtcgacatgt cgtcctggct cggg                                        24

<210> SEQ ID NO 57
<211> LENGTH: 24
<212> TYPE: DNA
<213> ORGANISM: Artificial Sequence
<220> FEATURE:
<223> OTHER INFORMATION: Synthetic primer
```

```
<400> SEQUENCE: 57
ctcgagctat tgctttaaaa ggtc                                        24

<210> SEQ ID NO 58
<211> LENGTH: 24
<212> TYPE: DNA
<213> ORGANISM: Artificial Sequence
<220> FEATURE:
<223> OTHER INFORMATION: Synthetic primer

<400> SEQUENCE: 58
catatgtcgt cctggcttgg gggc                                        24

<210> SEQ ID NO 59
<211> LENGTH: 25
<212> TYPE: DNA
<213> ORGANISM: Artificial Sequence
<220> FEATURE:
<223> OTHER INFORMATION: Synthetic primer

<400> SEQUENCE: 59
ggtaccttgc tttaaaaggt ctttc                                       25
```